US012535734B2

(12) United States Patent
Miyoshi et al.

(10) Patent No.: US 12,535,734 B2
(45) Date of Patent: Jan. 27, 2026

(54) ACTINIC-RAY-SENSITIVE OR RADIATION-SENSITIVE RESIN COMPOSITION, ACTINIC-RAY-SENSITIVE OR RADIATION-SENSITIVE FILM, METHOD FOR FORMING PATTERN, AND METHOD FOR PRODUCING ELECTRONIC DEVICE

(71) Applicant: FUJIFILM Corporation, Tokyo (JP)

(72) Inventors: Taro Miyoshi, Shizuoka (JP); Eiji Fukuzaki, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 655 days.

(21) Appl. No.: 17/948,838

(22) Filed: Sep. 20, 2022

(65) Prior Publication Data

US 2023/0075188 A1 Mar. 9, 2023

Related U.S. Application Data

(63) Continuation of application No. PCT/JP2021/010955, filed on Mar. 17, 2021.

(30) Foreign Application Priority Data

Mar. 31, 2020 (JP) ................................ 2020-065191

(51) Int. Cl.

| | |
|---|---|
| ***G03F 7/039*** | (2006.01) |
| ***C07C 25/18*** | (2006.01) |
| ***C07C 43/225*** | (2006.01) |
| ***C07C 309/04*** | (2006.01) |
| ***C07C 381/12*** | (2006.01) |
| ***C07D 307/00*** | (2006.01) |
| ***C07D 309/30*** | (2006.01) |
| ***C07D 327/06*** | (2006.01) |
| ***C07D 333/46*** | (2006.01) |
| ***C07D 333/76*** | (2006.01) |
| ***C07D 335/02*** | (2006.01) |
| ***C08F 212/14*** | (2006.01) |
| ***C08F 220/28*** | (2006.01) |
| ***C08F 220/30*** | (2006.01) |
| ***G03F 7/004*** | (2006.01) |
| ***G03F 7/038*** | (2006.01) |

(52) U.S. Cl.

CPC .............. *G03F 7/039* (2013.01); *C07C 25/18* (2013.01); *C07C 43/225* (2013.01); *C07C 309/04* (2013.01); *C07C 381/12* (2013.01); *C07D 307/00* (2013.01); *C07D 309/30* (2013.01); *C07D 327/06* (2013.01); *C07D 333/46* (2013.01); *C07D 333/76* (2013.01); *C07D 335/02* (2013.01); *C08F 212/24* (2020.02); *C08F 220/283* (2020.02); *C08F 220/301* (2020.02); *G03F 7/0045* (2013.01); *G03F 7/038* (2013.01)

(58) Field of Classification Search

CPC ... C07C 309/06; C07C 309/17; C07C 311/00; C07C 311/48; C07C 381/12

See application file for complete search history.

(56) References Cited

U.S. PATENT DOCUMENTS

| | | | | |
|---|---|---|---|---|
| 9,323,150 | B2 | 4/2016 | Hirano et al. | |
| 11,656,548 | B2 * | 5/2023 | Tsuchimura .......... | G03F 7/0045 430/5 |
| 11,687,001 | B2 * | 6/2023 | Yoshimura ............ | C08F 220/20 430/270.1 |
| 12,032,288 | B2 * | 7/2024 | Kojima ................. | C07C 309/12 |
| 2015/0331314 | A1 | 11/2015 | Yamaguchi et al. | |
| 2018/0120708 | A1 | 5/2018 | Tsubaki et al. | |
| 2021/0072642 | A1 * | 3/2021 | Asakawa .............. | C08F 220/24 |
| 2021/0165325 | A1 | 6/2021 | Miyoshi et al. | |
| 2021/0356862 | A1 * | 11/2021 | Kojima ................. | C07C 311/48 |
| 2021/0364917 | A1 * | 11/2021 | Uemura ................ | C07C 311/16 |
| 2021/0386264 | A1 * | 12/2021 | Yang ........................ | A47L 9/281 |
| 2022/0043347 | A1 * | 2/2022 | Takada ...................... | G03F 7/11 |

FOREIGN PATENT DOCUMENTS

| | | | | |
|---|---|---|---|---|
| CN | 101464628 | A | 6/2009 | |
| CN | 101464628 | B | 12/2012 | |
| CN | 108351592 | A | 7/2018 | |
| JP | 2005275153 | A * | 10/2005 | .......... G03F 7/0045 |
| JP | 2008-129433 | A | 6/2008 | |
| JP | 2014-149409 | A | 8/2014 | |
| JP | 2019-14704 | A | 1/2019 | |
| TW | 201435505 | A | 9/2014 | |
| TW | I551942 | B | 10/2016 | |

(Continued)

OTHER PUBLICATIONS

Machine translation of JP 2005-275153 (no date) (Year: 0000).*
Machine translation of JP 2019-014704 (no date) (Year: 0000).*
Communication issued from the Japan Patent Office on May 30, 2023 in corresponding Japanese Application No. 2022-511860.
Office Action issued Aug. 8, 2024 by the Korean Patent Office for KR Patent Application No. 10-2022-7032707.
International Search Report (PCT/ISA/210) issued by the International Searching Authority in International Application No. PCT/JP2021/010955 dated Jun. 1, 2021.
Written Opinion (PCT/IB/373, PCT/ISA/237) issued by the International Searching Authority in International Application No. PCT/JP2021/010955 dated Jun. 1, 2021.

(Continued)

*Primary Examiner* — Amanda C. Walke
(74) *Attorney, Agent, or Firm* — Sughrue Mion, PLLC

(57) ABSTRACT

The present invention provides an actinic ray-sensitive or radiation-sensitive resin composition containing (A) a resin having a polarity that increases by an action of an acid, and (B) a compound that generates an acid upon irradiation with actinic rays or radiation, represented by a specific general formula, is which the resin (A) includes a repeating unit represented by a specific general formula; and an actinic ray-sensitive or radiation-sensitive film formed of the actinic ray-sensitive or radiation-sensitive resin composition, a pattern forming method, and a method for manufacturing an electronic device.

12 Claims, No Drawings

(56) References Cited

FOREIGN PATENT DOCUMENTS

| | | | |
|---|---|---|---|
| WO | 2019/054311 | A1 | 3/2019 |
| WO | 2020/045534 | A1 | 3/2020 |
| WO | 2020/158366 | A1 | 8/2020 |

OTHER PUBLICATIONS

Office Action issued on Aug. 30, 2024 by the Chinese Patent Office in corresponding CN Patent Application No. 202180024024.9.

Extended European Search Report dated Aug. 17, 2023, issued by the European Patent Office in counterpart European Patent Application No. 21779362.9.

Office Action issued Apr. 25, 2025 by the Korean Intellectual Property Office in Korean Patent Application No. 10-2022-7032707.

Communication dated Jul. 2, 2025, issued by the Israeli Patent Office in Israeli Application No. 296306.

* cited by examiner

ACTINIC-RAY-SENSITIVE OR RADIATION-SENSITIVE RESIN COMPOSITION, ACTINIC-RAY-SENSITIVE OR RADIATION-SENSITIVE FILM, METHOD FOR FORMING PATTERN, AND METHOD FOR PRODUCING ELECTRONIC DEVICE

CROSS REFERENCE TO RELATED APPLICATION

This is a continuation of International Application No. PCT/JP2021/010955 filed on Mar. 17, 2021, and claims priority from Japanese Patent Application No. 2020-065191 filed on Mar. 31, 2020, the entire disclosures of which are incorporated herein by reference.

BACKGROUND OF THE INVENTION

1. Field of the Invention

The present invention relates to an actinic ray-sensitive or radiation-sensitive resin composition, an actinic ray-sensitive or radiation-sensitive film, a pattern forming method, and a method for manufacturing an electronic device. More specifically, the present invention relates to an actinic ray-sensitive or radiation-sensitive resin composition, an actinic ray-sensitive or radiation-sensitive film, a pattern forming method, and a method for manufacturing an electronic device, each of which is suitably used for an ultra-microlithography process applicable to a process for manufacturing an ultra-large scale integration (LSI) and a high-capacity microchip, a process for creating a mold for a nanoimprint, a process for manufacturing a high-density information recording medium, and the like, and other photofabrication processes.

2. Description of the Related Art

In processes for manufacturing semiconductor devices such as an integrated circuit (IC) and an LSI, microfabrication by lithography using a photoresist composition has been performed in the related art. In recent years, along with the high integration of integrated circuits, the formation of ultrafine patterns in a submicron region or quarter micron region has been required. Along with this, the exposure wavelength also tends to be shortened from g-line to i-line, and further to KrF excimer laser light, and an exposure machine using an ArF excimer laser having a wavelength of 193 nm as a light source is currently being developed. In addition, the development of a so-called liquid immersion method in which a liquid having a high refractive index (hereinafter also referred to as an "immersion liquid") is filled between a projection lens and a sample as a technique for further enhancing a resolving power has been in progress since the related art.

Furthermore, at present, the development of lithography using electron beams (EB), X-rays, extreme ultraviolet rays (EUV), or the like in addition to excimer laser light is also in progress. Along with this, chemically amplified resist compositions which are effectively sensitive to various radiations and are excellent in a sensitivity and a resolution have been developed.

For example, JP2014-149409A describes an actinic ray-sensitive or radiation-sensitive resin composition containing (A) a resin having a group that decomposes by the action of an acid to generate a polar group, and at least one of (C1) a compound having a group that generates a first acidic functional group upon a irradiation with actinic rays or radiation and a group that generates a second acidic functional group different from the first acidic functional group upon irradiation with actinic rays or radiation, or (C2) a compound having two or more groups that generate a specific structure upon irradiation with actinic rays or radiation.

In addition, WO2020/045534A describes an actinic ray-sensitive or radiation-sensitive resin composition containing a resin having a solubility in an alkali developer that increases through decomposition by an action of an acid, and a compound that generates an acid upon irradiation with actinic rays or radiation, represented by a specific formula.

SUMMARY OF THE INVENTION

However, in recent years, due to further miniaturization of a pattern formed, and the like, there has been a demand for an actinic ray-sensitive or radiation-sensitive resin composition capable of further improving line width roughness (LWR) and resolving power in a method for forming an ultrafine pattern (particularly having a line width or space width of 30 nm or less).

An object of the present invention is to provide an actinic ray-sensitive or radiation-sensitive resin composition capable of improving roughness performance and a resolving power at a high level in formation of an ultrafine pattern (particularly having a line width or space width of 30 nm or less). In addition, another object of the present invention is to provide an actinic ray-sensitive or radiation-sensitive film, a pattern forming method, and a method for manufacturing an electronic device, each of which uses the actinic ray-sensitive or radiation-sensitive resin composition.

The present inventors have found that the objects can be accomplished by the following configurations.

[1] An actinic ray-sensitive or radiation-sensitive resin composition comprising:

(A) a resin having a polarity that increases by an action of an acid; and (B) a compound that generates an acid upon irradiation with actinic rays or radiation, represented by General Formula (I), in which the resin (A) includes a repeating unit represented by General Formula (AI).

(AI)

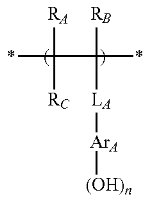

In General Formula (AI), $R_A$, $R_B$, and $R_C$ each independently represent a hydrogen atom, an alkyl group, a cycloalkyl group, a halogen atom, a cyano group, or an alkoxycarbonyl group. It should be noted that R may be bonded to $Ar_A$ to form a ring, in which case $R_C$ represents a single bond or an alkylene group.

$L_A$ represents a single bond or a divalent linking group.

$Ar_A$ represents an (n+1)-valent aromatic ring group. In a case where $Ar_A$ is bonded to $R_C$ to form a ring, $Ar_A$ represents an (n+2)-valent aromatic ring group.

n represents an integer of 1 to 5.

(I)

$$(M_1^+\ A_1^-)_m X - A_2^-\ M_2^+$$

In General Formula (I), $M_1^+$ and $M_2^+$ each independently represent a cation.

X represents a single bond or an (m+1)-valent linking group.

$A_1^-$ and $A_2^-$ each independently represent an anionic group. $A_1^-$ represents a structure different from the anionic group represented by $A_2^-$.

m represents 1 or 2. In a case where m represents 2, a plurality of $M_1^+$'s may be the same as or different from each other. In a case where m represents 2, a plurality of $A_1^-$'s may be the same as or different from each other.

It should be noted that a compound (PI) in which $M_1^+$ and $M_2^+$ of the compound represented by General Formula (I) are each substituted with a hydrogen atom has an acid dissociation constant a1 of a group represented by $HA_1$ and an acid dissociation constant a2 of a group represented by $A_2H$, the acid dissociation constant a1 is lower than the acid dissociation constant a2, and the acid dissociation constant at is −1.5 or more.

[2] The actinic ray-sensitive or radiation-sensitive resin composition as described in [1], in which in General Formula (I), $A_1^-$ and $A_2^-$ are each independently a group selected from the group consisting of groups represented by General Formulae (B-1) to (B-27).

(B-1)

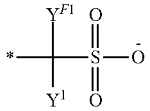

(B-2)

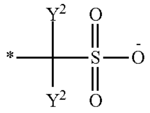

(B-3)

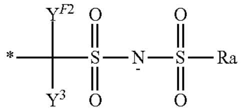

(B-4)

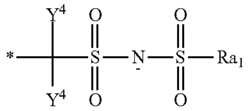

(B-5)

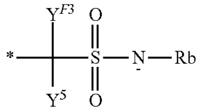

(B-6)

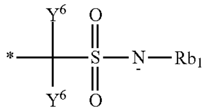

(B-7)

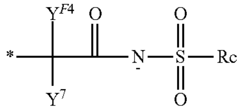

(B-8)

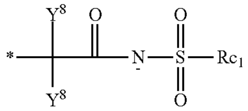

-continued (B-9)

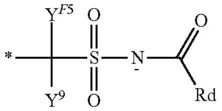

(B-10)

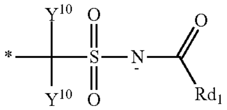

(B-11)

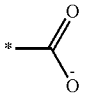

(B-12)

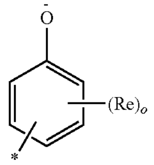

(B-13)

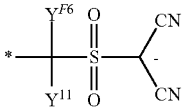

(B-14)

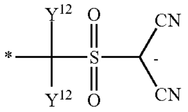

(B-15)

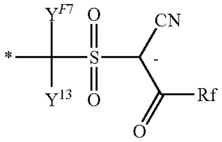

(B-16)

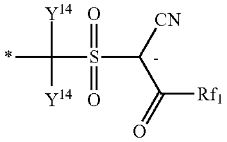

(B-17)

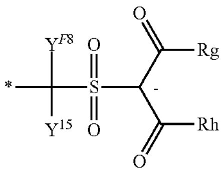

(B-18)

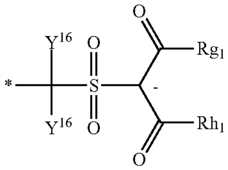

(B-19)

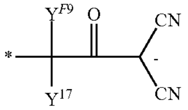

-continued (B-20)

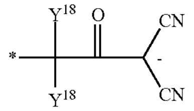

(B-21)

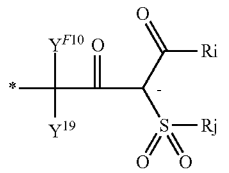

(B-22)

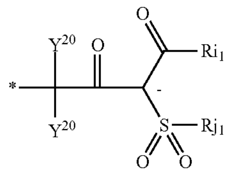

(B-23)

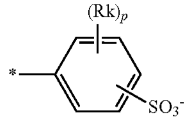

(B-24)

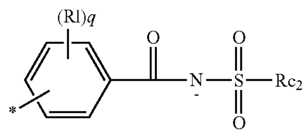

(B-25)

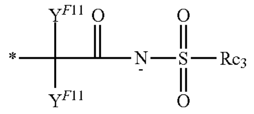

(B-26)

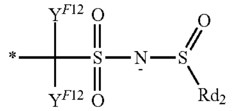

(B-27)

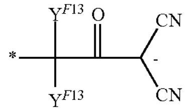

In General Formula (B-1), $Y^{F1}$ represents a fluorine atom or a perfluoroalkyl group.

$Y^1$ represents a hydrogen atom or a substituent having no fluorine atom.

In General Formula (B-2), $Y^2$'s each independently represent a hydrogen atom or a substituent having no fluorine atom.

In General Formula (B-3), $Y^{F8}$ represents a fluorine atom or a perfluoroalkyl group.

$Y^3$ represents a hydrogen atom or a substituent having no fluorine atom.

Ra represents an organic group.

In General Formula (B-4), $Y^4$'s each independently represent a hydrogen atom or a substituent having no fluorine atom.

$Ra_1$ represents an organic group.

In General Formula (B-5), $Y^{F3}$ represents a fluorine atom or a perfluoroalkyl group.

$Y^5$ represents a hydrogen atom or a substituent having no fluorine atom.

Rb represents a hydrogen atom or an organic group.

In General Formula (B-6), $Y^6$'s each independently represent a hydrogen atom or a substituent having no fluorine atom.

$Rb_1$ represents a hydrogen atom or an organic group.

In General Formula (B-7), $Y^{F4}$ represents a fluorine atom or a perfluoroalkyl group.

$Y^7$ represents a hydrogen atom or a substituent having no fluorine atom.

Rc represents an organic group.

In General Formula (B-8), $Y^8$'s each independently represent a hydrogen atom or a substituent having no fluorine atom.

$Rc_1$ represents an organic group.

In General Formula (B-9), $Y^{F5}$ represents a fluorine atom or a perfluoroalkyl group.

$Y^9$ represents a hydrogen atom or a substituent having no fluorine atom.

Rd represents an organic group.

In General Formula (B-10), $Y^{10}$'s each independently represent a hydrogen atom or a substituent having no fluorine atom.

$Rd_1$ represents an organic group.

In General Formula (R-12),

Re represents a hydrogen atom, an organic group, or a halogen atom.

represents an integer of 1 to 4.

In a case where o represents an integer of 2 or more, a plurality of Re's may be the same as or different from each other.

In General Formula (B-13).

$Y^{F6}$ represents a fluorine atom or a perfluoroalkyl group.

$Y^{11}$ represents a hydrogen atom or a substituent having no fluorine atom.

In General Formula (B-14), $Y^{12}$'s each independently represent a hydrogen atom or a substituent having no fluorine atom.

In General Formula (B-15).

$Y^{F7}$ represents a fluorine atom or a perfluoroalkyl group.

$Y^{13}$ represents a hydrogen atom or a substituent having no fluorine atom.

Rf represents an organic group.

In General Formula (B-16), $Y^{14}$'s each independently represent a hydrogen atom or a substituent having no fluorine atom.

$Rf_1$ represents an organic group.

In General Formula (B-17), $Y^{F8}$ represents a fluorine atom or a perfluoroalkyl group.

$Y^{15}$ represents a hydrogen atom or a substituent having no fluorine atom.

Rg represents an organic group.

Rh represents an organic group.

In General Formula (B-18), $Y^{16}$'s each independently represent a hydrogen atom or a substituent having no fluorine atom.

$Rg_1$ represents an organic group.

$Rh_1$ represents an organic group.

In General Formula (B-19), $Y^{F9}$ represents a fluorine atom or a perfluoroalkyl group.

$Y^{17}$ represents a hydrogen atom or a substituent having no fluorine atom.

In General Formula (B-20), $Y^{18}$s's each independently represent a hydrogen atom or a substituent having no fluorine atom.

In General Formula (B-21).

$Y^{F0}$ represents a fluorine atom or a perfluoroalkyl group.

$Y^{19}$ represents a hydrogen atom or a substituent having no fluorine atom.

Ri represents an organic group.

Rj represents an organic group.

In General Formula (B-22).

$Y^{20}$'s each independently represent a hydrogen atom or a substituent having no fluorine atom.

$Ri_1$ represents an organic group.

$Rj_1$ represents an organic group.

In General Formula (B-23),

Rk represents a hydrogen atom or a substituent having no fluorine atom.

p represents an integer of 1 to 4.

In a case where p represents an integer of 2 or more, a plurality of Rk's may be the same as or different from each other.

In General Formula (B-24).

Rl represents a hydrogen atom, an organic group, or a halogen atom.

q represents an integer of 1 to 4.

In a case where q represents an integer of 2 or more, a plurality of Rl's may be the same as or different from each other.

$R_2$ represents an organic group.

In General Formula (B-25).

$Y^{F11}$'s each independently represent a fluorine atom or a perfluoroalkyl group.

$Rc_3$ represents an organic group.

In General Formula (B-26), $Y^{F12}$'s each independently represent a fluorine atom or a perfluoroalkyl group.

$Rd_2$ represents an organic group.

In General Formula (B-27), $Y^{F13}$ 's each independently represent a fluorine atom or a perfluoroalkyl group.

In General Formulae (B-1) to (B-27).

* represents a bonding position.

[3] The actinic ray-sensitive or radiation-sensitive resin composition as described in [1] or [2], in which a difference between the acid dissociation constant a1 and the acid dissociation constant a2 is 2.0 or more in the compound (PI).

[4] The actinic ray-sensitive or radiation-sensitive resin composition as described in anyone of [1] to [3], in which the acid dissociation constant a2 is 2.0 or more in the compound (PI).

[5] The actinic ray-sensitive or radiation-sensitive resin composition as described in any one of [2] to [4], in which in General Formula (I), AC is the group represented by General Formula (B-2) or (B-23).

[6] The actinic ray-sensitive or radiation-sensitive resin composition as described in any one of [2] to [5], in which in General Formula (I), $A_1^-$ is the group represented by General Formula (B-2).

[7] The actinic ray-sensitive or radiation-sensitive resin composition as described in any one of [1] to [6], in which (A) the resin having a polarity that increases by an action of an acid includes a repeating unit having an acid-decomposable group, and the repeating unit having an acid-decomposable group is a repeating unit selected from the group consisting of a group that decomposes by an action of an acid to generate a carboxy group and a group that decomposes by an action of an acid to generate a phenolic hydroxyl group.

[8] The actinic ray-sensitive or radiation-sensitive resin composition as described in [7], in which the repeating unit having an acid-decomposable group includes one or more selected from repeating units represented by General Formulae (3) to (7).

(3)

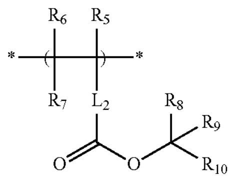

(4)

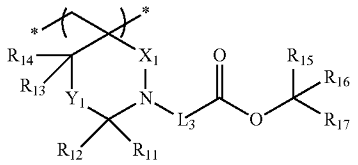

(5)

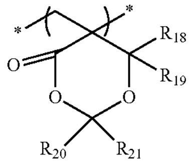

(6)

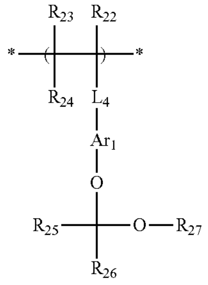

(7)

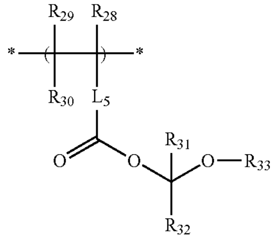

In General Formula (3), $R_5$, $R_6$, and $R_7$ each independently represent a hydrogen atom, an alkyl group, a cycloalkyl group, a halogen atom, a cyano group, or an alkoxycarbonyl group.

$L_2$ represents a single bond or a divalent linking group.

$R_8$ to $R_{10}$ each independently represent an alkyl group, a cycloalkyl group, an aryl group, an aralkyl group, or an alkenyl group. Furthermore, two of $R_8$ to $R_{10}$ may be bonded to each other to form a ring.

In General Formula (4), $R_{11}$ to $R_{14}$ each independently represent a hydrogen atom or an organic group. It should be noted that at least one of $R_{11}$ or $R_{12}$ represents an organic group.

$X_1$ represents —CO—, —SO—, or —$SO_2$—.

$Y_1$ represents —O—, —S—, —SO—, —$SO_2$—, or —$NR_{34}$—. $R_{34}$ represents a hydrogen atom or an organic group.

$L_3$ represents a single bond or a divalent linking group.

$R_{15}$ to $R_{17}$ each independently represent an alkyl group, a cycloalkyl group which may have a fluorine atom, an aryl group, an aralkyl group, or an alkenyl group. Furthermore, two of $R_{15}$ to $R_{17}$ may be bonded to each other to form a ring.

In General Formula (5), $R_{18}$ and $R_{19}$ each independently represent a hydrogen atom or an organic group. $R_{20}$ and $R_{21}$ each independently represent a hydrogen atom, an alkyl group, a cycloalkyl group, an aryl group, an aralkyl group, or an alkenyl group. Furthermore, $R_{20}$ and $R_{21}$ may be bonded to each other to form a ring.

In General Formula (6), $R_{22}$, $R_{23}$, and $R_{24}$ each independently represent a hydrogen atom, an alkyl group, a cycloalkyl group, a halogen atom, a cyano group, or an alkoxycarbonyl group.

$L_4$ represents a single bond or a divalent linking group.

$Ar_1$ represents an aromatic ring group.

$R_{25}$ to $R_{27}$ each independently represent a hydrogen atom, an alkyl group, a cycloalkyl group, an aryl group, an aralkyl group, or an alkenyl group. Furthermore, $R_{26}$ and $R_{27}$ may be bonded to each other to form a ring. In addition, $Ar_1$ may be bonded in $R_{24}$ or $R_{25}$ to form a ring.

In General Formula (7), $R_{28}$, $R_{29}$, and $R_{30}$ each independently represent a hydrogen atom, an alkyl group, a cycloalkyl group, a halogen atom, a cyano group, or an alkoxycarbonyl group.

$L_5$ represents a single bond or a divalent linking group.

$R_{31}$ and $R_{32}$ each independently represent a hydrogen atom, an alkyl group, a cycloalkyl group, an aryl group, an aralkyl group, or an alkenyl group.

$R_{33}$ represents an alkyl group, a cycloalkyl group, an aryl group, an aralkyl group, or an alkenyl group. Furthermore, $R_{32}$ and $R_{33}$ may be bonded to each other to form a ring.

[9] The actinic ray-sensitive or radiation-sensitive resin composition as described in [8], in which the repeating unit having an acid-decomposable group includes one or more selected from the repeating unit represented by General Formula (6) and the repeating unit represented by General Formula (7).

[10] The actinic ray-sensitive or radiation-sensitive resin composition as described in any one of [7] to [9], in which the repeating unit having an acid-decomposable group includes no halogen atom.

[11] An actinic my-sensitive or radiation-sensitive resin composition comprising:

(A) a resin having a polarity that increases by an action of an acid; and (B) a compound that generates an acid upon irradiation with actinic rays or radiation, represented by General Formula (I), in which the resin (A) includes a repeating unit represented by General Formula (AI).

(AI)

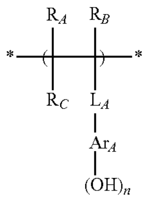

In General Formula (AI), $R_A$, $R_B$, and $R_c$ each independently represent a hydrogen atom, an alkyl group, a cycloalkyl group, a halogen atom, a cyano group, or an alkoxycarbonyl group. It should be noted that $R_C$ may be bonded to $Ar_A$ to form a ring, in which case $R_C$ represents a single bond or an alkylene group.

$L_A$ represents a single bond or a divalent linking group.

$Ar_A$ represents an (n+1)-valent aromatic ring group. In a case where $Ar_A$ is bonded to $R_C$ to form a ring, $Ar_A$ represents an (n+2)-valent aromatic ring group.

n represents an integer of 1 to 5.

(I)

$$(M_1^+\ A_1^-)_m\!-\!X-A_2^-\ M_2^+$$

In General Formula (I), $M_1^+$ and $M_2^+$ each independently represent a cation.

X represents an (m+1)-valent linking group.

$A_1^-$ and $A_2^-$ are each independently a group selected from the group consisting of groups represented by General Formulae (B-1) to (B-27).

(B-1)

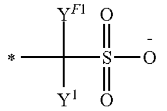

(B-2)

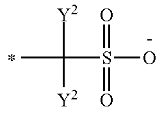

(B-3)

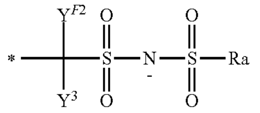

(B-4)

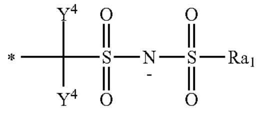

(B-5)

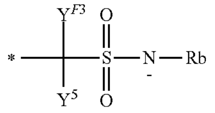

(B-6)

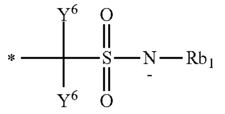

(B-7)

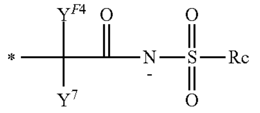

(B-8)

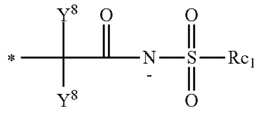

(B-9)

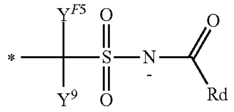

-continued (B-10)

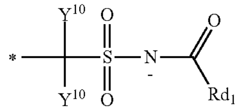

(B-11)

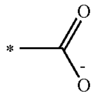

(B-12)

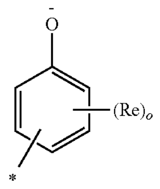

(B-13)

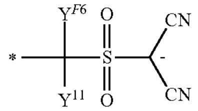

(B-14)

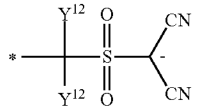

(B-15)

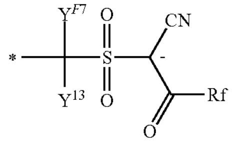

(B-16)

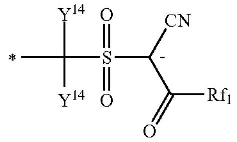

(B-17)

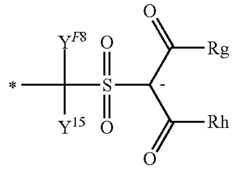

(B-18)

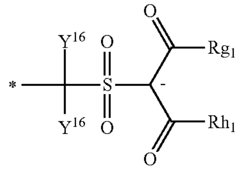

(B-19)

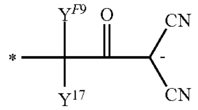

(B-20)

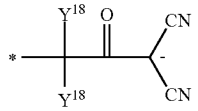

-continued (B-21)

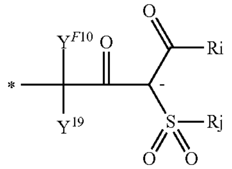

(B-22)

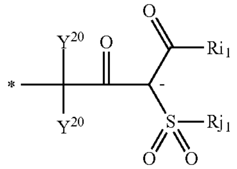

(B-23)

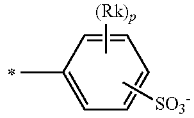

(B-24)

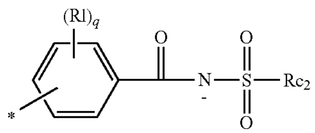

(B-25)

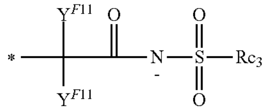

(B-26)

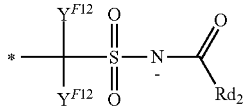

(B-27)

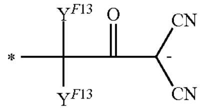

In General Formula (B-1), $Y^{F1}$ represents a fluorine atom or a perfluoroalkyl group.

$Y^1$ represents a hydrogen atom or a substituent having no fluorine atom.

In General Formula (B-2).

$Y^2$'s each independently represent a hydrogen atom or a substituent having no fluorine atom.

In General Formula (B-3).

$Y^{F2}$ represents a fluorine atom or a perfluoroalkyl group.

$Y^3$ represents a hydrogen atom or a substituent having no fluorine atom.

Ra represents an organic group.

In General Formula (B-4), $Y^4$'s each independently represent a hydrogen atom or a substituent having no fluorine atom.

$Ra_1$ represents an organic group.

In General Formula (B-5), $Y^{F3}$ represents a fluorine atom or a perfluoroalkyl group.

$Y^5$ represents a hydrogen atom or a substituent having no fluorine atom.

Rb represents a hydrogen atom or an organic group.

In General Formula (B-6), $Y^6$'s each independently represent a hydrogen atom or a substituent having no fluorine atom.

$Rb_1$ represents a hydrogen atom or an organic group.

In General Formula (B-7), $Y^{F3}$ represents a fluorine atom or a perfluoroalkyl group.

$Y^7$ represents a hydrogen atom or a substituent having no fluorine atom.

Rc represents an organic group.

In General Formula (B-8), $Y^8$'s each independently represent a hydrogen atom or a substituent having no fluorine atom.

$Rc_1$ represents an organic group.

In General Formula (B-9).

$Y^{F5}$ represents a fluorine atom or a perfluoroalkyl group.

$Y^9$ represents a hydrogen atom or a substituent having no fluorine atom.

Rd represents an organic group.

In General Formula (B-10), $Y^{10}$'s each independently represent a hydrogen atom or a substituent having no fluorine atom.

$Rd_1$ represents an organic group.

In General Formula (B-12).

Re represents a hydrogen atom, an organic group, or a halogen atom.

o represents an integer of 1 to 4.

In a case where o represents an integer of 2 or more, a plurality of Re's may be the same as or different from each other.

In General Formula (B-13), $Y^{F6}$ represents a fluorine atom or a perfluoroalkyl group.

$Y^{11}$ represents a hydrogen atom or a substituent having no fluorine atom.

In General Formula (B-14).

$Y^{12}$'s each independently represent a hydrogen atom or a substituent having no fluorine atom.

In General Formula (B-15).

$Y^{F7}$ represents a fluorine atom or a perfluoroalkyl group.

$Y^{13}$ represents a hydrogen atom or a substituent having no fluorine atom.

Rf represents an organic group.

In General Formula (B-16), $Y^{14}$'s each independently represent a hydrogen atom or a substituent having no fluorine atom.

$Rf_1$ represents an organic group.

In General Formula (B-17), $Y^{F8}$ represents a fluorine atom or a perfluoroalkyl group.

$Y^{15}$ represents a hydrogen atom or a substituent having no fluorine atom.

Rg represents an organic group.

Rh represents an organic group.

In General Formula (B-18), $Y^{16}$'s each independently represent a hydrogen atom or a substituent having no fluorine atom.

$Rg_1$ represents an organic group.

$Rh_1$ represents an organic group.

In General Formula (B-19), $Y^{F9}$ represents a fluorine atom or a perfluoroalkyl group.

$Y^{17}$ represents a hydrogen atom or a substituent having no fluorine atom.

In General Formula (B-20), $Y^{18}$'s each independently represent a hydrogen atom or a substituent having no fluorine atom.

In General Formula (B-21), $Y^{F10}$ represents a fluorine atom or a perfluoroalkyl group.

$Y^{19}$ represents a hydrogen atom or a substituent having no fluorine atom.

Ri represents an organic group.

Rj represents an organic group.

In General Formula (B-22), $Y^{20}$'s each independently represent a hydrogen atom or a substituent having no fluorine atom.

$Ri_1$ represents an organic group.

$Rj_1$ represents an organic group.

In General Formula (B-23),

Rk represents a hydrogen atom or a substituent having no fluorine atom.

p represents an integer of 1 to 4.

In a case where p represents an integer of 2 or more, a plurality of Rk's may be the same as or different from each other.

In General Formula (B-24),

Rl represents a hydrogen atom, an organic group, or a halogen atom.

q represents an integer of 1 to 4.

In a case where q represents an integer of 2 or more, a plurality of Rl's may be the same as or different from each other.

$Rc_2$ represents an organic group.

In General Formula (B-25), $Y^{F11}$ 's each independently represent a fluorine atom or a perfluoroalkyl group.

$Rc_3$ represents an organic group.

In General Formula (B-26), $Y^{F12}$'s each independently represent a fluorine atom or a perfluoroalkyl group.

$Rd_2$ represents an organic group.

In General Formula (B-27), $Y^{F13}$ 's each independently represent a fluorine atom or a perfluoroalkyl group.

In General Formulae (B-1) to (B-27),

* represents a bonding position.

$A_1^-$ represents a structure different from the group represented by $A_2^-$, m represents 1 or 2. In a case where m represents 2, a plurality of $M_1^+$'s may be the same as or different from each other. In a case where m represents 2, a plurality of $A_1^-$'s may be the same as or different from each other.

[12] An actinic ray-sensitive or mediation-sensitive film formed of the actinic ray-sensitive or radiation-sensitive resin composition as described in any one of [1] to [11].

[13] A pattern forming method comprising:

a resist film forming step of forming a resist film using the actinic ray-sensitive or radiation-sensitive resin composition as described in any one of [1] to [11];

an exposing step of exposing the resist film; and a developing step of developing the exposed resist film, using a developer.

[14] A method for manufacturing an electronic device, comprising the pattern forming method as described in [13].

According to the present invention, it is possible to provide an actinic ray-sensitive or radiation-sensitive resin composition capable of improving roughness performance and a resolving power at a high level in formation of an ultrafine pattern (particularly having a line width or space width of 30 nm or less). According to the present invention, it is possible to provide an actinic ray-sensitive or radiation-sensitive film, a pattern forming method, and a method for manufacturing an electronic device, each of which uses the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

"Actinic rays" or "radiation" in the present specification means, for example, a bright line spectrum of a mercury lamp, far ultraviolet rays typified by an excimer laser, extreme ultraviolet rays (EUV), X-rays, soft X-rays, electron beams (EB), or the like. "Light" in the present specification means actinic rays or radiation. Unless otherwise specified, "exposure" in the present specification encompasses not only exposure by a bright line spectrum of a mercury lamp, far ultraviolet rays typified by an excimer laser, extreme ultraviolet rays (EUV), X-rays, or the like, but also lithography by particle beams such as electron beams and ion beams.

In the present specification, a numerical range expressed using "to" is used in a meaning of a range that includes the preceding and succeeding numerical values of "to" as the lower limit value and the upper limit value, respectively.

The bonding direction of divalent groups cited in the present specification is not limited unless otherwise specified. For example, in a case where Y in a compound represented by General Formula "X—Y—Z" is —COO—, Y may be —CO—O— or —O—CO—. In addition, the compound may be "X—CO—O—Z" or "X—O—CO—Z".

In the present specification. (meth)acrylate represents at least one of acrylate or methacrylate. In addition, (meth) acrylic acid represents at least one of acrylic acid or methacrylic acid.

In the present specification, the weight-average molecular weight (Mw), the number-average molecular weight (Mn), and the dispersity (also referred to as a molecular weight distribution) (Mw/Mn) of a resin are each defined as a value expressed in terms of polystyrene by means of gel permeation chromatography (GPC) measurement (solvent: tetrahydrofuran, flow amount (amount of a sample injected): 10 μL, columns: TSK gel Multipore HXL-M manufactured by Tosoh Corporation, column temperature: 40° C., flow rate: 1.0 mL/min, detector: differential refractive index detector) using a GPC apparatus (HLC-8120 GPC manufactured by Tosoh Corporation).

In notations for a group (atomic group) in the present specification, in a case where the group is cited without specifying that it is substituted or unsubstituted, the group includes both a group having no substituent and a group having a substituent. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

Furthermore, in the present specification, the types of substituents, the positions of substituents, and the number of substituents in a case where it is described that "a substituent may be contained" are not particularly limited. The number of the substituents may be, for example, one, two, three, or more. Examples of the substituent include a monovalent non-metal atomic group excluding a hydrogen atom, and the substituent can be selected from, for example, the following substituent T.

(Substituent T)

Examples of the substituent T include halogen atoms such as a fluorine atom, a chlorine atom, a bromine atom, and an iodine atom; alkoxy groups such as a methoxy group, an ethoxy group, and a tert-butoxy group; aryloxy groups such as a phenoxy group and a p-tolyloxy group; alkoxycarbonyl groups such as a methoxycarbonyl group, a butoxycarbonyl group, and a phenoxycarbonyl group; acyloxy groups such as an acetoxy group, a propionyloxy group, and a benzoyloxy group; acyl groups such as an acetyl group, a benzoyl group, an isobutyryl group, an acryloyl group, a methacryloyl group, and a methoxalyl group; alkylsulfanyl groups such as a methylsulfanyl group and a tert-butylsulfanyl group; arylsulfanyl groups such as a phenylsulfanyl group and a p-tolylsulfanyl group; alkyl groups (for example, an alkyl group having 1 to 10 carbon atoms); cycloalkyl groups (for example, a cycloalkyl group having 3 to 20 carbon atoms); aryl groups (for example, an aryl group having 6 to 20 carbon atoms); heteroaryl groups: a hydroxyl group; a carboxy group; a formyl group; a sulfo group; a cyano group; an alkylaminocarbonyl group; an arylaminocarbonyl group; a sulfonamide group; a silyl group; an amino group; a monoalkylamino group; a dialkylamino group; an arylamino group, a nitro group; and a combination thereof.

In the present specification, an acid dissociation constant (pKa) represents a pKa in an aqueous solution, and is specifically a value determined by computation from a value based on a Hammett's substituent constant and database of publicly known literature values, using the following software package 1. Any of the pKa values described in the present specification indicate values determined by computation using the software package.

Software Package 1: Advanced Chemistry Development (ACD/Labs) Software V 8.14 for Solaris (1994-2007 ACD/Labs).

On the other hand, the pKa can also be determined by a molecular orbital computation method. Examples of a specific method therefor include a method for performing calculation by computing H' dissociation free energy in a solvent based on a thermodynamic cycle. (Furthermore, in the present specification, water is usually used as the solvent, and in a case where a pKa is not determined with water, dimethyl sulfoxide (DMSO) is used.)

With regard to the method for computing the H' dissociation free energy, the H' dissociation free energy can be computed by, for example, density functional theory (DFT), but various other methods have been reported in literature and the like, and are not limited thereto. Furthermore, there are a plurality of software applications capable of performing DFT, and examples thereof include Gaussian 16.

As described above, the pKa in the present specification refers to a value determined by computation from a value based on a Hammett's substituent constant and database of publicly known literature values, using the software package 1, but in a case where the pKa cannot be calculated by the method, a value obtained by Gaussian 16 based on density functional theory (DFT) shall be adopted.

[Actinic Ray-Sensitive or Radiation-Sensitive Resin Composition]

The actinic ray-sensitive or radiation-sensitive resin composition according to an embodiment of the present invention (hereinafter also referred to as a "composition of the embodiment of the present invention") is an actinic ray-sensitive or radiation-sensitive resin composition including:

(A) a resin having a polarity that increases by an action of an acid, and (B) a compound that generates an acid upon irradiation with actinic rays or radiation, represented by General Formula (I).

in which the resin (A) includes a repeating unit represented by General Formula (AI).

(AI)

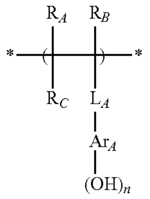

In General Formula (AI), $R_A$, $R_B$, and $R_C$ each independently represent a hydrogen atom, an alkyl group, a cycloalkyl group, a halogen atom, a cyano group, or an alkoxycarbonyl group. It should be noted that Re may be bonded to $Ar_A$ to form a ring, in which case $R_C$ represents a single bond or an alkylene group.

$L_A$ represents a single bond or a divalent linking group.

$Ar_A$ represents an (n+1)-valent aromatic ring group. In a case where $Ar_A$ is bonded to $R_C$ to form a ring, $Ar_A$ represents an (n+2)-valent aromatic ring group.

n represents an integer of 1 to 5.

$$(M_1^+\ A_1^-)_m\text{—}X\text{—}A_2^-\ M_2^+ \quad (I)$$

In General Formula (I), $M_1^+$ and $M_2^+$ each independently represent a cation.

X represents a single bond or an (m+1)-valent linking group.

$A_1^-$ and $A_2^-$ each independently represent an anionic group. $A_1^-$ represents a structure different from the anionic group represented by $A_2^-$.

m represents 1 or 2. In a case where m represents 2, a plurality of $M_1^+$'s may be the same as or different from each other. In a case where m represents 2, a plurality of $A_1^-$'s may be the same as or different from each other.

It should be noted that a compound (PI) in which $M_1^+$ and $M_2^+$ of the compound represented by General Formula (I) are each substituted with a hydrogen atom has an acid dissociation constant a1 of a group represented by $HA_1$ and an acid dissociation constant a2 of a group represented by $A_2H$, the acid dissociation constant a1 is lower than the acid dissociation constant a2, and the acid dissociation constant a1 is −1.5 or more.

The composition of the embodiment of the present invention is preferably a resist composition, and may be either a positive tone resist composition or a negative tone resist composition. In addition, the resist composition may be either a resist composition for alkali development or a resist composition for organic solvent development. Among those, the positive tone resist composition, which is a resist composition for alkali development, is preferable.

In addition, the composition of the embodiment of the present invention is preferably a chemically amplified resist composition, and more preferably a chemically amplified positive tone resist composition.

A reason why the composition of the embodiment of the present invention can accomplish both of improvement of roughness performance and improvement of a resolving power at a high level in formation of an ultrafine pattern (particularly having a line width or space width of 30 nm or less) has not been completely clarified, but is presumed as follows by the present inventors.

First, a resist composition including a photoacid generator and an acid diffusion control agent as individual compounds has been widely known since the related art. In a resist film formed from such the resist composition, it is considered that the acid diffusion control agent in the non-exposed portion captures an acid generated from the photoacid generator in the exposed portion, making it possible to suppress excessive diffusion in the non-exposed portion. As the acid diffusion control agent, a salt of an acid having an acid strength which is weaker than an acid generated by the photoacid generator (so-called a weak acid salt) is known.

As described above, although it is considered that a pattern having an excellent resolving power is formed by incorporating a photoacid generator and an acid diffusion control agent such as the weak acid salt into a resist composition, with regard to a demand for formation of an ultrafine pattern in recent years, it is more difficult to obtain required performance, for example, to accomplish excellent roughness performance at a high level at the same time, in addition to an excellent resolving power, with resist compositions in the related art.

The present inventors have conducted intensive studies, and as a result, they have considered that in a resist film formed by the resist composition in the related art, photoacid generators and acid diffusion control agents included as individual compounds are easily aggregated, and strictly speaking, the photoacid generators are easily aggregated to each other and the acid diffusion control agents are easily aggregated to each other; in other words, in the formed resist film, a portion having a high (or low) concentration of the photoacid generators and a portion having a high (or low) concentration of the acid diffusion control agents are likely to be present, and as a result, the concentration distribution of the photoacid generators and the acid diffusion control agents was non-uniform. It is considered that such non-uniformity has been a cause of, for example, deterioration of roughness performance, particularly in the formation of an ultrafine pattern in a case where the resist film was exposed.

On the other hand, the actinic ray-sensitive or radiation-sensitive resin composition of the embodiment of the present invention contains (B) the compound that generates an acid upon irradiation with actinic rays or radiation, represented by General Formula (I).

Since the compound represented by General Formula (I) includes both of a structural moiety ($A_1^-M_1^+$) having a function corresponding to a photoacid generator and a structural moiety ($A_2^-M_2^+$ (a structural moiety that captures an acid generated from $A_1^-M_1^+$)) having a function corresponding to an acid diffusion control agent) in one molecule, the compound that functions as both the photoacid generator and the acid diffusion control agent in the resist film can be more uniformly present.

Therefore, an excellent resolving power can be obtained, and at the same time, the width of a pattern obtained after development is easily stabilized. That is, it is considered that the roughness performance of the formed pattern is further improved.

The resin (A) in the composition of the embodiment of the present invention has a repeating unit represented by General Formula (A). It is considered that an interaction of the compound (B) with a hydroxy group at a terminal of the repeating unit further suppresses the aggregation of the compound (B) and further improves the roughness performance of the formed pattern.

In addition, in a case where the strength of an acid generated from the photoacid generator is too high, an acid generated in the exposed portion tends to cause excessive diffusion into the non-exposed portion, not staying in the exposed portion.

However, the acid dissociation constant a1 in the compound (PI) in which $M_1^+$ and $M_2^+$ of the compound represented by General Formula (I) are each substituted with a hydrogen atom is −1.5 or more. In other words, it is presumed that in the compound (B), the strength of an acid generated from the structural moiety ($A_1^-M_1^+$) having a function corresponding to the photoacid generator provides the acid with a strength moderately suppressed, and can suppress excessive diffusion of the acid into die non-exposed portion, and thus, the roughness performance of the formed pattern is further improved, particularly in the formation of an ultrafine pattern.

[(B) Compound that Generates Acid Upon Irradiation with Actinic Rays or Radiation, Represented by General Formula (I)]

As described above, the actinic ray-sensitive or radiation-sensitive resin composition of the embodiment of the present invention contains (B) a compound that generates an acid upon irradiation with actinic rays or radiation, represented by General Formula (I) (hereinafter also referred to as a "compound (B)" or a "photoacid generator (B)").

The compound (B) is a compound that generates an acid upon irradiation with actinic rays or radiation (photoacid generator).

<Compound Represented by General Formula (I)>

$$(M_1^+\ A_1^-)_m\text{—}X\text{—}A_2^-\ M_2^+ \qquad (I)$$

In General Formula (I), $M_1^+$ and $M_2^+$ each independently represent a cation.

X represents a single bond or an (m+1)-valent linking group.

$A_1^-$ and $A_2^-$ each independently represent an anionic group. $A_1^-$ represents a structure different from the anionic group represented by $A_2^-$.

m represents 1 or 2. In a case where m represents 2, a plurality of $M_1^+$'s may be the same as or different from each other. In ace where m represents 2, a plurality of $A_1^+$'s may be the same as or different from each other.

It should be noted that a compound (PI) in which $M_1^+$ and $M_2^+$ of the compound represented by General Formula (I) are each substituted with a hydrogen atom has an acid dissociation constant a1 of a group represented by $HA_1$ and an acid dissociation constant a2 of a group represented by $A_2H$, the acid dissociation constant a1 is lower than the acid dissociation constant a2, and the acid dissociation constant a1 is −1.5 or more.

In General Formula (I), the cations represented by $M_1^+$ and $M_2^+$ are as described later.

In General Formula (I), the divalent linking group represented by X in a case where m is 1 is not particularly limited, and examples thereof include —NR—, —CO—, —O—, an alkylene group (which preferably has 1 to 8 carbon atoms, and may be linear or branched), a cycloalkylene group (preferably having 3 to 15 carbon atoms), an alkenylene group (preferably having 2 to 6 carbon atoms), a divalent aliphatic heterocyclic group (preferably having a 5- to 10-membered ring, more preferably having a 5- to 7-membered ring, and still more preferably having a 5- or 6-membered ring, each having at least one of an N atom, an O atom, an S atom, or an Se atom in the ring structure), a divalent aromatic heterocyclic group (preferably having a 5- to 10-membered ring, more preferably having a 5- to 7-membered ring, and still more preferably having a 5- or 6-membered ring, each having at least one of an N atom, an O atom, an S atom, or an Se atom in the ring structure), a divalent aromatic hydrocarbon ring group (preferably having a 6- to 10-membered ring, and more preferably having a 6-membered ring), and a group formed by combination of a plurality of these groups. Examples of R include a hydrogen atom or a monovalent organic group. The monovalent organic group is not particularly limited, but is preferably, for example, an alkyl group (preferably having 1 to 6 carbon atoms).

The divalent linking group may further include a group selected from the group consisting of —S—, —SO—, and $—SO_2—$.

In addition, the alkylene group, the cycloalkylene group, the alkenylene group, the divalent aliphatic heterocyclic group, the divalent aromatic heterocyclic group, and the divalent aromatic hydrocarbon ring group may each have a substituent. The substituent is not particularly limited, and examples thereof include the above-mentioned substituent T.

Suitable specific examples of the trivalent linking group in a case where m is 2 include groups formed by removing any one hydrogen atom from the specific examples of the divalent linking group.

The anionic group represented by each of $A_1^-$ and $A_2^-$ is not particularly limited as long as the group has an acid dissociation constant a1 lower than the acid dissociation constant a2, and the acid dissociation constant a1 is −1.5 or more, but examples thereof each independently include a group selected from the group consisting of groups represented by General Formulae (B-1) to (B-27).

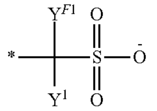
(B-1)

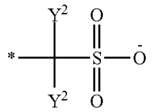
(B-2)

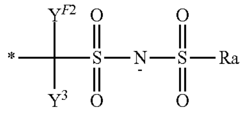
(B-3)

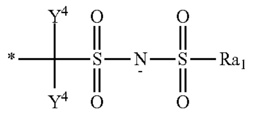
(B-4)

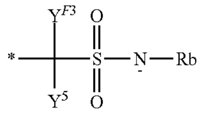
(B-5)

-continued
(B-6)
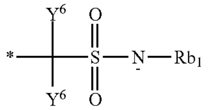
(B-7)
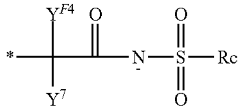
(B-8)
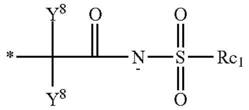
(B-9)
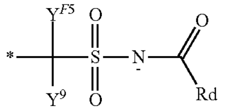
(B-10)
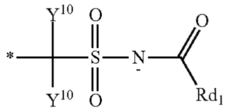
(B-11)
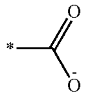
(B-12)
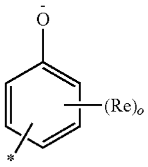
(B-13)
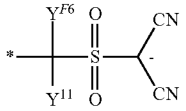
(B-14)
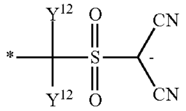
(B-15)
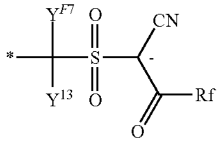
(B-16)
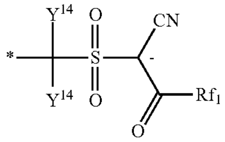
-continued
(B-17)
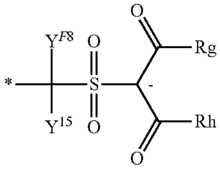
(B-18)
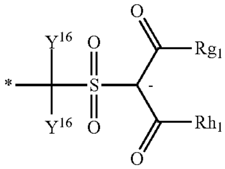
(B-19)
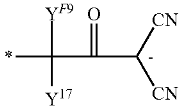
(B-20)
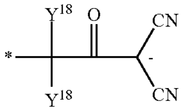
(B-21)
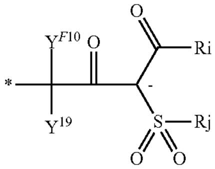
(B-22)
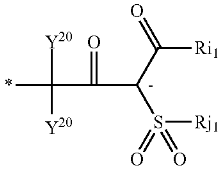
(B-23)
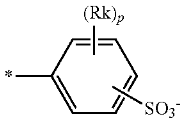
(B-24)
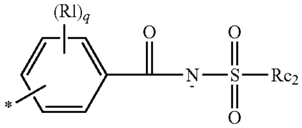
(B-25)
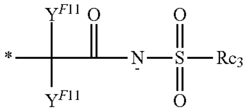
(B-26)
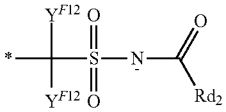

-continued (B-27)

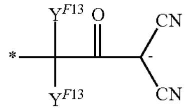

In General Formula (B-1), $Y^{F1}$ represents a fluorine atom or a perfluoroalkyl group.

$Y^1$ represents a hydrogen atom or a substituent having no fluorine atom.

In General Formula (B-2), $Y^2$'s each independently represent a hydrogen atom or a substituent having no fluorine atom.

In General Formula (B-3), $Y^{F2}$ represents a fluorine atom or a perfluoroalkyl group.

$Y^3$ represents a hydrogen atom or a substituent having no fluorine atom.

Ra represents an organic group.

In General Formula (B-4), $Y^4$'s each independently represent a hydrogen atom or a substituent having no fluorine atom.

$Ra_1$ represents an organic group.

In General Formula (B-5), $Y^{F3}$ represents a fluorine atom or a perfluoroalkyl group.

$Y^5$ represents a hydrogen atom or a substituent having no fluorine atom.

Rb represents a hydrogen atom or an organic group.

In General Formula (B-6), $Y^6$'s each independently represent a hydrogen atom or a substituent having no fluorine atom.

$Rb_1$ represents a hydrogen atom or an organic group.

In General Formula (B-7), $Y^{F4}$ represents a fluorine atom or a perfluoroalkyl group.

$Y^7$ represents a hydrogen atom or a substituent having no fluorine atom.

$R_C$ represents an organic group.

In General Formula (B-8), $Y^8$'s each independently represent a hydrogen atom or a substituent having no fluorine atom.

$Rc_1$ represents an organic group.

In General Formula (B-9), $Y^{F5}$ represents a fluorine atom or a perfluoroalkyl group.

$Y^9$ represents a hydrogen atom or a substituent having no fluorine atom.

Rd represents an organic group.

In General Formula (B-10).

$Y^{10}$'s each independently represent a hydrogen atom or a substituent having no fluorine atom.

$Rd_1$ represents an organic group.

In General Formula (B-12),

Re represents a hydrogen atom, an organic group, or a halogen atom.

o represents an integer of 1 to 4.

In a case where o represents an integer of 2 or more, a plurality of Re's may be the same as or different from each other.

In General Formula (B-13).

$Y^{F6}$ represents a fluorine atom or a perfluoroalkyl group.

$Y^{11}$ represents a hydrogen atom or a substituent having no fluorine atom.

In General Formula (B-14).

$Y^{12}$'s each independently represent a hydrogen atom or a substituent having no fluorine atom.

In General Formula (B-15).

$Y^{F7}$ represents a fluorine atom or a perfluoroalkyl group.

$Y^{13}$ represents a hydrogen atom or a substituent having no fluorine atom.

Rf represents an organic group.

In General Formula (B-16), $Y^{14}$'s each independently represent a hydrogen atom or a substituent having no fluorine atom.

$Rf_1$ represents an organic group.

In General Formula (B-17), $Y^{F8}$ represents a fluorine atom or a perfluoroalkyl group.

$Y^{15}$ represents a hydrogen atom or a substituent having no fluorine atom.

Rg represents an organic group.

Rh represents an organic group.

In General Formula (B-18).

$Y^{16}$'s each independently represent a hydrogen atom or a substituent having no fluorine atom.

$Rg_1$ represents an organic group.

$Rh_1$ represents an organic group.

In General Formula (B-19).

$Y^{F9}$ represents a fluorine atom or a perfluoroalkyl group.

$Y^{17}$ represents a hydrogen atom or a substituent having no fluorine atom.

In General Formula (B-20), $Y^{18}$'s each independently represent a hydrogen atom or a substituent having no fluorine atom.

In General Formula (B-21).

$Y^{F10}$ represents a fluorine atom or a perfluoroalkyl group.

$Y^{19}$ represents a hydrogen atom or a substituent having no fluorine atom.

Ri represents an organic group.

Rj represents an organic group.

In General Formula (B-22), $Y^{20}$'s each independently represent a hydrogen atom or a substituent having no fluorine atom.

$Ri_1$ represents an organic group.

$Rj_1$ represents an organic group.

In General Formula (B-23),

Rk represents a hydrogen atom or a substituent having no fluorine atom.

p represents an integer of 1 to 4.

In a case where p represents an integer of 2 or more, a plurality of Rk's may be the same as or different from each other.

In General Formula (B-24).

Rl represents a hydrogen atom, an organic group, or a halogen atom.

q represents an integer of 1 to 4.

In a case where q represents an integer of 2 or more, a plurality of Rl's may be the same as or different from each other.

$Rc_2$ represents an organic group.

General Formula (B-25).

$Y^{F11}$ 's each independently represent a fluorine atom or a perfluoroalkyl group.

$Rc_3$ represents an organic group.

In General Formula (B-26), $Y^{F12}$'s each independently represent a fluorine atom or a perfluoroalkyl group.

$Rd_2$ represents an organic group.

In General Formula (B-27), $Y^{F13}$'s each independently represent a fluorine atom or a perfluoroalkyl group.

In General Formulae (B-1) to (B-27),

* represents a bonding position.

In General Formula (B-1), The perfluoroalkyl group represented by $Y^{F1}$ preferably has 1 to 15 carbon atoms, more preferably has 1 to 10 carbon atoms, and still more preferably has 1 to 6 carbon atoms.

The substituent having no fluorine atom represented by $Y^1$ is not particularly limited as long as it is a substituent having no fluorine atom, but is preferably an organic group having no fluorine atom. Examples thereof include organic groups other than a fluorine atom and a perfluoroalkyl group, and an alkyl group (which may be linear or branched) and a cycloalkyl group other than the perfluoroalkyl group are preferable.

The alkyl group is not particularly limited, but may be linear or branched, and is preferably an alkyl group having 1 to 15 carbon atoms, and more preferably an alkyl group having 1 to 10 carbon atoms.

The cycloalkyl group may be monocyclic or polycyclic, and is not particularly limited, but is preferably a cycloalkyl group having 3 to 15 carbon atoms, and more preferably a cycloalkyl group having 3 to 10 carbon atoms.

The alkyl group and the cycloalkyl group may have a substituent other than a fluorine atom. The substituent is not particularly limited, and examples thereof include the substituent T (excluding a fluorine atom).

In General Formula (B-2), the substituent having no fluorine atom represented by $Y^2$ has the same definition as the substituent having no fluorine atom represented by $Y^1$ in General Formula (B-1), and a suitable aspect thereof is also the same.

In General Formula (B-3), the perfluoroalkyl group represented by $Y^{F2}$ has the same definition as the perfluoroalkyl group represented by $Y^{F1}$ in General Formula (B-1), and a suitable aspect thereof is also the same.

The substituent having no fluorine atom represented by $Y^3$ has the same definition as the substituent having no fluorine atom represented by $Y^1$ in General Formula (B-1), and a suitable aspect thereof is also the same.

The organic group represented by Ra is not particularly limited, and examples thereof include an organic group having 1 to 30 carbon atoms. The organic group is not particularly limited, and preferred examples thereof include an alkyl group, a cycloalkyl group, or an aryl group.

The alkyl group is not particularly limited, but may be linear or branched, and is preferably an alkyl group having 1 to 15 carbon atoms, and more preferably an alkyl group having 1 to 10 carbon atoms.

The cycloalkyl group may be monocyclic or polycyclic, and is not particularly limited, but is preferably a cycloalkyl group having 3 to 15 carbon atoms, and more preferably a cycloalkyl group having 3 to 10 carbon atoms.

The aryl group is not particularly limited, but is preferably an aryl group having 6 to 20 carbon atoms, and more preferably an aryl group having 6 to 10 carbon atoms.

The alkyl group, the cycloalkyl group, and the aryl group may have a substituent. The substituent is not particularly limited, and examples thereof include the substituent T.

In General Formula (B-4), the substituent having no fluorine atom represented by $Y^4$ has the same definition as the substituent having no fluorine atom represented by $Y^1$ in General Formula (B-1), and a suitable aspect thereof is also the same.

The organic group represented by $Ra_1$ has the same definition as the organic group represented by Ra in General Formula (B-3) mentioned above, and a suitable aspect thereof is also the same.

In General Formula (B-5), the perfluoroalkyl group represented by $Y^{F3}$ has the same definition as the perfluoroalkyl group represented by $Y^{F1}$ in General Formula (B-1), and a suitable aspect thereof is also the same.

The substituent having no fluorine atom represented by $Y^5$ has the same definition as the substituent having no fluorine atom represented by $Y^1$ in General Formula (B-1), and a suitable aspect thereof is also the same.

The organic group represented by Rb has the same definition as the organic group represented by Ra in General Formula (B-3), and a suitable aspect thereof is also the same.

In General Formula (B-6), the substituent having no fluorine atom represented by $Y^6$ has the same definition as the substituent having no fluorine atom represented by $Y^1$ in General Formula (B-1), and a suitable aspect thereof is also the same.

The organic group represented by $Rb_1$ has the same definition as the organic group represented by Ra in General Formula (B-3), and a suitable aspect thereof is also the same.

In General Formula (B-7), the perfluoroalkyl group represented by $Y^4$ has the same definition as the perfluoroalkyl group represented by $Y^{F1}$ in General Formula (B-1), and a suitable aspect thereof is also the same.

The substituent having no fluorine atom represented by $Y^7$ has the same definition as the substituent having no fluorine atom represented by $Y^1$ in General Formula (B-1), and a suitable aspect thereof is also the same.

The organic group represented by $Rc_1$ has the same definition as the organic group represented by Ra in General Formula (B-3), and a suitable aspect thereof is also the same.

In General Formula (B-8), the substituent having no fluorine atom represented by $Y^8$ has the same definition as the substituent having no fluorine atom represented by $Y^1$ in General Formula (B-1), and a suitable aspect thereof is also the same.

The organic group represented by $Rc_1$ has the same definition as the organic group represented by Ra in General Formula (B-3), and a suitable aspect thereof is also the same.

In General Formula (B-9), the perfluoroalkyl group represented by $Y^{F5}$ has the same definition as the perfluoroalkyl group represented by $Y^{F1}$ in General Formula (B-1), and a suitable aspect thereof is also the same.

The substituent having no fluorine atom represented by $Y^9$ has the same definition as the substituent having no fluorine atom represented by $Y^1$ in General Formula (B-1), and a suitable aspect thereof is also the same.

The organic group represented by Rd has the same definition as the organic group represented by Ra in General Formula (B-3), and a suitable aspect thereof is also the same.

In General Formula (B-10), the substituent having no fluorine atom represented by $Y^{10}$ has the same definition as the substituent having no fluorine atom represented by $Y^1$ in General Formula (B-1), and a suitable aspect thereof is also the same.

The organic group represented by $Rd_1$ has the same definition as the organic group represented by Ra in General Formula (B-3), and a suitable aspect thereof is also the same.

In General Formula (B-12), the organic group represented by Re has the same definition as the organic group represented by Ra in General Formula (B-3), and a suitable aspect thereof is also the same.

Examples of the halogen atom represented by Re include a fluorine atom, a chlorine atom, a bromine atom, or an iodine atom.

In General Formula (B-13), the perfluoroalkyl group represented by $Y^{F6}$ has the same definition as the perfluoroalkyl group represented by $Y^{F1}$ in General Formula (B-1), and a suitable aspect thereof is also the same.

The substituent having no fluorine atom represented by $Y^{11}$ has the same definition as the substituent having no fluorine atom represented by $Y^1$ in General Formula (B-1), and a suitable aspect thereof is also the same.

In General Formula (B-14), the substituent having no fluorine atom represented by $Y^{12}$ has the same definition as the substituent having no fluorine atom represented by $Y^1$ in General Formula (B-1), and a suitable aspect thereof is also the same.

In General Formula (B-15), the perflurooalkyl group represented by $Y^{F7}$ has the same definition as the perfluoroalkyl group represented by $Y^{F1}$ in General Formula (B-1), and a suitable aspect thereof is also the same.

The substituent having no fluorine atom represented by $Y^{13}$ has the same definition as the substituent having no fluorine atom represented by $Y^1$ in General Formula (B-1), and a suitable aspect thereof is also the same.

The organic group represented by Rf has the same definition as the organic group represented by Ra in General Formula (B-3), and a suitable aspect thereof is also the same.

In General Formula (B-16), the substituent having no fluorine atom represented by $Y^{14}$ has the same definition as the substituent having no fluorine atom represented by $Y^1$ in General Formula (B-1), and a suitable aspect thereof is also the same.

The organic group represented by $Rf_1$ has the same definition as the organic group represented by Ra in General Formula (B-3), and a suitable aspect thereof is also the same.

In General Formula (B-17), the perfluoroalkyl group represented by $Y^{F8}$ has the same definition as the perfluoroalkyl group represented by $Y^{F1}$ in General Formula (B-1), and a suitable aspect thereof is also the same.

The substituent having no fluorine atom represented by $Y^{15}$ has the same definition as the substituent having no fluorine atom represented by $Y^1$ in General Formula (B-1), and a suitable aspect thereof is also the same.

The organic groups represented by Rg and Rf each have the same definition as the organic group represented by Ra in General Formula (B-3), and suitable aspects thereof are also the same.

In General Formula (B-18), the substituent having no fluorine atom represented by $Y^{16}$ has the same definition as the substituent having no fluorine atom represented by $Y^1$ in General Formula (B-1), and a suitable aspect thereof is also the same.

The organic groups represented by $Rg_1$ and $Rf_1$ each have the same definition as the organic group represented by Ra in General Formula (B-3), and suitable aspects thereof are also the same.

In General Formula (B-19), the perfluoroalkyl group represented by $Y^{F9}$ has the same definition as the perfluoroalkyl group represented by $Y^{F1}$ in General Formula (B-1), and a suitable aspect thereof is also the same.

The substituent having no fluorine atom represented by $Y^{17}$ has the same definition as the substituent having no fluorine atom represented by $Y^1$ in General Formula (B-1), and a suitable aspect thereof is also the same.

In General Formula (B-20), the substituent having no fluorine atom represented by $Y^{18}$ has the same definition as the substituent having no fluorine atom represented by $Y^1$ in General Formula (B-1), and a suitable aspect thereof is also the same.

In General Formula (B-21), the perfluoroalkyl group represented by $Y^{F10}$ has the same definition as the perfluoroalkyl group represented by $Y^{F1}$ in General Formula (B-1), and a suitable aspect thereof is also the same.

The substituent having no fluorine atom represented by $Y^{19}$ has the same definition as the substituent having no fluorine atom represented by $Y^1$ in General Formula (B-1), and a suitable aspect thereof is also the same.

The organic groups represented by Ri and Rj each have the same definition as the organic group represented by Ra in General Formula (B-3), and a suitable aspect thereof is also the same.

In General Formula (B-22), the substituent having no fluorine atom represented by $Y^{20}$ has the same definition as the substituent having no fluorine atom represented by $Y^1$ in General Formula (B-1), and a suitable aspect thereof is also the same.

The organic groups represented by $Ri_1$ and $Rj_1$ each have the same definition as the organic group represented by Ra in General Formula (B-3), and suitable aspects thereof are also the same.

In General Formula (B-23), the substituent having no fluorine atom represented by Rk has the same definition as the substituent having no fluorine atom represented by $Y^1$ in General Formula (B-1), and a suitable aspect thereof is also the same.

In General Formula (B-24), the organic groups represented by Rl have the same definition as the organic group represented by Ra in General Formula (B-3), and suitable aspects thereof are also the same.

In addition, as a preferred aspect, the organic group represented by Rl is preferably an organic group having no fluorine atom.

Examples of the halogen atom represented by Rl include a fluorine atom, a chlorine atom, a bromine atom, or an iodine atom.

The organic group represented by $Rc_2$ has the same definition as the organic group represented by Ra in General Formula (B-3), and a suitable aspect thereof is also the same.

In General Formula (B-25), the perfluoroalkyl group represented by $Y^{F11}$ has the same definition as the perfluoroalkyl group represented by $Y^{F1}$ in General Formula (B-1), and a suitable aspect thereof is also the same.

The organic group represented by $Rc_3$ has the same definition as the organic group represented by Ra in General Formula (B-3), and a suitable aspect thereof is also the same.

In General Formula (B-26), the perfluoroalkyl group represented by $Y^{F12}$ has the same definition as the perfluoroalkyl group represented by $Y^{F1}$ in General Formula (B-1), and a suitable aspect thereof is also the same.

The organic group represented by $Rd_2$ has the same definition as the organic group represented by Ra in General Formula (B-3), and a suitable aspect thereof is also the same.

In General Formula (B-27), the perfluoroalkyl group represented by $Y^{F13}$ has the same definition as the perfluoroalkyl group represented by $Y^{F1}$ in General Formula (B-1), and a suitable aspect thereof is also the same.

In General Formula (I), $A_1^-$ is preferably the group represented by General Formula (B-1), (B-2), (B-3), (B-4), or (B-23), more preferably the group represented by General Formula (B-2) or (B-23), and still more preferably the group represented by General Formula (B-2).

In General Formula (I). A2 is preferably the group represented by General Formula (B-6), (B-8), (B-10), (B-11), (B-12), or (B-24), more preferably the group represented by General Formula (B-10), (B-11), (B-12), or (B-24), and still more preferably the group represented by General Formula (B-11) or (B-24).

In General Formula (I), the combination of $A_1^-$ and $A_2^-$ is more preferably a combination of groups in which each preferred $A_1^-$ and $A_2^-$.

Furthermore, the acid dissociation constant a1 and the acid dissociation constant a2 are determined by the above-mentioned method.

The acid dissociation constant a1 and the acid dissociation constant a2 of the compound (PI) will be specifically described below.

In a case where m represents 1 in General Formula (I), the pKa with which the compound (PI) (in which the compound (PI) corresponds to a "compound having $HA_1$ and $HA_2$") serves as a "compound having $A_1^-$ and $HA_2$" is the acid dissociation constant a1, and the pKa with which "compound having $A_1^-$ and $HA_2$" serves as a "compound having $A_1^-$ and $A_2^{+}$" is the acid dissociation constant a2 in a case where the acid dissociation constant of the compound (PI) is determined.

In a case where m represents 2 in General Formula (I), the compound (PI) corresponds to a "compound having two $HA_1$ and $HA_2$" in a case where the acid dissociation constant of the compound (PI) is determined. In a case where the acid dissociation constant of the compound (PI) was determined, the pKa in a case where the compound (PI) serves as a "compound having one $A_1^-$, one $HA_1$, and $HA_2$" is the acid dissociation constant a1, and the pKa in a case where the compound having two $A_1^-$'s and $HA_2$ serves as a "compound having two $A_1^-$'s and $A_2^-$" is the acid dissociation constant a2. That is, in a case where the compound (PI) has two acid dissociation constants derived from the acidic moiety represented by $HA_1$, the smallest value is considered as the acid dissociation constant a1.

In addition, the compound (PI) corresponds to an acid generated by irradiating a compound represented by General Formula (b with actinic rays or radiation.

From the viewpoint that the roughness performance of a pattern formed is more excellent, in the compound (PI), the difference between the acid dissociation constant a1 and the acid dissociation constant a2 is preferably 2.0 or more, and more preferably 3.0 or more. Furthermore, the upper limit value of the difference between the acid dissociation constant a1 and the acid dissociation constant a2 is not particularly limited, but is, for example, 15.0 or less.

In addition, from the suppression of excessive diffusion of the acid into the non-exposed portion is more excellent, in the compound (PI), the acid dissociation constant a2 is, for example, preferably 2.0 or more, more preferably 3.0 or more, and still more preferably 4.0 or more.

In addition, the upper limit value of the acid dissociation constant a2 is not particularly limited, but is, for example, 10.0 or less, and is preferably 7.0 or less, and more preferably 6.0 or less.

In addition, in the compound (PI), the acid dissociation constant a1 is −1.5 or more, more preferably −1.2 or more, and still more preferably −1.0 or more. Furthermore, the upper limit value of the acid dissociation constant a1 is not particularly limited, but is, for example, 2.0 or less, and is preferably 1.5 or less.

In General Formula (I), preferred forms of the cations represented by $M_1^+$ and $M_2^+$ will be described in detail.

In a case where m represents 1, $M_1^+$ and $M_2^+$ may be bonded via a single bond or a linking group to form a divalent cation.

In addition, in a case where m represents 2, at least two of the two cations, $M_1^+$ and $M_2^+$, may be bonded via a single bond or a linking group to form a divalent or trivalent cation.

The cations represented by $M_1^+$ and $M_2^+$ are not particularly limited, but are each independently preferably an onium cation, and a cation represented by General Formula (ZIA) or General Formula (ZIIA) is preferable.

(ZIA)

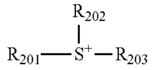

(ZIIA)

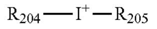

In General Formula (ZIA), $R_{201}$, $R_{202}$, and $R^{203}$ each independency represent a hydrogen atom or a substituent.

As the substituent as each of $R_{201}$, $R_{202}$, and $R_{203}$, an organic group is preferable, and the organic group generally has 1 to 30 carbon atoms, and preferably has 1 to 20 carbon atoms.

In addition, two of $R_{201}$ to $R_{203}$ may be bonded to each other to form a ring (also referred to as a ring structure), and the ring may include an oxygen atom, a sulfur atom, an ester bond, an amide bond, or a carbonyl group. Examples of the group formed by the mutual bonding of two of $R_{201}$ to $R_{203}$ include an alkylene group (for example, a butylene group and a pentylene group) and $-CH_2-CH_2-O-CH_2-CH_2-$.

Suitable aspects of the cation as General Formula (ZIA) include a cation (ZI-11), a cation (ZI-12), a cation represented by General Formula (ZI-13) (cation (ZI-13)), and a cation represented by General Formula (ZI-14) (cation (ZI-14)), each of which will be described later.

The cation may be a cation having a plurality of structures represented by General Formula (ZIA). Examples of such the cation include a divalent cation having a structure in which at least one of $R_{201}$, $R_{202}$, or $R_{203}$ of a cation represented by General Formula (ZIA) and at least one of $R_{201}$, $R_{202}$, or $R_{203}$ of another cation represented by General Formula (ZIA) are bonded via a single bond or a linking group.

First, the cation (ZI-11) will be described.

The cation (ZI-11) is a cation, that is, an arylsulfonium cation in which at least one of $R_{201}$, . . . , or $R_{203}$ of General Formula (ZIA) is an aryl group.

In the arylsulfonium cation, all of $R_{201}$ to $R_{203}$ may be aryl groups, or some of $R_{201}$ to $R_{203}$ may be an aryl group, and the rest may be an alkyl group or a cycloalkyl group.

Examples of the arylsulfonium cation include a triarylsulfonium cation, a diarylalkylsulfonium cation, an aryldialkylsulfonium cation, a diarylcycloalkylsulfonium cation, and an aryldicycloalkylsulfonium cation.

As the aryl group included in the arylsulfonium cation, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium cation has two or more aryl groups, the two or more aryl groups may be the same as or different from each other.

The alkyl group or the cycloalkyl group contained in the arylsulfonium cation, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of each of $R_{201}$ to $R_{203}$ may each independently have an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a halogen atom, a hydroxyl group, a lactone ring group, or a phenylthio group as a substituent.

Examples of the lactone ring group include groups obtained by removing a hydrogen atom from a structure represented by any of (LC1-1) to (LC1-21) which will be described later.

Next, the cation (ZI-12) will be described.

The cation (ZI-12) is a compound in which $R_{201}$ to $R^{203}$ in Formula (ZIA) each independently represent an organic group having no aromatic ring. Here, the aromatic ring also includes an aromatic ring including a heteroatom.

The organic group having no aromatic ring as each of $R_{201}$ to $R_{203}$ generally has 1 to 30 carbon atoms, and preferably 1 to 20 carbon atoms.

$R_{201}$ to $R_{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Preferred examples of the alkyl group and the cycloalkyl group of each of $R_{201}$ to $R_{203}$ include a linear alkyl group having 1 to 10 carbon atoms or branched alkyl group having 3 to 10 carbon atoms (for example, a methyl group, an ethyl group, a propyl group, a butyl group, and a pentyl group), and a cycloalkyl group having 3 to 10 carbon atoms (for example, a cyclopentyl group, a cyclohexyl group, and a norbornyl group).

$R_{201}$ to $R_{203}$ may be further substituted with a halogen atom, an alkoxy group (for example, having 1 to 5 carbon atoms), a hydroxyl group, a cyano group, or a nitro group.

Next, the cation (ZI-13) will be described.

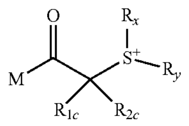

(ZI-13)

In General Formula (ZI-13), M represents an alkyl group, a cycloalkyl group, or an aryl group, and in a case where M has a ring structure, the ring structure may include at least one of an oxygen atom, a sulfur atom, an ester bond, an amide bond, or a carbon-carbon double bond. $R_{1c}$ and $R_{2c}$ each independently represent a hydrogen atom, an alkyl group, a cycloalkyl group, a halogen atom, a cyano group, or an aryl group. $R_{1c}$ and $R_{2c}$ may be bonded to each other to form a ring. $R_x$ and $R_y$ each independently represent an alkyl group, a cycloalkyl group, or an alkenyl group. $R_x$ and $R_y$ may be bonded to each other to form a ring. In addition, at least two selected from M, $R_{1c}$, or $R_{2c}$ may be bonded to each other to form a ring structure, and the ring structure may include a carbon-carbon double bond.

In General Formula (ZI-13), as the alkyl group and the cycloalkyl group represented by M, a linear alkyl group having 1 to 15 carbon atoms (preferably having 1 to 10 carbon atoms), a branched alkyl group having 3 to 15 carbon atoms (preferably having 3 to 10 carbon atoms), or a cycloalkyl group having 3 to 15 carbon atoms (preferably having 1 to 10 carbon atoms) is preferable, and specific examples thereof include a methyl group, an ethyl group, a propyl group, an n-butyl group, a sec-butyl group, a t-butyl group, a cyclopropyl group, a cyclobutyl group, a cyclohexyl group, and a norbornyl group.

The aryl group represented by M is preferably a phenyl group or a naphthyl group, and more preferably the phenyl group. The aryl group may be an aryl group which has a heterocyclic structure having an oxygen atom, a sulfur atom, or the like. Examples of the heterocyclic structure include a furan ring, a thiophene ring, a benzofuran ring, and a benzothiophene ring.

M may further have a substituent. In this aspect, examples of M include a benzyl group.

In addition, in a case where M has a ring structure, the ring structure may include at least one of an oxygen atom, a sulfur atom, an ester bond, an amide bond, or a carbon-carbon double bond.

Examples of the alkyl group, the cycloalkyl group, and the aryl group represented by each of $R_{1c}$ and $R_{2c}$ include the same ones as those of M as mentioned above, and preferred aspects thereof are also the same. In addition, $R_{1c}$ and $R_{2c}$ may be bonded to each other to form a ring.

Examples of the halogen atom represented by each of $R_{1c}$ and $R_{2c}$ include a fluorine atom, a chlorine atom, a bromine atom, and an iodine atom.

Examples of the alkyl group and the cycloalkyl group represented by each of $R_x$ and $R_y$ include the same ones as those of M as mentioned above, and preferred aspects thereof are also the same.

As the alkenyl group represented by each of $R_x$ and $R_y$, an allyl group or a vinyl group is preferable.

$R_x$ and $R_y$ may further have a substituent. In this aspect, examples of each of $R_x$ and $R_y$ include a 2-oxoalkyl group or an alkoxycarbonylalkyl group.

Examples of the 2-oxoalkyl group represented by each of $R_x$ and $R_y$ include those having 1 to 15 carbon atoms (preferably having 1 to 10 carbon atoms), and specifically a 2-oxopropyl group and a 2-oxobutyl group.

Examples of the alkoxycarbonylalkyl group represented by each of $R_x$ and $R_y$ include those having 1 to 15 carbon atoms (preferably having 1 to 10 carbon atoms). In addition, $R_x$ and $R_y$ may be bonded to each other to form a ring.

The ring structure formed by the mutual linkage of $R_x$ and $R_y$ may include an oxygen atom, a sulfur atom, an ester bond, an amide bond, or a carbon-carbon double bond.

In General Formula (ZI-13), M and $R_{1c}$ may be bonded to each other to form a ring structure, and the ring structure formed may include a carbon-carbon double bond.

Among those, the cation (ZI-13) is preferably a cation (ZI-13A).

The cation (ZI-13A) is a phenacylsulfonium cation represented by General Formula (ZI-13A).

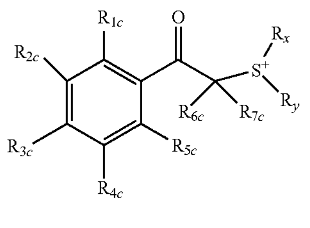

(ZI-13A)

In General Formula (ZI-13A), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ have the same definitions as $R_{1c}$ and $R_{2c}$, in General Formula (ZI-13) as mentioned above, respectively, and preferred aspects thereof are also the same.

$R_x$ and $R_y$ have the same definitions as $R_x$ and $R_y$, respectively, in General Formula (ZI-13) described above, and preferred aspects thereof are also the same.

Any two or more of $R_{1c}$, . . . , or $R_{5c}$, and $R_x$ and $R_y$ may be bonded to each other to form a ring structure, and the ring structure may each independently include an oxygen atom, a sulfur atom, an ester bond, an amide bond, or a carbon-carbon double bond. Furthermore, $R_{5c}$ and $R_{6c}$, or $R_{5c}$ and $R_x$ may be bonded to each other to form a ring structure, and the ring structure may each independently include a carbon-carbon double bond. In addition, $R_{6c}$ and $R_{7c}$ may be bonded to each other to form a ring structure.

Examples of the ring structure include an aromatic or non-aromatic hydrocarbon ring, an aromatic or non-aromatic heterocyclic ring, and a polycyclic fused ring in which two or more of these rings are combined. Examples of the ring structure include a 3- to 10-membered ring and the ring structure is preferably a 4- to 8-membered ring, and more preferably a 5- or 6-membered ring.

Examples of the group formed by the bonding of any two or more of $R_{1c}$, . . . , or $R_{5c}$, $R_{6c}$, and $R_{7c}$, and $R_x$ and $R_y$ include a butylene group and a pentylene group.

As the group formed by the bonding of $R_{5c}$ and $R_{6c}$, and $R_{5c}$ and $R_x$, a single bond or an alkylene group is preferable. Examples of the alkylene group include a methylene group and an ethylene group.

Next, the cation (ZI-14) will be described.

The cation (ZI-14) is represented by General Formula (ZI-14).

(ZI-14)

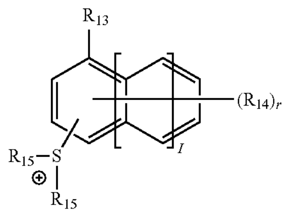

In General Formula (ZI-14).

l represents an integer of 0 to 2.

r represents an integer of 0 to 8.

$R_{13}$ represents a hydrogen atom, a fluorine atom, a hydroxyl group, an alkyl group, a cycloalkyl group, an alkoxy group, an alkoxycarbonyl group, or a group having a monocyclic or polycyclic cycloalkyl skeleton. These groups may have a substituent.

In a case where a plurality of $R_{14}$'s are present, $R_{14}$'s each independently represent an alkyl group, a cycloalkyl group, an alkoxy group, an alkylsulfonyl group, a cycloalkylsulfonyl group, an alkylcarbonyl group, an alkoxycarbonyl group, or an alkoxy group having a monocyclic or polycyclic cycloalkyl skeleton. These groups may have a substituent.

$R_{15}$'s each independently represent an alkyl group, a cycloalkyl group, or a naphthyl group. These groups may have a substituent. Two $R_{15}$'s may be bonded to each other to form a ring. In a case where two $R_{15}$'s are bonded to each other to form a ring, the ring skeleton may include a heteroatom such as an oxygen atom and a nitrogen atom. In one aspect, it is preferable that two $R_{15}$'s are alkylene groups and are bonded to each other to form a ring structure.

In General Formula (ZI-14), the alkyl group of each of $R_{13}$, $R_{14}$, and $R_{15}$ is linear or branched. The alkyl group preferably has 1 to 10 carbon atoms. As the alkyl group, a methyl group, an ethyl group, an n-butyl group, a t-butyl group, or the like is more preferable.

Next, General Formula (ZIIA) will be described.

In General Formula (ZIIA), $R_{204}$ and $R_{205}$ each independently represent an aryl group, an alkyl group, or a cycloalkyl group.

The aryl group of each of $R_{204}$ and $R_{205}$ is preferably a phenyl group or a naphthyl group, and more preferably the phenyl group. The aryl group of each of $R_{204}$ and $R_{205}$ may be an aryl group which has a heterocyclic structure having an oxygen atom, a nitrogen atom, a sulfur atom, or the like. Examples of the skeleton of the aryl group having a heterocyclic structure include pyrrole, furan, thiophene, indole, benzofuran, and benzothiophene.

As the alkyl group and the cycloalkyl group of each of $R_{204}$ and $R_{205}$, a linear alkyl group having 1 to 10 carbon atoms or branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R_{204}$ and $R_{205}$ may each independently have a substituent. Examples of the substituent which may be contained in the aryl group, the alkyl group, or the cycloalkyl group of each of $R_{204}$ to $R_{207}$ include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, a lactone ring group, and a phenylthio group.

Examples of the lactone ring group include groups obtained by removing a hydrogen atom from a structure represented by any of (LC1-1) to (LC1-21) which will be described later.

Preferred examples of the cations as $M_1^+$ and $M_2^+$ are shown below, but the present invention is not limited thereto. Me represents a methyl group.

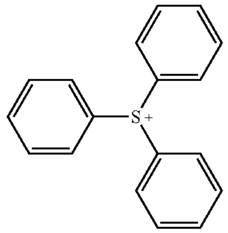

-continued
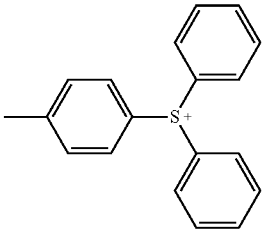
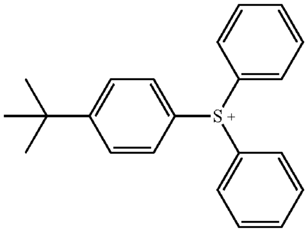
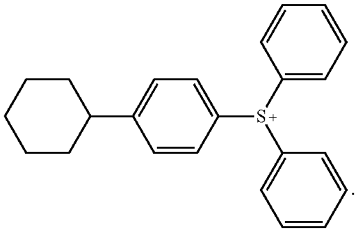
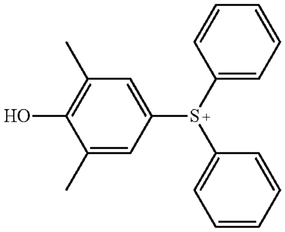
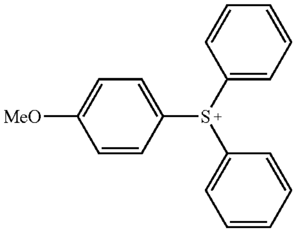
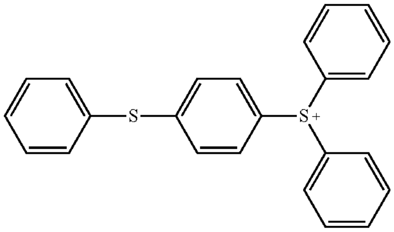
-continued
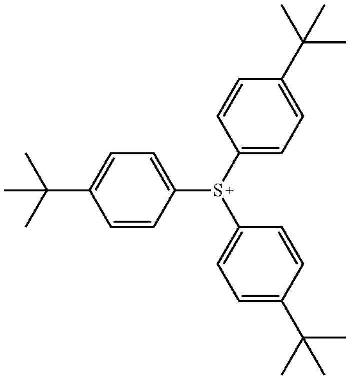
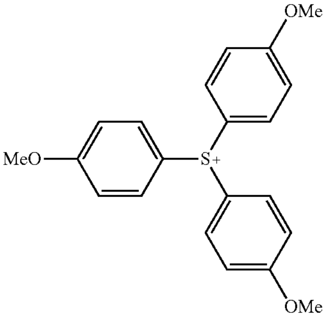
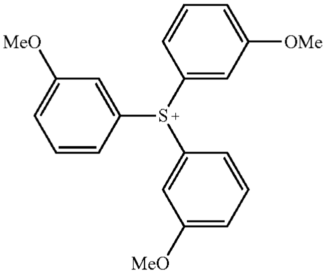
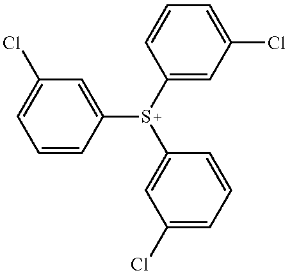
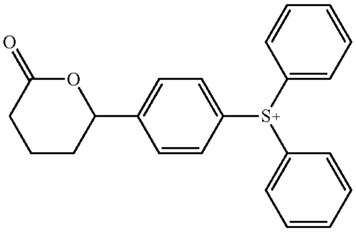

-continued
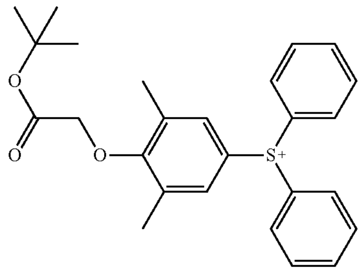
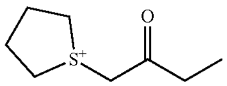
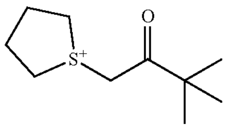
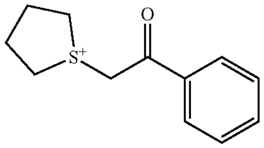
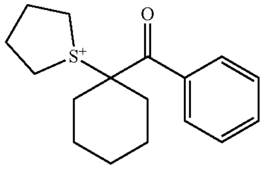
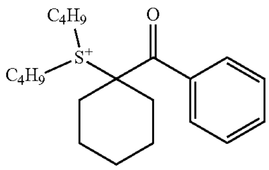
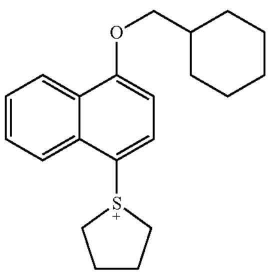
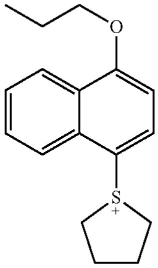
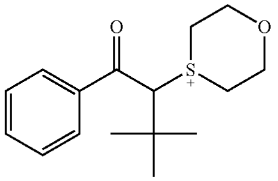
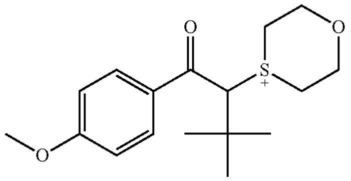
-continued
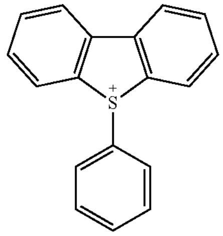
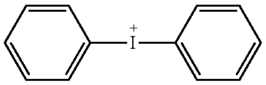
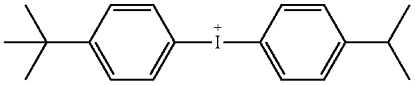
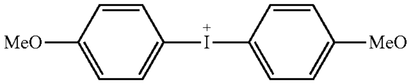
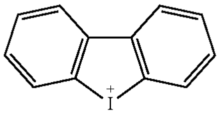
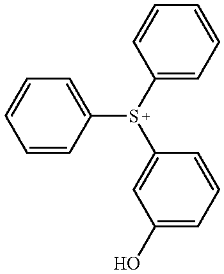
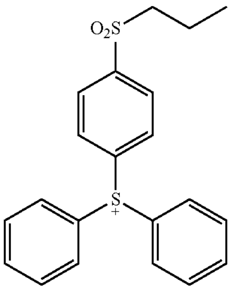
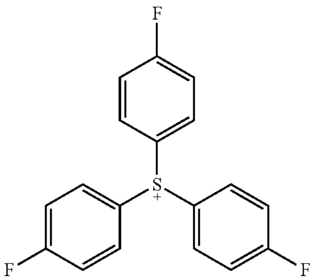
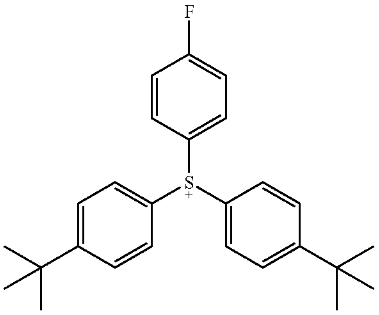

-continued
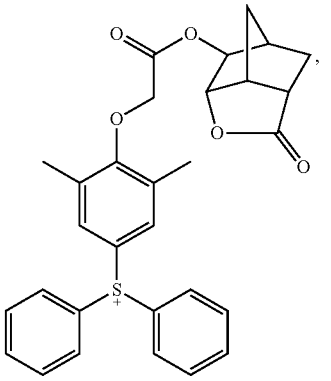
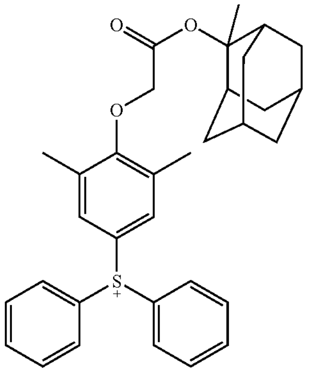
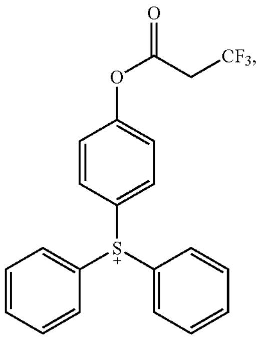
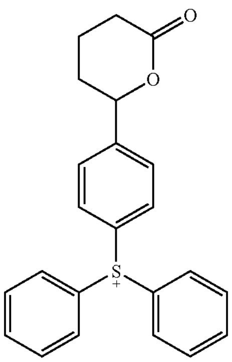
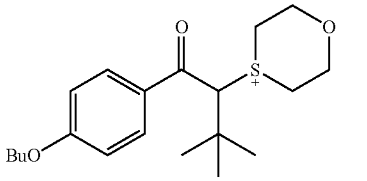
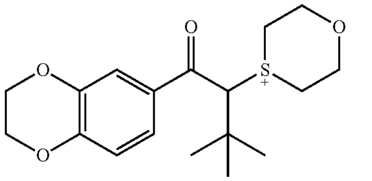
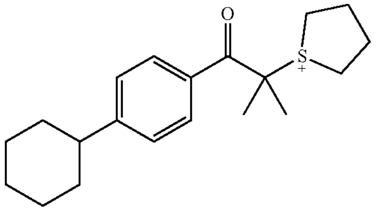
-continued
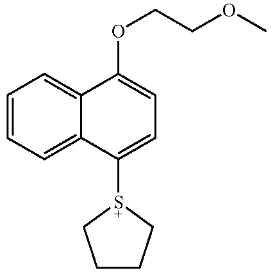
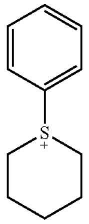
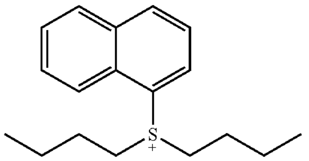
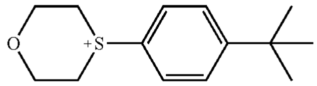
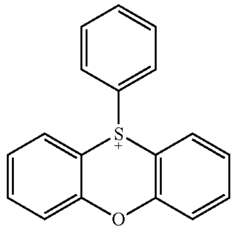
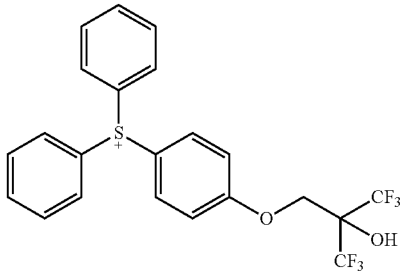
Preferred examples of the anionic moiety in the compound represented by General Formula (I) are shown below, but the present invention is not limited thereto. Me represents a methyl group.
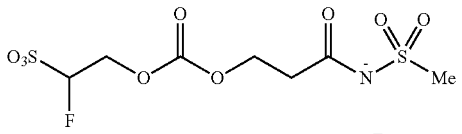
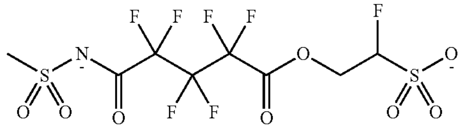
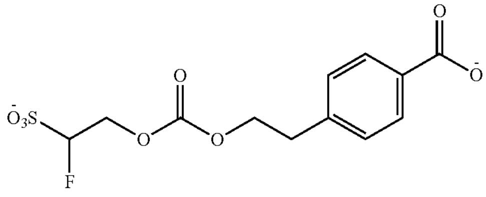

-continued
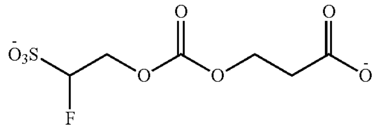
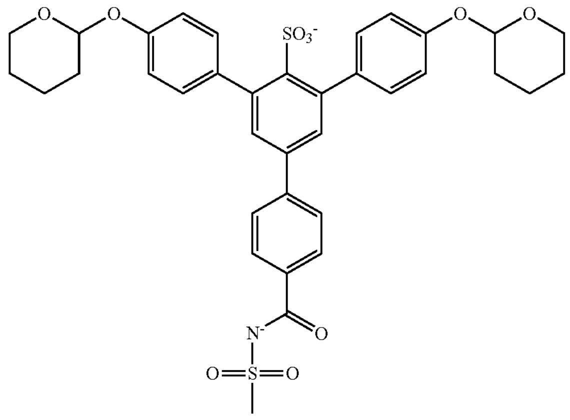
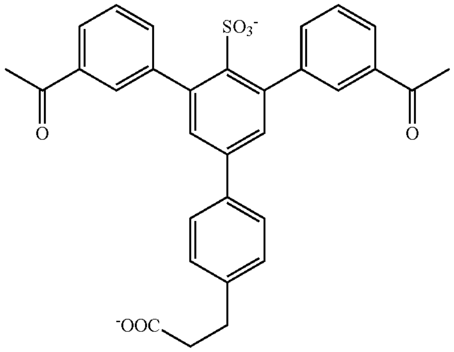
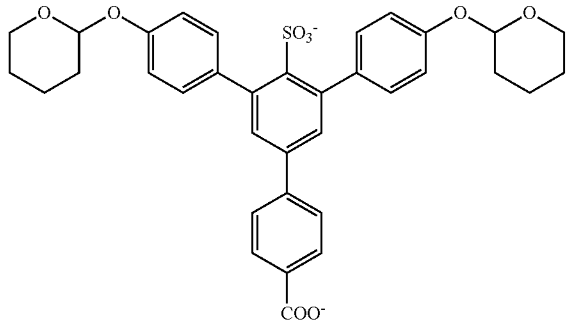
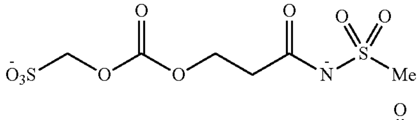
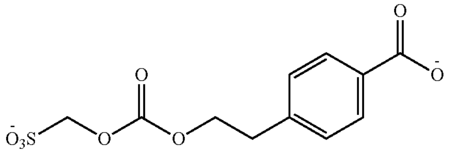
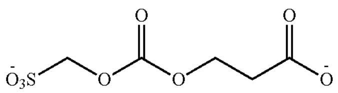
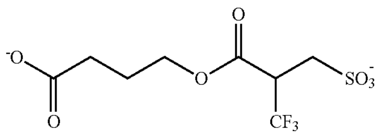
-continued
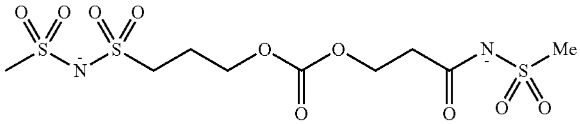
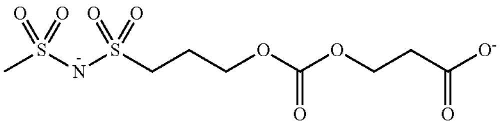
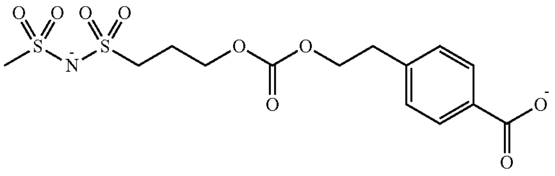
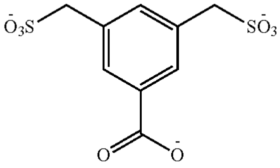
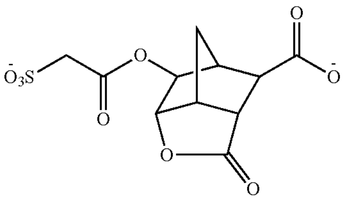
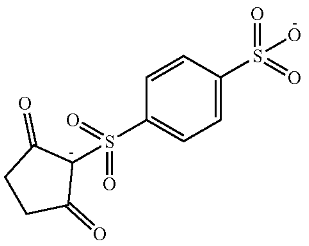
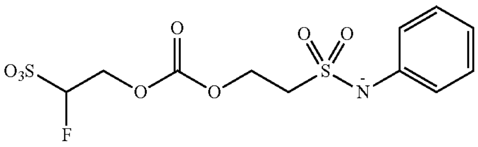
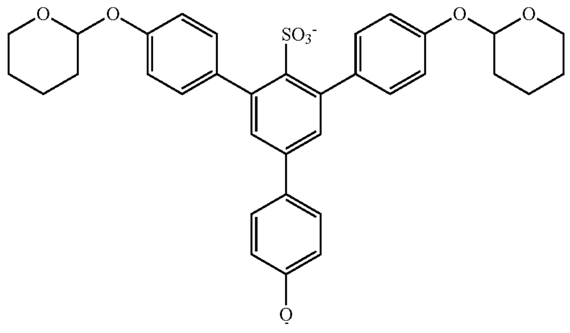

-continued
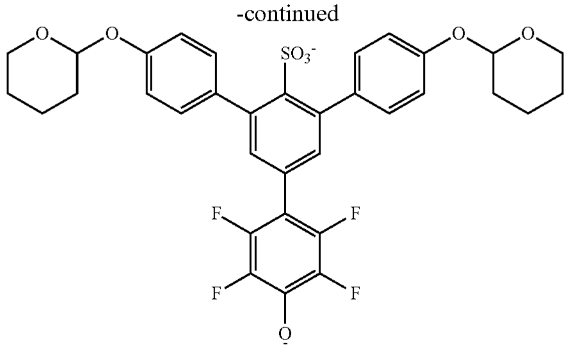
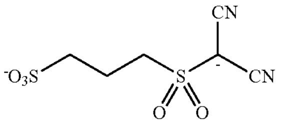
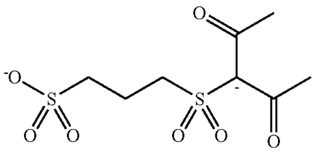
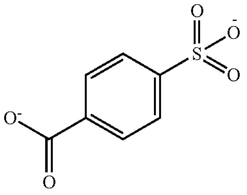
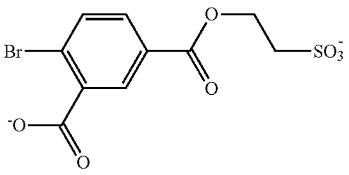
-continued
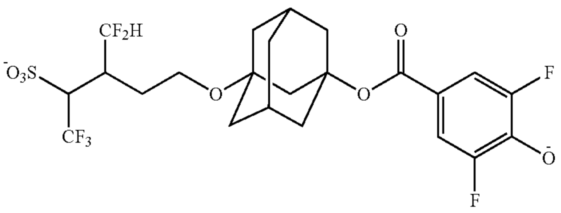
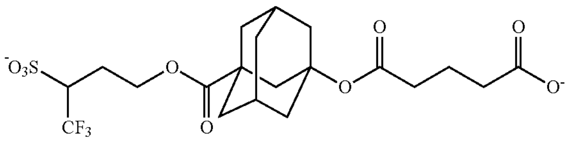
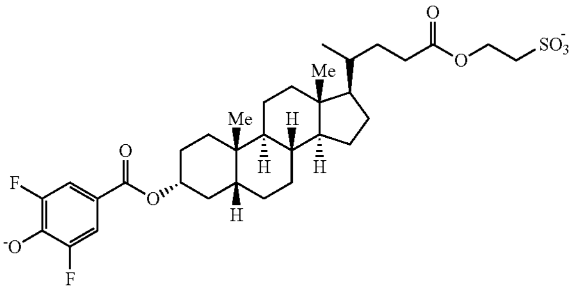
Preferred examples of the compound (B) are shown below, but the present invention is not limited thereto. Me represents a methyl group. Moreover, preferred examples of the compound (B) also include a compound obtained by combination of the anion and the cation.
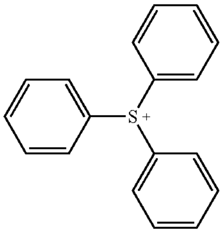
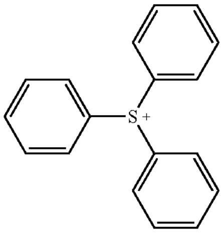
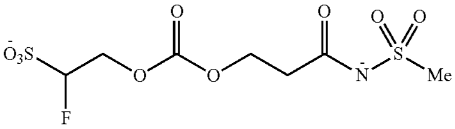

-continued
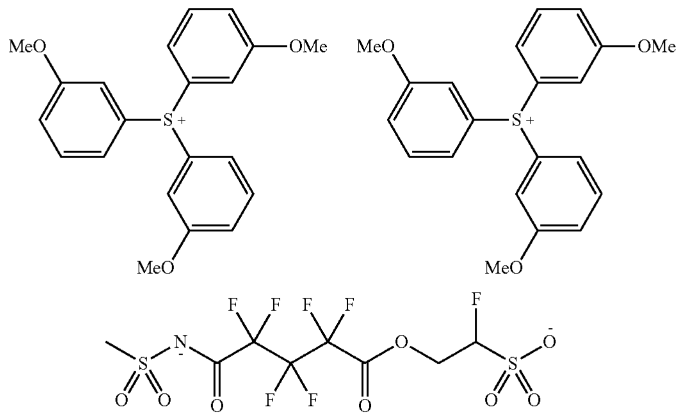
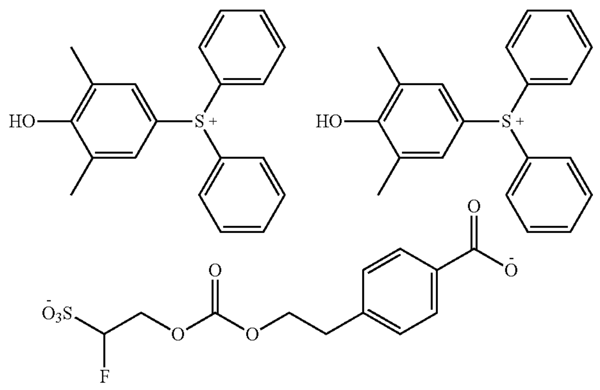
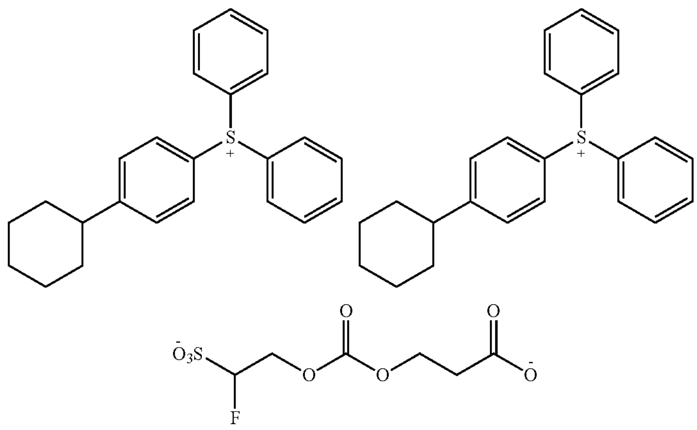

-continued
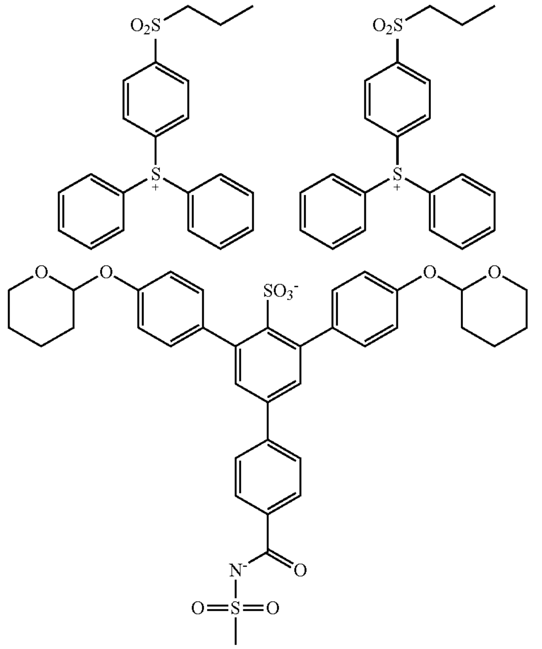
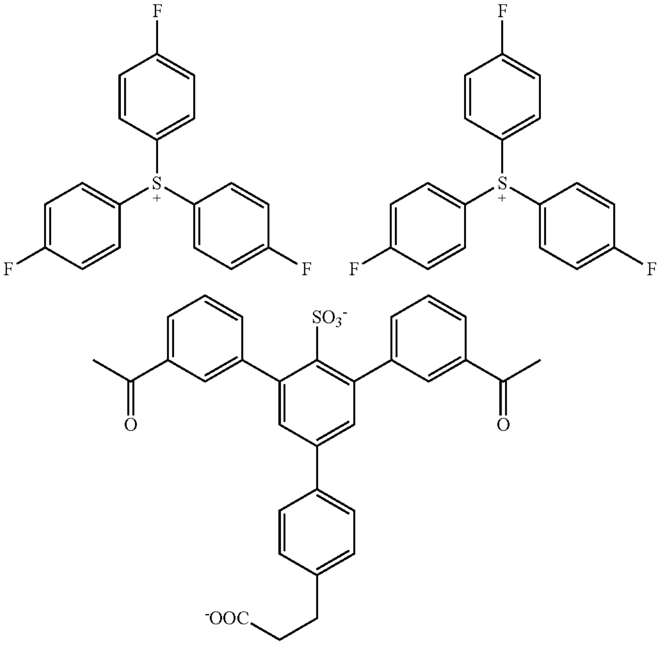
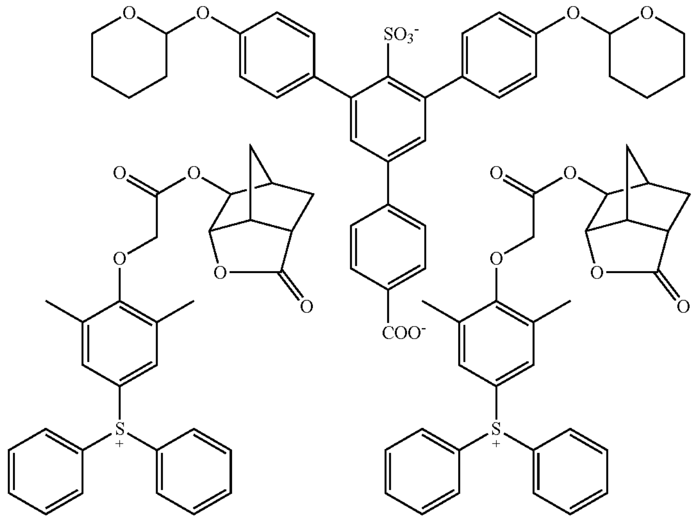
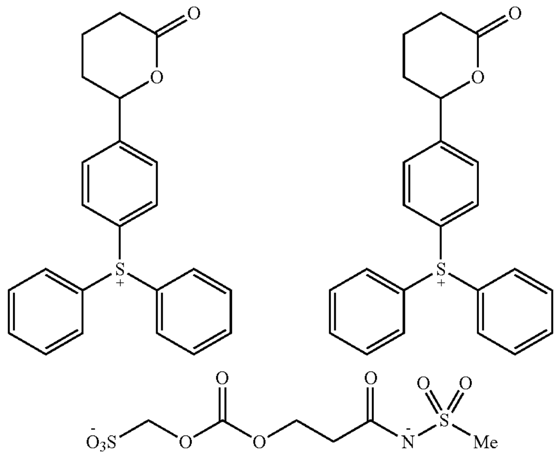
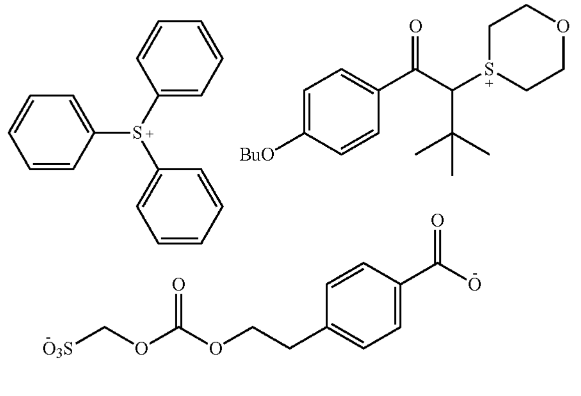

-continued
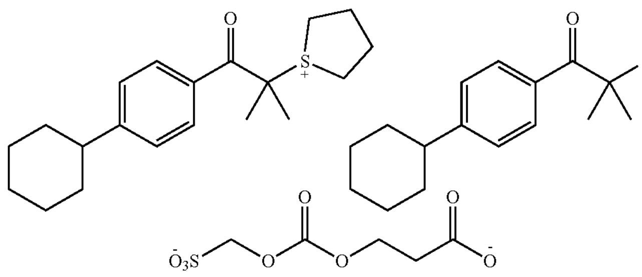
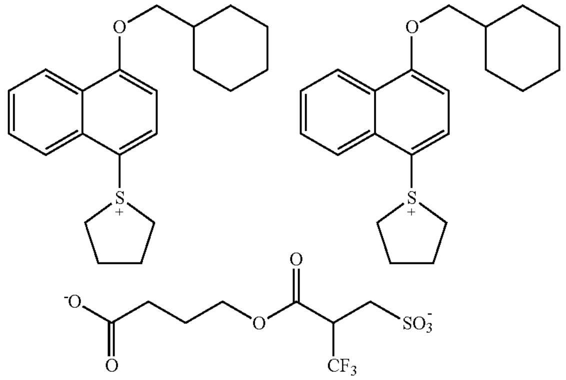
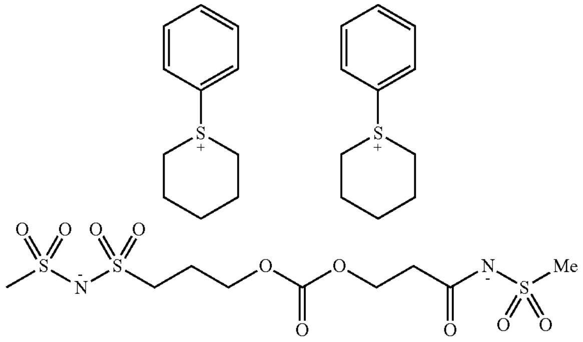
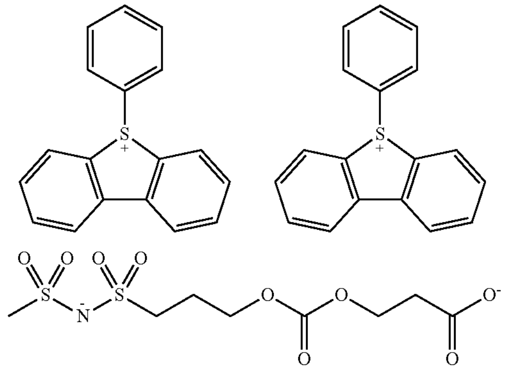
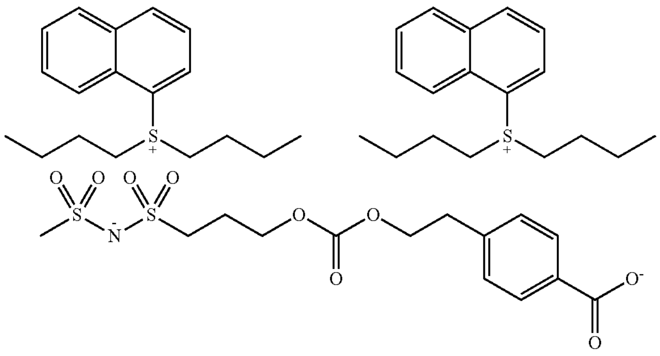
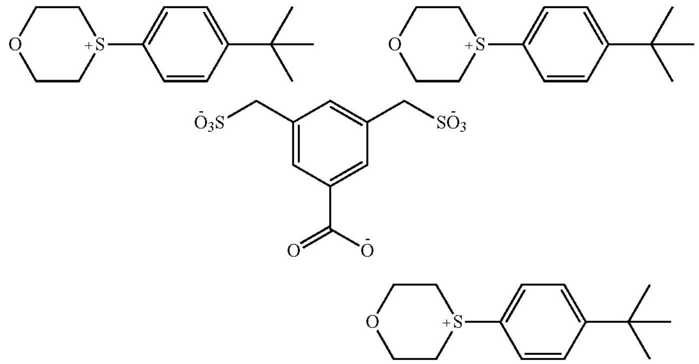

-continued
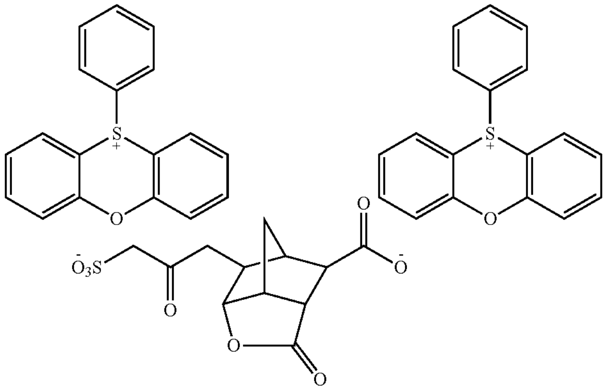
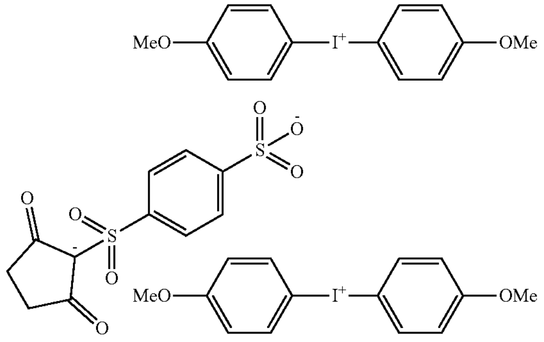
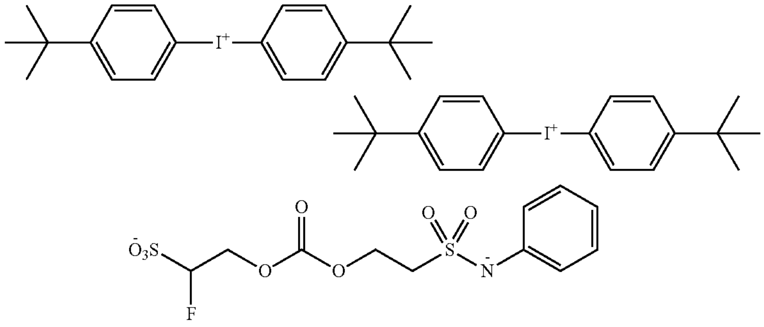
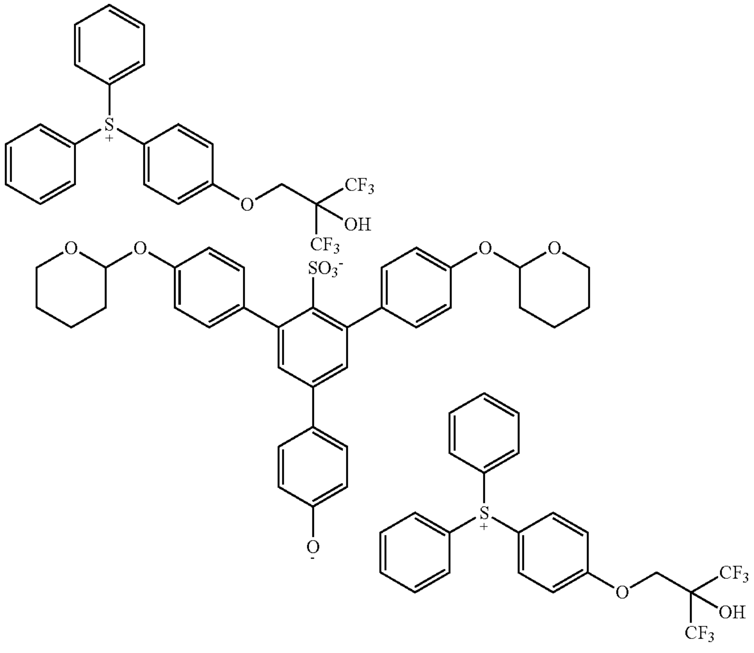

-continued
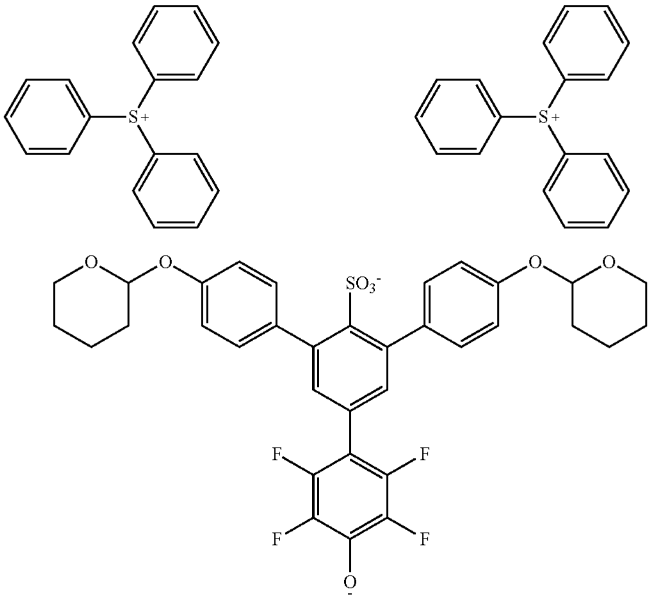
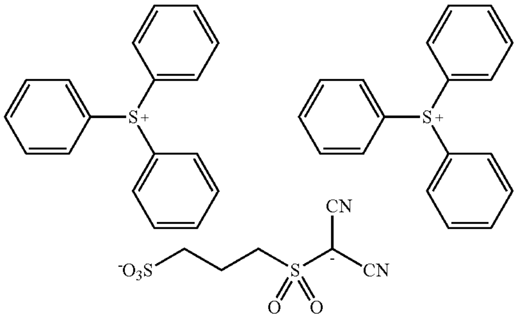
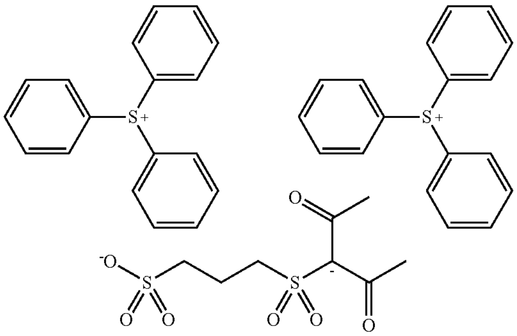
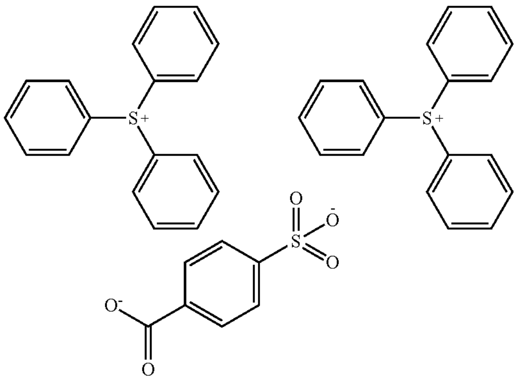
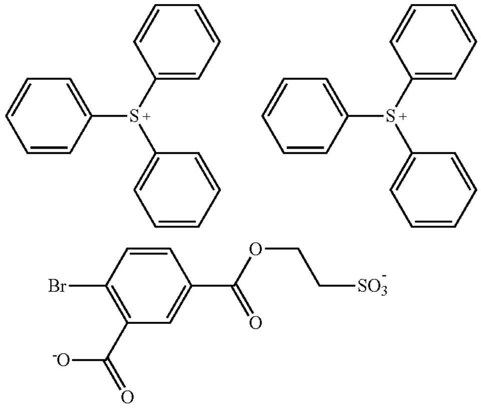

-continued

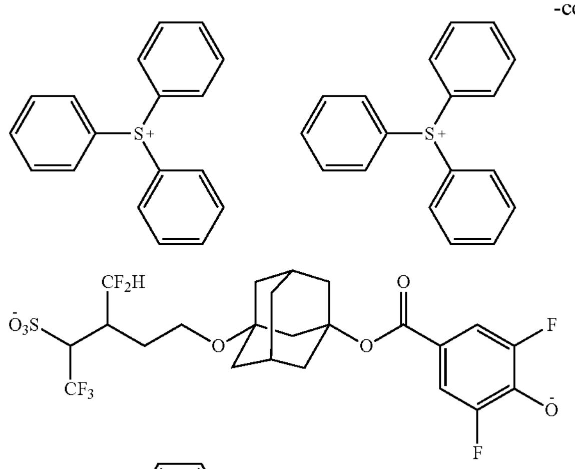

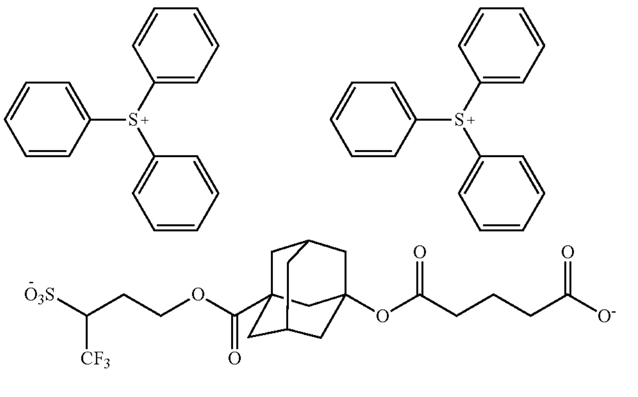

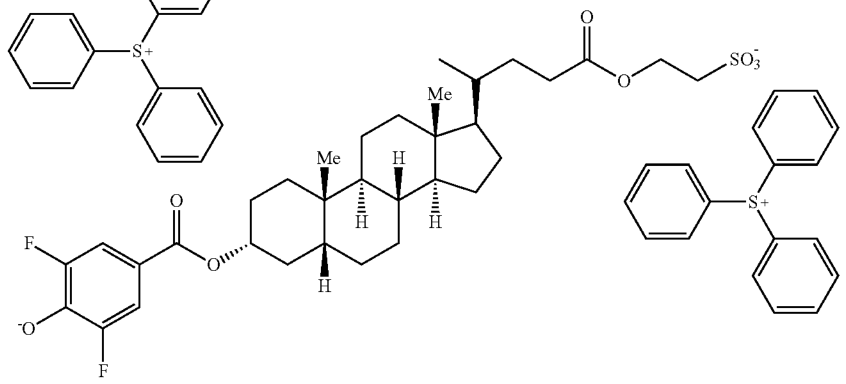

The molecular weight of the compound (B) is preferably 300 to 3,000, more preferably 300 to 2,000, and still more preferably 300 to 1,500.

The compound (B) may be used singly or in combination of two or more kinds thereof.

A content of the compound (B) (in a case where a plurality of the compounds (B) are present, a total content thereof) in the composition of the embodiment of the present invention is preferably 0.1% to 35% by mass, more preferably 0.5% to 25% by mass, still more preferably 1% to 20% by mass, and particularly preferably 5% to 20% by mass, with respect to a total solid content of the composition.

[(B') Compound that Generates Acid Upon Irradiation with Actinic Rays or Radiation Other than Compound (B)]

The composition of the embodiment of the present invention can contain a compound that generates an acid upon irradiation with actinic rays or radiation other than the compound (B) as long as the effect of the present invention is not impaired.

[(A) Resin Having Polarity that Increases by Action of Acid]

(A) The resin having a polarity that increases by the action of an acid (hereinafter also referred to as an "acid-decomposable resin" or a "resin (A)") will be described.

Further, as described later, the resin (A) may have a repeating unit having a photoacid generating group.

In pattern formation using a resist composition including the resin (A), typically, in a case where an alkali developer is adopted as the developer, a positive tone pattern is suitably formed, and in a case where an organic developer is adopted as the developer, a negative tone pattern is suitably formed.

The resin (A) usually includes a group having a polarity that increases through decomposition by the action of an acid (hereinafter also referred to as an "acid-decomposable group"), and preferably includes a repeating unit having an acid-decomposable group.

Hereinafter, the repeating unit which can be included in the resin (A) will be described.

The resin (A) includes a repeating unit represented by General Formula (AI).

(AI)

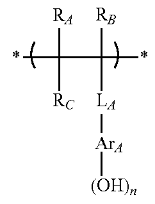

In General Formula (AI), $R_A$, $R_B$, and $R_C$ each independently represent a hydrogen atom, an alkyl group, a cycloalkyl group, a halogen atom, a cyano group, or an alkoxycarbonyl group. It should be noted that Re may be bonded to $Ar_A$ to form a ring, in which case Re represents a single bond or an alkylene group.

$L_A$ represents a single bond or a divalent linking group.

$Ar_A$ represents an (n+1)-valent aromatic ring group. In a case where $Ar_A$ is bonded to $R_C$ to form a ring, it represents an (n+2)-valent aromatic ring group.

n represents an integer of 1 to 5.

As the alkyl group represented by each of $R_A$, $R_B$, and $R_C$ in General Formula (AI), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group is preferable, an alkyl group having 8 or less carbon atoms is more preferable, and an alkyl group having 3 or less carbon atoms is still more preferable.

The cycloalkyl group of each of $R_A$, $R_B$, and $R_C$ in General Formula (AI) may be monocyclic or polycyclic. Among those, a monocyclic cycloalkyl group having 3 to 8 carbon atoms, such as a cyclopropyl group, a cyclopentyl group, and a cyclohexyl group, is preferable.

Examples of the halogen atom of each of $R_A$, $R_B$, and $R_C$ in General Formula (AI) include a fluorine atom, a chlorine atom, a bromine atom, and an iodine atom, and the fluorine atom is preferable.

As the alkyl group included in the alkoxycarbonyl group of each of $R_A$, $R_B$, and $R_C$ in General Formula (AI), the same ones as the alkyl group in each of $R_A$, $R_B$, and $R_C$ are preferable.

Each of the groups may have a substituent. The preferred substituent in each of the groups is not particularly limited, but examples thereof include an alkyl group, a cycloalkyl group, an aryl group, an amino group, an amide group, a ureide group, a urethane group, a hydroxyl group, a carboxy group, a halogen atom, an alkoxy group, a thioether group, an acyl group, an acyloxy group, an alkoxycarbonyl group, a cyano group, and a nitro group. The substituent preferably has 8 or less carbon atoms.

$Ar_A$ represents an (n+1)-valent aromatic ring group. The divalent aromatic ring group in a case where n is 1 is preferably, for example, an arylene group having 6 to 18 carbon atoms, such as a phenylene group, a tolylene group, a naphthylene group, and an anthracenylene group, or a divalent aromatic ring group including a heterocyclic ring such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Furthermore, the aromatic ring group may have a substituent.

Specific examples of the (n+1)-valent aromatic ring group in a case where n is an integer of 2 or more include groups formed by removing any (n−1) hydrogen atoms from the above-described specific examples of the divalent aromatic ring group.

The (n+1)-valent aromatic ring group may further have a substituent.

The substituent which can be contained in the alkyl group, the cycloalkyl group, the alkoxycarbonyl group, and the (n+1)-valent aromatic ring group, each mentioned above, is not particularly limited, but examples thereof include the alkyl groups; the alkoxy groups such as a methoxy group, an ethoxy group, a hydroxyethoxy group, a propoxy group, a hydroxypropoxy group, and a butoxy group; the aryl groups such as a phenyl group; and the like, as mentioned for each of $R_A$, $R_B$, and $R_C$ in General Formula (I).

The divalent linking group of $L_A$ is not particularly limited, but examples thereof include —COO—, —$CONR_{64}$—, an alkylene group, or a group formed by combination of two or more kinds of these groups. $R_{64}$ represents a hydrogen atom or an alkyl group.

The alkylene group is not particularly limited, but examples thereof include an alkylene group having 1 to 8 carbon atoms, such as a methylene group, an ethylene group, a propylene group, a butylene group, a hexylene group, and an octylene group, is preferable.

Examples of the alkyl group of $R_{64}$ include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, and an alkyl group having 8 or less carbon atoms, is preferable.

As $Ar_A$, an aromatic ring group having 6 to 18 carbon atoms is preferable, and a benzene ring group, a naphthalene ring group, and a biphenylene ring group are more preferable.

The repeating unit represented by General Formula (AI) preferably comprises a hydroxystyrene structure. That is, $Ar_A$ is preferably the benzene ring group.

n is preferably an integer of 1 to 3, and more preferably 1 or 2.

The repeating unit represented by General Formula (AI) will be exemplified below. In the formulae, a represents 1, 2, or 3.

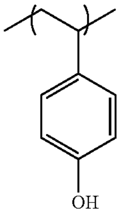

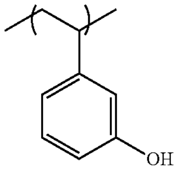

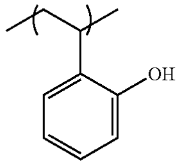

(B-1)

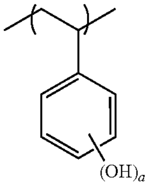

(B-2)

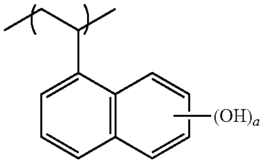

(B-3)

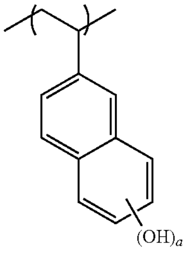

(B-4)

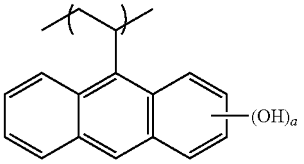

-continued
(B-5)
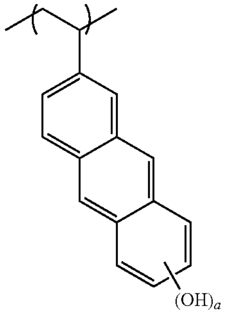
(B-6)
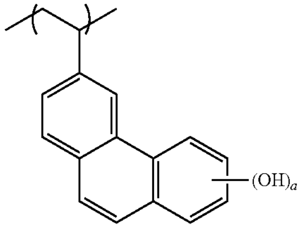
(B-7)
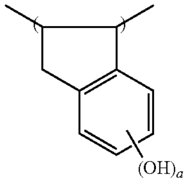
(B-8)
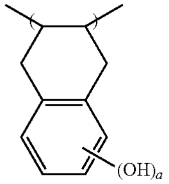
(B-9)
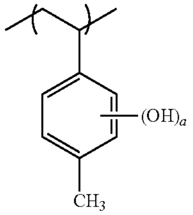
(B-10)
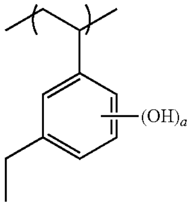
(B-11)
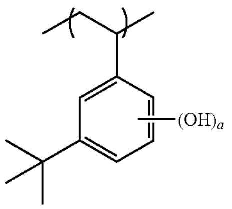
-continued
(B-12)
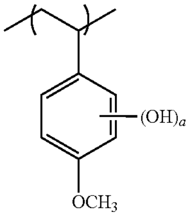
(B-13)
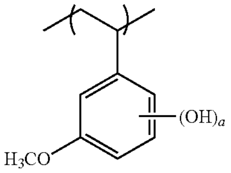
(B-14)
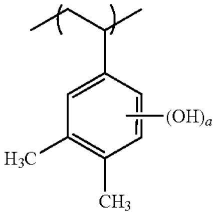
(B-15)
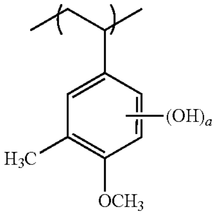
(B-16)
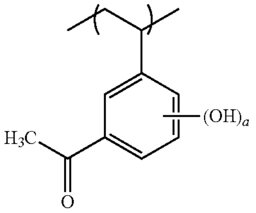
(B-17)
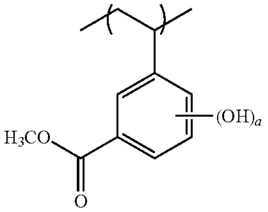
(B-18)
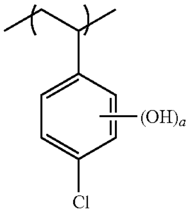

-continued
(B-19)
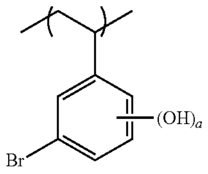
(B-20)
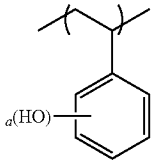
(B-21)
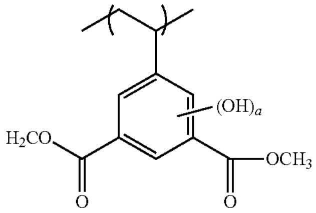
(B-22)
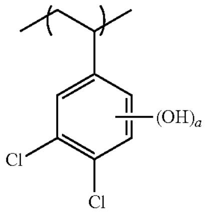
(B-23)
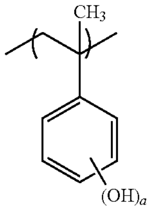
(B-24)
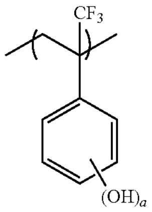
(B-25)
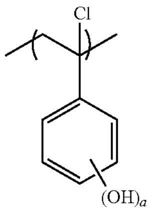
-continued
(B-26)
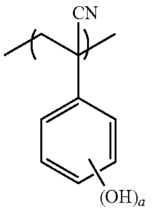
(B-27)
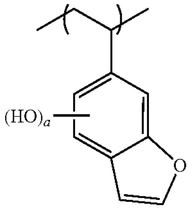
(B-28)
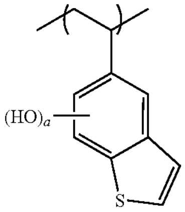
(B-29)
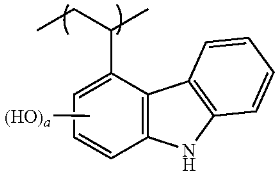
(B-30)
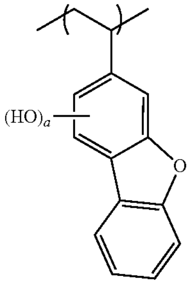
(B-31)
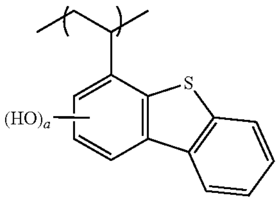
(B-32)
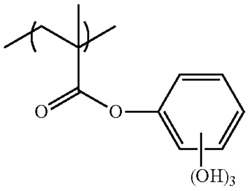

-continued
(B-33)
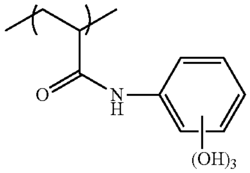
(B-34)
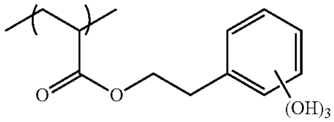
(B-35)
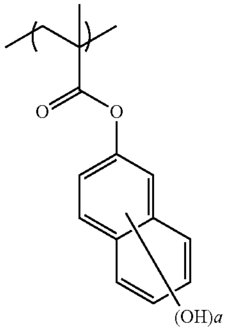
(B-36)
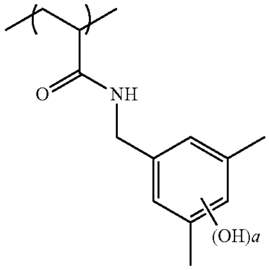
(B-37)
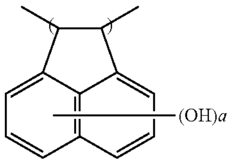
(B-38)
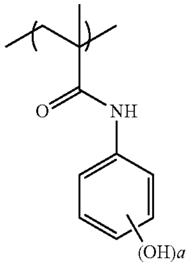
Moreover, as the repeating unit represented by General Formula (AI), repeating units specifically described below are preferable. In the formulae, R represents a hydrogen atom or a methyl group, and a represents 1, 2, or 3.
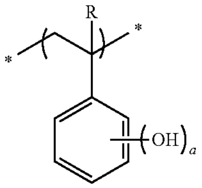
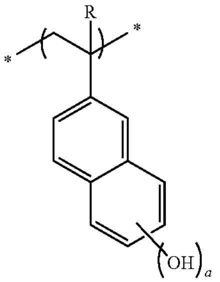
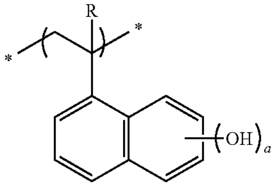
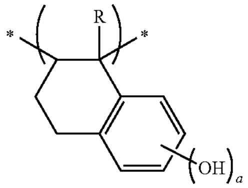
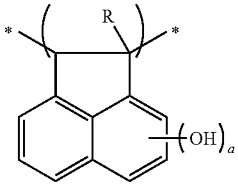
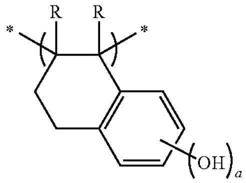
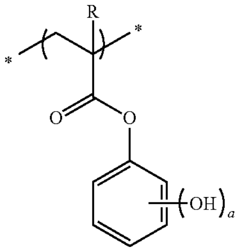
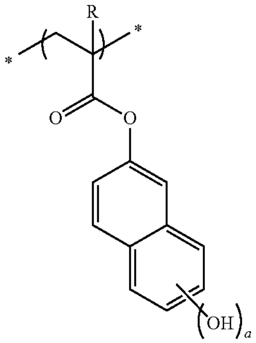
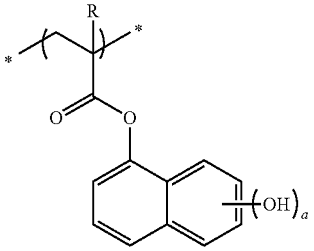
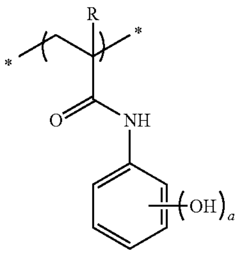
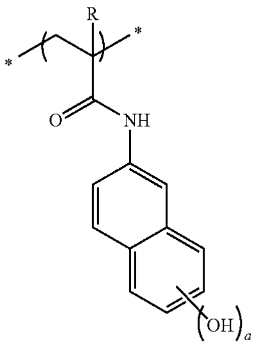

-continued

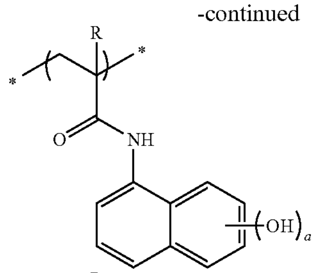

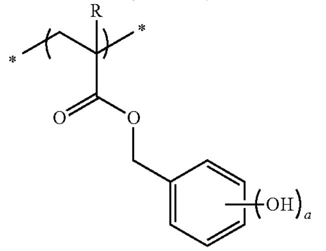

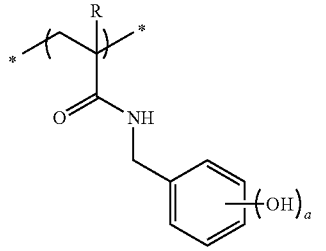

A content of the repeating unit represented by General Formula (AI) is preferably 30% by mole or more, and more preferably 40% by mole or more with respect to all repeating units in the resin (A). In addition, an upper limit value thereof is preferably 90% by mole or less, more preferably 85% by mole or less, and still more preferably 80% by mole or less.

(Repeating Unit Having Acid-Decomposable Group)

The acid-decomposable group refers to a group that decomposes by the action of an acid to generate a polar group. The acid-decomposable group preferably has a structure in which the polar group is protected by a leaving group that leaves by the action of an acid. That is, the resin (A) has a repeating unit having a group that decomposes by the action of an acid to generate a polar group. A resin having this repeating unit has an increased polarity by the action of an acid, and thus has an increased solubility in an alkali developer, and a decreased solubility in an organic solvent.

As the polar group, an alkali-soluble group is preferable, and examples thereof include an acidic group such as a carboxy group, a phenolic hydroxyl group, a fluorinated alcohol group, a sulfonic acid group, a phosphoric acid group, a sulfonamide group, a sulfonylimide group, an (alkylsulfonyl)(alkylcarbonyl)methylene group, an (alkylsulfonylxalkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris (alkylsulfonyl)methylene group, and an alcoholic hydroxyl group.

Among those, as the polar group, the carboxy group, the phenolic hydroxyl group, the fluorinated alcohol group (preferably a hexafluoroisopropanol group), or the sulfonic acid group is preferable. In particular, as the polar group, the carboxy group or the phenolic hydroxyl group is more preferable. That is, as the acid-decomposable group, a group that decomposes by the action of an acid to generate a carboxy group or a group that decomposes by the action of an acid to generate a phenolic hydroxyl group is preferable.

It is preferable that the resin (A) includes a repeating unit having an acid-decomposable group, and the repeating unit having an acid-decomposable group is a repeating unit selected from the group consisting of a group that decomposes by an action of an acid to generate a carboxy group and a group that decomposes by an action of an acid to generate a phenolic hydroxyl group.

Examples of the leaving group that leaves by the action of an acid include groups represented by Formulae (Y1) to (Y4).

$-C(Rx_1)(Rx_2)(Rx_3)$ Formula (Y1):

$-C(=O)OC(Rx_1)(Rx_2)(Rx_1)$ Formula (Y2):

$-C(R_{36})(R_{37})(OR_{38})$ Formula (Y3):

$-C(Rn)(H)(Ar)$ Formula (Y4):

In Formula (Y1) and Formula (Y2), $Rx_1$ to $Rx_3$ each independently represent an (linear or branched) alkyl group or (monocyclic or polycyclic) cycloalkyl group, an (monocyclic or polycyclic) aryl group, an (linear or branched) aralkyl group, or an (linear or branched) alkenyl group. Furthermore, in a case where all of $Rx_1$ to $Rx_3$ are (linear or branched) alkyl groups, it is preferable that at least two of $Rx_1$, $Rx_2$, or $Rx_3$ are methyl groups.

Above all, it is preferable that $Rx_1$ to $Rx_2$ each independently represent a linear or branched alkyl group, and it is more preferable that $Rx_1$ to $Rx_3$ each independently represent the linear alkyl group.

Two of $Rx_1$ to $Rx_3$ may be bonded to each other to form a ring (which may be either monocyclic or polycyclic).

As the alkyl group of each of $Rx_1$ to $Rx_3$, an alkyl group having 1 to 5 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the aryl group as each of $Rx_1$ to $Rx_3$, an aryl group having 6 to 10 carbon atoms is preferable, and examples thereof include a phenyl group, a naphthyl group, and an anthryl group.

As the aralkyl group of each of $Rx_1$ to $Rx_1$, a group formed by substituting one hydrogen atom in the alkyl group of each of $Rx_1$ to $Rx_1$ mentioned above with an aryl group having 6 to 10 carbon atoms (preferably a phenyl group) is preferable, and examples thereof include a benzyl group.

As the alkenyl group of each of $Rx_1$ to $Rx_3$, a vinyl group is preferable.

As a ring formed by the bonding of two of $Rx_1$ to $Rx_3$, a cycloalkyl group is preferable. As the cycloalkyl group formed by the bonding of two of $Rx_1$ to $Rx_3$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of two of $Rx_1$ to $Rx_3$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

With regard to the group represented by Formula (Y1) or Formula (Y2), for example, an aspect in which $Rx_1$ is a methyl group or an ethyl group, and $Rx_2$ and $Rx_3$ are bonded to each other to form a cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. It is also preferable that Rm is the hydrogen atom.

Furthermore, the alkyl group, the cycloalkyl group, the aryl group, and the aralkyl group may include a heteroatom such as an oxygen atom, and/or a group having a heteroatom, such as a carbonyl group. For example, in the alkyl group, the cycloalkyl group, the aryl group, and the aralkyl group, one or more of the methylene groups may be substituted with a heteroatom such as an oxygen atom, and/or a group having a heteroatom, such as a carbonyl group.

In addition, $R_{38}$ and another substituent contained in the main chain of the repeating unit may be bonded to each other to form a ring. A group formed by the mutual bonding of $R_{38}$ and another substituent on the main chain of the repeating unit is preferably an alkylene group such as a methylene group.

As Formula (Y3), a group represented by Formula (Y3-1) is preferable.

(Y3-1)

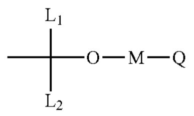

Here, $L_1$ and $L_2$ each independently represent a hydrogen atom, an alkyl group, a cycloalkyl group, an aryl group, or a group formed by combination thereof (for example, a group formed by combination of an alkyl group and an aryl group).

M represents a single bond or a divalent linking group.

Q represents an alkyl group which may include a heteroatom, a cycloalkyl group which may include a heteroatom, an aryl group which may include a heteroatom, an amino group, an ammonium group, a mercapto group, a cyano group, an aldehyde group, or a group formed by combination thereof (for example, a group formed by combination of an alkyl group and a cycloalkyl group).

In the alkyl group and the cycloalkyl group, for example, one of the methylene groups may be substituted with a heteroatom such as an oxygen atom or a group having a heteroatom, such as a carbonyl group.

In addition, it is preferable that one of $L_1$ or $L_2$ is a hydrogen atom, and the other is an alkyl group, a cycloalkyl group, an aryl group, or a group formed by combination of an alkylene group and an aryl group.

At least two of Q, M, or $L_1$ may be bonded to each other to form a ring (preferably a 5- or 6-membered ring).

From the viewpoint of pattern miniaturization, $L_2$ is preferably a secondary or tertiary alkyl group, and more preferably the tertiary alkyl group. Examples of the secondary alkyl group include an isopropyl group, a cyclohexyl group, and a norbornyl group, and examples of the tertiary alkyl group include a tert-butyl group and an adamantane group. In these aspects, since the glass transition temperature (Tg) and the activation energy are increased, it is possible to suppress fogging in addition to ensuring film hardness.

In Formula (Y4), Ar represents an aromatic ring group. Rn represents an alkyl group, a cycloalkyl group, or an aryl group. Rn and Ar may be bonded to each other to form a non-aromatic ring. Ar is more preferably the aryl group.

From the viewpoint that the acid decomposability of the repeating unit is excellent, in a case where a non-aromatic ring is directly bonded to a polar group (or a residue thereof) in a leaving group that protects the polar group, it is also preferable that a ring member atom adjacent to the ring member atom directly bonded to the polar group (or a residue thereof) in the non-aromatic ring has no halogen atom such as a fluorine atom as a substituent.

In addition, the leaving group that leaves by the action of an acid may be a 2-cyclopentenyl group having a substituent (an alkyl group and the like), such as a 3-methyl-2-cyclopentenyl group, and a cyclohexyl group having a substituent (an alkyl group and the like), such as a 1,1,4,4-tetramethylcyclohexyl group.

It is preferable that the repeating unit having an acid-decomposable group includes one or more selected from repeating units represented by the General formulae (3) to (7), and it is more preferable that the repeating unit having an acid-decomposable group includes one or more selected from the repeating unit represented by the General formula (6) and the repeating unit represented by the General formula (7).

(3)

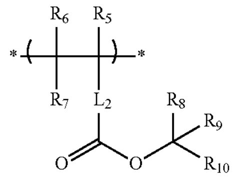

In General Formula (3), $R_5$, $R_6$, and $R_7$ each independently represent a hydrogen atom, an alkyl group, a cycloalkyl group, a halogen atom, a cyano group, or an alkoxycarbonyl group.

$L_2$ represents a single bond or a divalent linking group.

$R_8$ to $R_{10}$ each independently represent an alkyl group, a cycloalkyl group, an aryl group, an aralkyl group, or an alkenyl group. Furthermore, two of $R_8$ to $R_{10}$ may be bonded to each other to form a ring.

The alkyl group represented by each of $R_5$, $R_6$, and $R_7$ may be either linear or branched. The number of carbon atoms of the alkyl group is not particularly limited, but is preferably 1 to 5, and more preferably 1 to 3.

As the cycloalkyl group represented by each of $R_5$, $R_6$, and $R_7$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

Examples of the halogen atom represented by each of $R_5$, $R_6$, and $R_7$ include a fluorine atom, a chlorine atom, a bromine atom, and an iodine atom, and the fluorine atom or the iodine atom is preferable.

The alkyl group included in the alkoxycarbonyl group represented by each of $R_5$, $R_6$, and $R_7$ may be either linear or branched. The number of carbon atoms of the alkyl group included in the alkoxycarbonyl group is not particularly limited, but is preferably 1 to 5, and more preferably 1 to 3.

Examples of the divalent linking group represented by $L_2$ include —CO—, —O—, —S—, —SO—, —$SO_2$—, a hydrocarbon group (for example, an alkylene group, a cycloalkylene group, an alkenylene group, and an arylene group), and a linking group in which a plurality of these groups are linked.

The alkyl group represented by each of $R_8$ to $R_{10}$ may be either linear or branched. The number of carbon atoms of the alkyl group is not particularly limited, but is preferably 1 to 5, and more preferably 1 to 3. In the alkyl group represented by each of $R_8$ to $R_{10}$, the methylene group may be substituted with —CO— and/or —O—.

As the cycloalkyl group of each of $R_8$ to $R_{10}$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the aryl group represented by each of $R_8$ to $R_{10}$, a phenyl group is preferable.

As the aralkyl group represented by each of $R_8$ to $R_{10}$, a group formed by substituting one hydrogen atom in the above-mentioned alkyl group represented by each of $R_8$ to $R_{10}$ with an aryl group having 6 to 10 carbon atoms (preferably a phenyl group) is preferable, and examples thereof include a benzyl group.

As the alkenyl group represented by each of $R_8$ to $R_{10}$, a vinyl group is preferable.

As a ring formed by the bonding of two of $R_8$ to $R_{10}$, a cycloalkyl group is preferable. As the cycloalkyl group formed by the bonding of two of Re to $R_{10}$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of two of $R_8$ to $R_{10}$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

The group in General Formula (3) may have a substituent, and examples of the substituent include the substituent T.

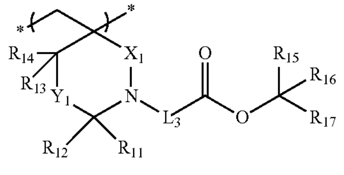

(4)

In General Formula (4), $R_{11}$ to $R_{14}$ each independently represent a hydrogen atom or an organic group. It should be noted that at least one of $R_{11}$ or $R_{12}$ represents an organic group.

$X_1$ represents —CO—, —SO—, or —$SO_2$—.

$Y_1$ represents —O—, —S—, —SO—, —$SO_2$—, or —$NR_{34}$—. $R_{34}$ represents a hydrogen atom or an organic group.

$L_3$ represents a single bond or a divalent linking group.

$R_{15}$ to $R_{17}$ each independently represent an alkyl group, a cycloalkyl group, an aryl group, an aralkyl group, or an alkenyl group. Furthermore, two of $R_{15}$ to $R_{17}$ may be bonded to each other to form a ring.

The organic group represented by each of $R_{11}$ to $R_{14}$ represents an alkyl group, a cycloalkyl group, an aryl group, an aralkyl group, or an alkenyl group.

Examples of the alkyl group, the cycloalkyl group, the aryl group, the aralkyl group, and the alkenyl group represented by each of $R_{11}$ to $R_{14}$ include the same ones as those of the alkyl group, the cycloalkyl group, the aryl group, the aralkyl group, and the alkenyl group represented by each of Ra to $R_{10}$ in General Formula (3) mentioned above.

As $X_1$, —CO— is preferable among those.

The organic group represented by $R_{11}$ has the same definition as the organic group represented by each of $R_{11}$ to $R_{14}$ mentioned above, and a suitable aspect thereof is also the same.

As $Y_1$, —O— is preferable.

The divalent linking group represented by $L_1$ has the same definition as the divalent linking group represented by $L_2$ in General Formula (3) mentioned above, and a suitable aspect thereof is also the same.

Examples of the alkyl group, the cycloalkyl group, the aryl group, the aralkyl group, and the alkenyl group represented by each of $R_{15}$ to $R_{17}$ include the same ones as those of the alkyl group, the cycloalkyl group, the aryl group, the aralkyl group, and the alkenyl group represented by each of $R_8$ to $R_{10}$ in General Formula (3) mentioned above.

As a ring formed by the bonding of two of $R_{15}$ to $R_{17}$, a cycloalkyl group is preferable. As the cycloalkyl group formed by the bonding of two of $R_{15}$ to $R_{17}$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of two of $R_{15}$ to $R_{17}$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

The group in General Formula (4) may have a substituent, and examples of the substituent include the substituent T.

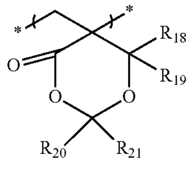

(5)

In General Formula (5), $R_{10}$ and $R_{19}$ each independently represent a hydrogen atom or an organic group.

$R_{20}$ and $R_{21}$ each independently represent a hydrogen atom, an alkyl group, a cycloalkyl group, an aryl group, an aralkyl group, or an alkenyl group. Furthermore, $R_{20}$ and $R_{21}$ may be bonded to each other to form a ring.

The organic group represented by each of $R_{18}$ and $R_{19}$ has the same definition as the organic group represented by each of $R_{11}$ to $R_{14}$ in General Formula (4) mentioned above, and a suitable aspect thereof is also the same.

Examples of the alkyl group, the cycloalkyl group, the aryl group, the aralkyl group, and the alkenyl group represented by each of $R_{20}$ and $R_{21}$ include the same ones as those of the alkyl group, the cycloalkyl group, the aryl group, the aralkyl group, and the alkenyl group represented by each of $R_8$ to $R_{10}$ in General Formula (3) mentioned above.

The alkyl group, the cycloalkyl group, the aryl group, the aralkyl group, and the alkenyl group represented by each of $R_{20}$ and $R_{21}$ may have a substituent, and examples of the substituent include the substituent T.

As the ring formed by the bonding of $R_{20}$ and $R_{21}$, a cycloalkyl group is preferable. As the cycloalkyl group formed by the bonding of $R_{20}$ and $R_{21}$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of $R_{20}$ and $R_{21}$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

(6)

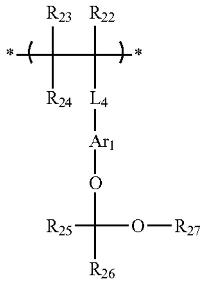

In General Formula (6), $R_{22}$, $R_{23}$, and $R_{24}$ each independently represent a hydrogen atom, an alkyl group, a cycloalkyl group, a halogen atom, a cyano group, or an alkoxycarbonyl group.

$L_4$ represents a single bond or a divalent linking group.

$Ar_1$ represents an aromatic ring group.

$R_{25}$ to $R_{27}$ each independently represent a hydrogen atom, an alkyl group, a cycloalkyl group, an aryl group, an aralkyl group, or an alkenyl group. Furthermore, $R_{26}$ and $R_{27}$ may be bonded to each other to form a ring. In addition, $Ar_1$ may be bonded to $R_{24}$ or $R_{25}$ to form a ring.

$R_{22}$, $R_{23}$, $R_{24}$, and $L_4$ have the same definitions as $R_5$, $R_6$, $R_7$, and $L_2$ in General Formula (3), respectively, and suitable aspects are also the same.

The aromatic ring group represented by $Ar_1$ is not particularly limited, examples thereof include a benzene ring and a naphthalene ring, and the benzene ring is preferable.

Examples of the alkyl group, the cycloalkyl group, the aryl group, the aralkyl group, and the alkenyl group represented by each of $R_{25}$ to $R_{27}$ include the same ones as those of the alkyl group, the cycloalkyl group, the aryl group, the aralkyl group, and the alkenyl group represented by each of $R_8$ to $R_{10}$ in General Formula (3) mentioned above.

The alkyl group, the cycloalkyl group, the aryl group, the aralkyl group, and the alkenyl group represented by each of $R_{25}$ to $R_{27}$ may have a substituent, and examples of the substituent include the substituent T.

A cycloalkyl group is preferable as the ring formed by the bonding of $R_{26}$ and $R_{27}$, $Ar_1$ and $R_{24}$, or $R_{25}$ and $Ar_1$. As the cycloalkyl group formed by the bonding of $R_{26}$ and $R_{27}$, $Ar_1$ and $R_4$, or $R_2$, and $Ar_1$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of $R_{26}$ and $R_{27}$, $Ar_1$ and $R_{24}$, or $R_{25}$ and $Ar_1$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

(7)

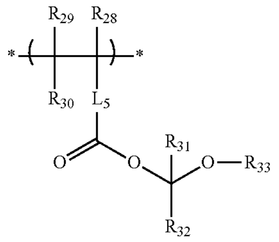

In General Formula (7), $R_{28}$, $R_{29}$, and $R_{30}$ each independently represent a hydrogen atom, an alkyl group, a cycloalkyl group, a halogen atom, a cyano group, or an alkoxycarbonyl group.

$L_5$ represents a single bond or a divalent linking group.

$R_{31}$ and $R_{32}$ each independently represent a hydrogen atom, an alkyl group, a cycloalkyl group, an aryl group, an aralkyl group, or an alkenyl group.

$R_{33}$ represents an alkyl group, a cycloalkyl group, an aryl group, an aralkyl group, or an alkenyl group. Furthermore, $R_{32}$ and $R_{33}$ may be bonded to each other to form a ring.

$R_{28}$, $R_{29}$, $R_{30}$, and $L_5$ have the same definitions as $R_5$, $R_6$, $R_7$, and $L_2$ in General Formula (3), respectively, and suitable aspects are also the same.

Examples of the alkyl group, the cycloalkyl group, the aryl group, the aralkyl group, and the alkenyl group represented by each of $R_{31}$, $R_{32}$, and $R_{33}$ include the same ones as those of the alkyl group, the cycloalkyl group, the aryl group, the aralkyl group, and the alkenyl group represented by each of $R_8$ to $R_{10}$ in General Formula (3) mentioned above.

The alkyl group, the cycloalkyl group, the aryl group, the aralkyl group, and the alkenyl group represented by each of $R_{31}$, $R_{32}$, and $R_{33}$ may have a substituent, and examples of the substituent include the substituent T.

A cycloalkyl group is preferable as the ring formed by the bonding of $R_{32}$ and $R_{33}$. As the cycloalkyl group formed by the bonding of $R_{32}$ and $R_{33}$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of $R_{32}$ and $R_{33}$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

The repeating unit having an acid-decomposable group may or may not include a halogen atom, but it is preferable that the repeating unit having an acid-decomposable group does not include a halogen atom.

The content of the repeating unit having an acid-decomposable group is preferably 5% by mole or more, more preferably 10% by mole or more, and still more preferably 15% by mole or more with respect to all repeating units in the resin (A). In addition, an upper limit value thereof is preferably 95% by mole or less, more preferably 90% by mole or less, and particularly preferably 85% by mole or less.

Specific examples of the repeating unit having an acid-decomposable group are shown below, but the present invention is not limited thereto. Furthermore, in the formulae, $Xa_1$ represents H, $CH_3$, $CF_3$, or $CH_2OH$, and Rxa and Rxb each represent a linear or branched alkyl group having 1 to 5 carbon atoms.

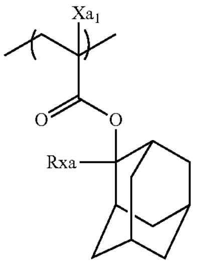
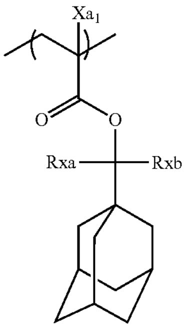
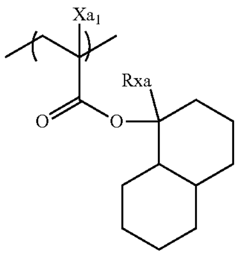
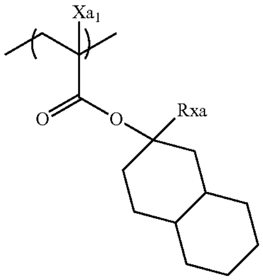
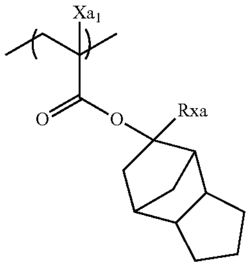
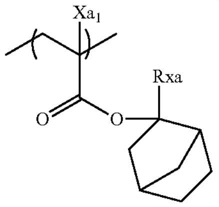

-continued

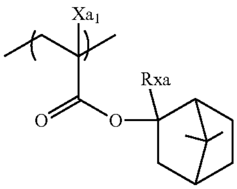
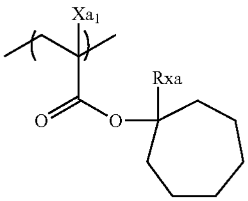
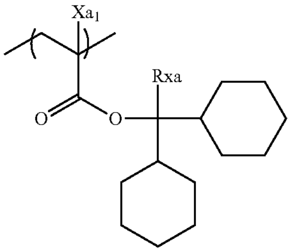
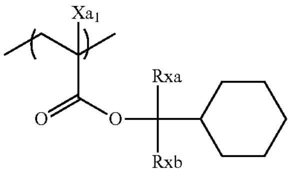
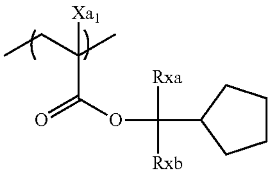
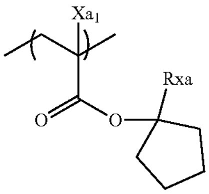
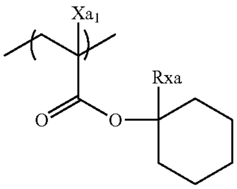
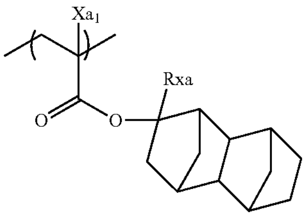
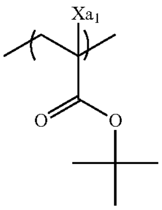
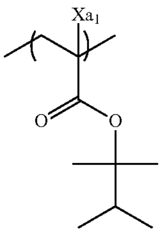
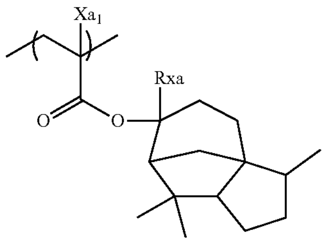
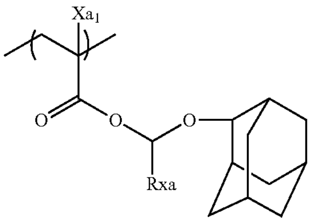

-continued
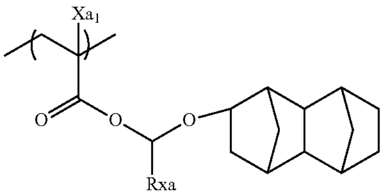
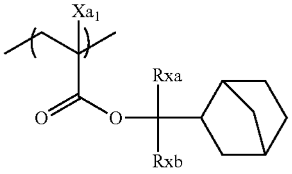
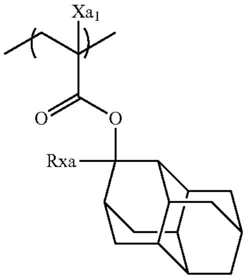
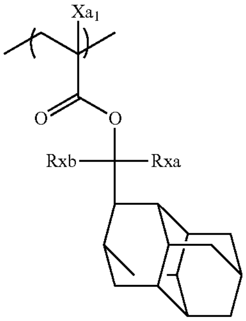
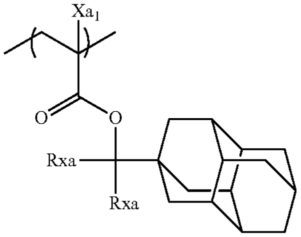
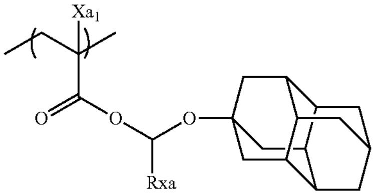
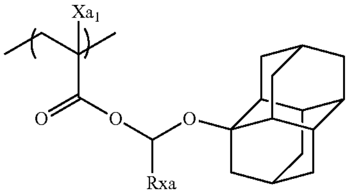
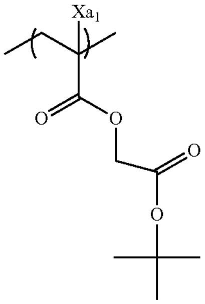
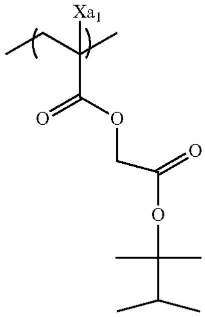
-continued
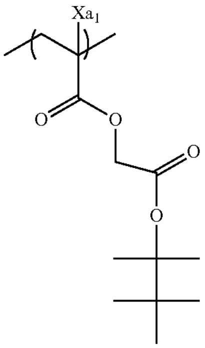
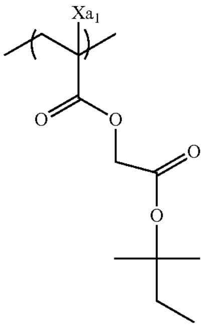
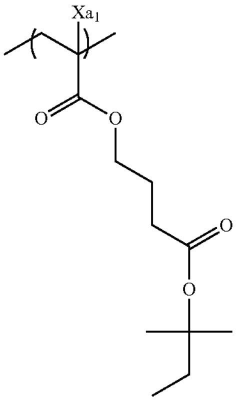
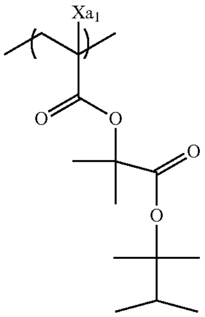
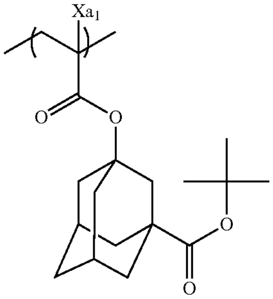
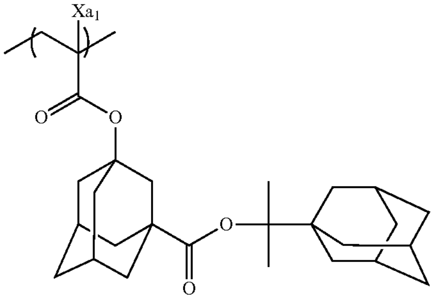
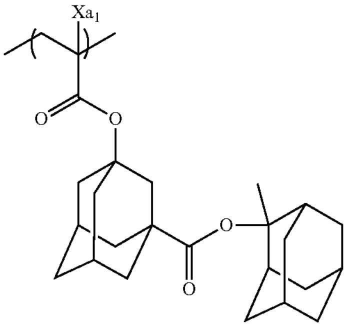

-continued
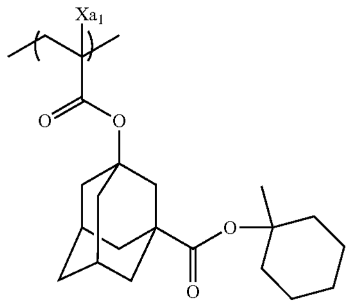
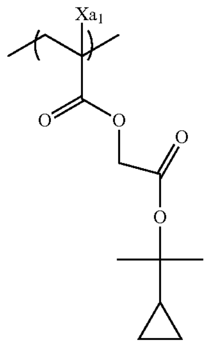
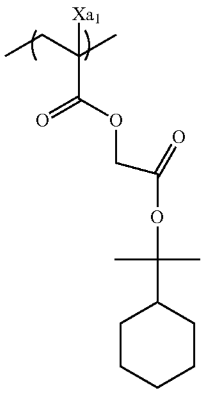
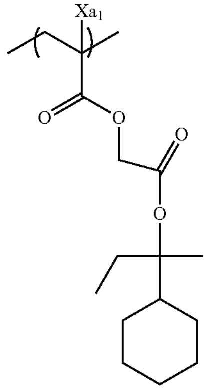
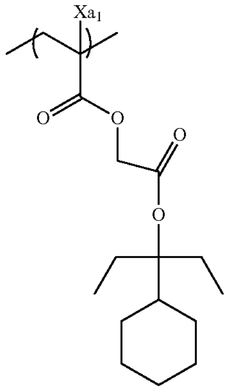
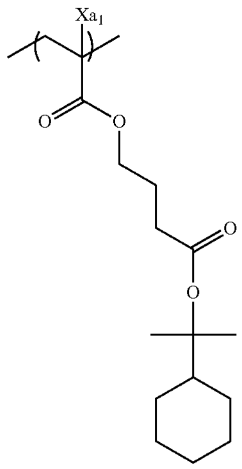
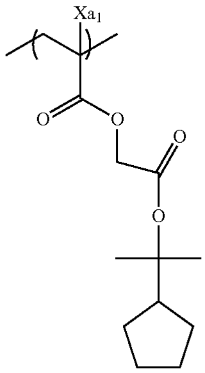
-continued
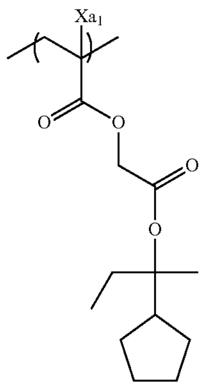
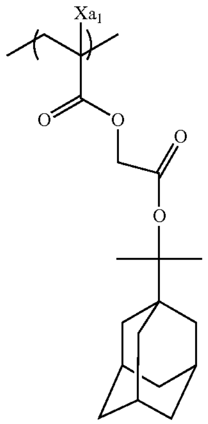
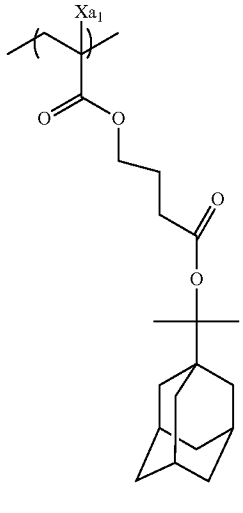
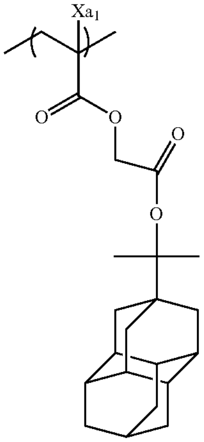
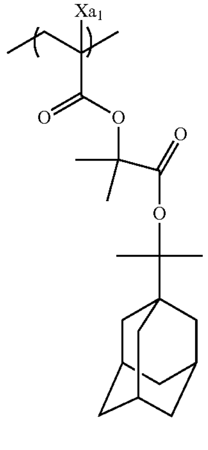
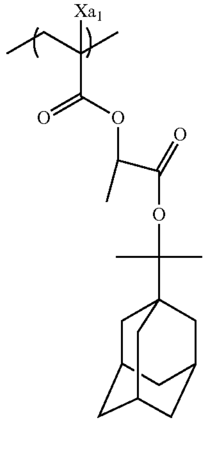

-continued
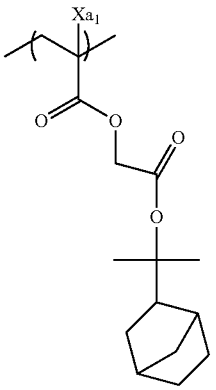
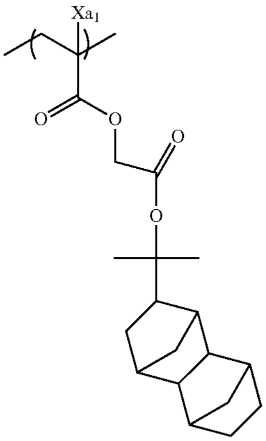
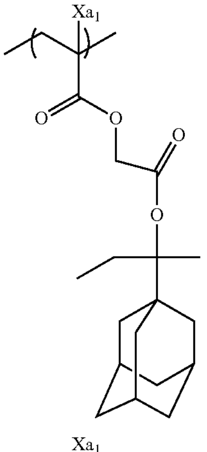
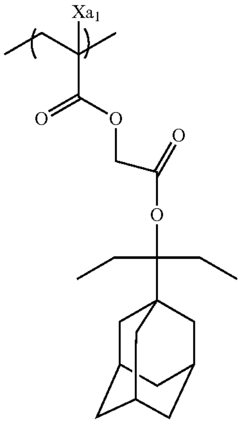
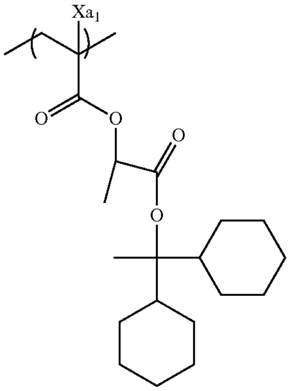
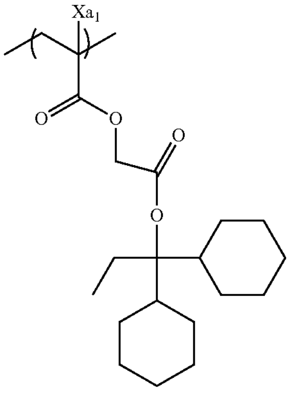
-continued
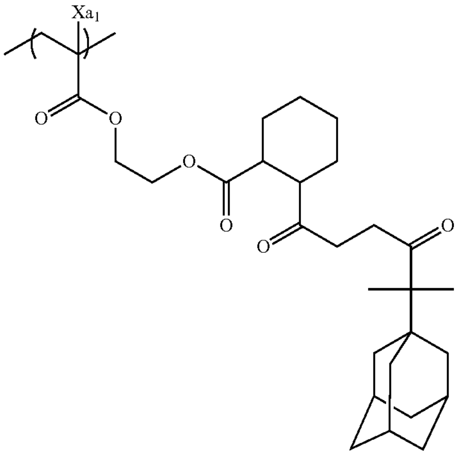
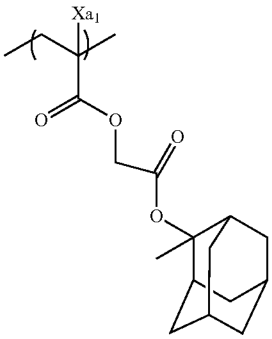
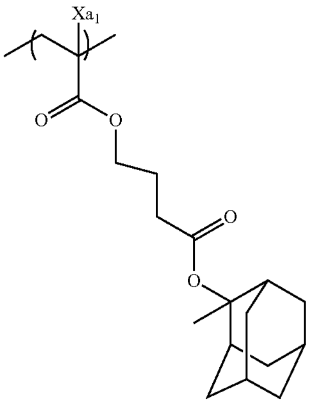
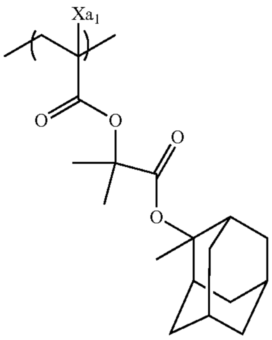

-continued
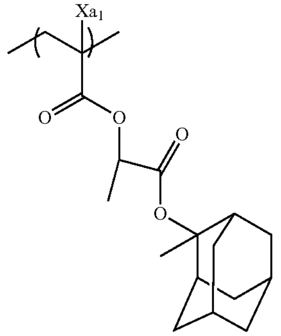
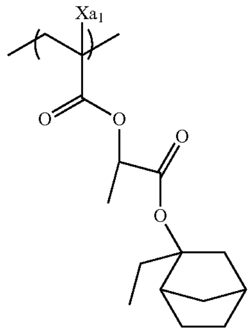
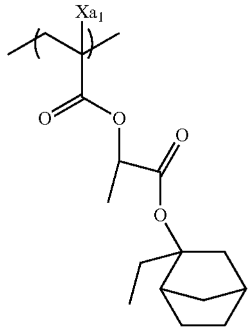
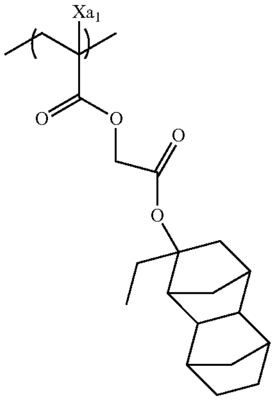
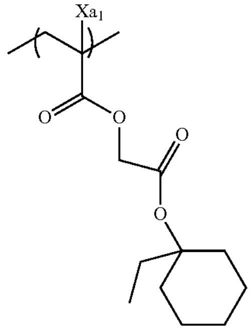
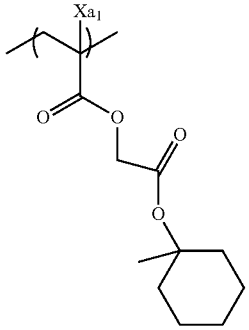
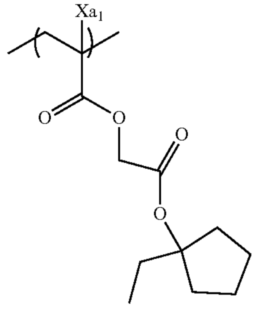
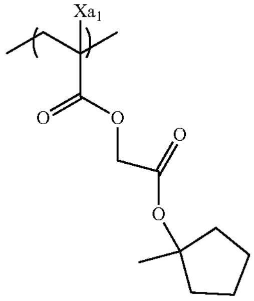
-continued
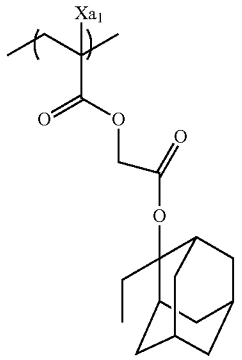
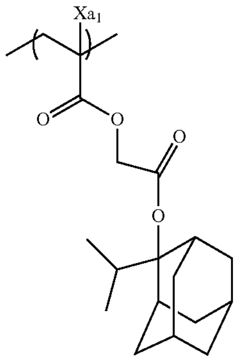
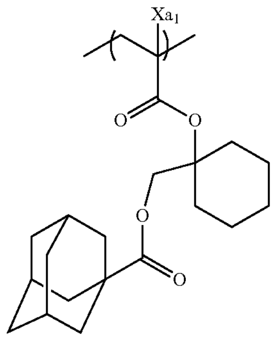
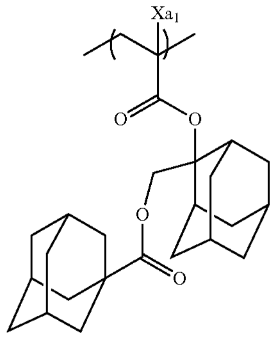
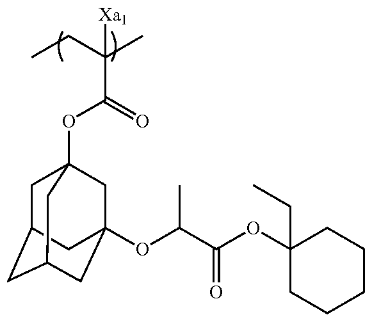
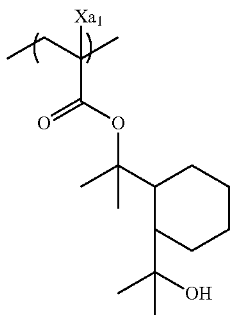
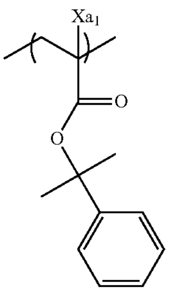

-continued
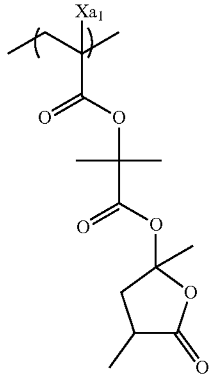
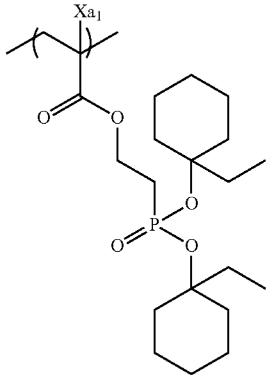
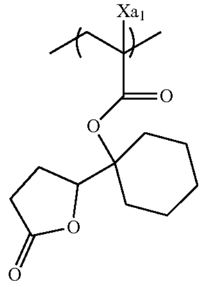
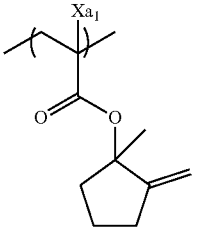
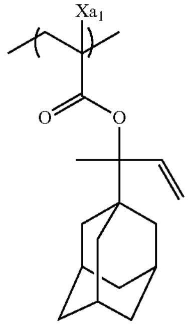
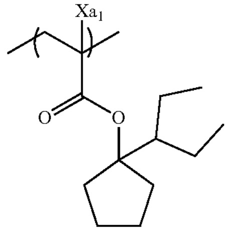
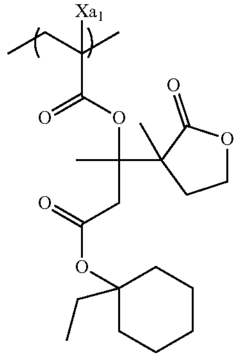
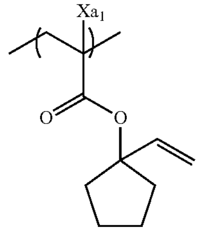
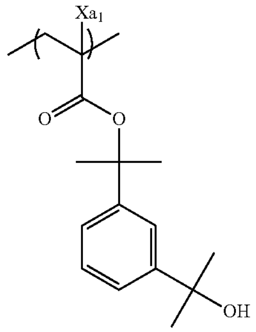
-continued
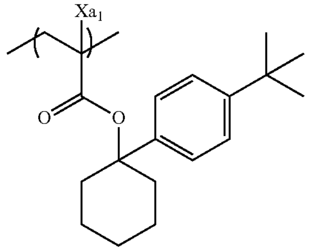
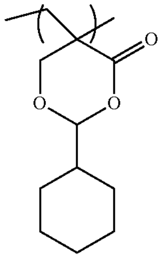
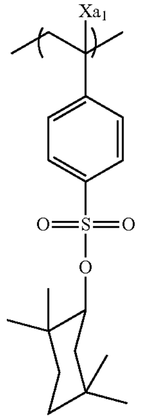
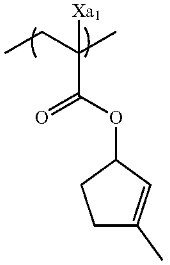
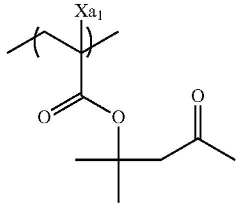
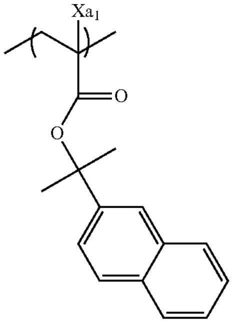
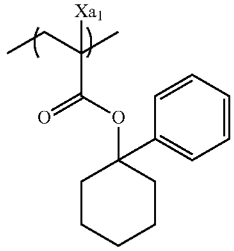
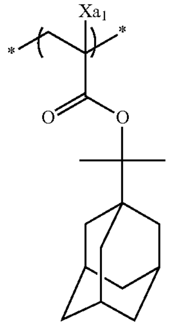
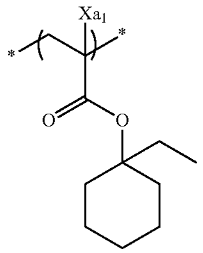
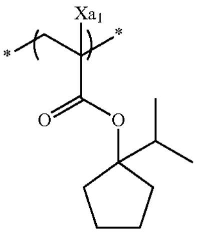

-continued
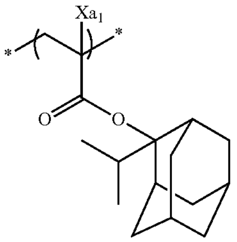
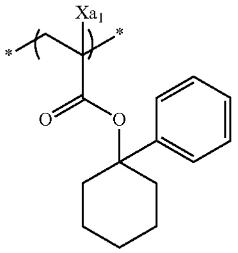
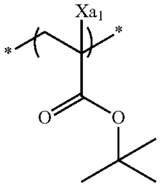
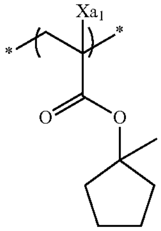
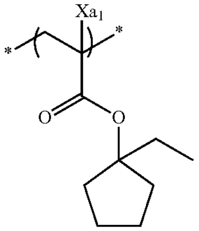
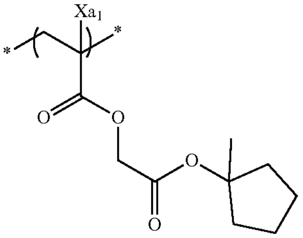
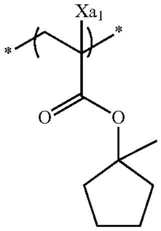
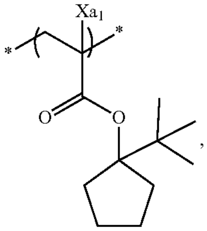
,
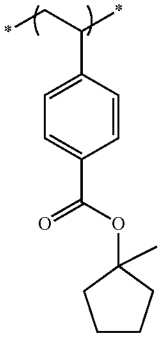
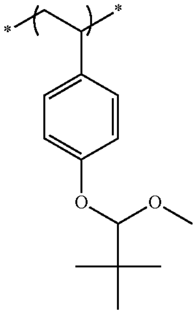
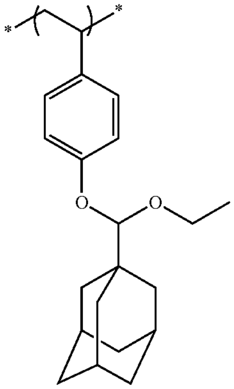
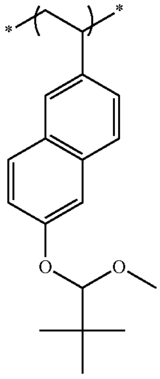
-continued
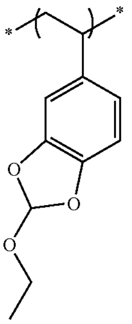
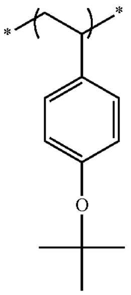
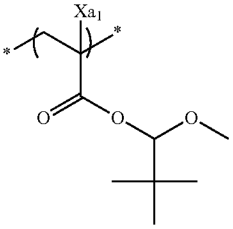
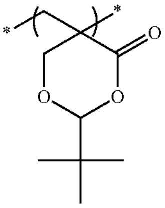
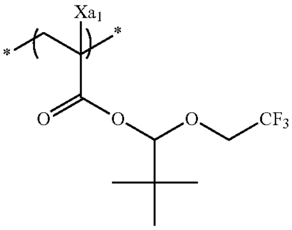
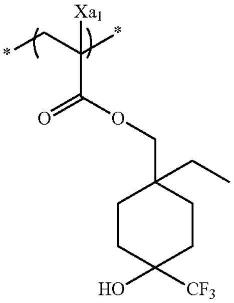
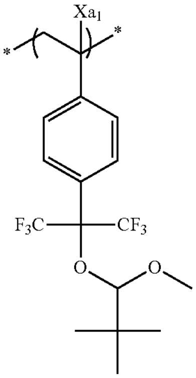
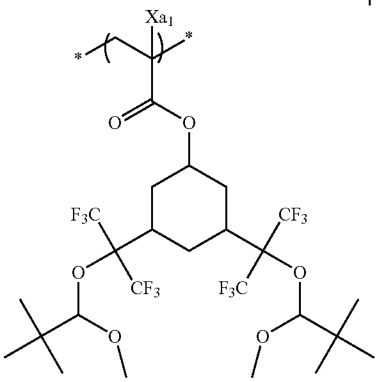
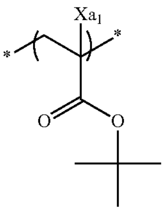
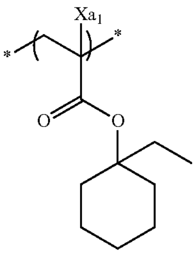
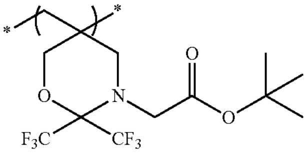

-continued

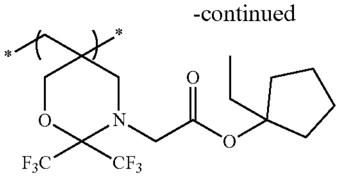

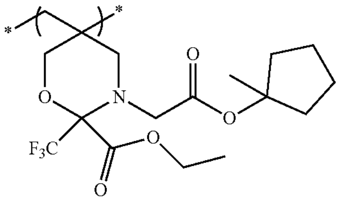

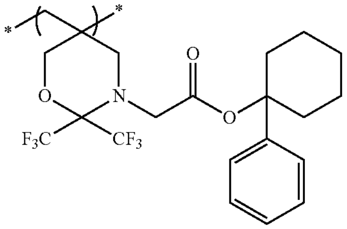

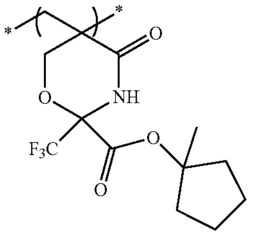

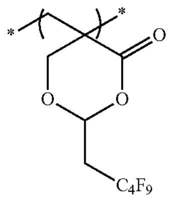

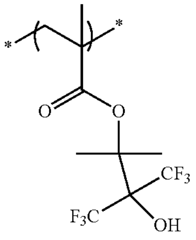

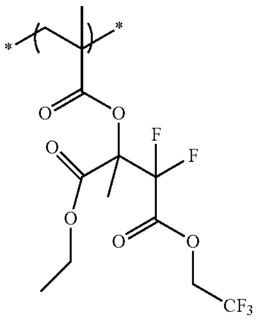

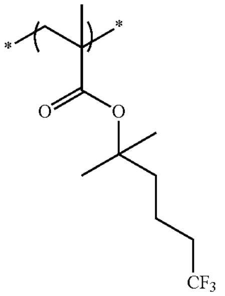

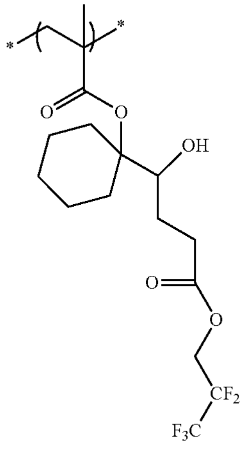

The resin (A) may include a repeating unit other than the above-mentioned repeating units.

For example, the resin (A) may include at least one repeating unit selected from the group consisting of the following group A and/or at least one repeating unit selected from the group consisting of the following group B.

Group A: A group consisting of the following repeating units (20) to (29).

(20) A repeating unit having an acid group, which will be described later

(21) A repeating unit having a fluorine atom or an iodine atom and not exhibiting acid decomposability, which will be described later

(22) A repeating unit having a lactose group, a sultone group, or a carbonate group, which will be described later

(23) A repeating unit having a photoacid generating group, which will be described later

(24) A repeating Unit represented by General Formula (V-1) or General Formula (V-2), which will be described later

(25) A repeating unit represented by Formula (A), which will be described later

(26) A repeating unit represented by Formula (B), which will be described later

(27) A repeating unit represented by Formula (C), which will be described later

(28) A repeating unit represented by Formula (D), which will be described later

(29) A repeating unit represented by Formula (E), which will be described later

Group B: A group consisting of the following repeating units (30) to (32)

(30) A repeating unit having at test one group selected from a lactone group, a sultone group, a carbonate group, a hydroxyl group, a cyano group, or an alkali-soluble group, which will be described later.

(31) A repeating unit having an alicyclic hydrocarbon structure and not exhibiting acid decomposability described later

(32) A repeating unit represented by General Formula (III) having neither a hydroxyl group nor a cyano group, which will be described later In a case where the composition of the embodiment of the present invention is used as an actinic ray-sensitive or radiation-sensitive resin composition for EUV, it is preferable that the resin (A) has at least one repeating unit selected from the group consisting of the group A.

In addition, in a case where the composition is used as the actinic ray-sensitive or radiation-sensitive resin composition for EUV, it is preferable that the resin (A) includes at least one of a fluorine atom or an iodine atom, and it is more preferable that the resin (A) includes the fluorine atom. In a case where the resin (A) includes both a fluorine atom and an iodine atom, the resin (A) may have one repeating unit including both a fluorine atom and an iodine atom, and the resin (A) may include two kinds of repeating units, that is, a repeating unit having a fluorine atom and a repeating unit having an iodine atom.

In addition, in a case where the composition is used as an actinic ray-sensitive or radiation-sensitive resin composition for EUV, it is also preferable that the resin (A) has a repeating unit having an aromatic group.

(Repeating Unit Having Acid Group)

The resin (A) may have a repeating unit having an acid group that is different from the repeating unit represented by General Formula (AI).

As the acid group, for example, a carboxy group, a fluorinated alcohol group (preferably a hexafluoroisopropanol group), a sulfonic acid group, a sulfonamide group, or an isopropanol group is preferable.

In addition, in the hexafluoroisopropanol group, one or more (preferably one or two) fluorine atoms may be substituted with a group (an alkoxycarbonyl group and the like) other than a fluorine atom. $—C(CF_3)(OH)—CF_2—$ formed as above is also preferable as the acid group. In addition, one or more fluorine atoms may be substituted with a group other than a fluorine atom to form a ring including $—C(CF)(OH)—CF_2—$.

The repeating unit having an acid group is preferably a repeating unit different from a repeating unit having the structure in which a polar group is protected by the leaving group that leaves by the action of an acid as described above, and a repeating unit having a lactone group, a sultone group, or a carbonate group which will be described later.

The repeating unit having an acid group may have a substituent, and examples of the substituent include the substituent T.

As the repeating unit having an acid group, a repeating unit represented by Formula (B) is preferable.

(B)

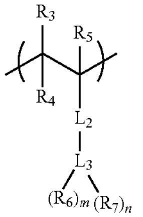

$R_3$ represents a hydrogen atom or a monovalent organic group.

As the monovalent organic group, a group represented by $-L_4-R_8$ is preferable. $L_4$ represents a single bond or an ester group. Examples of $R_x$ include an alkyl group, a cycloalkyl group, an aryl group, and a group formed by combination thereof.

$R_4$ to $R_5$ each independently represent a hydrogen atom, a fluorine atom, an iodine atom, or an alkyl group.

$L_2$ represents a single bond or an ester group.

$L_3$ represents an (n+m+1)-valent alicyclic hydrocarbon ring group. The alicyclic hydrocarbon ring group may be either a monocycle or a polycycle, and examples thereof include a cycloalkyl ring group.

$R_6$ represents a hydroxyl group or a fluorinated alcohol group (preferably a hexafluoroisopropanol group).

$R_7$ represents a halogen atom. Examples of the halogen atom include a fluorine atom, a chlorine atom, a bromine atom, or an iodine atom.

m represents an integer of 1 or more m is preferably an integer of 1 to 3 and more preferably an integer of 1 or 2.

n represents 0 or an integer of 1 or more. n is preferably an integer of 1 to 4.

Furthermore, (n+m+1) is preferably an integer of 1 to 5.

The group in Formula (B) may have a substituent, and examples of the substituent include the substituent T.

The repeating unit having an acid group is exemplified below.

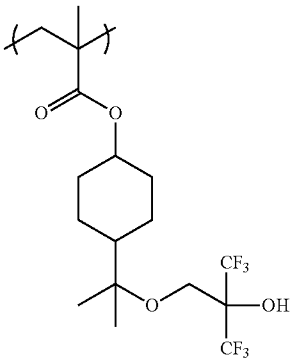

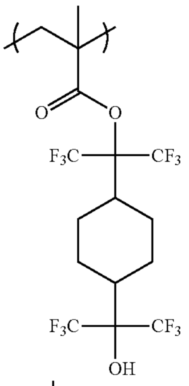

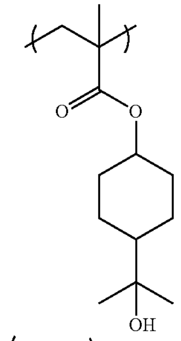

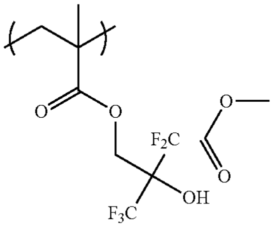

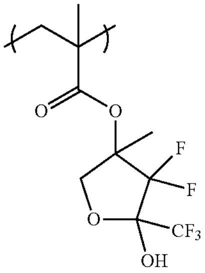

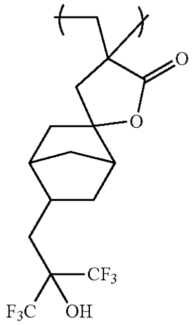

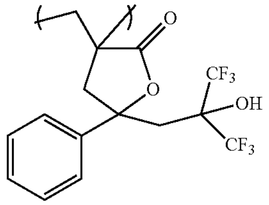

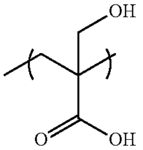

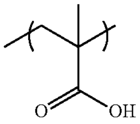

The content of the repeating unit having an acid group is preferably 5% by mole or more, and more preferably 10% by mole or more with respect to all repeating units in the resin (A). In addition, an upper limit value thereof is preferably 70% by mole or less, more preferably 60% by mole or less, and still more preferably 50% by mole or less.

(Repeating Unit Having Fluorine Atom or Iodine Atom and not Exhibiting Acid Decomposability)

The resin (A) may have a repeating unit having a fluorine atom or an iodine atom, in addition to "(Repeating Unit Having Acid-Decomposable Group)" and "(Repeating Unit Having Acid Group)", each mentioned above. In addition, the "repeating unit having a fluorine atom or an iodine atom"

as mentioned herein is preferably different from other kinds of repeating units belonging to the group A, such as "(Repeating Unit Having Lactone Group, Sultone Group, or Carbonate Group)" and "(Repeating Unit Having Photoacid Generating Group)", each of which will be described late.

Furthermore, in "(Repeating Unit Having Fluorine Atom or Iodine Atom and Not Exhibiting Acid Decomposability)" mentioned above, it is preferable that the main chain does not include a ring member atom (in other words, an atom constituting a ring structure).

As the repeating unit having a fluorine atom or an iodine atom and not exhibiting acid decomposability, a repeating unit represented by Formula (C) is preferable.

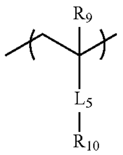

(C)

$L_5$ represents a single bond or an ester group.

$R_9$ represents a hydrogen atom, or an alkyl group which may have a fluorine atom or an iodine atom.

$R_{10}$ represents a hydrogen atom, an alkyl group which may have a fluorine atom or an iodine atom, a cycloalkyl group which may have a fluorine atom or an iodine atom, an aryl group which may have a fluorine atom or an iodine atom, or a group formed by combination thereof.

A repeating unit having a fluorine atom or an iodine atom and not exhibiting acid decomposability will be exemplified below.

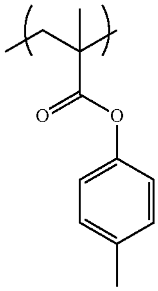

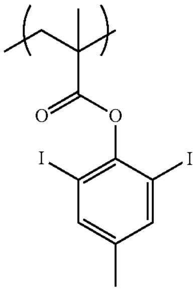

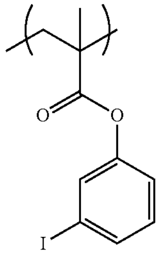

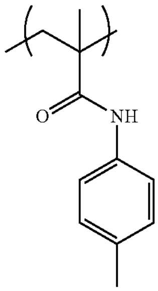

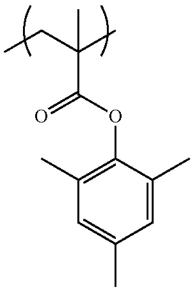

-continued

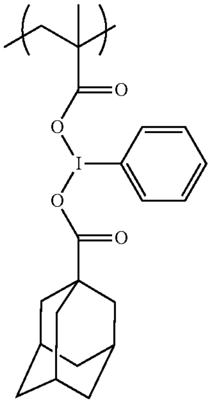

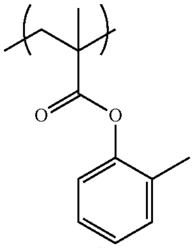

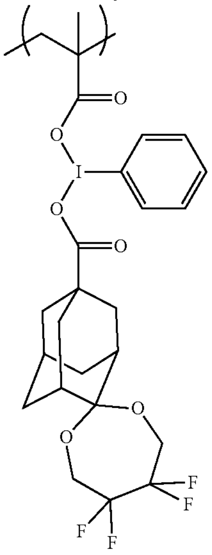

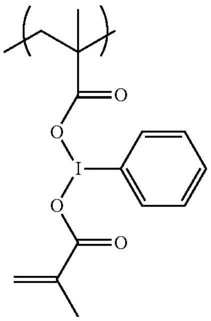

The content of the repeating unit having a fluorine atom or an iodine atom and not exhibiting acid decomposability is preferably 0% by mole or more, more preferably 5% by mole or more, and still more preferably 10% by mole or more with respect to all repeating units in the resin (A). In addition, an upper limit value thereof is preferably 50% by mole or less, more preferably 45% by mole or less, and still more preferably 40% by mole or less.

(Repeating Unit Having Lactone Group, Sultone Group, or Carbonate Group)

The resin (A) may have a repeating unit having at least one selected from the group consisting of a lactone group, a sultone group, and a carbonate group (hereinafter also collectively referred to as a "repeating unit having a lactone group, a sultone group, or a carbonate group").

It is also preferable that the repeating unit having a lactone group, a sultone group, or a carbonate group has no acid group such as a hexafluoropropanol group.

The lactone group or the sultone group may have a lactone structure or a sultone structure. The lactone structure or the sultone structure is preferably a 5- to 7-membered ring lactone structure or a 5- to 7-membered ring sultone structure. Among those, the structure is more preferably a 5- to 7-membered ring lactone structure with which another ring structure is fused so as to form a bicyclo structure or a spiro structure or a 5- to 7-membered ring sultone structure with which another ring structure is fused so as to form a bicyclo structure or a spiro structure.

The resin (A) preferably has a repeating unit having a lactone group or a sultone group, formed by extracting one or more hydrogen atoms from a ring member atom of a lactone structure represented by any of General Formulae (LC1-1) to (LC1-21) or a sultone structure represented by any of General Formulae (SL1-1) to (SL1-3).

In addition, the lactone group or the sultone group may be bonded directly to the main chain. For example, a ring member atom of the lactone group or the sultone group may constitute the main chain of the resin (A).

LC1-1

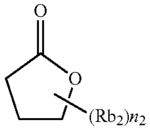

LC1-2

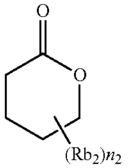

LC1-3

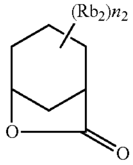

LC1-4

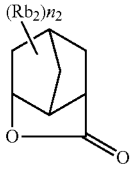

LC1-5

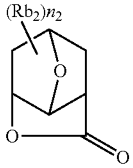

LC1-6

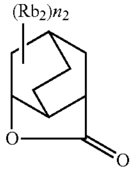

LC1-7

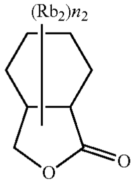

-continued

LC1-8

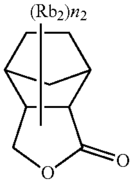

LC1-9

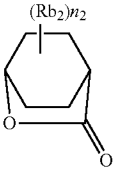

LC1-10

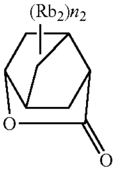

LC1-11

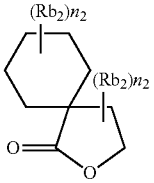

LC1-12

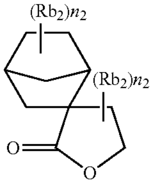

LC1-13

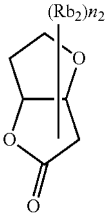

LC1-14

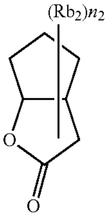

LC1-15

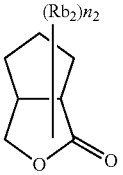

-continued

LC1-16

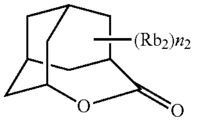

LC1-17

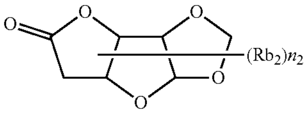

LC1-18

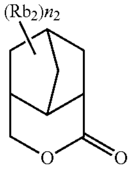

LC1-19

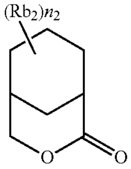

LC1-20

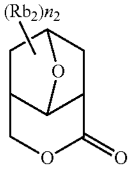

LC1-21

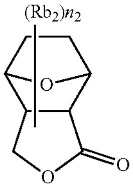

SL1-1

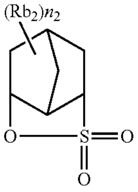

SL1-2

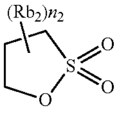

SL1-3

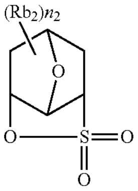

The moiety of the lactone structure or the sultone structure may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxy group, a halogen atom, a hydroxyl group, a cyano group, and an acid-decomposable group. $n_2$ represents an integer of 0 to 4. In a case where $n_2$ is 2 or more, $Rb_2$'s which are present in a plural number may be different from each other, and $Rb_2$'s which are present in a plural number may be bonded to each other to form a ring.

Examples of the repeating unit having a group having the lactone structure represented by any of General Formulae (LC1-1) to (LC1-21) or the sultone structure represented by any of General Formulae (SL1-1) to (SL1-3) include a repeating unit represented by General Formula (AI).

(AI)

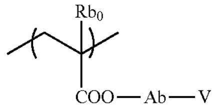

In General Formula (AI), $Rb_0$ represents a hydrogen atom, a halogen atom, or an alkyl group having 1 to 4 carbon atoms.

Preferred examples of the substituent which may be contained in the alkyl group of $Rb_0$ include a hydroxyl group and a halogen atom.

Examples of the halogen atom of $Rb_0$ include a fluorine atom, a chlorine atom, a bromine atom, and an iodine atom. $Rb_0$ is preferably the hydrogen atom or a methyl group.

Ab represents a single bond, an alkylene group, a divalent linking group having a monocyclic or polycyclic alicyclic hydrocarbon structure, an ether group, an ester group, a carbonyl group, a carboxy group, or a divalent group formed by combination thereof. Among those, the single bond or a linking group represented by $-Ab_1-CO_2-$ is preferable. $Ab_1$ is a linear or branched alkylene group, or a monocyclic or polycyclic cycloalkylene group, and is preferably a methylene group, an ethylene group, a cyclohexylene group, an adamantylene group, or a norbornylene group.

V represents a group formed by extracting one hydrogen atom from a ring member atom of the lactone structure represented by any of General Formulae (LC1-1) to (LC1-21) or a group formed by extracting one hydrogen atom from a ring member atom of the sultone structure represented by any of General Formulae (SL1-1) to (SL1-3).

In a case where an optical isomer is present in the repeating unit having a lactone group or a sultone group, any of the optical isomer may be used. In addition, one kind of optical isomers may be used alone or a plurality of kinds of optical isomers may be mixed and used. In a case where one kind of optical isomers is mainly used, an optical purity (ee) thereof is preferably 90 or more, and more preferably 95 or more.

As the carbonate group, a cyclic carbonic acid ester group is preferable.

As the repeating unit having a cyclic carbonic acid ester group, a repeating unit represented by General Formula (A-1) is preferable.

(A-1)

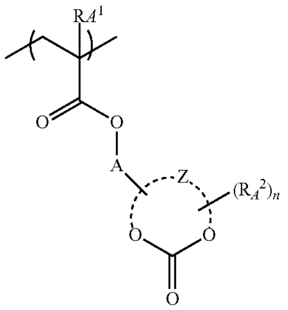

In General Formula (A-1), $R_A^1$ represents a hydrogen atom, a halogen atom, or a monovalent organic group (preferably a methyl group).

n represents an integer of 0 or more.

$R_A^2$ represents a substituent. In a case where n is 2 or more, $R_A^2$ which are present in a plural number may be the same as or different from each other.

A represents a single bond or a divalent linking group. As the divalent linking group, an alkylene group, a divalent linking group having a monocyclic or polycyclic alicyclic hydrocarbon structure, an ether group, an ester group, a carbonyl group, a carboxy group, or a divalent group formed by combination thereof is preferable.

Z represents an atomic group that forms a monocycle or polycycle with a group represented by —O—CO—O— in the formula.

The repeating unit having a lactone group, a sultone group, or a carbonate group will be exemplified below.

(in the formulae, $R_8$ represents H, $CH_3$, $CH_2OH$, or $CF_3$)

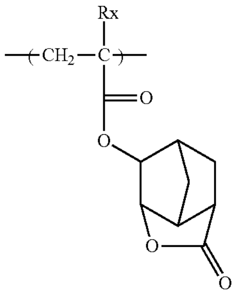

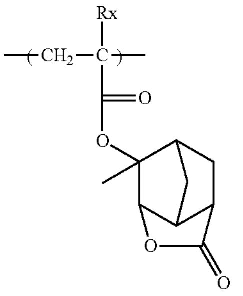

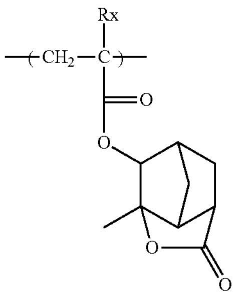

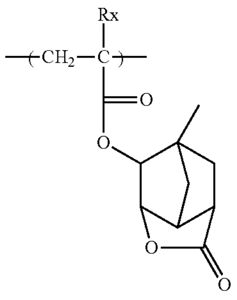

-continued

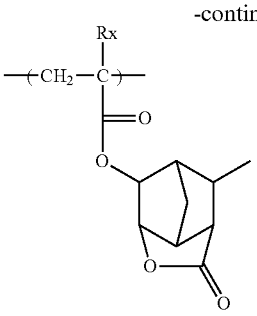

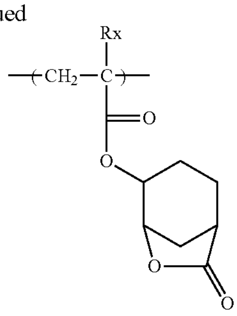

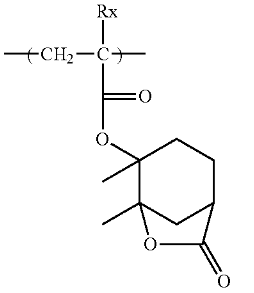

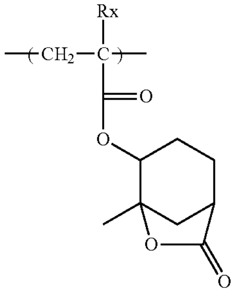

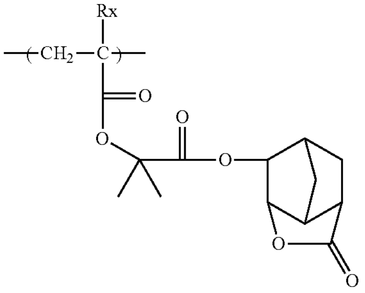

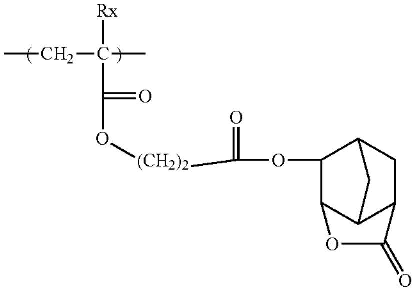

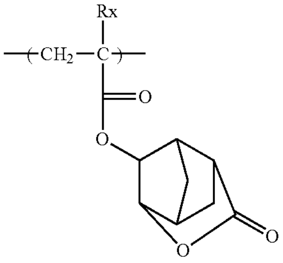

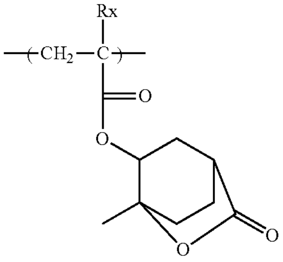

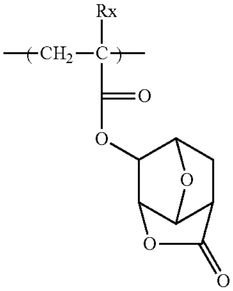

-continued
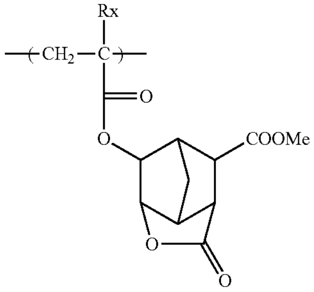
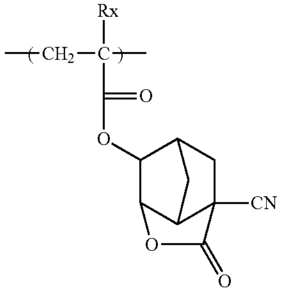
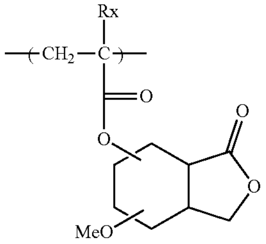
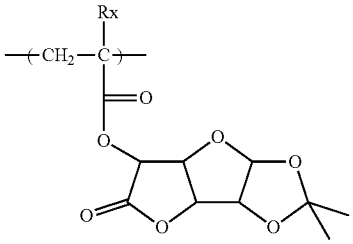
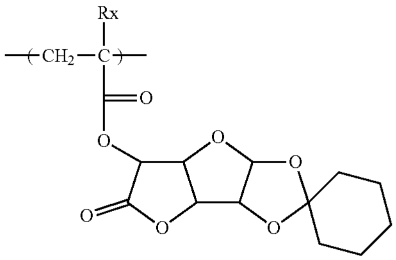
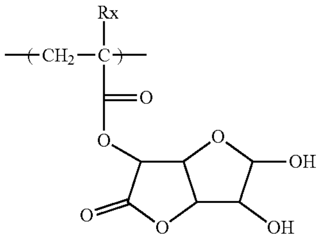
-continued
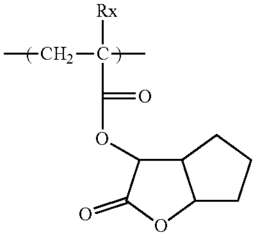
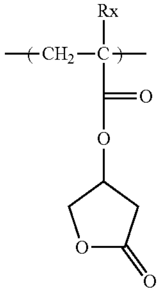
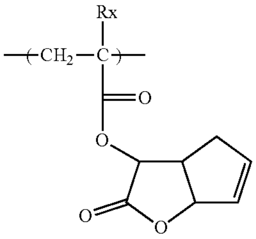
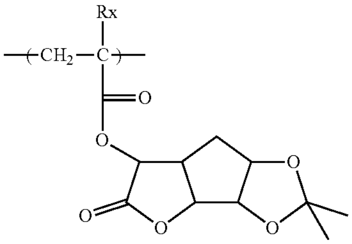
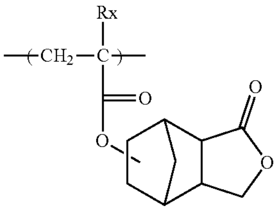
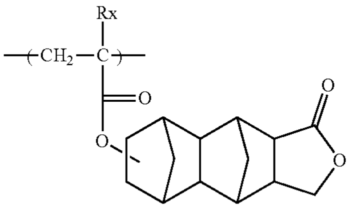
(in the formulae, Rx represents H, $CH_3$, $CH_2OH$, or $CF_3$)
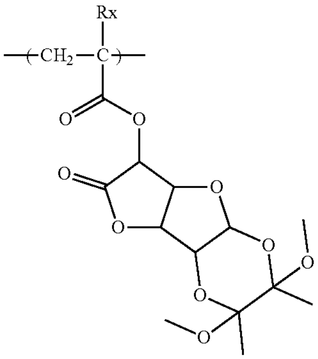
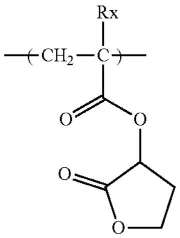

-continued
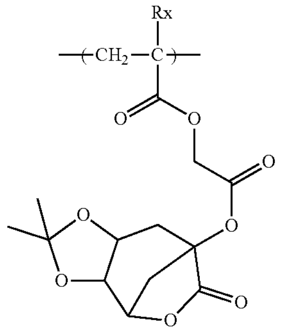
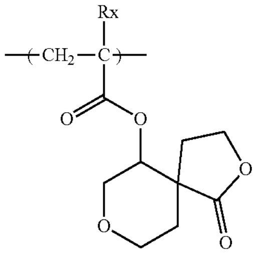
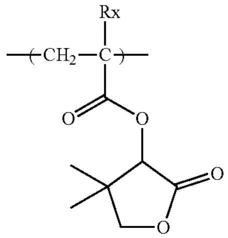
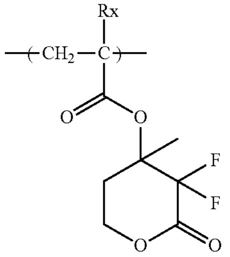
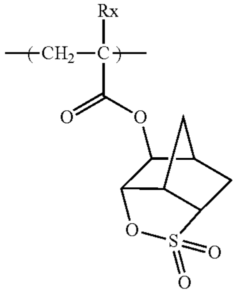
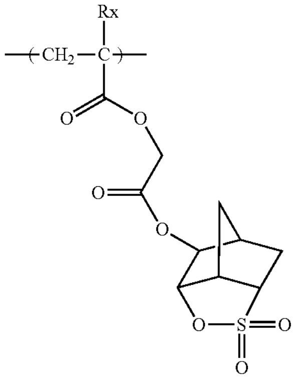
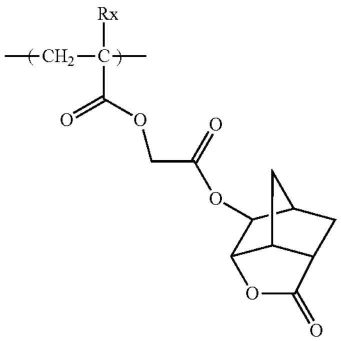
-continued
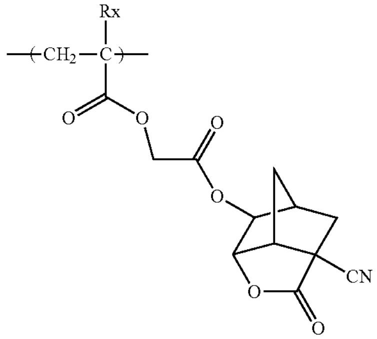
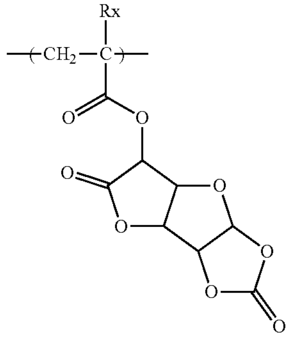
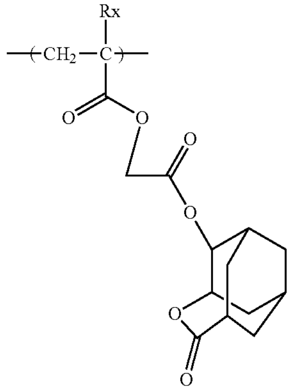
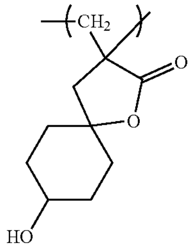
(in the formulae, Rx represents H, $CH_3$, $CH_2OH$, or $CF_3$)
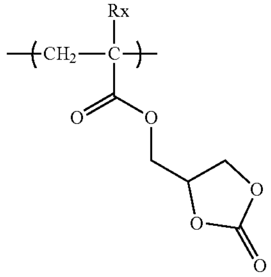

-continued

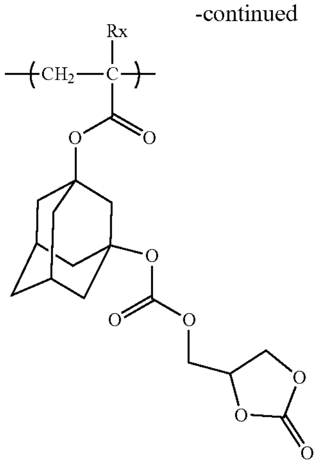

The content of the repeating unit having a lactone group, a sultone group, or a carbonate group is preferably 1% by mole or more, and more preferably 10% by mole or more with respect to all repeating units in the resin (A). In addition, an upper limit value thereof is preferably 85% by mole or less, more preferably 80% by mole or less, still more preferably 70% by mole or less, and particularly preferably 60% by mole or less.

(Repeating Unit Having Photoacid Generating Group)

The resin (A) may have, as a repeating unit other than those above, a repeating unit having a group that generates an acid upon irradiation with actinic rays or radiation (hereinafter also referred to as a "photoacid generating group").

In this case, it can be considered that the repeating unit having a photoacid generating group corresponds to a compound that generates an acid upon irradiation with actinic rays or radiation which will be described later (also referred to as a "photoacid generator").

Examples of such the repeating unit include a repeating unit represented by General Formula (4).

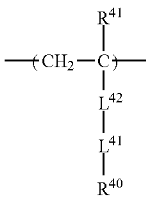

(4)

$R^{41}$ represents a hydrogen atom or a methyl group. $L^{41}$ represents a single bond or a divalent linking group. $L^{42}$ represents a divalent linking group. Ra represents a structural moiety that decomposes upon irradiation with actinic rays or radiation to generate an acid in a side chain.

The repeating unit having a photoacid generating group is exemplified below.

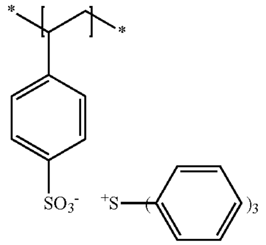

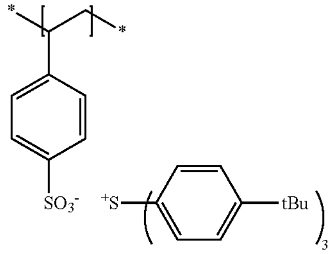

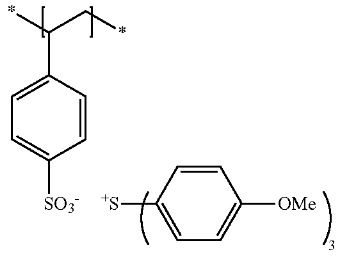

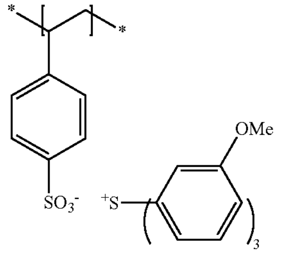

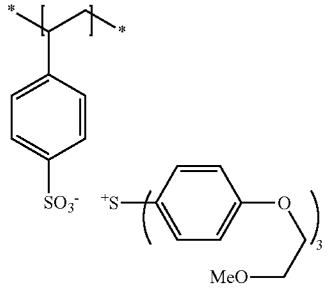

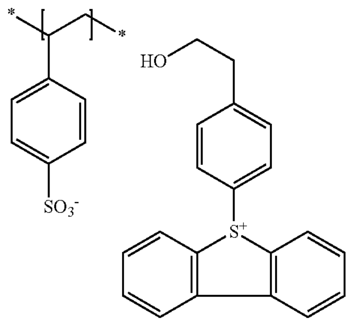

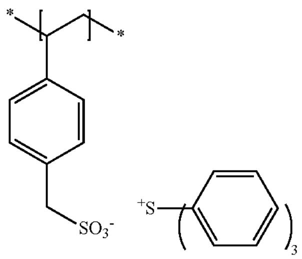
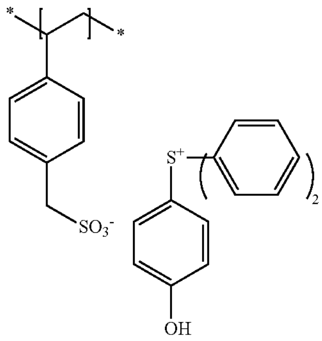
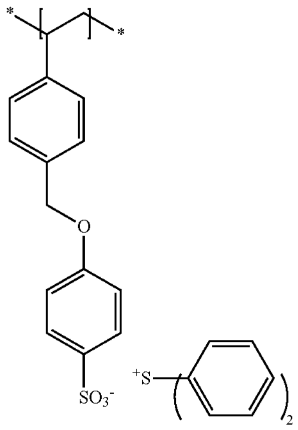
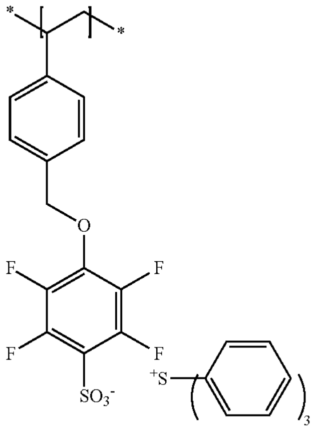
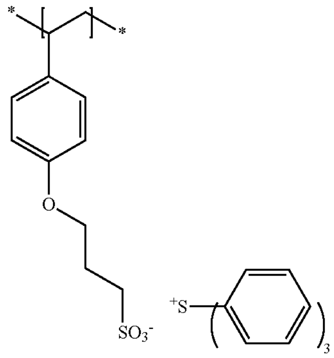
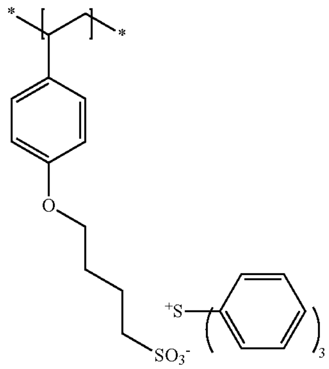
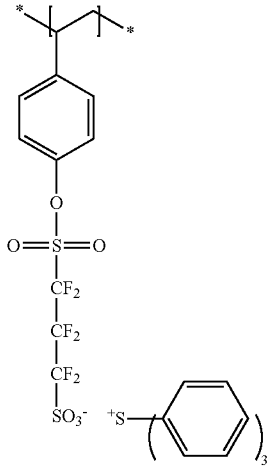

-continued

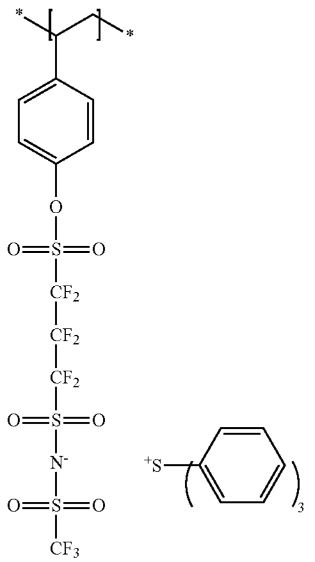

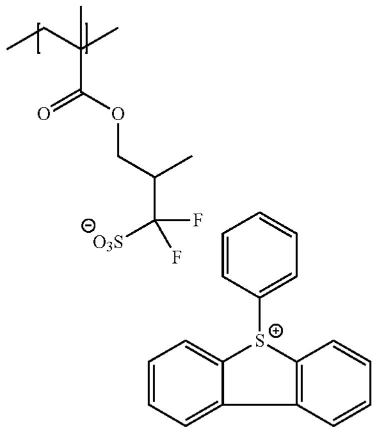

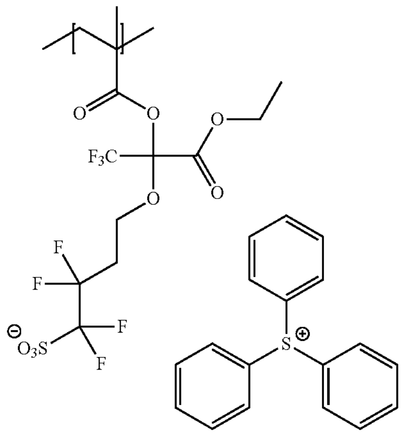

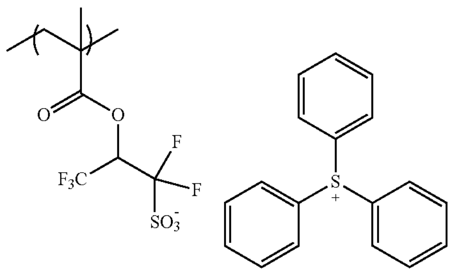

-continued

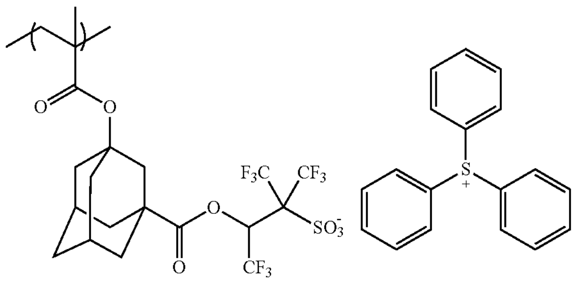

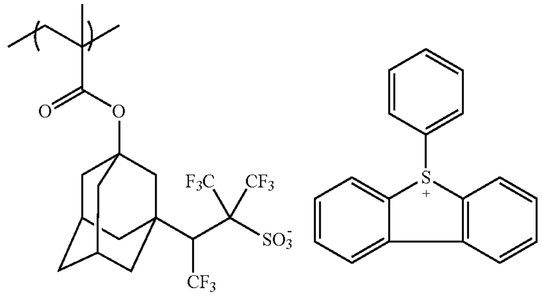

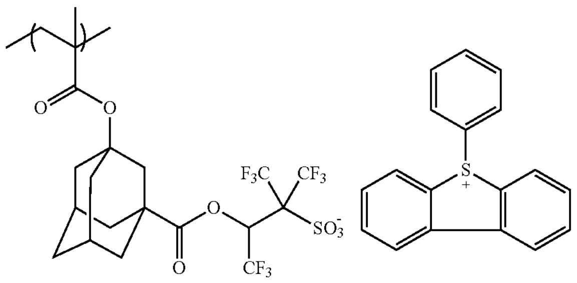

In addition, examples of the repeating unit represented by General Formula (4) include the repeating units described in paragraphs [0094] to [0105] of JP2014-041327A.

The content of the repeating unit having a photoacid generating group is preferably 1% by mole or more, and more preferably 5% by mole or more with respect to all repeating units in the resin (A). In addition, an upper limit value thereof is preferably 40% by mole or less, more preferably 35% by mole or less, and still more preferably 30% by mole or less.

(Repeating Unit Represented by General Formula (V-1) or General Formula (V-2))

The resin (A) may have a repeating unit represented by General Formula (V-1) or General Formula (V-2).

The repeating unit represented by General Formula (V-1) and General Formula (V-2) is preferably a repeating unit different from the above-mentioned repeating units.

(V-1)

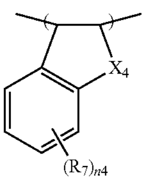

-continued (V-2)

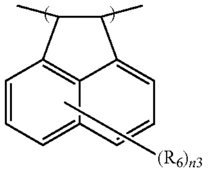

In the formulae, $R_6$ and $R_7$ each independently represent a hydrogen atom, a hydroxyl group, an alkyl group, an alkoxy group, an acyloxy group, a cyano group, a nitro group, an amino group, a halogen atom, an ester group (—OCOR or —COOR: R is an alkyl group or fluorinated alkyl group having 1 to 6 carbon atoms), or a carboxy group. As the alkyl group, a linear, branched, or cyclic alkyl group having 1 to 10 carbon atoms is preferable.

$n_3$ represents an integer of 0 to 6.

$n_4$ represents an integer of 0 to 4.

$X_4$ is a methylene group, an oxygen atom, or a sulfur atom.

The repeating unit represented by General Formula (V-1) or (V-2) will be exemplified below.

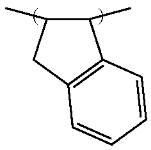
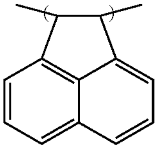
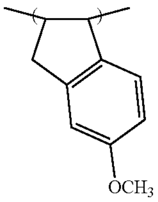
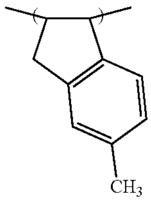
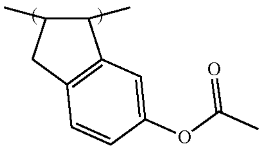
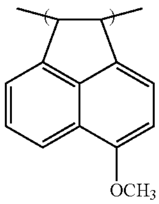
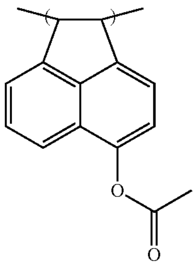
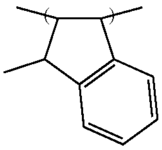

(Repeating Unit for Reducing Motility of Main Chain)

The resin (A) preferably has a high glass transition temperature (Tg) from the viewpoint that excessive diffusion of an acid generated or pattern collapse during development can be suppressed. Tg is preferably higher than 90° C., more preferably higher than 100° C., still more preferably higher than 110° C., and particularly preferably higher than 125° C. In addition, since an excessive increase in Tg causes a decrease in the dissolution rate in a developer, Tg is preferably 400° C. or lower, and more preferably 350° C. or lower.

Furthermore, in the present specification, the glass transition temperature (Tg) of a polymer such as the resin (A) is calculated by the following method. First, the Tg of a homopolymer consisting only of each repeating unit included in the polymer is calculated by a Bicerano method. Hereinafter, the calculated Tg is referred to as the "Tg of the repeating unit". Next, the mass proportion (%) of each repeating unit to all repeating units in the polymer is calculated. Then, the Tg at each mass proportion is calculated using a Fox's equation (described in Materials Letters 62 (2008) 3152, and the like), and these are summed to obtain the Tg (° C.) of the polymer.

The Bicerano method is described in Prediction of polymer properties. Marcel Dekker Inc., New York (1993), and the like. The calculation of a Tg by the Bicerano method can be carried out using MDL Polymer (MDL Information Systems, Inc.), which is software for estimating physical properties of a polymer.

In order to raise the Tg of the resin (A)(preferably to raise the Tg to higher than 90° C.), it is preferable to reduce the motility of the main chain of the resin (A). Examples of a method for reducing the motility of the main chain of the resin (A) include the following (a) to (e) methods.

(a) Introduction of a bulky substituent into the main chain (b) Introduction of a plurality of substituents into the main chain (c) Introduction of a substituent that induces an interaction between the resins (A) near the main chain (d) Formation of the main chain in a cyclic structure (e) Linking of a cyclic structure to the main chain Furthermore, the resin (A) preferably has a repeating unit having a Tg of a homopolymer exhibiting 130° C. or higher.

In addition, the type of the repeating unit having a Tg of the homopolymer exhibiting 130° C. or higher is not particularly limited, and may be any of repeating units having a Tg of a homopolymer of 130° C. or higher calculated by the Bicerano method. Moreover, it corresponds to a repeating unit having a Tg of a homopolymer exhibiting 130° C. or higher, depending on the type of a functional group in the repeating units represented by Formula (A) to Formula (E) which will be described later.

(Repeating Unit Represented by Formula (A))

As an example of a specific unit for accomplishing (a) above, a method of introducing a repeating unit represented by Formula (A) is to the resin (A) may be mentioned.

(A)

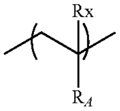

In Formula (A), $R_A$ represents a group having a polycyclic structure. $R_x$ represents a hydrogen atom, a methyl group, or an ethyl group. The group having a polycyclic structure is a group having a plurality of ring structures, and the plurality of ring structures may or may not be fused.

Specific examples of the repeating unit represented by Formula (A) include the following repeating units.

(A-1)

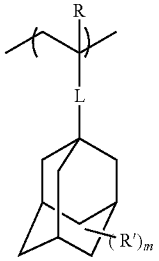

(A-2)

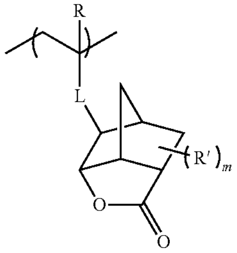

(A-3)

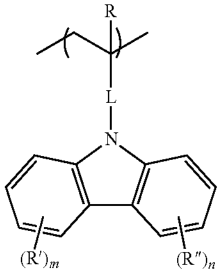

(A-4)

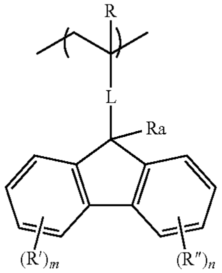

(A-5)

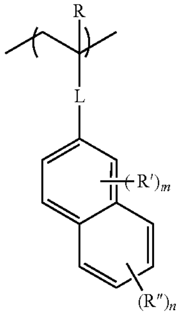

-continued (A-6)

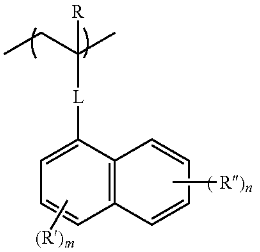

(A-7)

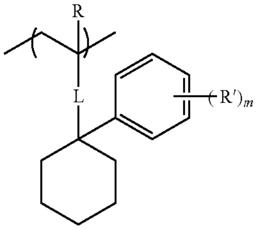

(A-8)

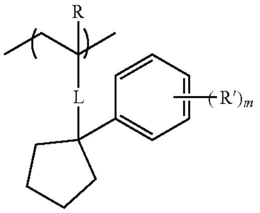

(A-9)

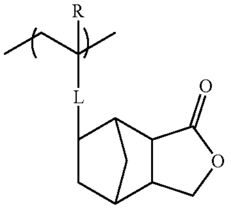

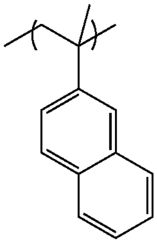

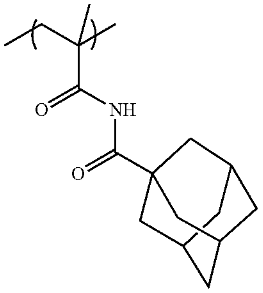

In the formulae. R represents a hydrogen atom, a methyl group, or an ethyl group.

Ra represents a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR''' or —COOR''': R''' is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, a hydrogen atom bonded to the carbon atom in the group represented by Ra may be substituted with a fluorine atom or an iodine atom.

Moreover, R' and R'' each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR''' or —COOR'''; R''' is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, a hydrogen atom bonded to the carbon atom in the group represented by each of R' and R'' may be substituted with a fluorine atom or an iodine atom.

L represents a single bond or a divalent linking group. Examples of the divalent linking group include —COO—, —CO—, —O—, —S—, —SO—, $—SO_2—$, an alkylene group, a cycloalkylene group, an alkenylene group, and a linking group in which a plurality of these groups are linked.

m and n each independently represent an integer of 0 or more. An upper limit of each of m and n is not particularly limited, but is 2 or less in many cases, and 1 or less in more cases.

(Repeating Unit Represented by Formula (B))

As an example of a specific unit for accomplishing (b) above, a method of introducing a repeating unit represented by Formula (B) into the resin (A) may be mentioned.

(B)

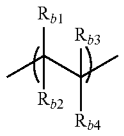

In Formula (B), $R_{b1}$ to $R_{b4}$ each independently represent a hydrogen atom or an organic group, and at least two or more of $R_{b1}$, . . . , or $R_{b4}$ represent an organic group.

Furthermore, in a case where at least one of the organic groups is a group in which a ring structure is directly linked to the main chain in the repeating unit, the types of the other organic groups are not particularly limited.

In addition, in a case where none of the organic groups is a group in which a ring structure is directly linked to the main chain in the repeating unit, at least two or more of the organic groups are substituents having three or more constituent atoms excluding hydrogen atoms.

Specific examples of the repeating unit represented by Formula (B) include the following repeating units.

(B-1)

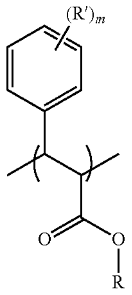

-continued (B-2)

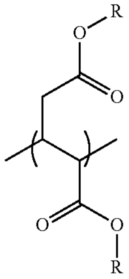

(B-3)

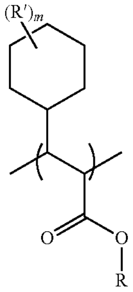

(B-4)

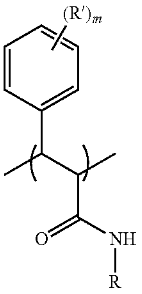

(B-5)

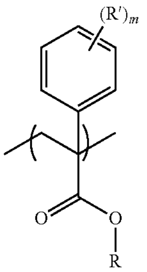

(B-6)

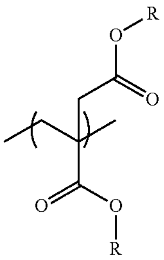

In the formula, R's each independently represent a hydrogen atom or an organic group. Examples of the organic group include an organic group such as an alkyl group, a cycloalkyl group, an aryl group, an aralkyl group, and an alkenyl group, each of which may have a substituent.

R''s each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. An upper limit of m is not particularly limited, but is 2 or less in many cases, and 1 or less in more cases.

(Repeating Unit Represented by Formula (C))

As an example of a specific unit for accomplishing (c) above, a method of introducing a repeating unit represented by Formula (C) into the resin (A) may be mentioned.

(C)

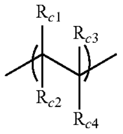

In Formula (C), $R_{c1}$ to $R_{c4}$ each independently represent a hydrogen atom or an organic group, and at least one of $R_{c1}$, . . . , or $R_{c4}$ is a group having a hydrogen-bonding hydrogen atom with a number of atoms of 3 or less from the main chain carbon. Among those, it is preferable that the group has hydrogen-bonding hydrogen atoms with a number of atoms of 2 or less (on a side closer to the vicinity of the main chain) to induce an interaction between the main chains of the resin (A).

Specific examples of the repeating unit represented by Formula (C) include the following repeating units.

(C-1)

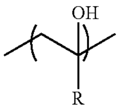

(C-2)

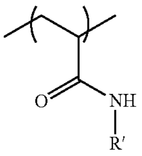

(C-3)

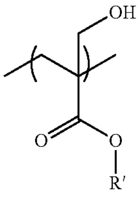

In the formula, R represents an organic group. Examples of the organic group include an alkyl group, a cycloalkyl group, an aryl group, an aralkyl group, an alkenyl group, and an ester group (—OCOR or —COOR: R represents an alkyl group or fluorinated alkyl group having 1 to 20 carbon atoms), each of which may have a substituent.

R' represents a hydrogen atom or an organic group. Examples of the organic group include an organic group such as an alkyl group, a cycloalkyl group, an aryl group, an aralkyl group, and an alkenyl group. In addition, a hydrogen atom in the organic group may be substituted with a fluorine atom or an iodine atom.

(Repeating Unit Represented by Formula (D))

As an example of a specific unit for accomplishing (d) above, a method of introducing a repenting unit represented by Formula (D) into the resin (A) may be mentioned.

(D)

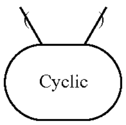

In Formula (D), "Cyclic" is a group that forms a main chain with a cyclic structure. The number of the ring-constituting atoms is not particularly limited.

Specific examples of the repeating unit represented by Formula (D) include the following repeating units.

(D-1)

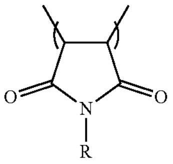

(D-2)

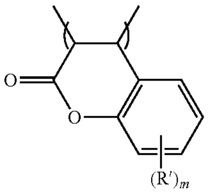

(D-3)

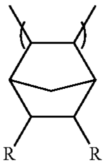

(D-4)

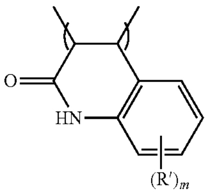

(D-5)

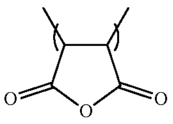

(D-6)

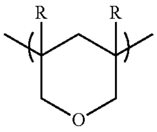

(D-7)

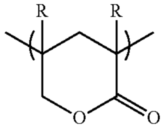

(D-8)

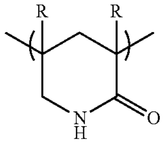

(D-9)

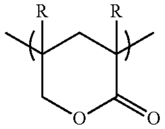

(D-10)

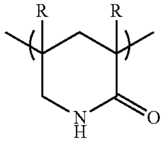

(D-11)

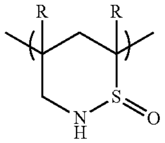

(D-12)

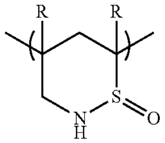

(D-13)

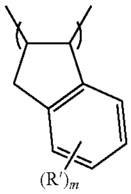

(D-14)

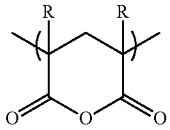

(D-15)

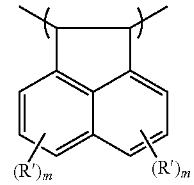

(D-16)

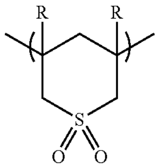

-continued (D-17)

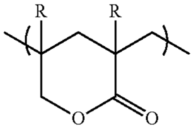

(D-18)

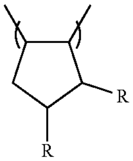

(D-19)

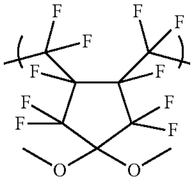

In the formula, R's each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, the hydrogen atom bonded to the carbon atom in the group represented by R may be substituted with a fluorine atom or an iodine atom.

In the formula, R"s each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. An upper limit of m is not particularly limited, but is 2 or less in many cases, and 1 or less in more cases.

(Repeating Unit Represented by Formula (E))

As an example of a specific unit for accomplishing (e) above, a method of introducing a repeating unit represented by Formula (E) into the resin (A) may be mentioned.

(E)

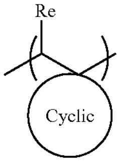

In Formula (E), Re's each independently represent a hydrogen atom or an organic group. Examples of the organic group include an alkyl group, a cycloalkyl group, an aryl group, an aralkyl group, and an alkenyl group, which may have a substituent.

"Cyclic" is a cyclic group including a carbon atom of the main chain. The number of atoms included in the cyclic group is not particularly limited.

Specific examples of the repeating unit represented by Formula (E) include the following repeating units.

(E-1)

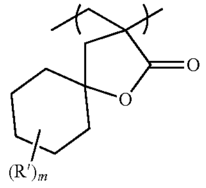

(E-2)

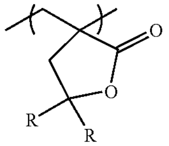

(E-3)

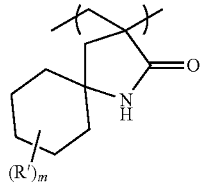

(E-4)

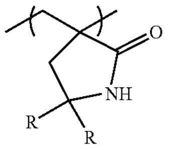

(E-5)

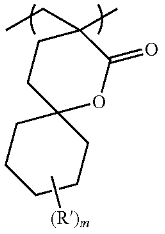

(E-6)

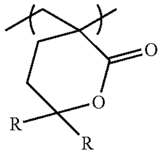

(E-7)

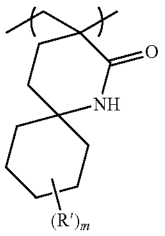

-continued (E-8)

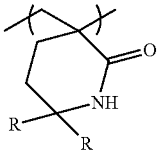

(E-9)

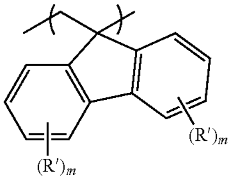

(E-10)

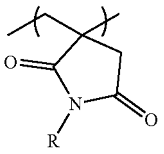

(E-11)

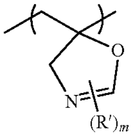

(E-12)

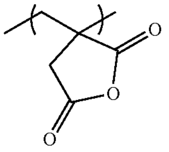

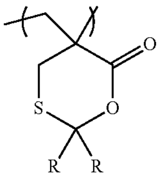

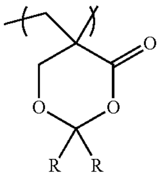

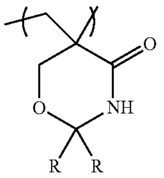

Furthermore, as a specific example of the repeating unit represented by Formula (E), a repeating unit derived from the following monomer can also be suitably used.

(M001)

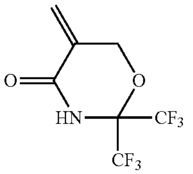

(M002)

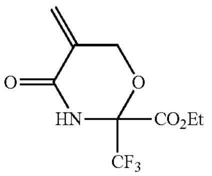

-continued (M003)

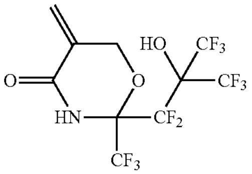

(M004)

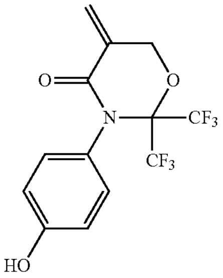

(M005)

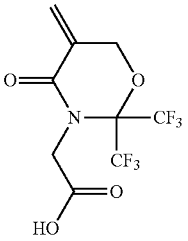

(M006)

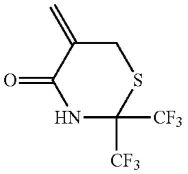

(M007)

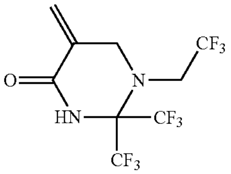

(M008)

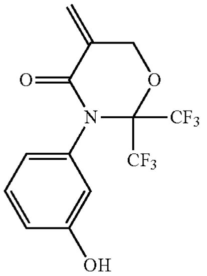

-continued (M009)

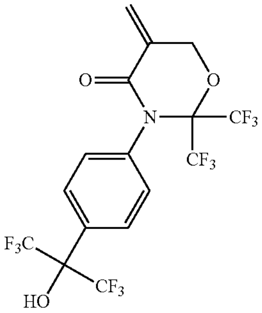

(M010)

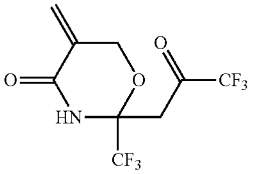

(M011)

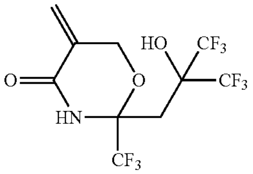

(M012)

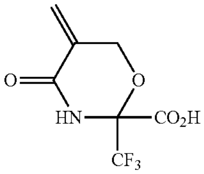

(M013)

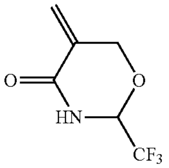

(M014)

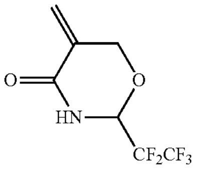

(M015)

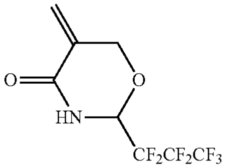

In the formula, R's each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, the hydrogen atom bonded to the carbon atom in the group represented by R may be substituted with a fluorine atom or an iodine atom.

R"s each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxy group. Furthermore, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. An upper limit of m is not particularly limited, but is 2 or less in many cases, and 1 or less in more cases.

In addition, in Formula (E-2), Formula (E-4), Formula (E-6), and Formula (E-8), two R's may be bonded to each other to form a ring.

A content of the repeating units represented by Formula (A) to Formula (E) is preferably 5% by mole or more, and more preferably 10% by mole or more with respect to all repeating units in the resin (A). In addition, an upper limit value thereof is preferably 60% by mole or less, and more preferably 55% by mole or less.

(Repeating Unit Having at Least One Group Selected from Lactone Group, Sultone Group, Carbonate Group, Hydroxyl Group, Cyano Group, or Alkali-Soluble Group)

The resin (A) may have a repeating unit having at least one group selected from a lactone group, a sultone group, a carbonate group, a hydroxyl group, a cyano group, or an alkali-soluble group.

Examples of the repeating unit having a lactone group, a sultone group, or a carbonate group contained in the resin (A) include the repeating units described in "(Repeating Unit Having Lactone Group, Sultone Group, or Carbonate Group)" mentioned above. A preferred content thereof is also the same as described in "(Repeating Unit Having Lactone Group, Sultone Group, or Carbonate Group)" mentioned above.

The resin (A) may have a repeating unit having a hydroxyl group or a cyano group. As a result, the adhesiveness to a substrate and the affinity for a developer are improved.

The repeating unit having a hydroxyl group or a cyano group is preferably a repeating unit having an alicyclic hydrocarbon structure substituted with a hydroxyl group or a cyano group.

The repeating unit having a hydroxyl group or a cyano group preferably has no acid-decomposable group. Examples of the repeating unit having a hydroxyl group or a cyano group include repeating units represented by General Formulae (AIIa) to (AIId).

(AIIa)

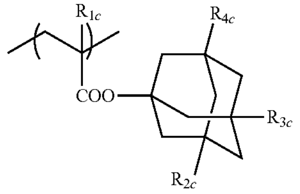

-continued (AIIb)

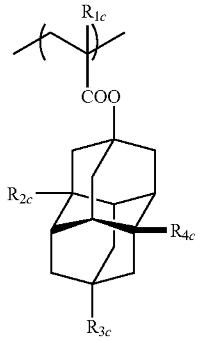

(AIIc)

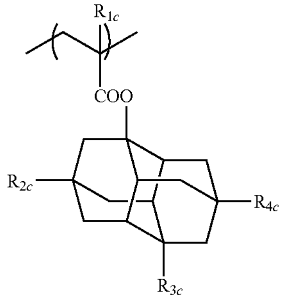

(AIId)

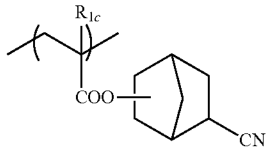

In General Formulae (AIIa) to (AIId), $R_{1c}$ represents a hydrogen atom, a methyl group, a trifluoromethyl group, or a hydroxymethyl group.

$R_{2c}$ to $R_{4c}$ each independently represent a hydrogen atom, a hydroxyl group, or a cyano group. It should be noted that at least one of $R_{2c}$, . . . , or $R_{4c}$ represents a hydroxyl group or a cyano group. It is preferable that one or two of $R_{2c}$ to $R_{4c}$ are hydroxyl groups, and the rest are hydrogen atoms. It is more preferable that two of $R_{2c}$ to $R_{4c}$ are hydroxyl groups and the rest are hydrogen atoms.

A content of the repeating unit having a hydroxyl group or a cyano group is preferably 5% by mole or more, and more preferably 10% by mole or more with respect to all repeating units in the resin (A). In addition, an upper limit value thereof is preferably 40% by mole or less, more preferably 35% by mole or less, and still more preferably 30% by mole or less.

Specific examples of the repeating unit having a hydroxyl group or a cyano group are shown below, but the present invention is not limited thereto.

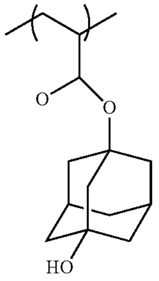
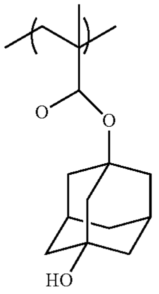
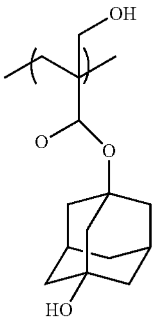
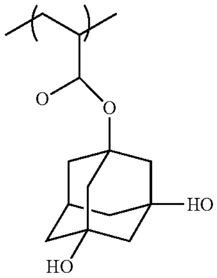
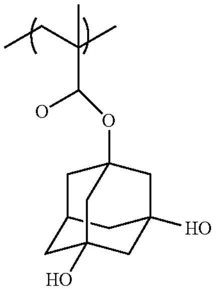
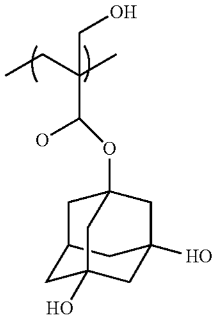
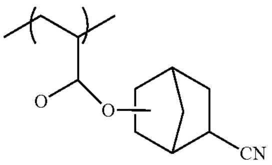
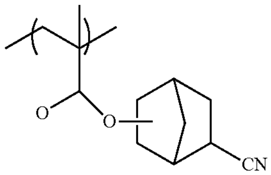
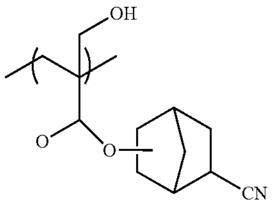
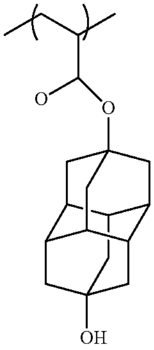

-continued

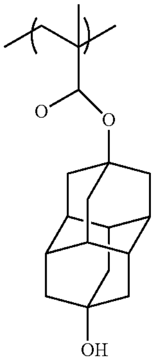
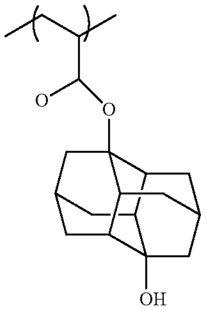
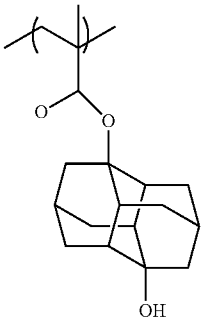

The resin (A) may have a repeating unit having an alkali-soluble group.

Examples of the alkali-soluble group include a carboxy group, a sulfonamide group, a sulfonylimide group, a bis-sulfonylamide group, or an aliphatic alcohol group (for example, a hexafluoroisopropanol group) in which the a-position is substituted with an electron-withdrawing group, and the carboxy group is preferable. In a case where the resin (A) includes a repeating unit having an alkali-soluble group, the resolution for use in contact holes increases.

Examples of the repeating unit having an alkali-soluble group include a repeating unit in which an alkali-soluble group is directly bonded to the main chain of a resin such as a repeating unit with acrylic acid and methacrylic acid, or a repeating unit in which an alkali-soluble group is bonded to the maim chain of the resin through a linking group. Furthermore, the linking group may have a monocyclic or polycyclic cyclic hydrocarbon structure.

The repeating unit having an alkali-soluble group is preferably a repeating unit with acrylic acid or methacrylic acid.

A content of the repeating unit having an alkali-soluble group is preferably 0% by mole or more, more preferably 3% by mole or more, and still more preferably 5% by mole or more with respect to all repeating units in the resin(A). An upper limit value thereof is preferably 20% by mole or less, more preferably 15% by mole or less, and still more preferably 10% by mole or less.

Specific examples of the repeating unit having an alkali-soluble group are shown below, but the present invention is not limited thereto. In the specific examples. Rx represents H, $CH_3$, $CH_2OH$, or $CF_3$.

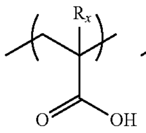
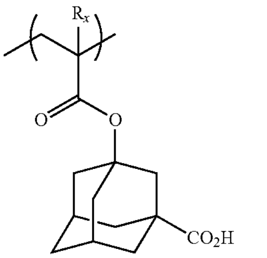
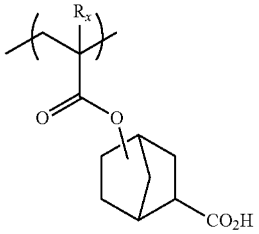
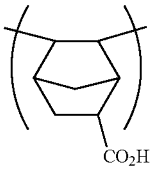
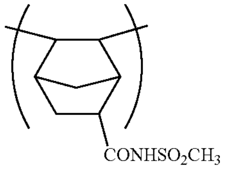
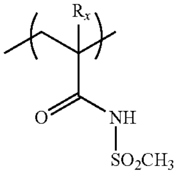
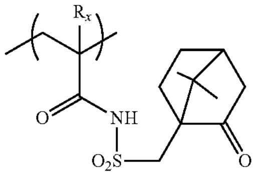
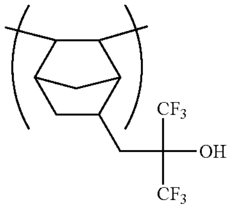
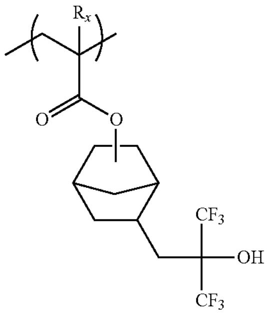
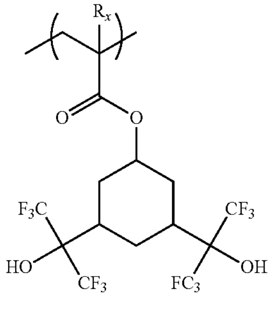

As the repeating unit having at least one group selected from a lactone group, a hydroxyl group, a cyano group, or an alkali-soluble group, a repeating unit having at least two selected from a lactone group, a hydroxyl group, a cyano group, or an alkali-soluble group is preferable, a repeating unit having a cyano group and a lactone group is more preferable, and a repeating unit having a structure in which a cyano group is substituted in the lactone structure represented by General Formula (LC1-4) is still more preferable.

(Repeating Unit Having Alicyclic Hydrocarbon Structure and not Exhibiting Acid Decomposability)

The resin (A) may have a repeating unit having an alicyclic hydrocarbon structure and not exhibiting acid decomposability. This can reduce the elution of low-molecular-weight components from the resist film into an immersion liquid during liquid immersion exposure. Examples of such the repeating unit include repeating units derived from I-adamantyl (meth)acrylate, diadamantyl (meth)acrylate, tricyclodecanyl (meth)acrylate, and cyclohexyl (meth)acrylate.

(Repeating Unit Represented by General Formula (III) Having Neither Hydroxyl Group Nor Cyano Group)

The resin (A) may have a repeating unit represented by General Formula (III), which has neither a hydroxyl group nor a cyano group.

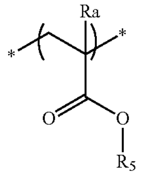

(III)

In General Formula (III), $R_5$ represents a hydrocarbon group having at least one cyclic structure and having neither a hydroxyl group nor a cyano group.

Ra represents a hydrogen atom, an alkyl group, or a —CH—O—$Ra_2$ group. In the formula, $Ra_2$ represents a hydrogen atom, an alkyl group, or an acyl group.

The cyclic structure contained in $R_5$ includes a monocyclic hydrocarbon group and a polycyclic hydrocarbon group. Examples of the monocyclic hydrocarbon group include a cycloalkyl group having 3 to 12 carbon atoms (more preferably 3 to 7 carbon atoms) or a cycloalkenyl group having 3 to 12 carbon atoms.

Examples of the polycyclic hydrocarbon group include a ring-assembled hydrocarbon group and a crosslinked cyclic hydrocarbon group. Examples of the crosslinked cyclic hydrocarbon ring include a bicyclic hydrocarbon ring, a tricyclic hydrocarbon ring, and a tetracyclic hydrocarbon ring. Furthermore, examples of the crosslinked cyclic hydrocarbon ring also include a fused ring formed by fusing a plurality of 5- to 8-membered cycloalkane rings.

As the crosslinked cyclic hydrocarbon group, a norbornyl group, an adamantyl group, a bicyclooctanyl group, or a tricyclo[5,2,1,$0^{2,6}$] decanyl group is preferable, and the norbornyl group or the adamantyl group is more preferable.

The alicyclic hydrocarbon group may have a substituent, and examples of the substituent include a halogen atom, an alkyl group, a hydroxyl group protected by a protective group, and an amino group protected by a protective group.

The halogen atom is preferably a bromine atom, a chlorine atom, or a fluorine atom.

As the alkyl group, a methyl group, an ethyl group, a butyl group, or a t-butyl group is preferable. The alkyl group may further have a substituent, and examples of the substituent include a halogen atom, an alkyl group, a hydroxyl group protected by a protective group, and an amino group protected by a protective group.

Examples of the protective group include an alkyl group, a cycloalkyl group, an aralkyl group, a substituted methyl group, a substituted ethyl group, an alkoxycarbonyl group, and an aralkyloxycarbonyl group.

As the alkyl group, an alkyl group having 1 to 4 carbon atoms is preferable.

As the substituted methyl group, a methoxymethyl group, a methoxythiomethyl group, a benzyloxymethyl group, a t-butoxymethyl group, or a 2-methoxyethoxymethyl group is preferable.

The substituted ethyl group is preferably a 1-ethoxyethyl group or a 1-methyl-1-methoxyethyl group.

As the acyl group, an aliphatic acyl group having 1 to 6 carbon atoms, such as a formyl group, an acetyl group, a propionyl group, a butyryl group, an isobutyryl group, a valeryl group, and a pivaloyl group, is preferable.

As the alkoxycarbonyl group, an alkoxycarbonyl group having 1 to 4 carbon atoms is preferable.

A content of the repeating unit represented by General Formula (III), which has neither a hydroxyl group nor a cyano group, is preferably 0% to 40% by mole, and more preferably 0% to 20% by mole with respect to all repeating units in the resin (A).

Specific examples of the repeating unit represented by General Formula (III) are shown below, but the present invention is not limited thereto. In the formulae. Ra represents H, $CH_3$, $CH_2OH$, or $CF_3$

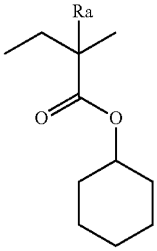
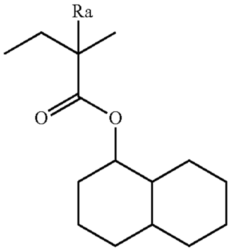

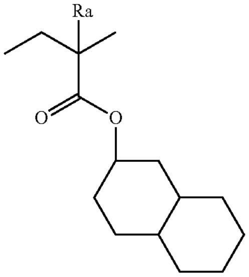
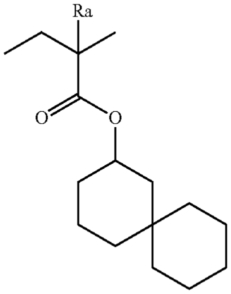

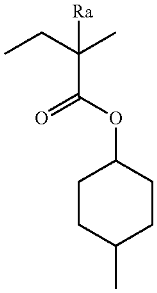
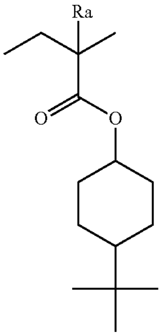
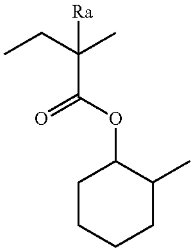

-continued

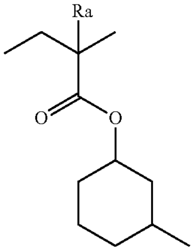
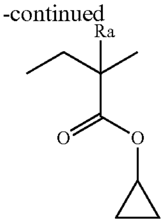
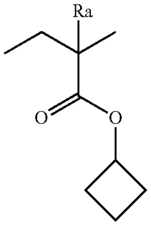

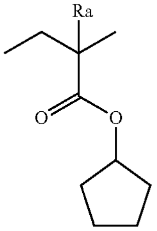
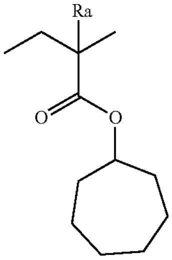
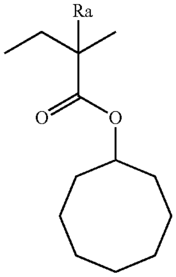

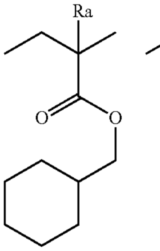
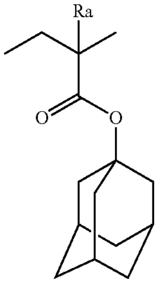
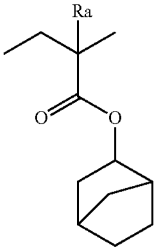

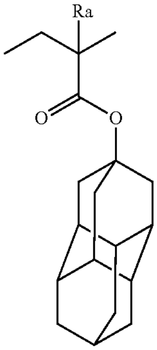
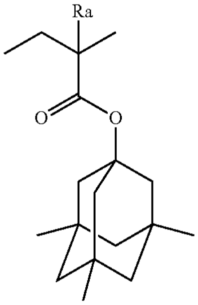

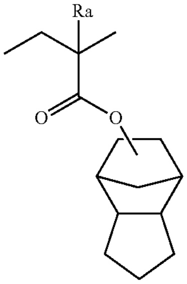

(Other Repeating Units)

The resin (A) may further have a repeating unit other than the above-mentioned repeating units.

For example, the resin (A) may have a repeating unit selected from the group consisting of a repeating unit having an oxathiane ring group, a repeating unit having an oxazolone ring group, a repeating unit having a dioxane ring group, and a repeating unit having a hydantoin ring group.

Such repeating units will be exemplified below.

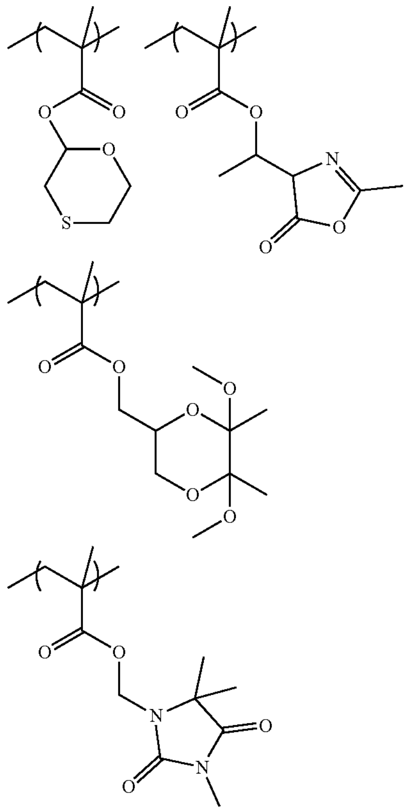

The resin (A) may have a variety of repeating structural units, in addition to the repeating structural units described above, for the purpose of adjusting dry etching resistance, suitability for a standard developer, adhesiveness to a substrate, a resist profile, resolving power, heat resistance, sensitivity, and the like.

The resin (A) can be synthesized in accordance with an ordinary method (for example, radical polymerization).

The weight-average molecular weight of the resin (A) as a value expressed in terms of polystyrene by a GPC method is preferably 1,000 to 200,000, more preferably 2,000 to 30,000, and still more preferably 3,000 to 20,000. By setting the weight-average molecular weight of the resin (A) to 1,000 to 200,000, deterioration of heat resistance and dry etching resistance can be further suppressed. In addition, deterioration of developability and deterioration of film forming property due to high viscosity can also be further suppressed.

The dispersity (molecular weight distribution) of the resin (A) is usually 1.0 to 5.0, preferably 1.0 to 3.0, more preferably 1.0 to 2.5, and still more preferably 1.0 to 2.0. The smaller the dispersity, the more excellent the resolution and the resist shape, and the smoother the side wall of the resist pattern, the more excellent the roughness.

In the composition of the embodiment of the present invention, a content of the resin (A) is preferably 50% to 99.9% by mass, and more preferably 60% to 99.0% by mass with respect to the total solid content of the composition.

Furthermore, the solid content is intended to be components excluding the solvent in the composition, and any of components other than the solvent are regarded as the solid content even in a case where they are liquid components.

In addition, the resin (A) may be used alone or in combination of a plurality thereof.

[Acid Diffusion Control Agent]

The composition of the embodiment of the present invention preferably contains an acid diffusion control agent. The acid diffusion control agent acts as a quencher that suppresses a reaction of an acid-decomposable resin in the non-exposed portion by excessive generated acids by trapping the acids generated from a photoacid generator and the like upon exposure.

For example, a basic compound (DA), a basic compound (DB) having basicity reduced or lost upon irradiation with actinic rays or radiation, an onium salt (DC) which is a weak acid relative to an acid generator, a low-molecular-weight compound (DD) having a nitrogen atom and a group that leaves by an action of an acid, an onium salt compound (DE) having a nitrogen atom in a cationic moiety, or the like, can be used as the acid diffusion control agent. In the composition of the embodiment of the present invention, a known acid diffusion control agent can be appropriately used. For example, the known compounds disclosed in paragraphs 106271 to 106641 of US2016/0070167A1, paragraphs 100951 to 101871 of US2015/0004544A1, paragraphs [0403] to [0423] of US2016/0237190A1, and paragraphs [0259] to 103281 of US2016/0274458A1 can be suitably used as the acid diffusion control agent.

As the basic compound (DA), compounds having structures represented by General Formulae (A) to (E) are preferable.

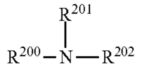

(A)

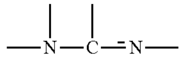

(B)

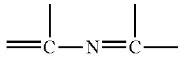

(C)

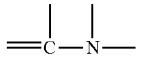

(D)

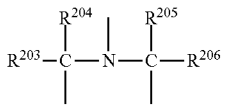

(E)

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (having 6 to 20 carbon atoms). $R^{201}$ and $R^{202}$ may be bonded to each other to form a ring.

$R^{203}$, $R^{204}$, $R^{205}$, and $R^{201}$ may be the same as or different from each other and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl group in each of General Formulae (A) and (E) are more preferably unsubstituted.

As the basic compound (DA), thiazole, benzothiazole, oxazole, benzoxazole, guanidine, aminopyrrolidine, pyrazole, pyrazoline, piperazine, aminomorpholine, aminoalkylmorpholine, piperidine, or compounds having these structures are preferable; and a compound having a thiazole structure, a benzothiazole structure, an oxazole structure, a benzoxazole structure, an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond, or the like is more preferable.

The basic compound (DB) having basicity reduced or lost upon irradiation with actinic rays or radiation (hereinafter also referred to as a "compound (DB)") is a compound which has a proton-accepting functional group, and decomposes under irradiation with actinic rays or radiation to exhibit reduced proton-accepting properties, no proton-accepting properties, or a change from the proton-accepting properties to acidic properties.

The proton-accepting functional group refers to a functional group having a group or an electron which is capable of electrostatically interacting with a proton, and for example, means a functional group with a macrocyclic structure, such as a cyclic polyether, or a functional group having a nitrogen atom having as unshared electron pair not contributing to π-conjugation. The nitrogen atom having an unshared electron pair not contributing to π-conjugation is, for example, a nitrogen atom having a partial structure represented by the following formula.

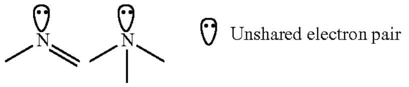

Preferred examples of the partial structure of the proton-accepting functional group include a crown ether structure, an azacrown ether structure, primary to tertiary amine structures, a pyridine structure, an imidazole structure, and a pyrazine structure.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting reduced proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (DB) having the proton-accepting functional group and the proton.

The proton-accepting properties can be confirmed by performing pH measurement.

The acid dissociation constant pKa of the compound generated by decomposition of the compound (DB) upon irradiation with actinic rays or radiation preferably satisfies $pKa<-1$, and more preferably satisfies $-13<pKa<-1$, and still more preferably satisfies $-13<pKa<-3$.

In the composition of the embodiment of the present invention, the onium salt (DC) which is a relatively weak acid with respect to a photoacid generator can be used as the acid diffusion control agent.

In a case where the photoacid generator and the onium salt that generates an acid which is a weak acid relative to an acid generated from the photoacid generator are mixed and used, an acid generated from the photoacid generator upon irradiation with actinic rays or radiation generates an onium salt having a strong acid anion by discharging the weak acid through salt exchange in a case where the acid collides with an onium salt having an unreacted weak acid anion. In this process, the strong acid is exchanged with a weak acid having a lower catalytic activity, and thus, the acid is apparently deactivated and the acid diffusion can be controlled.

As the onium salt which serves as a relatively weak acid with respect to the photoacid generator, compounds represented by General Formulae (d1-1) to (d1-3) are preferable.

(dl-1)

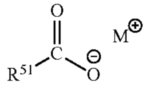

(dl-2)

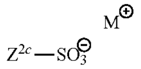

(dl-3)

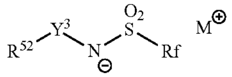

In the formula, $R^{51}$ is a hydrocarbon group which may have a substituent. $Z^{2c}$ is a hydrocarbon group having 1 to 30 carbon atoms, which may have a substituent (provided that carbon adjacent to 5 is not substituted with a fluorine atom), $R^{52}$ is an organic group, $Y^3$ is a linear, branched, or cyclic alkylene group or an arylene group, Rf is a hydrocarbon group including a fluorine atom, and M"s are each independently an ammonium cation, a sulfonium cation, or an iodonium cation.

Preferred examples of the sulfonium cation or iodonium cation represented by $M^+$ include the sulfonium cation exemplified for General Formula (ZIA) and the iodonium cation exemplified for General Formula (ZIIA).

The onium salt (DC) which is a weak acid relative to a photoacid generator may be a compound having a cationic moiety and an anionic moiety in the same molecule, in which the cationic moiety and the anionic moiety are licked by a covalent bond (hereinafter also referred to as a "compound (DCA)").

The compound (DCA) is preferably a compound represented by any of General Formulae (C-1) to (C-3).

(C-1)

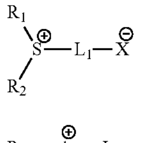

(C-2)

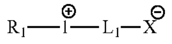

(C-3)

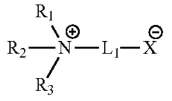

In General Formulae (C-1) to (C-3), $R_1$, $R_2$, and $R_3$ each independently represent a substituent having 1 or more carbon atoms.

$L_1$ represents a divalent linking group that links a cationic moiety with an anionic moiety, or a single bond.

$—X^-$ represents an anionic moiety selected from —COO—, $—SO_3^-$, $—SO_2^-$, and $—N^-—R_4$. $R_4$ represents at least one of a monovalent substituent having a carbonyl group: —C(═O)—, a sulfonyl group: $—S(═O)_2—$, or a sulfinyl group: —S(═O)— at a site for linking to an adjacent N atom.

$R_1$, $R_2$, $R_3$, $R_4$, and L, may be bonded to each other to form a ring structure. In addition, in General Formula (C-3), two of $R_1$ to $R_3$ are combined with each other to represent one divalent substituent, and may be bonded to an N atom via a double bond.

Examples of the substituent having 1 or more carbon atoms in each of $R_1$ to Ra include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group. The alkyl group, a cycloalkyl group, or the aryl group is preferable.

Examples of $L_1$ as a divalent linking group include a linear or branched alkylene group, a cycloalkylene group, an arylene group, a carbonyl group, an ether bond, an ester bond, an amide bond, a urethane bond, a urea bond, and a group formed by a combination of two or more of these groups. $L_1$ is preferably the alkylene group, the arylene group, the ether bond, the ester bond, and the group formed by a combination of two or more of these groups.

The low-molecular-weight compound (DD) having a nitrogen atom and having a group that leaves by the action of an acid (hereinafter also referred to as a "compound (DD)") is preferably an amine derivative having a group that leaves by the action of an acid on the nitrogen atom.

As the group that leaves by the action of an acid, an acetal group, a carbonate group, a carbamate group, a tertiary ester group, a tertiary hydroxyl group, or a hemiaminal ether group is preferable, and the carbamate group or the hemiaminal ether group is more preferable.

The molecular weight of the compound (DD) is preferably 100 to 1,000, more preferably 100 to 700, and still more preferably 100 to 500.

The compound (DD) may have a carbamate group having a protective group on the nitrogen atom. The protective group constituting the carbamate group is represented by General Formula (d-1).

(d-1)

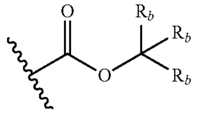

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). Rb's may be bonded to each other to form a ring.

The alkyl group, the cycloalkyl group, the aryl group, or the aralkyl group represented by $R_b$ may be each independently substituted with a functional group such as a hydroxyl group, a cyano group, an amino group, a pyrrolidino group, a piperidino group, a morpholino group, and an oxo group, an alkoxy group, or a halogen atom. The same applies to the alkoxyalkyl group represented by $R_b$.

As $R_b$, a linear or branched alkyl group, a cycloalkyl group, or an aryl group is preferable, and the linear or branched alkyl group, or the cycloalkyl group is more preferable.

Examples of the ring formed by the mutual linkage of two $R_b$'s include an alicyclic hydrocarbon, an aromatic hydrocarbon, a heterocyclic hydrocarbon, and derivatives thereof.

Examples of the specific structure of the group represented by General Formula (d-1) include, but are not limited to, the structures disclosed in paragraph 104661 of US2012/0135348A 1.

The compound (DD) preferably has a structure represented by General Formula (6).

(6)

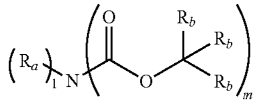

In General Formula (6).

l represents an integer of 0 to 2, m represents an integer of 1 to 3, and these satisfy 1+m=3.

$R_a$ represents a hydrogen atom, an alkyl group, a cycloalkyl group, an aryl group, or an aralkyl group. In a case where l is 2, two $R_a$'s may be the same as or different from each other, and the two $R_a$'s may be linked to each other to form a heterocyclic ring with the nitrogen atom in the formula. This heterocyclic ring may include a heteroatom other than the nitrogen atom in the formula.

$R_b$ has the same definition as $R_b$ in General Formula (d-1), and preferred examples are also the same.

In General Formula (6), the alkyl group, the cycloalkyl group, the aryl group, and the aralkyl group as $R_a$ may be each independently substituted with the same groups as the group mentioned above as a group which may be substituted in the alkyl group, the cycloalkyl group, the aryl group, and the aralkyl group as $R_b$.

Specific examples of the alkyl group, the cycloalkyl group, the aryl group, and the aralkyl group (these groups may be substituted with the groups) of $R_a$ include the same groups as the specific examples described above with respect to $R_b$.

Specific examples of the particularly preferred compound (DD) in the present invention include, but are not limited to, the compounds disclosed in paragraph [0475] of US2012/0135348A1.

The onium salt compound (DE) having a nitrogen atom in a cationic moiety (hereinafter also referred to as a "compound (DE)") is preferably a compound having a basic moiety including a nitrogen atom in the cationic moiety. The basic moiety is preferably an amino group, and more preferably an aliphatic amino group. All of the atoms adjacent to the nitrogen atom in the basic moiety are still more preferably hydrogen atoms or carbon atoms. In addition, from the viewpoint of improving basicity, it is preferable that an electron-withdrawing functional group (such as a carbonyl group, a sulfonyl group, a cyano group, and a halogen atom) is not directly linked to the nitrogen atom.

Preferred specific examples of the compound (DE) include, but are not limited to, the compounds disclosed in paragraph 102031 of US2015/0309408A 1.
Preferred examples of the acid diffusion control agent are shown below, but the present invention is not limited thereto. Me represents a methyl group.
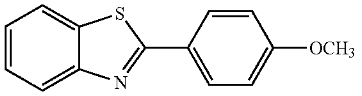
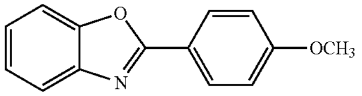
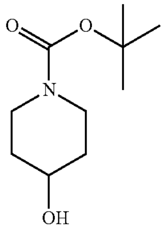
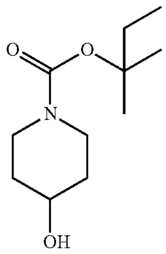
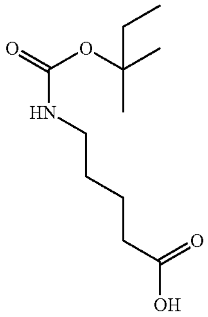
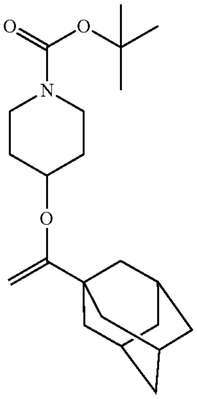
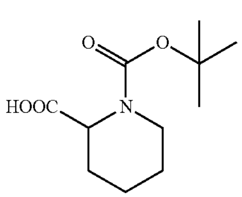
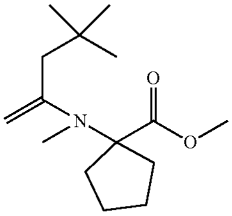
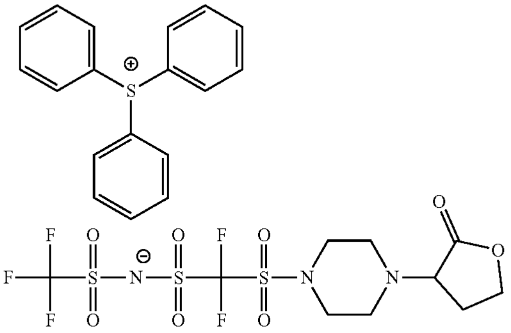
-continued
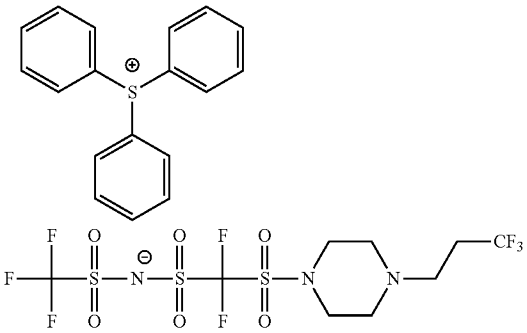
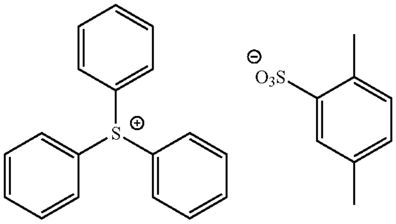
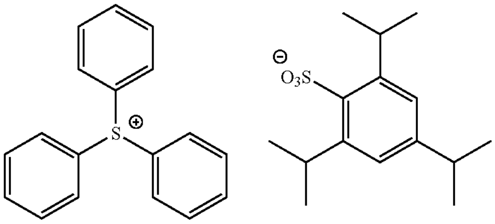
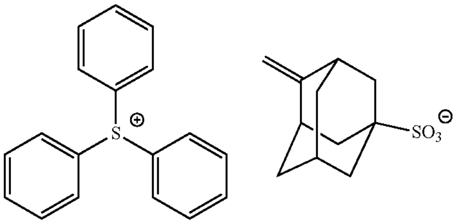
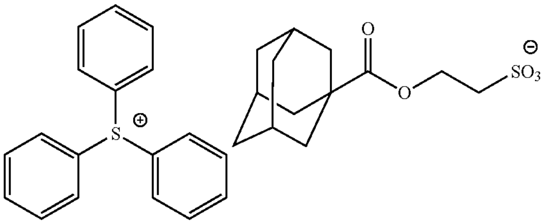
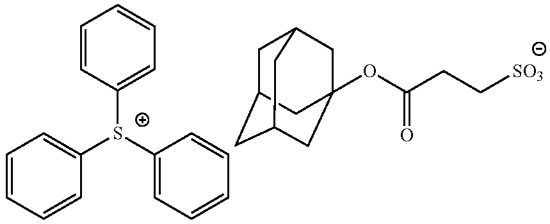
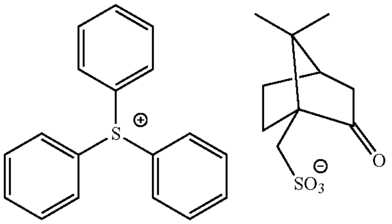

-continued
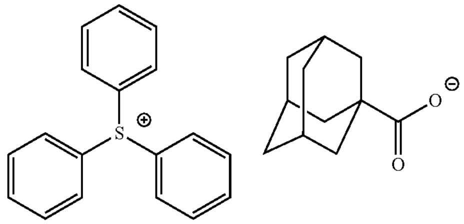
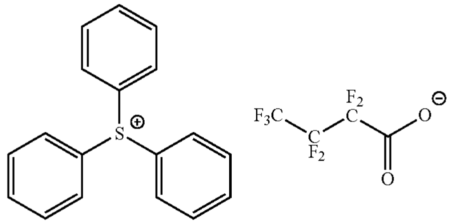
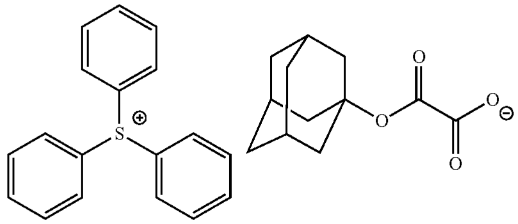
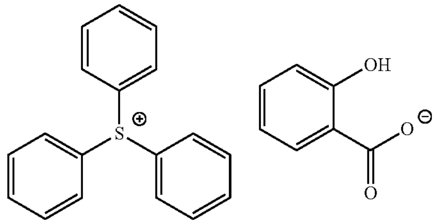
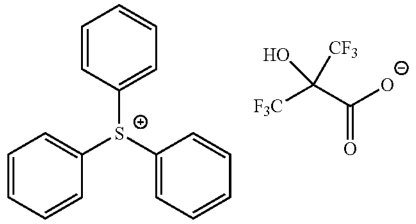
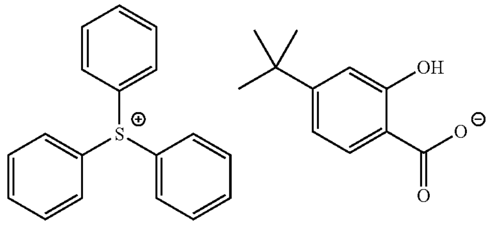
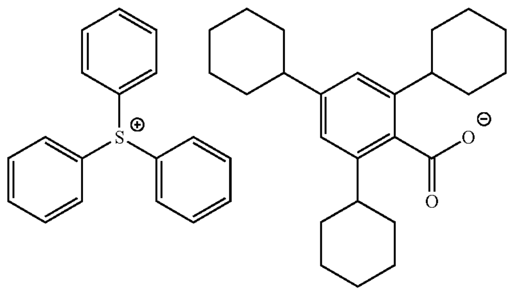
-continued
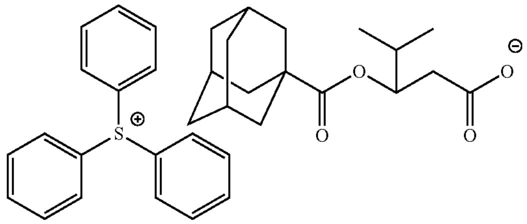
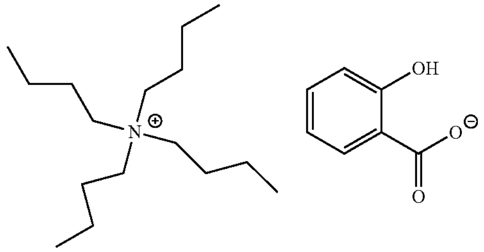
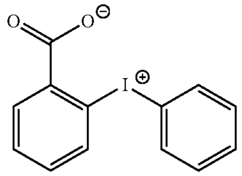
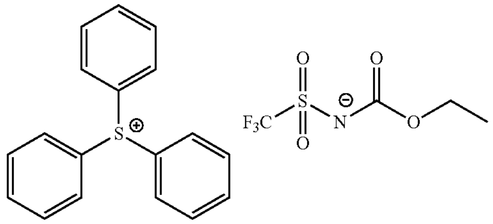
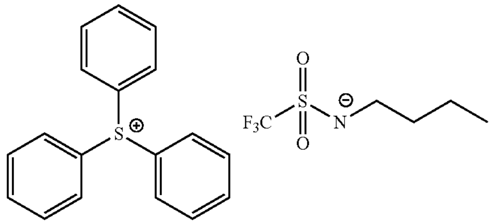
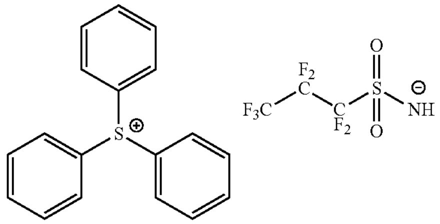
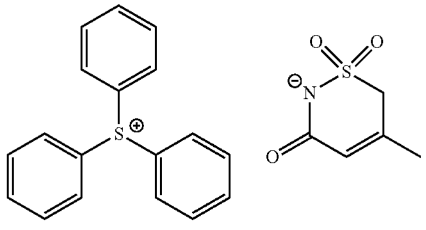

-continued

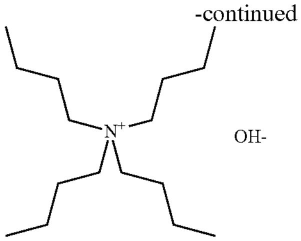

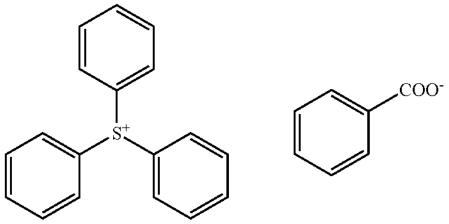

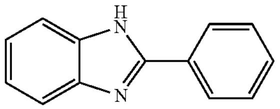

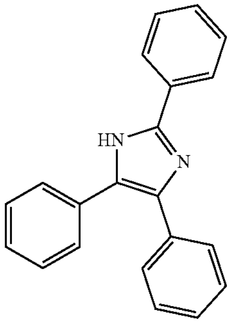

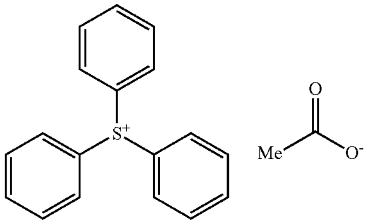

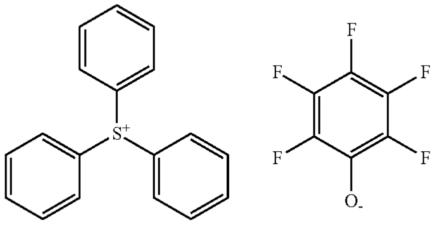

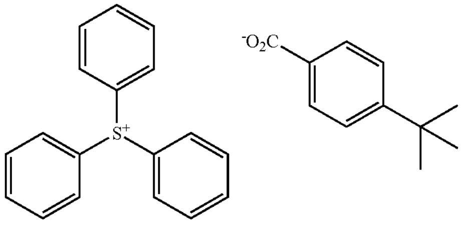

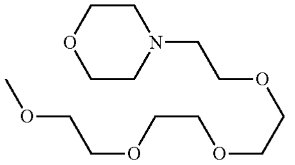

-continued

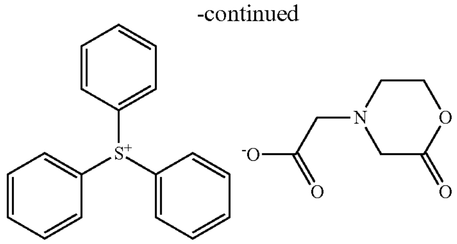

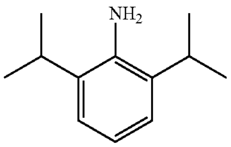

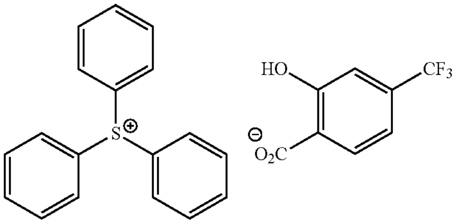

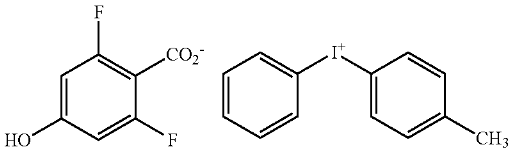

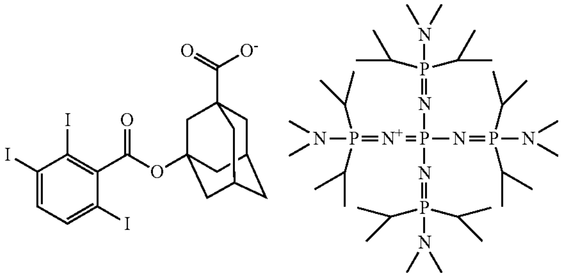

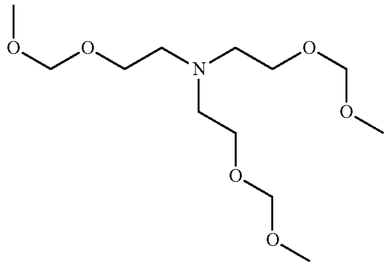

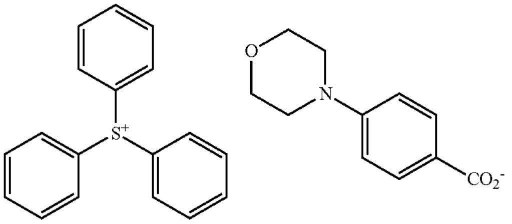

In the composition of the embodiment of the present invention, the acid diffusion control agents may be used alone or in combination of two or more kinds thereof.

A content of the acid diffusion control agent (in a case where a plurality of kinds of the acid diffusion control agents are present, a total content thereof) in the composition of the embodiment of the present invention is preferably 0.001% to 20% by mass, and more preferably 0.01% to 5% by mass with respect to the total solid content of the composition.

[Solvent]

The composition of the embodiment of the present invention preferably contains a solvent.

In the composition of the embodiment of the present invention, a known resist solvent can be appropriately used. For example, the known solvents disclosed in paragraphs 106651 to 106701 of US2016/0070167A1, paragraphs [0210] to [0235] of US2015/0004544A1, paragraphs [0424] to [0426] of US2016/0237190A1, and paragraphs [0357] to [0366] of US2016/0274458A1 can be suitably used.

Examples of the solvent which can be used in the preparation of the composition include organic solvents such as alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

As the organic solvent, a mixed solvent obtained by mixing a solvent having a hydroxyl group in the structure and a solvent having no hydroxyl group may be used.

As the solvent having a hydroxyl group and the solvent having no hydroxyl group, the above-exemplified compounds can be appropriately selected, but as the solvent having a hydroxyl group, alkylene glycol monoalkyl ether or alkyl lactate is preferable, and propylene glycol monomethyl ether (PGME), propylene glycol monoethyl ether (PGEE), methyl 2-hydroxyisobutyrate, or ethyl lactate is more preferable. In addition, as the solvent having no hydroxyl group, alkylene glycol monoalkyl ether acetate, alkyl alkoxypropionate, a monoketone compound which may have a ring, a cyclic lactone, alkyl acetate, or the like is preferable, and among these, propylene glycol monomethyl ether acetate (PGEX), ethyl ethoxypropionate, 2-heptanone, y-butyrolactone, cyclohexanone, cyclopentanone, or butyl acetate is more preferable, and propylene glycol monomethyl ether acetate, γ-butyrolactone, ethyl ethoxypropionate, cyclohexanone, cyclopentanone, or 2-heptanone is still more preferable. As a solvent having no hydroxyl group, propylene carbonate is also preferable.

A mixing ratio (mass ratio) of the solvent having a hydroxyl group to the solvent having no hydroxyl group is 1/99 to 99/1, preferably 10/90 to 90/10, and more preferably 20/80 to 60/40. A mixed solvent containing 50% by mass or more of the solvent having no hydroxyl group is preferable from the viewpoint of coating evenness.

The solvent preferably contains propylene glycol monomethyl ether acetate, and may be either a single solvent of propylene glycol monomethyl ether acetate or a mixed solvent of two or more kinds containing propylene glycol monomethyl ether acetate.

[Surfactant]

The composition of the embodiment of the present invention may further include a surfactant. By containing the surfactant, in a case where an exposure light source at a wavelength of 250 nm or less, in particular, 220 nm or less is used, it is possible to form a pattern with good sensitivity and resolution, excellent adhesiveness, and fewer development defects.

It is particularly preferable to use a fluorine-based and/or silicon-based surfactant as the surfactant.

Examples of the fluorine- and/or silicon-based surfactants include the surfactants described in 102761 of US2008/0248425A. In addition. EFTOP EF301 or EF303 (manufactured by Shin-Akita Chemical Co., Ltd.); FLORAD FC430, 431, or 4430 (manufactured by Sumitomo 3M Inc.); MEGAFACE F171, F173, F176, F189, F113, F110. F177, F120, or R08 (manufactured by DIC Corporation), SURFLON S-382, SC101, 102, 103, 104, 105, or 106 (manufactured by Asahi Glass Co., Ltd.); TROYSOL S-366 (manufactured by Troy Chemical Corporation); GF-300 or GF-150 (manufactured by Toagosei Chemical Industry Co., Ltd.); SURFLON S-393 (manufactured by Seimi Chemical Co., Ltd.); EFTOP EF121, EF122A, EF1228, RF122C, EF125M, EF135M, EF351, EF352, EF801, EF802, or EF601 (manufactured by JEMCO Inc.); PF636, PF656, PF6320, or PF6520 (manufactured by OMNOVA Solutions Inc.); or FTX-204G, 208G, 218G, 230G, 204D, 208D, 212D, 218D, or 222D (manufactured by NEOS COMPANY LIMITED) may be used. In addition, a polysiloxane polymer, KP-341 (manufactured by Shin-Etsu Chemical Co., Ltd.), can also be used as the silicon-based surfactant.

In addition, the surfactant may be synthesized using a fluoroaliphatic compound produced by a telomerization method (also referred to as a telomer method) or an oligomerization method (also referred to as an oligomer method), in addition to the known surfactants as shown above. Specifically, a polymer including a fluoroaliphatic group derived from fluoroaliphatic compound may be used as the surfactant. The fluoroaliphatic compound can be synthesized in accordance with the method described in JP2002-90991A.

In addition, another surfactant other than the fluorine-based and/or silicon-based surfactants, described in [0280] of US2008/0248425A, may also be used.

These surfactants may be used alone or in combination of two or more kinds thereof.

In a case where the composition of the embodiment of the present invention includes a surfactant, a content thereof is preferably more than 0% to 2% by mass, more preferably 0.0001% to 2% by mass, and still more preferably 0.0005% to 1% by mass with respect to the total solid content of the composition.

[Other Additives]

The composition of the embodiment of the present invention can contain, in addition to the components described above, a carboxylic acid, an onium carboxylate salt, a dissolution inhibiting compound having a molecular weight of 3,000 or less described in Proceeding of SPIE, 2724,355 (1996) and the like, a dye, a plasticizer, a photosensitizer, a light absorber, an antioxidant, and the like as appropriate.

In particular, the carboxylic acid can be suitably used for improving the performance. The carboxylic acid is preferably an aromatic carboxylic acid such as benzoic acid or naphthoic acid.

In a case where the composition of the embodiment of the present invention includes a carboxylic acid, the content of the carboxylic acid is preferably 0.01% to 10% by mass, more preferably 0.01% to 5% by mass, and still more preferably 0.01% to 3% by mass with respect to the total solid content of the composition.

The actinic ray-sensitive or radiation-sensitive resin composition of the embodiment of the present invention is used with a film thickness of preferably 10 to 250 nm, more preferably 20 to 200 nm, and still more preferably 30 to 100 nm, from the viewpoint of improving a resolving power. Such a film thickness can be obtained by setting the concentration of solid contents in the composition to an appropriate range to provide the composition with a suitable viscosity and improve the coating property and the film forming property.

The concentration of solid contents of the actinic ray-sensitive or radiation-sensitive resin composition in the embodiment of the present invention is usually 1.0% to 10% by mass, preferably 1.5% to 5.7% by mass, and more preferably 1.8% to 5.3% by mass. By setting the concentration of solid contents within the range, the resist solution can be uniformly applied onto a substrate, and further, it is possible to form a resist pattern having excellent line width roughness.

The concentration of solid contents is a mass percentage of the mass of other components excluding the solvent with respect to the total mass of the actinic ray-sensitive or radiation-sensitive resin composition.

[Use]

The composition of the embodiment of the present invention relates to an actinic ray-sensitive or radiation-sensitive resin composition having properties which change by undergoing a reaction upon irradiation with actinic rays or radiation. More specifically, the composition of the embodiment of the present invention relates to an actinic ray-sensitive or radiation-sensitive resin composition which is used in a step of manufacturing a semiconductor such as an integrated circuit (IC), for the manufacture of a circuit board for a liquid crystal, a thermal head, or the like, the manufacture of a mold structure for imprinting, other photofabrication steps, or production of a planographic printing plate or an acid-curable composition. A pattern formed in the present invention can be used in an etching step, an ion implantation step, a bump electrode forming step, a rewiring forming step, a microelectromechanical system (MEMS), or the like.

[Actinic Ray-Sensitive or Radiation-Sensitive Film]

The present invention also relates to an actinic ray-sensitive or radiation-sensitive film (preferably a resist film) formed with the actinic my-sensitive or radiation-sensitive resin composition of the embodiment of the present invention. Such a film is formed, for example, by applying the composition of the embodiment of the present invention onto a support such as a substrate. The thickness of this film is preferably 0.02 to 0.1 μm. As a method for applying the composition on the substrate, a suitable application method such as spin coating, roll coating, flow coating, dip coating, spray coating, and doctor coating is used to apply the composition onto a substrate, but the spin coating is preferable and the rotation speed is preferably 1,000 to 3,000 rotations per minute (rpm). The coating film is preheated at 60° C. to 150° C. for 1 to 20 minutes, and preferably at 80° C. to 120° C. for 1 to 10 minutes to form a thin film.

For a material constituting a substrate to be processed and an outermost layer thereof, for example, in a case of a semiconductor wafer, a silicon wafer can be used, and examples of the material forming the outermost layer include Si, $SiO_2$, SiN, SiON, and TiN, WSi, BPSG SOG, and an organic antireflection film.

Before forming the resist film, an antireflection film may be previously coated on the substrate.

As the antireflection film, any of an inorganic film type antireflection film such as titanium, titanium dioxide, titanium nitride, chromium oxide, carbon, and amorphous silicon, and an organic film type antireflection film formed of a light absorber and a polymer material can be used. Furthermore, as the organic antireflection film, a commercially available organic antireflection film such as DUV30 series or DUV-40 series manufactured by Brewer Science Inc., or AR-2, AR-3, or AR-5 manufactured by Shipley Co., Ltd. can be used.

Moreover, in the pattern forming method of the embodiment of the present invention, a topcoat may be formed on the upper layer of the resist film. It is preferable that the topcoat is not mixed with the resist film and can be uniformly applied to the upper layer of the resist film.

The topcoat is not particularly limited, a topcoat known in the related art can be formed by a method known in the related an, and for example, the topcoat can be formed in accordance with the description in paragraphs 0072 to 0082 of JP2014-059543A.

For example, it is preferable that a topcoat containing a basic compound as described in JP2013-61648A is formed on a resist film. Specific examples of the basic compound which can be included in the topcoat include the same ones as those for the above-mentioned acid diffusion control agent.

In addition, the topcoat preferably includes a compound which includes at least one group or bond selected from the group consisting of an ether bond, a thioether bond, a hydroxyl group, a thiol group, a carbonyl bond, and an ester bond.

Furthermore, the topcoat preferably contains a resin. The resin which can be contained in the topcoat is not particularly limited, but the same resin as the hydrophobic resin which can be included in the actinic ray-sensitive or radiation-sensitive resin composition can be used.

With regard to the hydrophobic resin, reference can be made to the descriptions in [0017] to [0023] of JP2013-61647A ([0017] to [0023] of the corresponding US2013/244438A), and [0016] to [0165] of JP2014-56194A, the contents of which are incorporated herein by reference.

The topcoat preferably includes a resin containing a repeating unit having an aromatic ring. By containing the repeating unit having an aromatic ring, a secondary electron-generating efficiency and an acid-generating efficiency from a compound that generates an acid with actinic rays or radiation increase, particularly upon irradiation with electron beams or EUV exposure, and thus, an effect of realizing a high sensitivity and a high resolution in the formation of a pattern can be expected.

In a case where the topcoat includes a plurality of resins, it is preferable that the topcoat includes at least one resin (XA) having a fluorine atom and/or a silicon atom. It is more preferable that the topcoat composition includes at least one resin (XA) having a fluorine atom and/or a silicon atom, and a resin (XB) having a content of a fluorine atom and/or silicon atom which is smaller than that of the resin (XA). As a result, in a case where a topcoat film is formed, the resin (XA) is unevenly distributed on a surface of the topcoat film, and thus, it is possible to improve performance such as development characteristics and immersion liquid followability.

In addition, the topcoat may contain an acid generator and a crosslinking agent.

The topcoat is typically formed from a composition for forming a topcoat.

For the composition for forming a topcoat, it is preferable that the respective components are dissolved in a solvent and filtered using a filter. The filter is preferably made of polytetrafluoroethylene, polyethylene, or nylon, which has a pore size of 0.1 μm or less, more preferably 0.05 μm or less, and still more preferably 0.03 μm or less. Furthermore, in a case where the concentration of solid contents of the composition is high (for example, 25% by mass or more), the pore size of a filter used for filtration using a filter is preferably 3 μm or less, more preferably 0.5 μm or less, still more preferably 0.3 μm or less. The filter is preferably a polytetrafluoroethylene-made, polyethylene-made, or nylon-made filter. In the filtration using a filter, for example, as disclosed in JP2002-62667A, circulation-filtration may be performed or the filtration may be performed by connection of a plurality of kinds of filters in series or in parallel. In addition, the composition may be filtered in plural times. Furthermore, the composition may be subjected to a deaeration treatment or the like before or after filtration using a filter.

The composition for forming a topcoat preferably does not include impurities such as a metal. The content of the metal components included in these materials is preferably 10 ppm or less, more preferably 5 ppm or less, and still more preferably 1 ppm or less, and it is particularly preferable that substantially no metal component is included (below a detection limit of the measuring apparatus).

It is also preferable to partially or wholly subject the inside of a device used in a producing step (a step for synthesizing a raw material, and the like) of a raw material (a resin, a photoacid generator, and the like) of a resist composition to a glass lining treatment such that a content of metal impurities of the resist composition is adjusted to be small (for example, on the order of ppm by mass). Such a method is described, for example, in The Chemical Daily, Dec. 21, 2017.

In a case where the exposure which will be described later is liquid immersion exposure, the topcoat is arranged between the resist film and the immersion liquid, and also functions as a layer which does not bring the resist film into direct contact with the immersion liquid. In this case, preferred characteristics required for the topcoat (composition for forming a topcoat) are coating suitability onto the resist film, transparency to radiation, particularly to radiation at a wavelength of 193 nm, and sparing solubility in an immersion liquid (preferably water). Furthermore, it is preferable that the topcoat is not mixed with the resist film and can be uniformly applied onto a surface of the resist film.

Moreover, in order to uniformly apply the composition for forming a topcoat onto a surface of the resist film while not dissolving the resist film, it is preferable that the composition for forming a topcoat contains a solvent in which the resist film is not dissolved. It is more preferable to use a solvent of a component different from a developer (organic developer) containing an organic solvent which will be described in detail later as the solvent in which the resist film is not dissolved.

A method for applying the composition for forming a topcoat is not particularly limited, and a spin coating method, a spray method, a roller coating method, a dip method, or the like which is known in the related art can be used.

The thickness of the topcoat is not particularly limited, but is usually 5 nm to 300 nm, preferably 10 nm to 300 nm, more preferably 20 nm to 200 nm, and still more preferably 30 nm to 100 nm, from the viewpoint of transparency to an exposure light source.

After forming the topcoat, the substrate is post-baked (PB) as necessary.

From the viewpoint of resolution, it is preferable that the refractive index of the topcoat is close to that of the resist film.

The topcoat is preferably insoluble in an immersion liquid, and more preferably insoluble in water.

With regard to the receding contact angle of the topcoat, the receding contact angle (23° C.) of the immersion liquid with respect to the topcoat is preferably 50 to 100 degrees, and more preferably 80 to 100 degrees, from the viewpoint of immersion liquid followability.

In the liquid immersion exposure, from the viewpoint that the immersion liquid needs to move on a wafer following the movement of an exposure head that is scanning the wafer at a high speed and forming an exposure patters, the contact angle of the immersion liquid with respect to the topcoat in a dynamic state is important, and in order to obtain better resist performance, it is preferable that the immersion liquid has a receding contact angle in the range.

During the release of the topcoat, an organic developer may be used, and another release agent may be separately used. As the release agent, a solvent hardly permeating the resist film is preferable. From the viewpoint that the release of the topcoat can be carried out at the same time as the development of the resist film, the topcoat is preferably releasable by an organic developer. The organic developer used for the release is not particularly limited as long as it makes it possible to dissolve and remove a less exposed portion of the resist film.

From the viewpoint of the release with the organic developer, the dissolution rate of the topcoat in the organic developer is preferably 1 to 300 nm/sec, and more preferably 10 to 100 nm/sec.

Here, the dissolution rate of the topcoat in the organic developer is a film thickness decreasing rate in a case where the topcoat is exposed to a developer after film formation, and in the present invention, it is a rate in a case where the topcoat is dipped in butyl acetate at 23° C.

An effect of reducing development defects after developing a resist film is accomplished by adjusting the dissolution rate of a topcoat in an organic developer to 1/sec or more, and preferably 10 nm/sec or more. In addition, by setting the dissolution rate to 300 nm/sec or less, and preferably 100 nm/sec, an effect that the line edge roughness of a pattern after the development of the resist film is improved is accomplished, possibly due to an effect of reducing the exposure unevenness during the liquid immersion exposure.

The topcoat may be removed using another known developer, for example, an aqueous alkali solution. Specific examples of the usable aqueous alkali solution include an aqueous tetramethylammonium hydroxide solution.

[Pattern Forming Method]

The present invention also relates to a pattern forming method including a resist film forming step of forming a resist film using the actinic my-sensitive or radiation-sensitive resin composition of the embodiment of the present invention, an exposing step of exposing the resist film, and a developing step of developing the exposed resist film, using a developer.

In the present invention, the exposure is preferably carried out using electron beams, an ArF excimer laser, or extreme ultraviolet rays, and more preferably electron beams or extreme ultraviolet rays.

For exposure (pattern forming step) on a resist film in the production of a precision integrated circuit element, first, irradiation with an ArF excimer laser, electron beams, or extreme ultraviolet rays (EUV) is preferably performed patternwise on the resist film of the present invention. In a case of the ArF excimer laser, the exposure amount is approximately 1 to 100 mJ/cm$^2$, preferably approximately 20 to 60 mi/cm$^2$; in a case of the electron beams, the exposure amount is approximately 0.1 to 20 μC/cm$^2$, and preferably approximately 3 to 10 μC/cm$^2$; and in a case of the extreme ultraviolet rays, the exposure amount is approximately 0.1 to 20 mJ/cm$^2$, and preferably approximately 3 to 15 mJ/cm$^2$.

Subsequently, post-exposure baking is performed on a hot plate, preferably at 60° C. to 150° C. for S seconds to 20 minutes, more preferably at 80° C. to 120° C. for 15 seconds to 10 minutes, and still more preferably at 80° C. to 120° C. for 1 to 10 minutes, and then development, rinsing, and drying are performed to form a pattern. Here, the post-exposure baking is appropriately adjusted depending on the acid decomposability of the repeating unit having an acid-decomposable group in the resin (A). In a case where the acid decomposability is low, it is also preferable that the temperature for post-exposure baking is 110° C. or higher and the heating time is 45 seconds or longer.

The developer is appropriately selected, but an alkali developer (typically an aqueous alkali solution) or a developer containing an organic solvent (also referred to as an organic developer) is preferably used. In a case where the developer is an aqueous alkali solution, development is performed with an aqueous alkali solution of tetramethylammonium hydroxide (TMAH), tetrabutylammonium hydroxide (TBAH), or the like at 0.1% to 5% by mass, and preferably 2% to 3% by mass for 0.1 to 3 minutes, and preferably 0.5 to 2 minutes by an ordinary method such as a dip method, a puddle method, a spray method, or the like. An appropriate amount of an alcohol and/or a surfactant may be added to the alkali developer. Thus, in the formation of a negative tone pattern, the film in the non-exposed portion is dissolved and the exposed portion is hardly dissolved in the developer, and in the formation of a positive tone pattern, the film in the exposed portion is dissolved and the film in the non-exposed portion is hardly dissolved in the developer, such that a desired pattern is formed on the substrate.

In a case where the pattern forming method of the embodiment of the present invention has a step of performing development using an alkali developer, as the alkali developer, for example, an aqueous alkali solution of inorganic alkalis such as sodium hydroxide, potassium hydroxide, sodium carbonate, sodium silicate, sodium metasilicate, and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, tetraalkylammonium hydroxides such as tetramethylammonium hydroxide, tetraethylammonium hydroxide, tetrapropylammonium hydroxide, tetrabutylammonium hydroxide, tetrapentylammonium hydroxide, tetrahexylammonium hydroxide, tetraoctylammonium hydroxide, ethyltrimethylammonium hydroxide, butyltrimethylammonium hydroxide, methyltriamylammonium hydroxide, and dibutyldipentylammonium hydroxide, quaternary ammonium salts such as trimethylphenylammonium hydroxide, trimethylbenzylammonium hydroxide, triethylbenzylammonium hydroxide, and dimethylbis(2-hydroxyethyl)ammonium hydroxide, or cyclic amines such as pyrrole and piperidine can be used.

Furthermore, the aqueous alkali solution can be used after adding an appropriate amount of alcohols or a surfactant thereto.

The alkali concentration of the alkali developer is usually 0.1% to 20% by mass.

The pH of the alkali developer is usually 10.0 to 15.0.

In particular, a 2.38%-by-mass aqueous tetramethylammonium hydroxide solution is desirable.

Pure water may be used as the rinsing liquid in the rinse treatment performed after the alkali development, and an appropriate amount of a surfactant may be added to the pure water.

In addition, after the developing treatment or the rinsing treatment, a treatment of removing the developer or the rinsing liquid adhering to a pattern with a supercritical fluid can be performed.

In a case where the pattern forming method of the embodiment or the present invention has a step or performing development using a developer containing an organic solvent, as the developer in the step (hereinafter also referred to as an organic developer), a polar solvent such as a ketone-based solvent, an ester-based solvent, an alcohol-based solvent, an amide-based solvent, and an ether-based solvent, or a hydrocarbon-based solvent can be used.

In the present invention, the ester-based solvent is a solvent having an ester group in the molecule, the ketone-based solvent is a solvent having a ketone group in the molecule, the alcohol-based solvent is a solvent having an alcoholic hydroxyl group in the molecule, the amide-based solvent is a solvent having an amide group in the molecule, and the ether-based solvent is a solvent having an ether bond in die molecule. Among those, a solvent having a plurality of the functional groups in one molecule is also present, but in this case, it is applicable to any of solvent species including the functional group contained in the solvent. For example, diethylene glycol monomethyl ether is applicable to any of the alcohol-based solvent and the ether-based solvent in the classification. In addition, the hydrocarbon-based solvent is a hydrocarbon-based solvent having no substituent.

In particular, a developer containing at least one solvent selected from the ketone-based solvent, the ester-based solvent, the alcohol-based solvent, or the ether-based solvent is preferable.

It is preferable to use an ester-based solvent having 7 or more carbon atoms (preferably 7 to 14 carbon atoms, more preferably 7 to 12 carbon atoms, and still more preferably 7 to 10 carbon atoms), and 2 or less heteroatoms as the developer from the viewpoint that the swelling of the resist film can be suppressed.

The heteroatom of the ester-based solvent is an atom other than a carbon atom and a hydrogen atom, and examples thereof include an oxygen atom, a nitrogen atom, and a sulfur atom. The number of the heteroatoms is preferably 2 or less.

Preferred examples of the ester-based solvents having 7 or more carbon atoms and 2 or less heteroatoms include amyl acetate, isoamyl acetate, 2-methylbutyl acetate, 1-methylbutyl acetate, hexyl acetate, pentyl propionate, hexyl propionate, heptyl propionate, butyl butanoate, and isobutyl isobutanoate, and isoamyl acetate or isobutyl isobutanoate is particularly preferably used.

As the developer, a mixed solvent of the ester-based solvent and the hydrocarbon-based solvent or a mixed solvent of the ketone-based solvent and the hydrocarbon-based solvent may be used instead of the ester-based solvent having 7 or more carbon atoms and having 2 or less heteroatoms as mentioned above. Also in this case, it is effective in suppressing the swelling of the resist film.

In a case where the ester-based solvent and the hydrocarbon-based solvent are used in combination, it is preferable to use isoamyl acetate as the ester-based solvent. In addition, from the viewpoint of adjusting the solubility of the resist film, a saturated hydrocarbon-based solvent (for example, octane, nonane, decane, dodecane, undecane, and hexadecane) is preferably used as the hydrocarbon-based solvent.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, 2,5-dimethyl-4-hexanone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate, and diisobutyl ketone and 2,5-dimethyl-4-hexanone are particularly preferably used.

Examples of the ester-based solvent include methyl acetate, butyl acetate, ethyl acetate, isopropyl acetate, isoamyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, and methyl 2-hydroxyisobutyrate.

Examples of the alcohol-based solvent include alcohols such as methyl alcohol, ethyl alcohol, n-propyl alcohol, isopropyl alcohol, n-butyl alcohol, sec-butyl alcohol, 4-methyl-2-pentanol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, and glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol.

Examples of the ether-based solvent include anisole, dioxane, and tetrahydrofuran, in addition to the glycol ether-based solvents.

As the amide-based solvent, for example, N-methyl-2-pyrrolidone, N,N-dimethylacetamide, N,N-dimethylfomamide, hexamethylphosphoric triamide, 1,3-dimethyl-2-imidazolidinone, or the like can be used.

Examples of the hydrocarbon-based solvent include aromatic hydrocarbon-based solvents such as toluene and xylene, and aliphatic hydrocarbon-based solvents such as pentane, hexane, octane, decane, and undecane.

In addition, the aliphatic hydrocarbon-based solvent which is a hydrocarbon-based solvent may be a mixture of compounds having the same number of carbon atoms but different structures. For example, in a case where decane is used as the aliphatic hydrocarbon-based solvent, 2-methylnonane, 2,2-dimethyloctane, 4-ethyloctane, isooctane, or the like which is a compound having the same number of carbon atoms and different structures, may be included in the aliphatic hydrocarbon-based solvent.

In addition, only one kind or a plurality of kinds of the compounds as described above having the same number of carbon atoms and different structures may be included.

A plurality of the solvents may be mixed or the solvent may be used in admixture with a solvent other than those described above or water. It should be noted that in order to fully exert the effects of the present invention, the moisture content of the developer as a whole is preferably less than 10% by mass, and the developer is more preferably substantially free of the moisture.

The concentration of the organic solvent (in a case of mixing a plurality of the organic solvents, a total thereof) in the organic developer is preferably 50% by mass or more, more preferably 50% to 100% by mass, still more preferably 85% to 100% by mass, even still more preferably 90% to 100% by mass, and particularly preferably 95% to 100% by mass. Most preferably, the organic solvent consists substantially only of an organic solvent. In addition, a case of consisting substantially only of an organic solvent includes a case of containing a trace amount of a surfactant, an antioxidant, a stabilizer, an antifoaming agent, or the like.

In particular, the organic developer is preferably a developer containing at least one organic solvent selected from the group consisting of a ketone-based solvent, an ester-based solvent, an alcohol-based solvent, an amide-based solvent, and an ether-based solvent.

The vapor pressure of the organic developer at 20° C. is preferably 5 kPa or less, more preferably 3 kPa or less, and particularly preferably 2 kPa or less. By setting the vapor pressure of the organic developer to 5 kPa or less, evaporation of the developer on the substrate or in the development cup is suppressed, the temperature uniformity in a wafer plane is improved, and as a result, the dimensional uniformity in the wafer plane is improved.

Specific examples of the organic developer having a vapor pressure of 5 kPa or less include ketone-based solvents such as 1-octanone, 2-octanone, 1-nonanone, 2-nonanone, 2-heptanone (methyl amyl ketone), 4-heptanone, 2-hexanone, diisobutyl ketone, cyclohexanone, methylcyclohexanone, phenylacetone, and methyl isobutyl ketone, ester-based solvents such as butyl acetate, pentyl acetate, isoamyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate, and propyl lactate, alcohol-based solvents such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol, ether-based solvents such as tetrahydrofuran, amide-based solvents such as N-methyl-2-pyrrolidone, N,N-dimethylacetamide, and N,N-dimethylformamide, aromatic hydrocarbon-based solvents such as toluene and xylene, and aliphatic hydrocarbon-based solvents such as octane and decane.

Specific examples of the organic developer having a vapor pressure of 2 kPa or less, which is a particularly preferred range, include ketone-based solvents such as 1-octanone, 2-octanone, 1-nonanone, 2-nonanone, 2-heptanone, 4-heptanone, 2-hexanone, diisobutyl ketone, cyclohexanone, methylcyclohexanone, and phenylacetone, ester-based solvents such as butyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate, and propyl lactate, alcohol-based solvents such as n-butyl alcohol, sec-butyl alcohol, tert-butyl alcohol, isobutyl alcohol, n-hexyl alcohol, n-heptyl alcohol, n-octyl alcohol, and n-decanol, glycol-based solvents such as ethylene glycol, diethylene glycol, and triethylene glycol, glycol ether-based solvents such as ethylene glycol monomethyl ether, propylene glycol monomethyl ether, ethylene glycol monoethyl ether, propylene glycol monoethyl ether, diethylene glycol monomethyl ether, triethylene glycol monoethyl ether, and methoxymethyl butanol, amide-based solvents such as N-methyl-2-pyrrolidone, N,N-dimethylacetamide, and N,N-dimethylformamide, aromatic hydrocarbon-based solvents such as xylene, and aliphatic hydrocarbon-based solvents such as octane, decane, and undecane.

The organic developer may include a basic compound. Specific examples and preferred examples of the basic compound which can be included in the developer used in the present invention are the same ones as those in the basic compound which can be included in the above-described actinic ray-sensitive or radiation-sensitive resin composition.

An appropriate amount of a surfactant can be added to the organic developer, as necessary.

The surfactant is not particularly limited, but, for example, an ionic or nonionic fluorine-based and/or silicon-based surfactant or the like can be used. Examples of such the fluorine- and/or silicon-based surfactant include the surfactants described in, for example, JP1987-36663A (JP-S62-36663A), JP1986-226746A (JP-S61-226746A). JP1986-226745A (JP-S61-226745A), JP1987-170950A (JP-S62-170950A), JP1988-34540A (JP-S63-34540A), JP1995-230165A (JP-H07-230165A), JP1996-62834A (JP-H08-62834A), JP1997-54432A (JP-H09-54432A), JP1997-5998A (JP-H09-5988A), U.S. Pat. Nos. 5,405,720A, 5,360,692A, 5,529,881A, 5,296,330A, 5,436,098A, 5,576,143A, 5,294,511A, and 5,824,451A, and nonionic surfactants are preferable. The nonionic surfactant is not particularly limited, but it is more preferable to use a fluorine-based surfactant or a silicon-based surfactant.

The amount of the surfactant to be used is preferably 0.0001% to 2% by mass, more preferably 0.0001% to 1% by mass, and particularly preferably 0.0001% to 0.1% by mass with respect to the total amount of the developer.

As the developing method, for example, a method in which a substrate is dipped in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), a method in which a developer is continuously jetted onto a substrate rotating at a constant rate while scanning a developer jetting nozzle at a constant rate (a dynamic dispense method), or the like can be applied.

In a case where the various developing methods include a step of jetting a developer from developing nozzles of a developing device toward the resist film, the jetting pressure of the developer to be jetted (flow rate per unit area of the developer to be jetted) is preferably 2 $mL/sec/mm^2$ or less, more preferably 1.5 $mL/sec/mm^2$ or less, and still more preferably 1 $mL/sec/mm^2$ or less. There is no particular lower limit to the flow rate, but the lower limit is preferably 0.2 $mL/sec/mm^2$ or more in consideration of a throughput.

By setting the jetting pressure of the developer to be jetted within the range, it is possible to significantly reduce the pattern defects derived from resist residues after development.

Although the details of this mechanism are not clear, it is considered that by setting the jetting pressure to be in the range, the pressure applied to the resist film by the developer is likely to be reduced and the resist film/pattern is prevented from being scraped or broken carelessly.

In addition, the jetting pressure ($mL/sec/mm^2$) of the developer is a value at the outlet of the developing nozzle in the developing device.

Examples of the method of adjusting the jetting pressure of the developer include a method of adjusting a jetting pressure with a pump or the like, and a method of changing a jetting pressure by adjusting the pressure with a supply from a pressure tank.

Furthermore, after a step of performing development using a developer including an organic solvent, a step of stopping the development may be carried out while substituting the solvent with another solvent.

A step of performing washing using a rinsing liquid may be included after the step of performing development using a developer including an organic solvent, but from the viewpoint of a throughput (productivity), an amount of the rinsing liquid to be used, and the like, a step of performing washing using a rinsing liquid may not be included.

The rinsing liquid used in the rinsing step after the developing step using a developer including an organic solvent is not particularly limited as long as the rinsing liquid does not dissolve the resist pattern, and a solution including a common organic solvent can be used. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent include the same ones as those described for the developer including an organic solvent, and in particular, suitable examples thereof include butyl acetate and methyl isobutyl carbinol.

It is preferable to perform a step of performing washing, more preferably using a rinsing liquid containing at least one organic solvent selected from the group consisting of an ester-based solvent, an alcohol-based solvent, and a hydrocarbon-based solvent, and still more preferably using a rinsing liquid containing the alcohol-based solvent or the hydrocarbon-based solvent, after the step of performing development using a developer including an organic solvent.

Among the organic solvents, the hydrocarbon-based solvent is also preferably used, and the aliphatic hydrocarbon-based solvent is more preferably used, as the organic solvent included in the rinsing liquid. As the aliphatic hydrocarbon-based solvent used in the rinsing liquid, from the viewpoint of further improving the effects, an aliphatic hydrocarbon-based solvent having 5 or more carbon atoms (for example, pentane, hexane, octane, decane, undecane, dodecane, and hexadecane) is preferable, an aliphatic hydrocarbon-based solvent having 8 or more carbon atoms is more preferable, and an aliphatic hydrocarbon-based solvent having 10 or more carbon atoms is still more preferable.

Incidentally, the upper limit value of the number of carbon atoms in the aliphatic hydrocarbon-based solvent is not particularly limited, and for example, is 16 or less, preferably 14 or less, and more preferably 12 or less.

Among the aliphatic hydrocarbon-based solvents, decane, undecane, or dodecane is particularly preferable, and undecane is the most preferable.

By using the hydrocarbon-based solvent (in particular, the aliphatic hydrocarbon-based solvent) as the organic solvent included in the rinsing liquid as described above, the developer permeating into the resist film slightly after development is washed away, the swelling is further suppressed, and thus, an effect of suppressing pattern collapse is further exhibited.

The respective components in a plural number may be mixed or the components may also be used in admixture with an organic solvent other than the solvents.

The moisture content of the rinsing liquid is preferably 10% by mass or less, more preferably 5% by mass or less, and particularly preferably 3% by mass or less. By setting the moisture content to 10% by mass or less, good development characteristics can be obtained.

The vapor pressure at 20° C. of the rinsing liquid which is used alter the step of performing development using a developer including an organic solvent is preferably from 0.05 kPa to 5 kPa, more preferably from 0.1 kPa to 5 kPa, and most preferably from 0.12 kPa to 3 kPa. By setting the vapor pressure of the rinsing liquid to be from 0.05 kPa to 5 kPa, the temperature uniformity in a wafer plane is improved, and further, the dimensional uniformity in a wafer plane is enhanced by suppression of swelling due to the permeation of the rinsing liquid.

The rinsing liquid can be used ater an appropriate amount of a surfactant is added thereto.

In the rinsing step, a wafer which has been developed using a developer including an organic solvent is subjected to a washing treatment using a rinsing liquid including an organic solvent. A method for the washing treatment is not particularly limited, for example, a method in which a rinsing liquid is continuously jetted on a substrate rotating at a constant rate (a rotation application method), a method in which a substrate is dipped in a tank filled with a rinsing liquid for a certain period of time (a dip method), a method in which a rinsing liquid is sprayed on a substrate surface (a spray method), or the like can be applied, and among these, a method in which a washing treatment is performed using the rotation application method, and a substrate is rotated at a rotation speed of 2,000 rpm to 4,000 rpm after washing, thereby removing the rinsing liquid from the substrate, is preferable. Furthermore, it is also preferable that a heating step (postbaking) is included after the rinsing step. The developer and the rinsing liquid remaining between and inside the patterns are removed by the baking. The heating step after the rinsing step is performed, usually at 40° C. to 160° C., and preferably 70° C. to 95° C., usually for 10 seconds to 3 minutes, and preferably for 30 seconds to 90 seconds.

In a case where there is no step of performing washing with a rinsing liquid, for example, the developing treatment method described in paragraphs [0014] to [0086] of JP2015-216403A can be adopted.

Moreover, the pattern forming method of the embodiment of the present invention may include a developing step using an organic developer and a developing step using an alkali developer. A portion having a low exposure intensity is removed by development using an organic developer, and a portion having a high exposure intensity is removed by performing development using an alkali developer. By virtue of multiple development processes in which development is performed a plurality of times in such a manner, a pattern can be formed by keeping only a region with an intermediate exposure intensity from not being dissolved, such that a finer pattern than usual can be formed (the same mechanism as in paragraph [0077] of JP2008-292975A).

It is preferable that various materials (for example, a resist solvent, a developer, a rinsing liquid, a composition for forming an antireflection film, and a composition for forming a topcoat) used in the actinic ray-sensitive or radiation-sensitive resin composition in the embodiment of the present invention, and the pattern forming method of the embodiment of the present invention include no impurities such as metals, metal salts including halogen, acids, alkalis, and components including a sulfur atom or a phosphorus atom. Here, examples of the impurities including a metal atom include Na, K, Ca, Fe, Cu, Mn, Mg, Al, Cr, Ni, Zn, Ag, Sn, Pb, Li, and salts thereof.

The content of the impurities included in these materials is preferably 1 ppm or less, more preferably 1 ppb or less, still more preferably 100 parts per trillion (ppt) or less, and particularly preferably 10 ppt or less, and it is the most preferable that substantially no impurities is included (below a detection limit of the measuring apparatus).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a filter made of polytetrafluoroethylene, polyethylene, nylon, or the like is preferable. The filter may be a composite material in which these materials are combined with an ion exchange medium. As the filter, a filter which has been washed with an organic solvent in advance may be used. In the step of filter filtration, a plurality of kinds of filters connected in series or in parallel may be used. In a case of using a plurality of kinds of filters, a combination of filters having different pore diameters and/or materials may be used. In addition, various materials may be filtered plural times, and the step of filtering plural times may be a circulation-filtration step.

Moreover, examples of a method for reducing the impurities such as metals included in various materials include a method in which a raw material having a low metal content is selected as a raw material constituting various materials and the raw material constituting the various materials is subjected to filtration using a filter; and a method in which distillation under conditions suppressing contamination as much as possible by performing a lining with TEFLON (registered trademark), or the like in the inside of a device is performed. Preferred conditions for the filtration using a filter performed on the raw materials constituting various materials are the same ones as the above-mentioned conditions.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

In addition, as a method for reducing the impurities such as metals included in the organic treatment liquid of the present invention, a method in which a raw material having a low metal content is selected as a raw material constituting various materials, the raw material constituting the various materials is subjected to filtration using a filter: distillation under conditions suppressing contamination as much as possible by performing a lining with TEFLON (registered trademark) in the inside of a device; or the like. Preferred conditions for the filtration using a filter performed on the raw materials constituting various materials are the same ones as the above-mentioned conditions.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used.

[Storage Container]

As an organic solvent (also referred to as an "organic treatment liquid") which can be used for a developer and a rinsing liquid, it is preferable to use one stored in a storage container for storing an organic treatment liquid for patterning a chemically amplified or non-chemically amplified resist film, in which the storage container has a storage part. The storage container is preferably, for example, a storage container for storing an organic treatment liquid for patterning a resist film, in which the inner wall of the storage part being in contact with the organic treatment liquid is formed from a resin different from any of a polyethylene resin, a polypropylene resin, and a polyethylene-polypropylene resin, or of a metal subjected to a rust prevention/metal elation prevention treatment. An organic solvent to be used as an organic treatment liquid for patterning a resist film is stored in the storage part of the storage container, and the organic solvent jetted from the storage part can be used at the time of patterning the resist film.

In a case where the storage container further has a sealing part for sealing the storage part, the sealing part is also preferably formed of a resin different from one or more resins selected from the group consisting of a polyethylene resin, a polypropylene resin, and a polyethylene-polypropylene resin, or of a metal which has been subjected to a rust prevention/metal elution prevention treatment.

Here, the sealing part refers to a member capable of shielding the storage part from the outside air, and suitable examples thereof include a packing and an O ring.

The resin different from one or more resins selected from the group consisting of a polyethylene resin, a polypropylene resin, and a polyethylene-polypropylene resin is preferably a perfluoro resin.

Examples of the perfluoro resin include a tetrafluoroethylene resin (PTFE), a tetrafluoroethylene-perfluoroalkyl vinyl ether copolymer (PFA), a tetrafluoroethylene-hexafluoropropylene copolymerized resin (FEP), a tetrafluoroethylene-ethylene copolymerized resin (ETFE), a trifluoroethylene chloride-ethylene copolymerized resin (ECME), a polyvinylidene fluoride resin (PVDF), a trifluoroethylene chloride copolymerized resin (PCTFE), and a polyvinyl fluoride resin (PVF).

Particularly preferred examples of the perfluoro resin include a tetrafluoroethylene resin, a tetrafluoroethylene-perfluoroalkyl vinyl ether copolymer, and a tetrafluoroethylene-hexafluoropropylene copolymerized resin.

Examples of the metal in the metal which has been subjected to a rust prevention/metal elution prevention treatment include carbon steel, alloy steel, nickel chromium steel, nickel chromium molybdenum steel, chromium steel, chromium molybdenum steel, and manganese steel.

As the rust prevention/metal elution prevention treatment, a coating technique is preferably applied.

The coating technique is roughly divided into three types of metal coating (various plating), inorganic coating (various chemical conversion treatments, glass, concrete, ceramics, and the like), and organic coating (a rust preventive oil, a paint, rubber, and plastics).

Preferred examples of the coating technique include a rust preventive oil, a rust inhibitor, a corrosion inhibitor, a chelate compound, a strippable plastic, and a surface treatment with a lining agent.

Among those, corrosion inhibitors, such as various chromates, nitrites, silicates, phosphates, oleic acid, dimer acid, carboxylic acids such as naphthenic acid, carboxylic acid metal soaps, sulfonates, amine salts, and esters (glycerol esters of higher fatty acids and phosphate esters), chelate compounds such as ethylenediaminetetraacetic acid, gluconic acid, nitrilotriacetic acid, hydroxyethylethylenediaminetriacetic acid, and diethylenetriaminepentaacetic acid, and a fluorine resin lining are preferable. A phosphate treatment and the fluorine resin lining are particularly preferable.

Although it does not directly prevent rust as compared with a direct coating treatment, it is also preferable to adopt a "pretreatment" which is a step prior to, rust prevention treatment, as a treatment method leading to prolongation of the rust prevention period by a coating treatment.

As a specific example of such a pretreatment, a treatment for removing a variety of corrosive factors such as chlorides and sulfates present on the metal surface by washing or polishing can be suitably mentioned.

Specific examples of the storage container include the following ones.

FluoroPurePFA composite drum manufactured by Entegris Inc. (wetted inner surface: PFA resin lining)

Steel drum manufactured by JFE Corporation (wetted inner surface: zinc phosphate-coated film)

Furthermore, examples of the storage container which can be used in the present invention include the containers described in paragraphs [0013] to [0030] of JP1999-021393A (JP-H11-021393A) and paragraphs [0012] to [0024] of JP1998-4591A (JP-H10-45961 A).

In order to prevent breakdown of a chemical liquid pipe and various pans (a filter, an O-ring, a tube, and the like) due to electrostatic charging and subsequent electrostatic discharging, a conductive compound may be added to the organic treatment liquid of the present invention. The conductive compound is not particularly limited, but examples thereof include methanol. The addition amount of the conductive compound is not particularly limited, but is preferably 10% by mass or less, and more preferably 5% by mass or less from the viewpoint of maintaining preferable development characteristics. With regard to the members of the chemical liquid pipe, it is possible to use various pipes coated with stainless steel (SUS), or a polyethylene resin, a polypropylene resin, or a fluorine resin (a polytetrafluoroethylene resin, a perfluoroalkoxy resin, or the like), which has been subjected to an antistatic treatment. Similarly, a polyethylene resin, a polypropylene resin, or a fluorine resin (a polytetrafluoroethylene resin, a perfluoroalkoxy resin, or the like), which has been subjected to an antistatic treatment, can be used for a filter and an O-ring.

Moreover, generally, the developer and the rinsing liquid are stored in a waste liquid tank through a pipe after use. At that time, in a case where a hydrocarbon-based solvent is used as the rinsing liquid, there is a method of passing a solvent in which a resist is dissolved through a pipe again in order to prevent the resist dissolved in the developer from being precipitated and adhering to the back surface of the wafer, the side surface of the pipe or the like. Examples of the method of passing the solvent through the pipe include a method in which the hack surface, the side surface, and the like of a substrate are washed with a solvent in which a resist is dissolved and then the solvent is allowed to flow after performing washing with a rinsing liquid, and a method of flowing a solvent in which a resist is dissolved so as to pass through a pipe while being not in contact with the resist.

The solvent to be passed through the pipe is not particularly limited as long as it can dissolve the resist, examples thereof include the above-mentioned organic solvents, and propylene glycol monomethyl ether acetate (PGMEA), propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate, ethylene glycol monoethyl ether acetate, propylene glycol monomethyl ether (PGME), propylene glycol monoethyl ether, propylene glycol monopropyl ether, propylene glycol monobutyl ether, ethylene glycol monomethyl ether, ethylene glycol monoethyl ether, 2-heptanone, ethyl lactate, I-propanol, acetone, or the like can be used. Among those, PGMEA, PGME, or cyclohexanone can be preferably used.

[Method for Manufacturing Electronic Device]

In addition, the present invention further relates to a method for manufacturing an electronic device, including the above-described pattern forming method. The electronic device manufactured by the method for manufacturing an electronic device of an embodiment of the present invention is suitably mounted on electric or electronic equipment (for example, home appliances, office automation (OA)-related equipment, media-related equipment, optical equipment, and telecommunication equipment).

In addition, the present invention also relates to the following actinic ray-sensitive or radiation-sensitive resin composition.

An actinic ray-sensitive or radiation-sensitive resin composition including:

(A) a resin having a polarity that increases by an action of an acid, and (B) a compound that generates an acid upon irradiation with actinic rays or radiation, represented by General Formula (I), in which the resin (A) includes a repeating unit represented by General Formula (AI).

(AI)

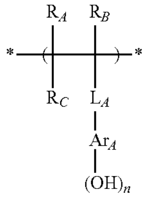

In General Formula (AI), $R_A$, $R_B$, and $R_C$ each independently represent a hydrogen atom, an alkyl group, a cycloalkyl group, a halogen atom, a cyano group, or an alkoxycarbonyl group. It should be noted that $R_C$ may be bonded to $Ar_A$ to form a ring, in which case $R_C$ represents a single bond or an alkylene group.

$L_A$ represents a single bond or a divalent linking group.

$Ar_A$ represents an (n+1)-valent aromatic ring group. In a case where $Ar_A$ is bonded to $R_C$ to form a ring. $Ar_A$ represents an (n+2)-valent aromatic ring group.

n represents an integer of 1 to 5.

(I)

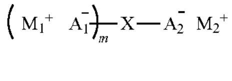

In General Formula (I), $M_1^+$ and $M_2^+$ each independently represent a cation.

X represents an (m+1)-valent linking group.

$A_1^-$ and $A_2^-$ are each independently a group selected from the group consisting of groups represented by each of Formulae (B-1) to (B-27).

(B-1)

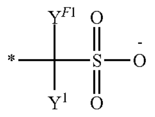

(B-2)

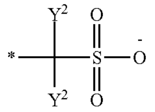

(B-3)

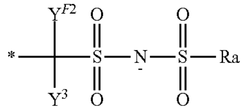

(B-4)

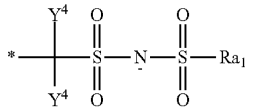

(B-5)

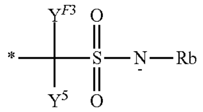

(B-6)

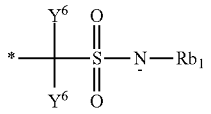

(B-7)

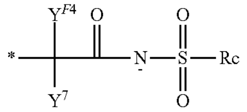

(B-8)

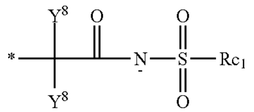

(B-9)

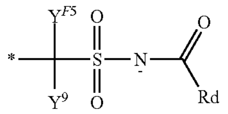

(B-10)

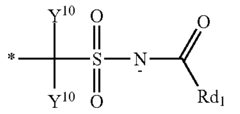

(B-11)

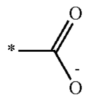

-continued (B-12)

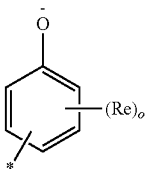

(B-13)

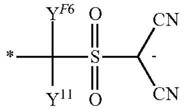

(B-14)

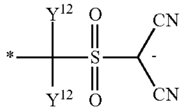

(B-15)

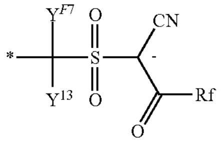

(B-16)

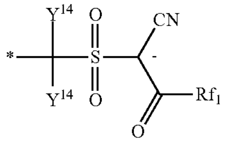

(B-17)

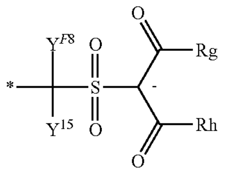

(B-18)

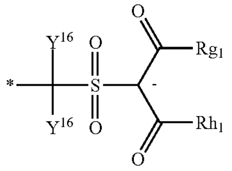

(B-19)

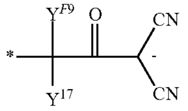

(B-20)

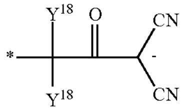

(B-21)

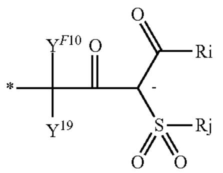

-continued (B-22)

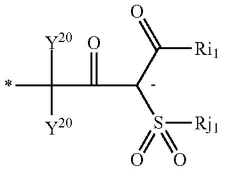

(B-23)

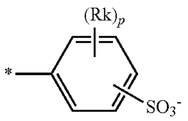

(B-24)

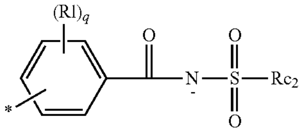

(B-25)

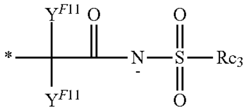

(B-26)

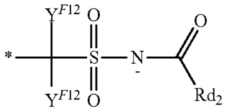

(B-27)

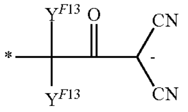

In General Formula (B-1).

$Y^{F1}$ represents a fluorine atom or a perfluoroalkyl group.

$Y^1$ represents a hydrogen atom or a substituent having no fluorine atom.

In General Formula (B-2), $Y^2$'s each independently represent a hydrogen atom or a substituent having no fluorine atom.

In General Formula (B-3), $Y^{F2}$ represents a fluorine atom or a perfluoroalkyl group.

$Y^3$ represents a hydrogen atom or a substituent having no fluorine atom.

Ra represents an organic group.

In General Formula (B-4), $Y^4$'s each independently represent a hydrogen atom or a substituent having no fluorine atom.

$Ra_1$ represents an organic group.

In General Formula (B-5), $Y^{F3}$ represents a fluorine atom or a perfluoroalkyl group.

$Y^5$ represents a hydrogen atom or a substituent having no fluorine atom.

$R_b$ represents a hydrogen atom or an organic group.

In General Formula (B-6), $Y^6$'s each independently represent a hydrogen atom or a substituent having no fluorine atom.

$Rb_1$ represents a hydrogen atom or an organic group.

In General Formula (B-7), $Y^{F4}$ represents a fluorine atom or a perfluoroalkyl group.

$Y^7$ represents a hydrogen atom or a substituent having no fluorine atom.

Rc represents an organic group.

In General Formula (B-8), $Y^8$'s each independently represent a hydrogen atom or a substituent having no fluorine atom.

$Rc_1$ represents an organic group.

In General Formula (B-9), $Y^{F5}$ represents a fluorine atom or a perfluoroalkyl group.

$Y^9$ represents a hydrogen atom or a substituent having no fluorine atom.

Rd represents an organic group.

In General Formula (B-10), $Y^{10}$'s each independently represent a hydrogen atom or a substituent having no fluorine atom.

$Rd_1$ represents an organic group.

In General Formula (B-12),

Re represents a hydrogen atom, an organic group, or a halogen atom.

o represents an integer of 1 to 4.

In a case where o represents an integer of 2 or more, a plurality of Re's may be the same as or different from each other.

In General Formula (B-13).

$Y^{F6}$ represents a fluorine atom or a perfluoroalkyl group.

$Y^{11}$ represents a hydrogen atom or a substituent having no fluorine atom.

In General Formula (B-14), $Y^{12}$'s each independently represent a hydrogen atom or a substituent having no fluorine atom.

In General Formula (B-1S).

$Y^{F7}$ represents a fluorine atom or a perfluoroalkyl group.

$Y^{13}$ represents a hydrogen atom or a substituent having no fluorine atom.

Rf represents an organic group.

In General Formula (B-16), $Y^{14}$'s each independently represent a hydrogen atom or a substituent having no fluorine atom.

$Rf_1$ represents an organic group.

In General Formula (B-17), $Y^{F8}$ represents a fluorine atom or a perfluoroalkyl group.

$Y^{15}$ represents a hydrogen atom or a substituent having no fluorine atom.

Rg represents an organic group.

Rh represents an organic group.

In General Formula (B-18), $Y^{16}$'s each independently represent a hydrogen atom or a substituent having no fluorine atom.

$Rg_1$ represents an organic group.

$Rh_1$ represents an organic group.

In General Formula (B-19).

$Y^{F9}$ represents a fluorine atom or a perfluoroalkyl group.

$Y^{17}$ represents a hydrogen atom or a substituent having no fluorine atom.

In General Formula (B-20), $Y^{18}$'s each independently represent a hydrogen atom or a substituent having no fluorine atom.

In General Formula (B-21), $Y^{F10}$ represents a fluorine atom or a perfluoroalkyl group.

$Y^{19}$ represents a hydrogen atom or a substituent having no fluorine atom.

Ri represents an organic group.

Rj represents an organic group.

In General Formula (B-22), $Y^{20}$'s each independently represent a hydrogen atom or a substituent having no fluorine atom.

Ri represents an organic group.

$Rj_1$ represents an organic group.

In General Formula (B-23),

Rk represents a hydrogen atom or a substituent having no fluorine atom.

p represents an integer of 1 to 4.

In a case where p represents an integer of 2 or more, a plurality of Rk's may be the same as or different from each other.

In General Formula (B-24),

Rl represents a hydrogen atom, an organic group, or a halogen atom.

q represents an integer of 1 to 4.

In a case where q represents an integer of 2 or more, a plurality of Rl's may be the same as or different from each other.

$Rc_2$ represents an organic group.

In General Formula (B-25), $Y^{F11}$'s each independently represent a fluorine atom or a perfluoroalkyl group.

$Rc_3$ represents an organic group.

In General Formula (B-26), $Y^{F12}$'s each independently represent a fluorine atom or a perfluoroalkyl group.

$Rd_2$ represents an organic group.

In General Formula (B-27), $Y^{F13}$ 's each independently represent a fluorine atom or a perfluoroalkyl group.

In General Formulae (B-1) to (B-27),

* represents a bonding position.

$A_1^-$ represents a structure different from the group represented by $A_2^-$.

m represents 1 or 2. In a case where m represents 2, a plurality of $M_1^+$'s may be the same as or different from each other. In a case where m represents 2, a plurality of $A_1^-$'s may be the same as or different from each other.

$R_A$, $R_B$, $R_C$, $L_A$, $Ar_A$, and n in General Formula (AI) are the same as $R_A$, $R_B$, $R_C$, $L_A$, $Ar_A$, and n in General Formula (A 1) in the resin (A), respectively.

$M_1^+$, $M_2^+$, and X in General Formula (I), and each group in General Formulae (B-1) to (B-27) are the same as $M_1^+$, $M_2^+$, and X in General Formula (I), and each group in General Formulae (B-1) to (B-27), respectively, in the compound (B).

Examples

Hereinbelow, the present invention will be described in more detail with reference to Examples. The materials, the amounts of materials used, the proportions, the treatment details, the treatment procedure, and the like shown in Examples below may be appropriately modified as long as the modifications do not depart from the spirit of the present invention. Therefore, the scope of the present invention should not be construed as being limited to Examples shown below.

<Resin (A)>

The structures of the repeating nits and contents (molar ratios) thereof, the weight-average molecular weights (Mw), and the dispersities (Mw/Mn) of the resin (A) used are shown below.

Furthermore, the resin A'-1 is not the resin (A), but will be described below for convenience.

(A-1)
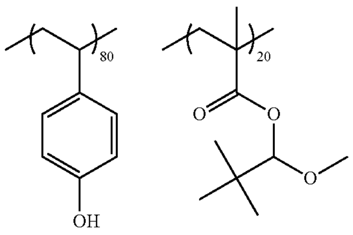
Mw = 8800
Mw/Mn = 1.6
(A-2)
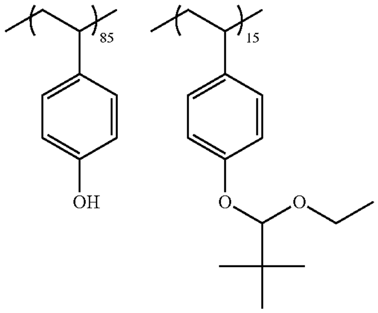
Mw = 4600
Mw/Mn = 1.2
(A-3)
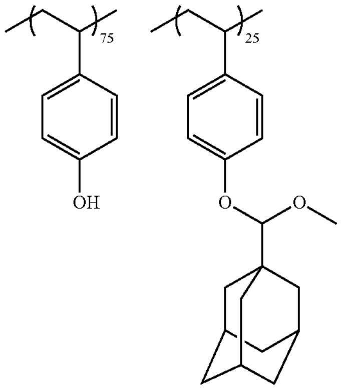
Mw = 5000
Mw/Mn = 1.4
(A-4)
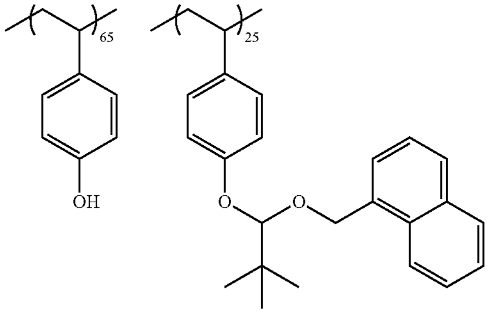
-continued
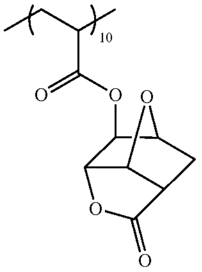
Mw = 9000
Mw/Mn = 1.6
(A-5)
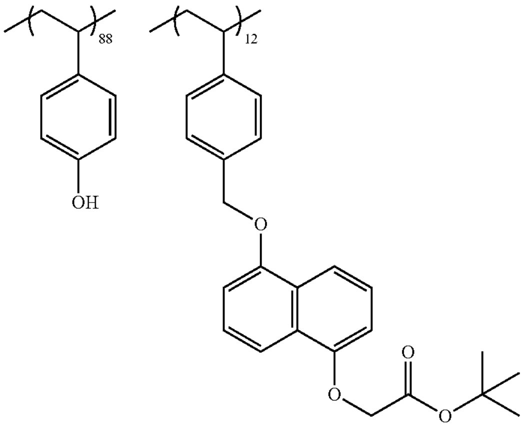
Mw = 7000
Mw/Mn = 1.4
(A-6)
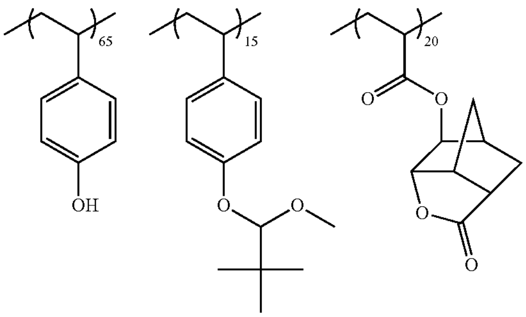
Mw = 6000
Mw/Mn = 1.6
(A-7)
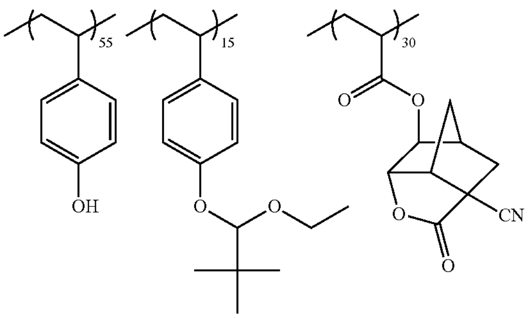
Mw = 12000
Mw/Mn = 1.7

-continued
(A-8)
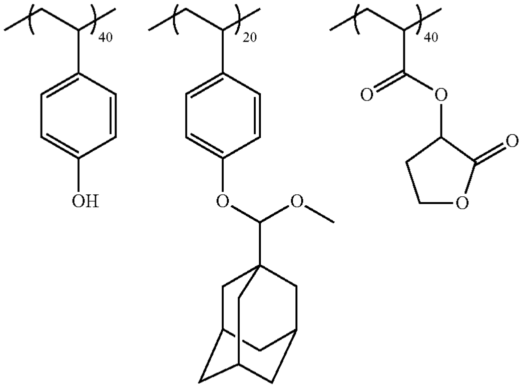
Mw = 5000
Mw/Mn = 1.7
(A-9)
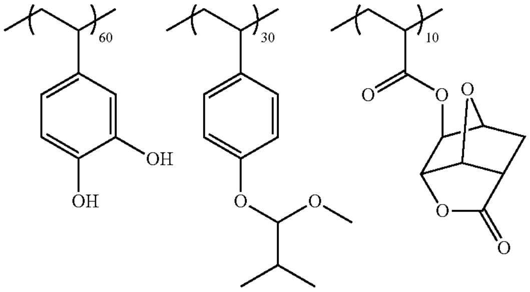
Mw = 9000
Mw/Mn = 1.6
(A-10)
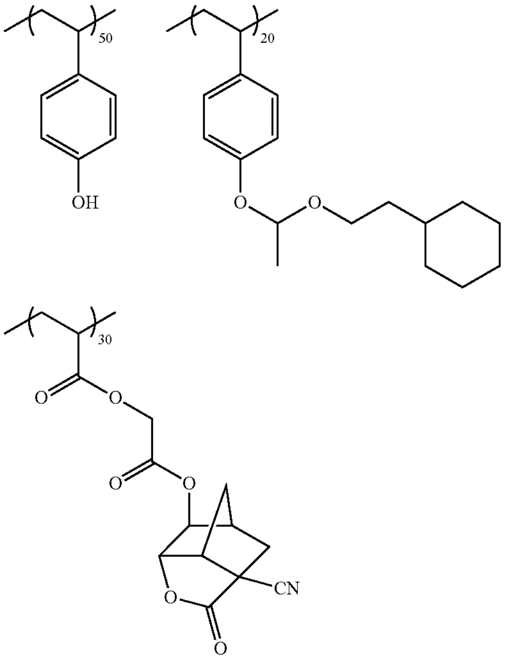
Mw = 15000
Mw/Mn = 1.7
-continued
(A-11)
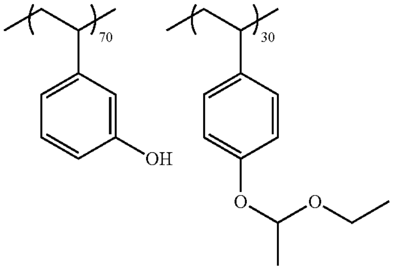
Mw = 8000
Mw/Mn = 1.7
(A-12)
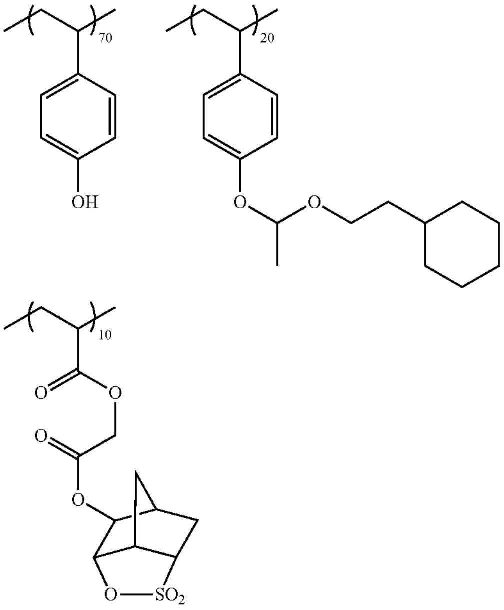
Mw = 7300
Mw/Mn = 1.5
(A-13)
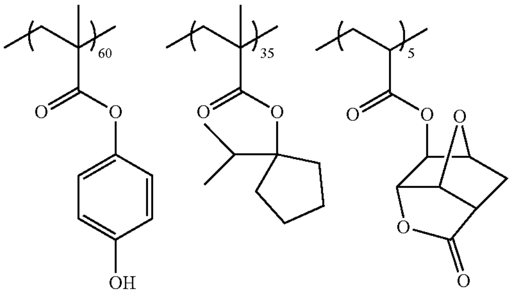
Mw = 12000
Mw/Mn = 1.6
(A-14)
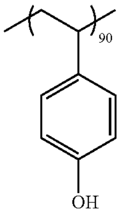

-continued
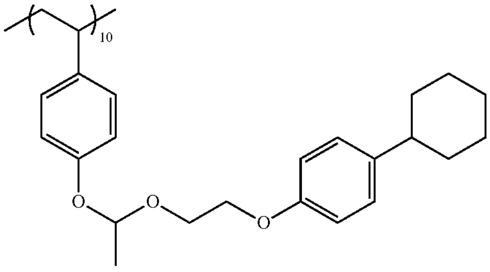
Mw = 18000
Mw/Mn = 1.2
(A-15)
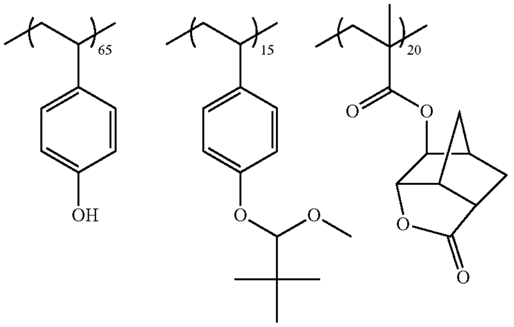
Mw = 5500
Mw/Mn = 1.7
(A-16)
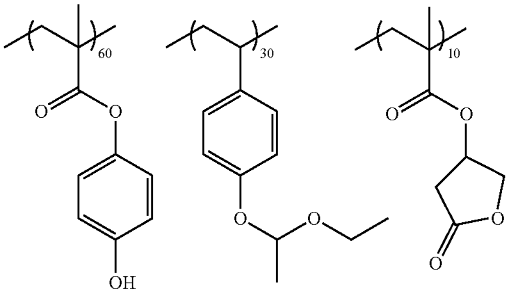
Mw = 9000
Mw/Mn = 1.6
(A-17)
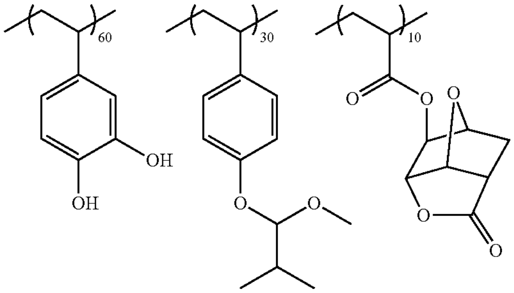
Mw = 9000
Mw/Mn = 1.6
-continued
(A-18)
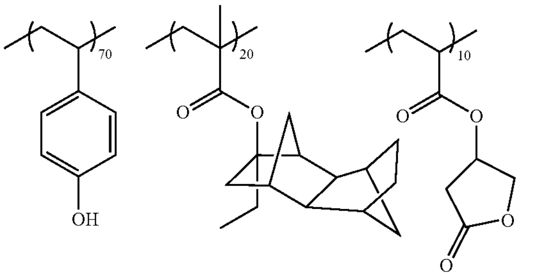
Mw = 10000
Mw/Mn = 1.6
(A-19)
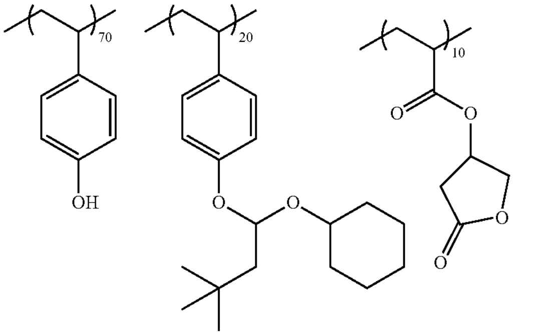
Mw = 5500
Mw/Mn = 1.7
(A-20)
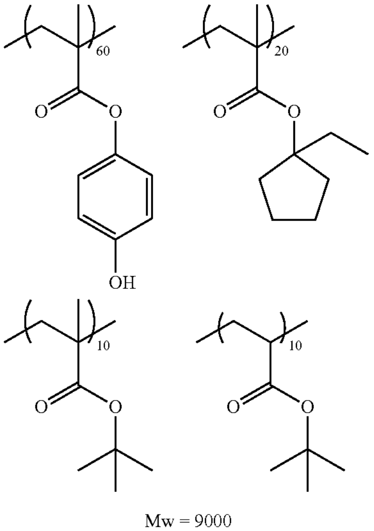
Mw = 9000
Mw/Mn = 1.7
(A-21)
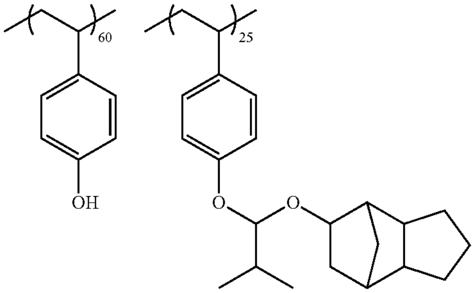

-continued
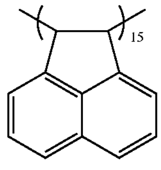
Mw = 5000
Mw/Mn = 1.8
(A-22)
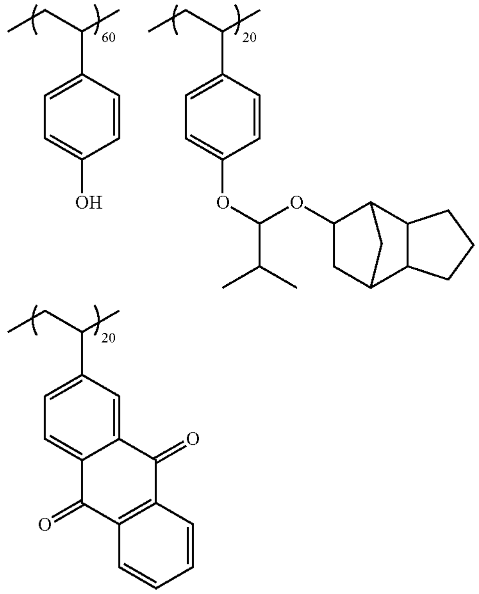
Mw = 10000
Mw/Mn = 1.7
(A-23)
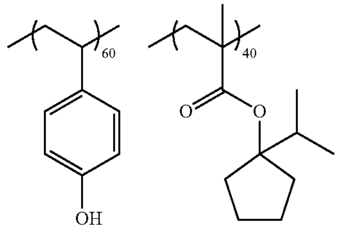
Mw = 7000
Mw/Mn = 1.7
(A-24)
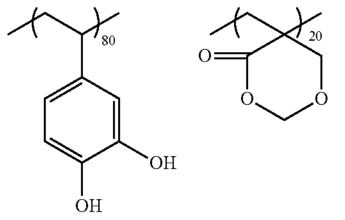
Mw = 5000
Mw/Mn = 1.8
-continued
(A-25)
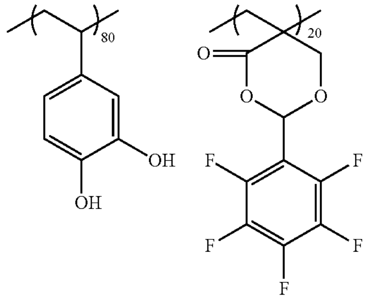
Mw = 8000
Mw/Mn = 1.8
(A-26)
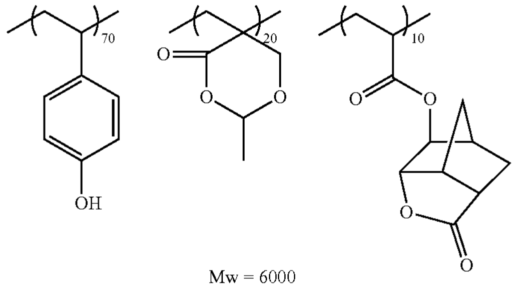
Mw = 6000
Mw/Mn = 1.7
(A-27)
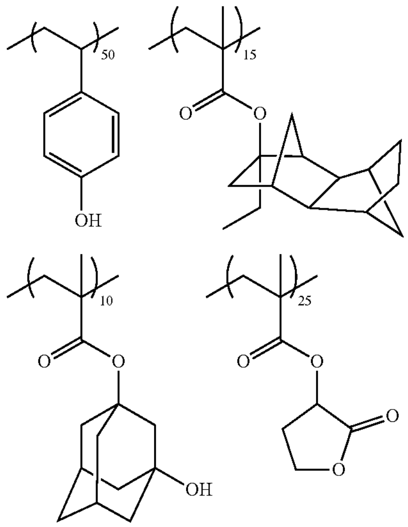
Mw = 8000
Mw/Mn = 1.8
(A-28)
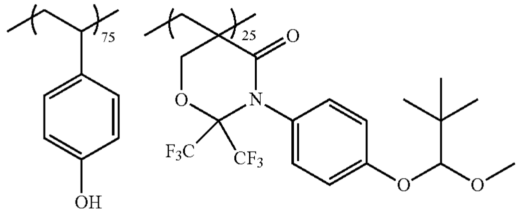
Mw = 7000
Mw/Mn = 1.8

-continued
(A-29)
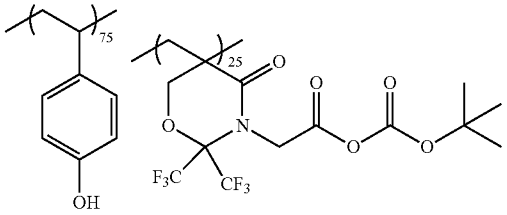
Mw = 10000
Mw/Mn = 1.8
(A-30)
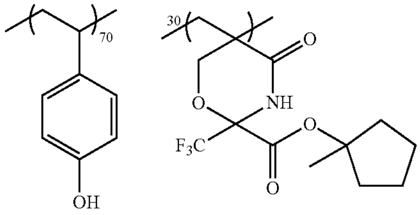
Mw = 8000
Mw/Mn = 1.8
(A-31)
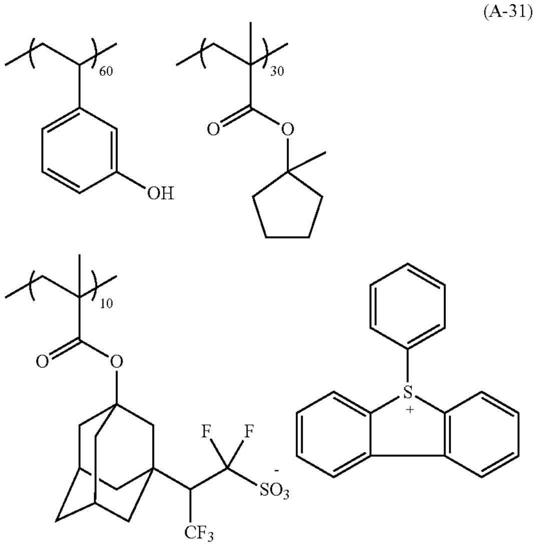
Mw = 7000
Mw/Mn = 1.7
(A-32)
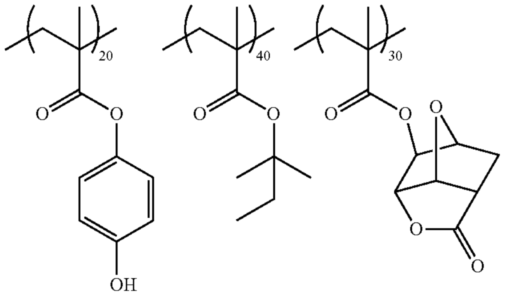
-continued
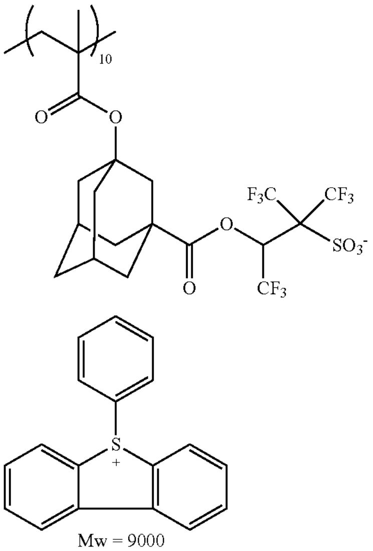
Mw = 9000
Mw/Mn = 1.8
(A-33)
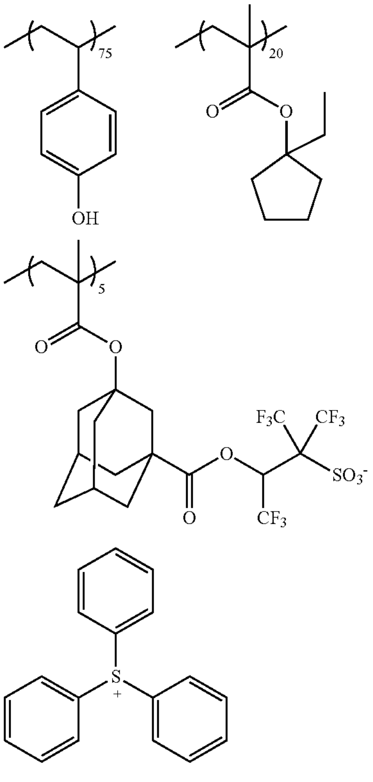
Mw = 10000
Mw/Mn = 1.5
(A-34)
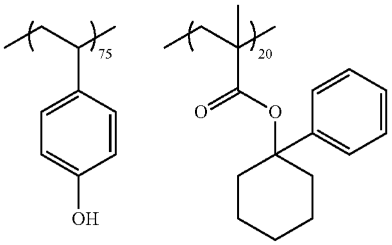

-continued

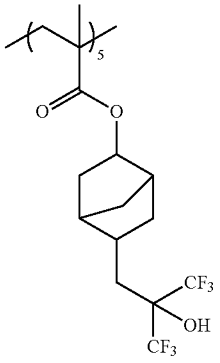

Mw = 7500
Mw/Mn = 1.6

(A'-1)

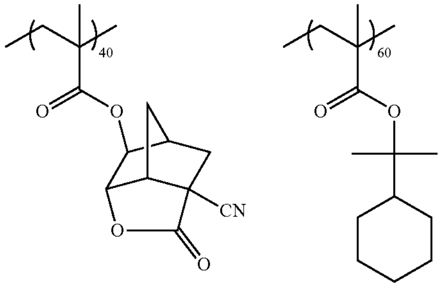

Mw = 11000
Mw/Mn = 1.7

The number attached to the repeating unit on the left side in the resin (A-30) represents a content (molar ratio) of the repeating unit.

<Photoacid Generator (B)>

The compounds (B-1) to (B-27) are each a compound obtained by a combination of a cation shown in Table 1 and an anion shown in Table 1. Furthermore, with regard to the cations, the number of cations included in the compound is also described.

The following compound (B'-1) was used in Comparative Examples.

(B'-1)

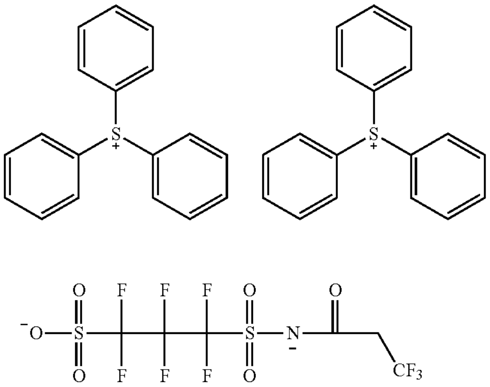

TABLE 1

| Photoacid | Cation | | Anion |
|---|---|---|---|
| generator | Type | Number | Type |
| B-1 | 1 | 2 | 1 |
| B-2 | 2 | 2 | 2 |
| B-3 | 3 | 2 | 3 |
| B-4 | 4 | 2 | 4 |
| B-5 | 5 | 2 | 5 |
| B-6 | 6 | 2 | 6 |
| B-7 | 7 | 2 | 7 |
| B-8 | 8 | 2 | 8 |
| B-9 | 1 | 1 | 9 |
| | 9 | 1 | |
| B-10 | 10 | 2 | 10 |
| B-11 | 11 | 2 | 11 |
| B-12 | 12 | 2 | 12 |
| B-13 | 13 | 2 | 13 |
| B-14 | 14 | 2 | 14 |
| B-15 | 15 | 3 | 15 |
| B-16 | 16 | 2 | 16 |
| B-17 | 17 | 2 | 17 |
| B-18 | 18 | 2 | 18 |
| B-19 | 19 | 2 | 19 |
| B-20 | 1 | 2 | 20 |
| B-21 | 1 | 2 | 21 |
| B-22 | 1 | 2 | 22 |
| B-23 | 1 | 2 | 23 |
| B-24 | 1 | 2 | 24 |
| B-25 | 1 | 2 | 25 |
| B-26 | 1 | 2 | 26 |
| B-27 | 1 | 2 | 27 |

The structures of cations shown in Table 1 are shown below. Me represents a methyl group and Bu represents an n-butyl group.

1

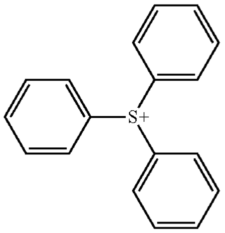

2

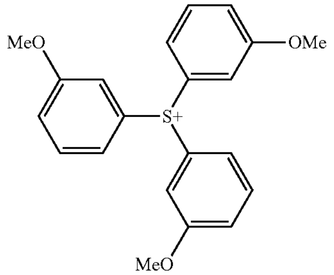

3

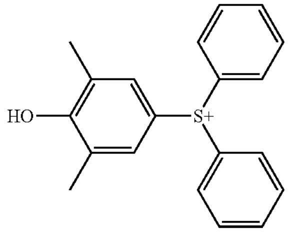

-continued
4
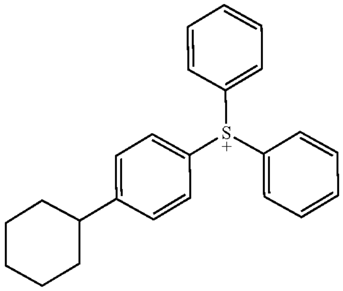
5
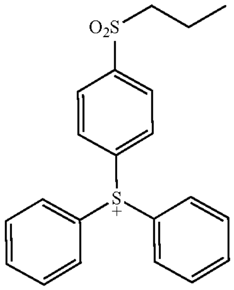
6
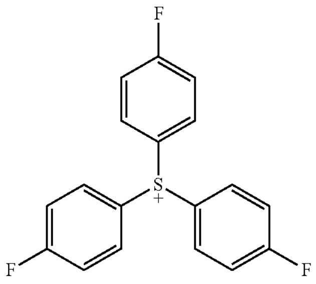
7
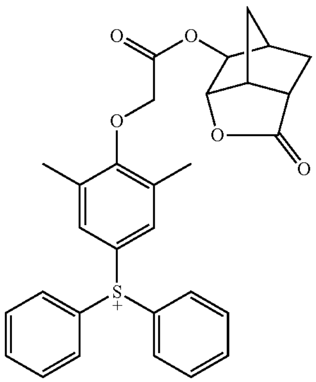
8
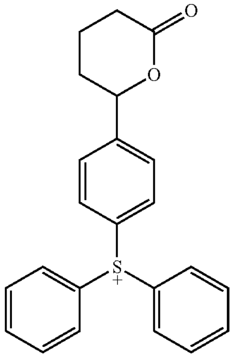
-continued
9
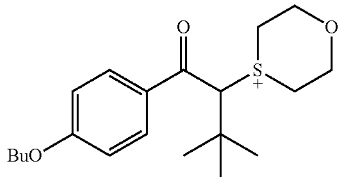
10
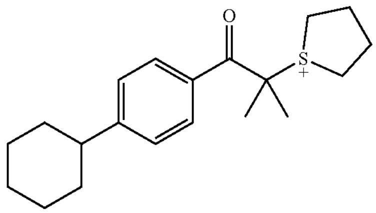
11
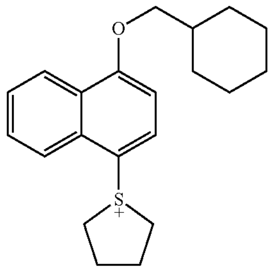
12
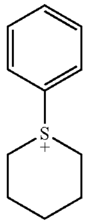
13
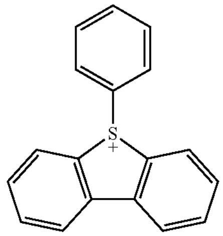
14
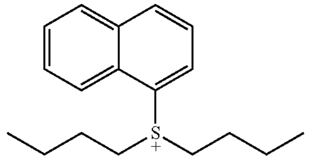
15
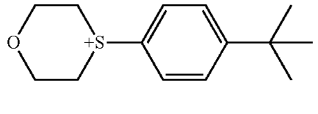

-continued
16
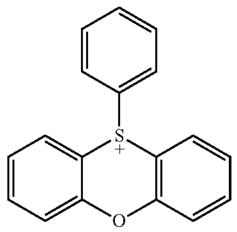
17
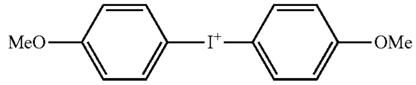
18
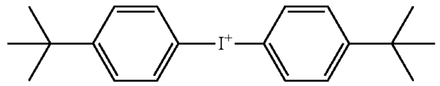
19
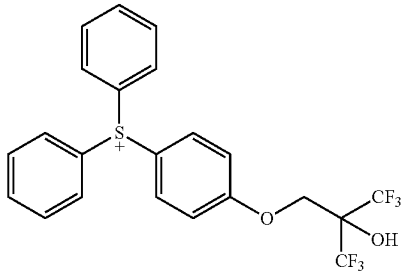
The structures of anions shown in Table 1 are shown below. Me represents a methyl group and Bu represents an n-butyl group.
1
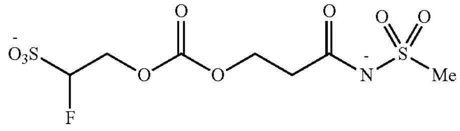
2
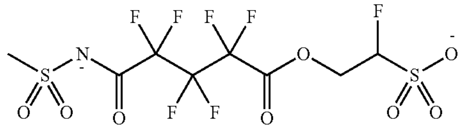
3
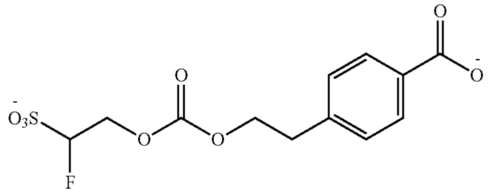
4
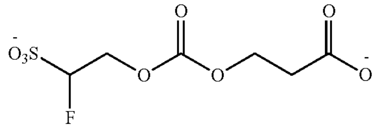
-continued
5
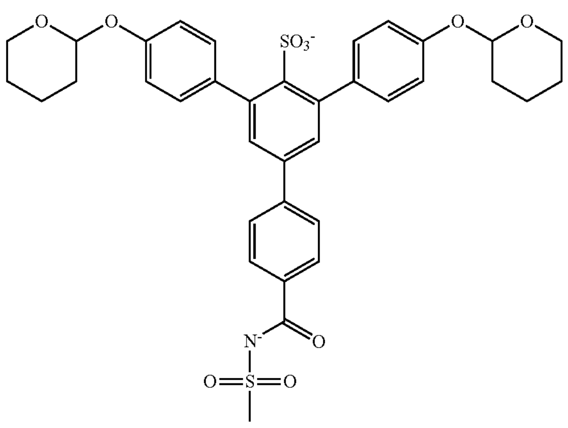
6
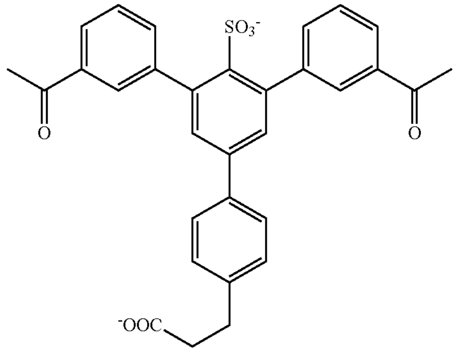
7
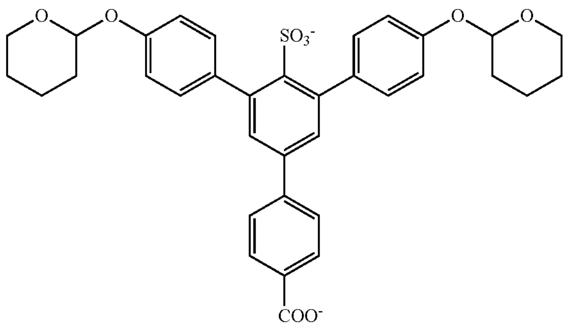
8
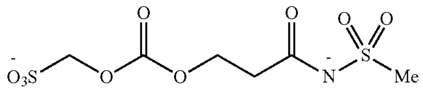
9
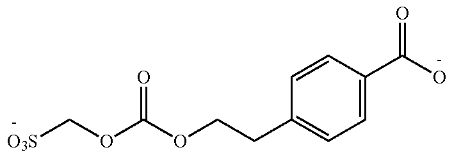
10
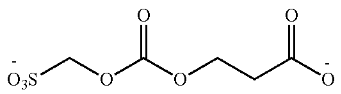

-continued
11
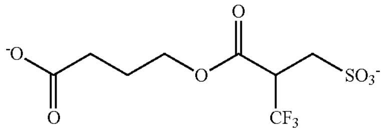
12
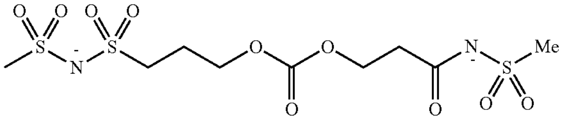
13
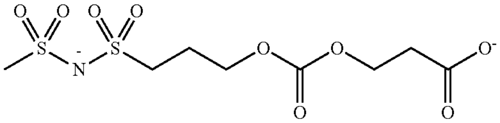
14
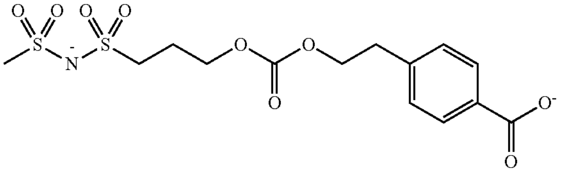
15
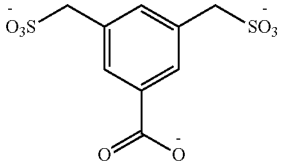
16
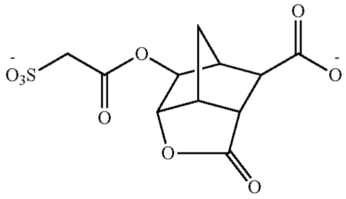
17
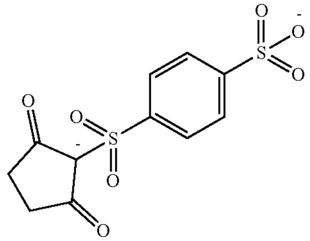
18
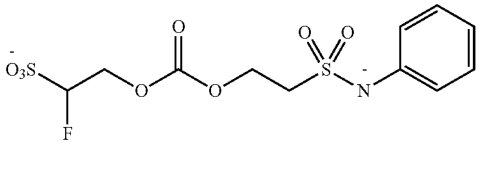
-continued
19
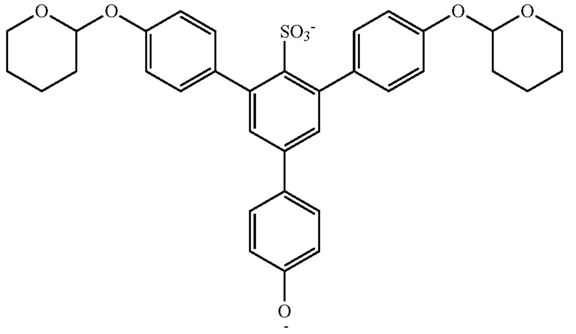
20
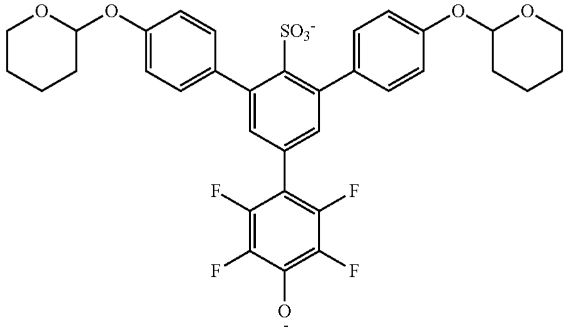
21
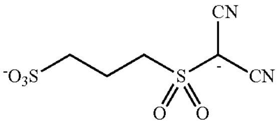
22
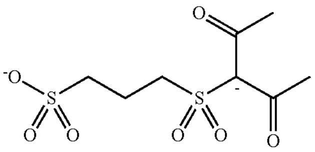
23
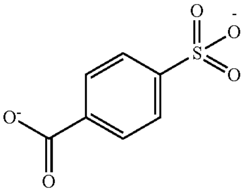
24
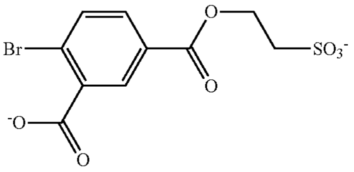

-continued

25

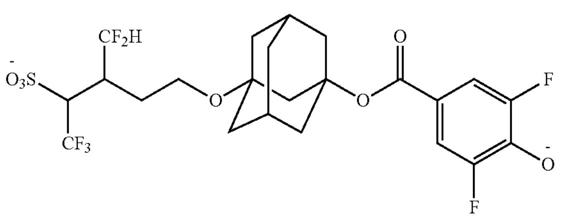

26

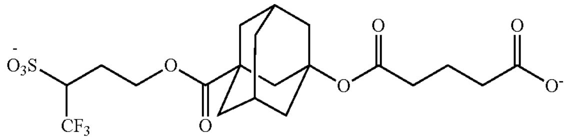

27

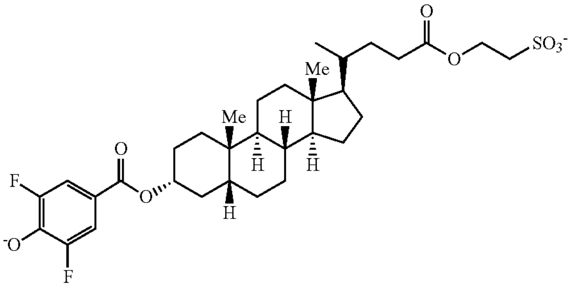

(Acid Dissociation Constant pKa of Acid Generated from Photoacid Generator)

The acid dissociation constant pKa of an acid generated from the photoacid generator is shown in Table 2.

Furthermore, in the measurement of the acid dissociation constant pKa of an acid generated from the photoacid generator, specifically, the pKa is a value determined by subjecting a compound formed by substituting each cationic moiety in the compounds B-1 to B-27 with H' (for example, in a case of the compound B-1, a compound formed by substituting the triphenylsulfonium cation with H') to computation from a value based on a Hammett's substituent constant and database of publicly known literature values, using Software Package 1 of ACD/Labs, as described above. In addition, in a case where pKa could not be calculated by the method, a value obtained by Gaussian 16 based on density functional theory (DFT) was adopted.

In the following table, "pKa1" represents an acid dissociation constant of the first stage, "pKa2" represents an acid dissociation constant of the second stage, and "pKa3" represents an acid dissociation constant of the third stage. A smaller value of pKa means a higher acidity.

As described above, the compounds B-1 to B-14, and B-16 to B-27 correspond to the above-mentioned compound (B). Here, pKa1 corresponds to the above-mentioned acid dissociation constant a1, and pKa2 corresponds to the above-mentioned acid dissociation constant a2.

In addition, as described above, the compound B-15 also corresponds to the above-mentioned compound (B). Here, pKa1 corresponds to the above-mentioned acid dissociation constant a1, and pKa3 corresponds to the above-mentioned acid dissociation constant a2.

Since an acid (a compound formed by substituting the sulfonium cation of the compound B-15 with H') generated from the compound B-15 has a symmetric structure, the acid dissociation constants pKa of the two first acidic moieties ($HA_1$) are theoretically the same value. However, in the above-mentioned calculation method, the acid dissociation constants of the two first acidic moieties ($HA_1$) are obtained as the acid dissociation constant pKa1 of the first stage and the acid dissociation constant pKa2 of the second stage. For the acid generated from the compound B-15, the smallest value (that is, the acid dissociation constant pKa1) of the acid dissociation constants pKa of the two first acidic moieties ($HA_1$) corresponds to the above-mentioned acid dissociation constant a1.

TABLE 2

| Photoacid generator B | pKa1 | pKa2 | pKa3 |
|---|---|---|---|
| B-1 | −0.83 | 4.14 | — |
| B-2 | −0.92 | 1.92 | — |
| B-3 | −0.82 | 4.24 | — |
| B-4 | −0.83 | 3.96 | — |
| B-5 | −0.86 | 3.32 | — |
| B-6 | −0.95 | 4.58 | — |
| B-7 | −0.8 | 3.90 | — |
| B-8 | 0.05 | 4.15 | — |
| B-9 | 0.07 | 4.24 | — |
| B-10 | 0.05 | 3.98 | — |
| B-11 | 0.86 | 4.49 | — |
| B-12 | −0.05 | 4.15 | — |
| B-13 | −0.05 | 3.97 | — |
| B-14 | −0.05 | 4.24 | — |
| B-15 | 0.79 | 1.53 | 4.16 |
| B-16 | 0.42 | 4.06 | — |
| B-17 | −0.82 | −0.56 | — |
| B-18 | −0.92 | 1.92 | — |
| B-19 | −0.58 | 9.09 | — |
| B-20 | −1.3 | 4.64 | — |
| B-21 | 1.64 | 2.3 | — |
| B-22 | 1.44 | 4.86 | — |
| B-23 | −1.47 | 3.89 | — |
| B-24 | 1.01 | 2.5 | — |
| B-25 | −0.54 | 5.72 | — |
| B-26 | −0.29 | 4.61 | — |
| B-27 | 1.08 | 5.68 | — |
| B'-1 | −3.41 | −0.24 | — |

<Acid Diffusion Control Agent>

The structures of the acid diffusion control agents used are shown below.

(C-1)

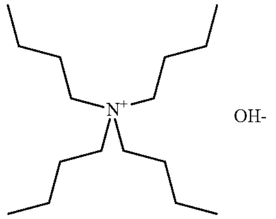

(C-2)

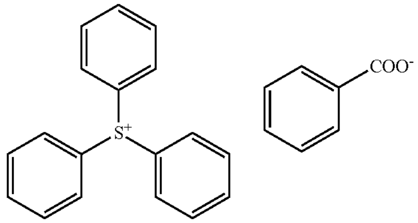

(C-3)

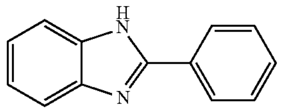

-continued
(C-4)
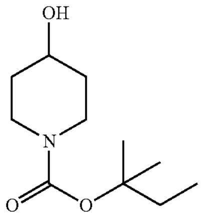
(C-5)
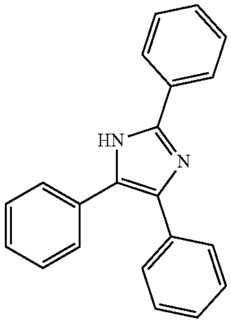
(C-6)
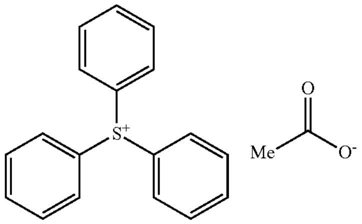
(C-7)
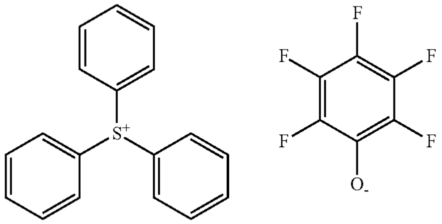
(C-8)
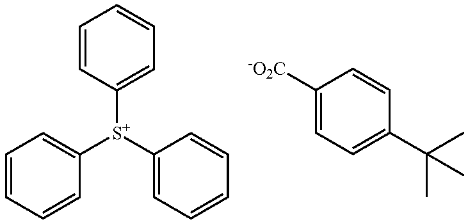
(C-9)
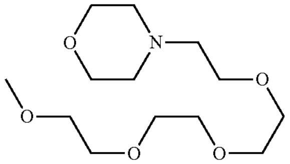
-continued
(C-10)
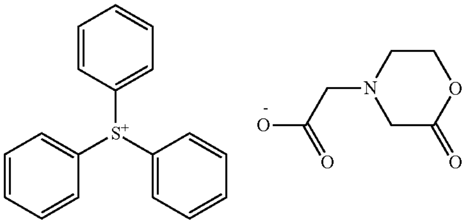
(C-11)
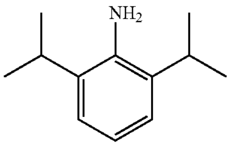
(C-12)
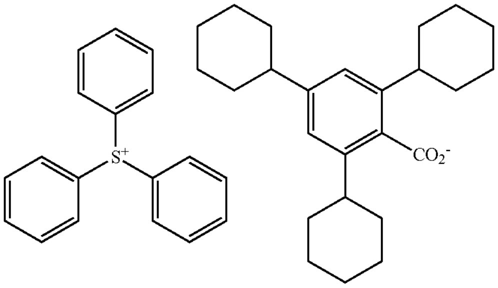
(C-13)
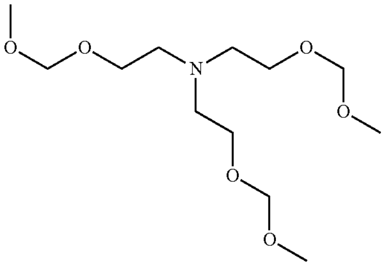
(C-14)
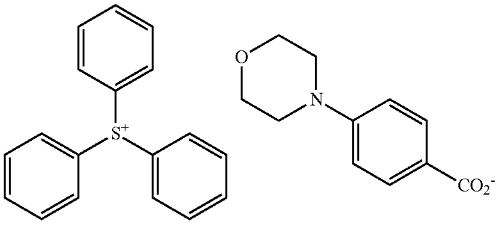
(C-15)
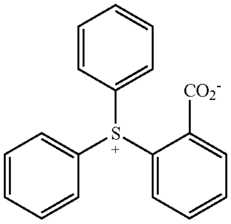

-continued
(C-16)
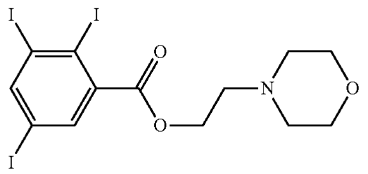
<Photoacid Generator (B')>
The structures of the photoacid generators (B') used are shown below.
(D-1)
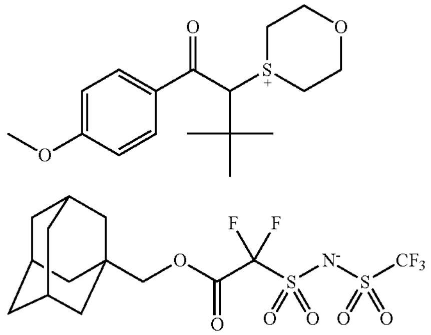
(D-2)
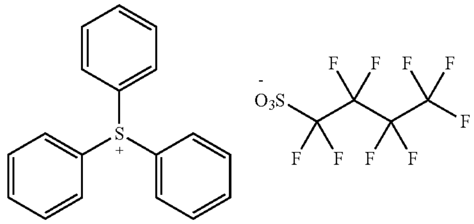
(D-3)
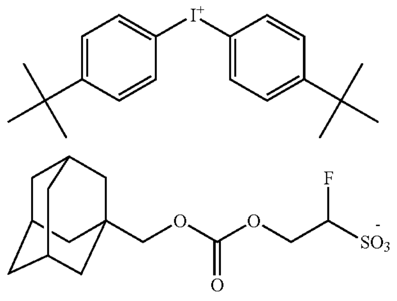
(D-4)
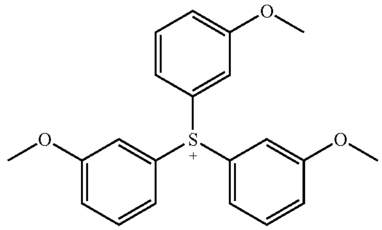
-continued
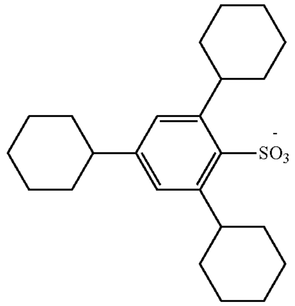
(D-5)
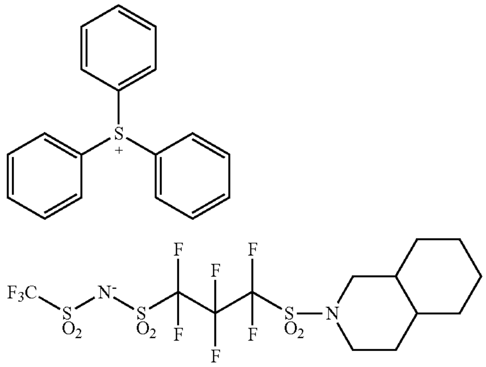
(D-6)
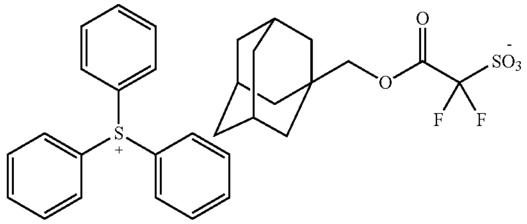
(D-7)
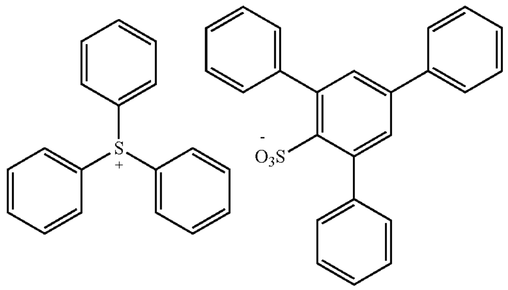
(D-8)
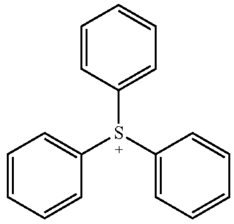

-continued

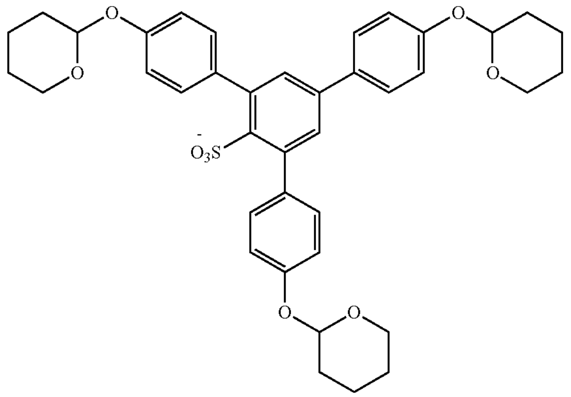

(D-9)

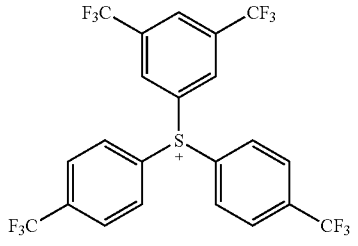

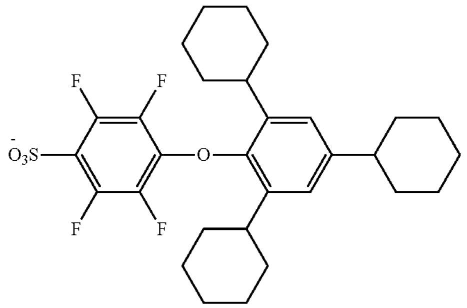

(D-10)

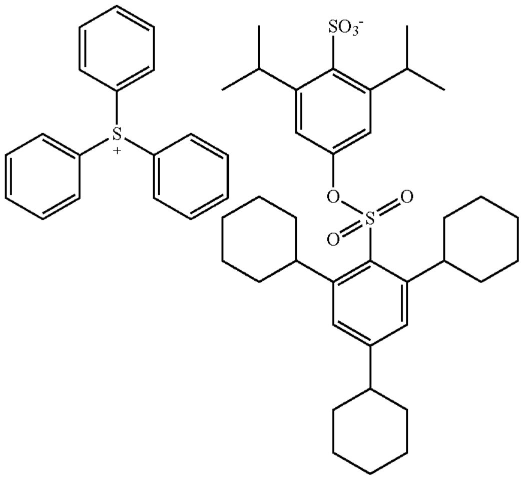

-continued (D-11)

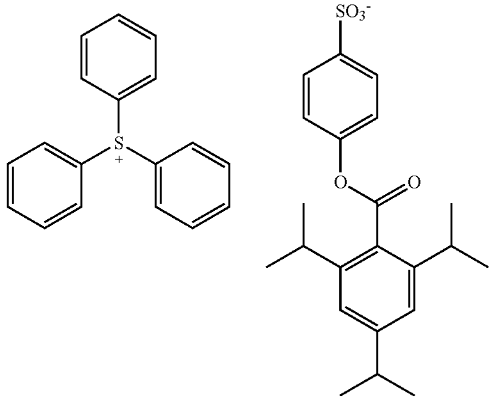

<Surfactant>

The following W-1 to W-4 were used as a surfactant.

W-1: MEGAFACE R08 (manufactured by Dainippon Ink and Chemicals Inc.; fluorine- and silicon-based)

W-2: Polysiloxane Polymer KP-341 (manufactured by Shin-Etsu Chemical Co., Ltd.; silicon-based)

W-3: TROYSOL S-366 (manufactured by Troy Chemical Corporation: fluorine-based)

W-4: PF6320 (manufactured by OMNOVA Solutions Inc.; fluorine-based)

<Solvent>

The solvents used are shown below.

S-1: Propylene glycol monomethyl ether acetate (PGMEA)

S-2: Propylene glycol monomethyl ether (PGME)

S-3: Ethyl lactate (EL)

S-4: Ethyl 3-ethoxypropionate (EEP)

S-5: 2-Heptanone (MAK)

S-6: Methyl 3-methoxypropionate (MMP)

S-7: 3-Methoxybutyl acetate

[Preparation and Coating of Coating Liquid of Resist Composition]

(1) Preparation of Support

An 8-inch wafer on which Cr oxynitride had been vapor-deposited (a product for which a shielding film treatment used for an ordinary photomask blank had been carried out) was prepared.

(2) Preparation of Resist Composition

The components-shown in Table 3 were dissolved in the solvents shown in the same table to prepare solutions, which were filtered through a polyethylene filter having a pore size of 0.03 μm to prepare resist compositions.

(3) Manufacture of Resist Film

A resist composition was applied onto the 8-inch wafer using a spin coater Mark8 manufactured by Tokyo Electron Limited, and dried on a hot plate at 120° C. for 600 seconds to obtain a resist film having a film thickness of 100 nm. That is, a resist-coated wafer was obtained.

[EB Exposure and Development]

(4) Manufacture of Resist Pattern

The resist film obtained in (3) above was subjected to patternwise irradiation using an electron beam drawing apparatus (manufactured by Advantest Corporation; F7000S, accelerating voltage: 50 KeV). After the irradiation, the film was heated on a hot plate at 100° C. for 600 seconds, dipped using a 2.38%-by-mass aqueous tetramethylammonium hydroxide (TMAH) solution for 60 seconds, then rinsed with water for 30 seconds, and dried.

[Evaluation]

(5) Evaluation of Resist Pattern

The obtained pattern was evaluated on a resolution and roughness performance by the following methods. The results are shown in Table 4 later.

The irradiation energy upon resolution of a 1:1 line-and-space pattern with a line width of 50 nm was defined as a sensitivity (Eop).

<L/S Resolution>

A marginal resolving power (a minimum line width at which lines and spaces (line:space=1:1) are separated and resolved) at an exposure amount showing the sensitivity (Eop) was taken as a resolving power (nm).

<Isolated Space Pattern (IS) Resolution>

A marginal resolving power (a minimum space width at which lines and spaces are separated and resolved) of an isolated space (line:space=100:1) at the sensitivity (Eop) was determined. Then, this value was defined as an "isolated space pattern resolving power (nm)". A smaller value thereof indicates better performance.

<Roughness Performance (LWR)>

In a case where a 30 nm (1:1) line-and-space pattern resolved with an optimum exposure amount upon resolving a line pattern having an average line width of 20 nm was observed from the upper part of the pattern using a critical dimension scanning electron microscope (SEM (S-938011 manufactured by Hitachi. Ltd.)), the line width was observed at any points, and a measurement deviation thereof was evaluated as 3a (nm). A smaller value thereof indicates better performance.

Furthermore, in Table 3 below, the content (% by mass) of each component other than the solvent means a content ratio with respect to the total solid content. In addition, a content ratio (% by mass) with respect to the total solvent of the solvents used is described in Table 3 below.

TABLE 3

| Resist composition | Resin (A) Type | Resin (A) Content (% by mass) | Photoacid generator (B) Type | Photoacid generator (B) Content (% by mass) | Acid diffusion control agent (C) Type | Acid diffusion control agent (C) Content (% by mass) | Photoacid generator (B') Type | Photoacid generator (B') Content (% by mass) | Surfactant Type (0.01% by mass) |
|---|---|---|---|---|---|---|---|---|---|
| R-1 | (A-1) | 89.79 | (B-1) | 10.00 | (C-1) | 0.20 | — | — | W-1 |
| R-2 | (A-2) | 84.90 | (B-2) | 15.00 | (C-2) | 0.10 | — | — | — |
| R-3 | (A-3) | 89.79 | (B-3) | 10.00 | (C-3) | 0.20 | — | — | W-1 |
| R-4 | (A-4) | 88.90 | (B-4) | 10.00 | (C-4) | 0.10 | (D-1) | 1.00 | — |
| R-5 | (A-5) | 77.29 | (B-5) | 20.00 | (C-5) | 0.20 | (D-2) | 2.50 | W-2 |
| R-6 | (A-6) | 79.80 | (B-6) | 20.00 | (C-6) | 0.20 | — | — | — |
| R-7 | (A-7) | 79.80 | (B-7) | 15.00 | (C-7) | 0.20 | (D-3) | 5.00 | — |
| R-8 | (A-8) | 77.20 | (B-8) | 20.00 | (C-8) | 0.30 | (D-4) | 2.50 | — |
| R-9 | (A-9) | 84.89 | (B-9) | 15.00 | (C-9) | 0.10 | — | — | W-4 |
| R-10 | (A-10) | 89.70 | (B-10) | 10.00 | (C-10) | 0.30 | — | — | — |
| R-11 | (A-11) | 84.80 | (B-11) | 15.00 | (C-11) | 0.20 | — | — | — |
| R-12 | (A-12) | 79.70 | (B-12) | 20.00 | (C-12) | 0.30 | — | — | — |
| R-13 | (A-13) | 89.89 | (B-13) | 10.00 | (C-13) | 0.10 | — | — | W-1 |
| R-14 | (A-14) | 82.30 | (B-14) | 15.00 | (C-14) | 0.20 | (D-5) | 2.50 | — |
| R-15 | (A-15) | 89.80 | (B-15) | 10.00 | (C-1) | 0.20 | — | — | — |
| R-16 | (A-16) | 84.79 | (B-16) | 15.00 | (C-2) | 0.20 | — | — | W-2 |
| R-17 | (A-17) | 79.90 | (B-17) | 20.00 | (C-3) | 0.10 | — | — | — |
| R-18 | (A-18) | 94.70 | (B-18) | 5.00 | (C-4) | 0.30 | — | — | — |
| R-19 | (A-19) | 88.90 | (B-19) | 10.00 | (C-5) | 0.10 | (D-6) | 1.00 | — |
| R-20 | (A-20) | 94.69 | (B-20) | 5.00 | (C-6) | 0.30 | — | — | W-1 |

| Resist composition | Solvent 1 | Content ratio of solvent 1 (% by mass) | Solvent 2 | Content ratio of solvent 2 (% by mass) | Solvent 3 | Content ratio of solvent 3 (% by mass) | Concentration of solid contents (% by mass) |
|---|---|---|---|---|---|---|---|
| R-1 | S-1 | 70 | S-2 | 30 | — | — | 2.5 |
| R-2 | S-1 | 80 | S-2 | 10 | S-3 | 10 | 3.0 |
| R-3 | S-1 | 70 | S-2 | 20 | S-3 | 10 | 3.0 |
| R-4 | S-1 | 60 | S-2 | 20 | S-3 | 20 | 2.5 |
| R-5 | S-1 | 80 | S-2 | 10 | S-3 | 10 | 3.0 |
| R-6 | S-1 | 50 | S-2 | 20 | S-4 | 30 | 3.0 |
| R-7 | S-1 | 60 | S-3 | 30 | S-5 | 10 | 2.5 |
| R-8 | S-1 | 70 | S-2 | 20 | S-3 | 10 | 3.0 |
| R-9 | S-1 | 50 | S-2 | 20 | S-6 | 30 | 3.0 |
| R-10 | S-1 | 60 | S-4 | 20 | S-5 | 20 | 3.0 |
| R-11 | S-1 | 70 | S-2 | 20 | S-4 | 10 | 2.5 |
| R-12 | S-1 | 50 | S-2 | 30 | S-3 | 20 | 3.0 |
| R-13 | S-1 | 60 | S-2 | 20 | S-3 | 20 | 2.5 |
| R-14 | S-1 | 80 | S-3 | 20 | — | — | 2.5 |
| R-15 | S-1 | 50 | S-2 | 20 | S-3 | 30 | 2.5 |
| R-16 | S-1 | 70 | S-4 | 20 | S-5 | 10 | 2.0 |
| R-17 | S-1 | 60 | S-3 | 30 | S-4 | 10 | 3.0 |
| R-18 | S-1 | 80 | S-4 | 10 | S-5 | 10 | 2.5 |

TABLE 3-continued

| | | | | | | | |
|---|---|---|---|---|---|---|---|
| R-19 | S-1 | 50 | S-2 | 20 | S-3 | 30 | 2.0 |
| R-20 | S-1 | 80 | S-3 | 10 | S-7 | 10 | 3.0 |

TABLE 4

| | Resin (A) | | Photoacid generator (B) | | Acid diffusion control agent (C) | | Photoacid generator (B') | | Surfactant |
|---|---|---|---|---|---|---|---|---|---|
| Resist composition | Type | Content (% by mass) | Type | Content (% by mass) | Type | Content (% by mass) | Type | Content (% by mass) | Type (0.01% by mass) |
| R-21 | (A-21) | 89.80 | (B-21) | 10.00 | (C-7) | 0.20 | — | — | — |
| R-22 | (A-22) | 94.70 | (B-22) | 5.00 | (C-8) | 0.30 | — | — | — |
| R-23 | (A-23) | 79.90 | (B-23) | 20.00 | (C-9) | 0.10 | — | — | — |
| R-24 | (A-24) | 89.80 | (B-24) | 10.00 | (C-10) | 0.20 | — | — | — |
| R-25 | (A-25) | 84.90 | (B-25) | 15.00 | (C-11) | 0.10 | — | — | — |
| R-26 | (A-26) | 89.89 | (B-26) | 10.00 | (C-12) | 0.10 | — | — | W-1 |
| R-27 | (A-27) | 94.80 | (B-27) | 5.00 | (C-13) | 0.20 | — | — | — |
| R-28 | (A-28) | 87.30 | (B-1) | 10.00 | (C-10) | 0.20 | (D-7) | 2.50 | — |
| R-29 | (A-29) | 79.90 | (B-2) | 15.00 | (C-11) | 0.10 | (D-8) | 5.00 | — |
| R-30 | (A-30) | 89.89 | (B-3) | 10.00 | (C-12) | 0.10 | — | — | W-1 |
| R-31 | (A-31) | 94.80 | (B-4) | 5.00 | (C-13) | 0.20 | — | — | — |
| R-32 | (A-32) | 89.69 | (B-5) | 10.00 | (C-14) | 0.30 | — | — | W-2 |
| R-33 | (A-33) | 78.90 | (B-6) | 20.00 | (C-15) | 0.10 | (D-9) | 1.00 | — |
| R-34 | (A-34) | 89.79 | (B-7) | 10.00 | (C-16) | 0.20 | — | — | W-3 |
| R-35 | (A-1) | 95.00 | (B-8) | 5.00 | — | — | — | — | — |
| R-36 | (A-2) | 89.89 | (B-9) | 10.00 | (C-1) | 0.10 | — | — | W-1 |
| R-37 | (A-1) | 94.90 | — | — | (C-1) | 0.10 | (D-10) | 5.00 | — |
| R-38 | (A-1) | 89.80 | — | — | (C-2) | 0.20 | (D-11) | 10.00 | — |
| R-39 | (A-1) | 84.69 | (B'-1) | 15.00 | (C-3) | 0.30 | — | — | W-1 |
| R-40 | (A'-1) | 79.79 | (B-1) | 20.00 | (C-4) | 0.20 | — | — | W-2 |

| | Solvent | | | | | | |
|---|---|---|---|---|---|---|---|
| Resist composition | Solvent 1 | Content ratio of solvent 1 (% by mass) | Solvent 2 | Content ratio of solvent 2 (% by mass) | Solvent 3 | Content ratio of solvent 3 (% by mass) | Concentration of solid contents (% by mass) |
| R-21 | S-1 | 70 | S-2 | 20 | S-3 | 10 | 2.5 |
| R-22 | S-1 | 60 | S-4 | 20 | S-7 | 20 | 2.0 |
| R-23 | S-1 | 80 | S-2 | 10 | S-3 | 10 | 2.5 |
| R-24 | S-1 | 70 | S-3 | 20 | S-7 | 10 | 3.0 |
| R-25 | S-1 | 40 | S-4 | 20 | S-6 | 40 | 2.0 |
| R-26 | S-1 | 50 | S-2 | 20 | S-3 | 30 | 2.5 |
| R-27 | S-1 | 80 | S-2 | 10 | S-3 | 10 | 2.0 |
| R-28 | S-1 | 70 | S-3 | 20 | S-7 | 10 | 3.0 |
| R-29 | S-1 | 40 | S-4 | 20 | S-6 | 40 | 2.0 |
| R-30 | S-1 | 50 | S-2 | 20 | S-3 | 30 | 2.5 |
| R-31 | S-1 | 80 | S-2 | 10 | S-3 | 10 | 2.0 |
| R-32 | S-1 | 50 | S-4 | 30 | S-5 | 20 | 3.0 |
| R-33 | S-1 | 70 | S-4 | 20 | S-6 | 10 | 2.5 |
| R-34 | S-1 | 40 | S-2 | 30 | S-3 | 30 | 2.0 |
| R-35 | S-2 | 80 | S-4 | 10 | S-5 | 10 | 3.0 |
| R-36 | S-1 | 50 | S-2 | 20 | S-3 | 30 | 3.0 |
| R-37 | S-1 | 60 | S-2 | 20 | S-3 | 20 | 2.5 |
| R-38 | S-1 | 60 | S-2 | 20 | S-3 | 20 | 2.5 |
| R-39 | S-1 | 60 | S-2 | 20 | S-3 | 20 | 2.5 |
| R-40 | S-1 | 60 | S-2 | 20 | S-3 | 20 | 2.5 |

TABLE 5

| | Resist composition | L/S resolution [nm] | Isolated space pattern (IS) resolution [nm] | LWR [nm] |
|---|---|---|---|---|
| Example 1a | R-1 | 24 | 22 | 4.6 |
| Example 2a | R-2 | 25 | 23 | 4.7 |
| Example 3a | R-3 | 23 | 21 | 4.6 |
| Example 4a | R-4 | 24 | 21 | 4.5 |
| Example 5a | R-5 | 23 | 20 | 4.6 |
| Example 6a | R-6 | 21 | 18 | 4.4 |

TABLE 5-continued

| | Resist composition | L/S resolution [nm] | Isolated space pattern (IS) resolution [nm] | LWR [nm] |
|---|---|---|---|---|
| Example 7a | R-7 | 22 | 19 | 4.5 |
| Example 8a | R-8 | 20 | 19 | 4.2 |
| Example 9a | R-9 | 21 | 19 | 4.3 |
| Example 10a | R-10 | 20 | 18 | 4.3 |
| Example 11a | R-11 | 21 | 19 | 4.2 |
| Example 12a | R-12 | 24 | 22 | 4.6 |

TABLE 5-continued

| | Resist composition | L/S resolution [nm] | Isolated space pattern (IS) resolution [nm] | LWR [nm] |
|---|---|---|---|---|
| Example 13a | R-13 | 26 | 24 | 4.7 |
| Example 14a | R-14 | 23 | 22 | 4.6 |
| Example 15a | R-15 | 24 | 22 | 4.5 |
| Example 16a | R-16 | 20 | 19 | 4.2 |
| Example 17a | R-17 | 26 | 24 | 4.8 |
| Example 18a | R-18 | 25 | 24 | 4.7 |
| Example 19a | R-19 | 21 | 18 | 4.5 |
| Example 20a | R-20 | 23 | 20 | 4.6 |

TABLE 6

| | Resist composition | L/S resolution [nm] | Isolated space pattern (IS) resolution [nm] | LWR [nm] |
|---|---|---|---|---|
| Example 21a | R-21 | 22 | 18 | 4.4 |
| Example 22a | R-22 | 21 | 19 | 4.3 |
| Example 23a | R-23 | 22 | 18 | 4.5 |
| Example 24a | R-24 | 23 | 22 | 4.5 |
| Example 25a | R-25 | 23 | 20 | 4.6 |
| Example 26a | R-26 | 22 | 18 | 4.4 |
| Example 27a | R-27 | 22 | 19 | 4.5 |
| Example 28a | R-28 | 25 | 23 | 4.8 |
| Example 29a | R-29 | 29 | 26 | 5.1 |
| Example 30a | R-30 | 27 | 26 | 4.9 |
| Example 31a | R-31 | 27 | 24 | 4.9 |
| Example 32a | R-32 | 25 | 23 | 4.8 |
| Example 33a | R-33 | 25 | 23 | 4.7 |
| Example 34a | R-34 | 26 | 24 | 4.7 |
| Example 35a | R-35 | 21 | 19 | 4.2 |
| Example 36a | R-36 | 20 | 18 | 4.3 |
| Comparative Example 1a | R-37 | 28 | 33 | 7.1 |
| Comparative Example 2a | R-38 | 29 | 28 | 6.8 |
| Comparative Example 3a | R-39 | 41 | 35 | 4.7 |
| Comparative Example 4a | R-40 | 41 | 35 | 4.7 |

From the results in Table 4, it can be seen that the pattern obtained by the pattern forming method of the present invention has excellent resolution and roughness performance.

[Extreme Ultraviolet Ray (EUV) Exposure and Development]

(4) Manufacture of Resist Pattern

A wafer on which the resist film obtained in (3) had been applied was subjected to pattern exposure through an exposure mask (line/space=1/1) using an EUV exposure device (Micro Exposure Tool, manufactured by Exitech, numerical aperture (NA): 0.3, Quadrupole, outer sigma: 0.68, inner sigma: 0.36). Alter the exposure, the film was heated on a hot plate at 100° C. for 90 seconds, dipped using a 2.38%-by-mass aqueous tetramethylammonium hydroxide (TMAH) solution for 60 seconds, and then rinsed with water for 30 seconds. Then, the wafer was rotated at a rotation speed of 4,000 rpm for 30 seconds, baked at 95° C. for 60 seconds, and dried.

[Evaluation]

(5) Evaluation of Resist Pattern

The obtained pattern was evaluated on a resolution and roughness performance by the following methods. The results are shown in Table 5 later.

The irradiation energy upon resolution of a 1:1 line-and-space pattern with a line width of 30 nm was defined as a sensitivity (Eop).

<L/S Resolution>

A marginal resolving power (a minimum line width at which lines and spaces (line:space=1:1) are separated and resolved) at an exposure amount showing the sensitivity (Eop) was taken as a resolving power (nm).

<Isolated Space Pattern (IS) Resolution>

A marginal resolving power (a minimum space width at which lines and spaces are separated and resolved) of an isolated space (line:space=100:1) at the sensitivity (Eop) was determined. Then, this value was defined as an "isolated space pattern resolving power (nm)". A smaller value thereof indicates better performance.

<Roughness Performance (LWR)>

In a case where a 30 nm (1:1) line-and-space pattern resolved with an optimum exposure amount upon resolving a line pattern having an average line width of 20 nm was observed from the upper part of the pattern using a critical dimension scanning electron microscope (SEM (S-938011 manufactured by Hitachi, Ltd.)), the line width was observed at any points, and a measurement deviation thereof was evaluated as 30 (nm). A smaller value thereof indicates better performance.

TABLE 7

| | Resist composition | L/S resolution [nm] | Isolated space pattern (IS) resolution [nm] | LWR [nm] |
|---|---|---|---|---|
| Example 1b | R-1 | 24 | 21 | 4.5 |
| Example 2b | R-2 | 25 | 23 | 4.7 |
| Example 3b | R-3 | 24 | 22 | 4.6 |
| Example 4b | R-4 | 24 | 23 | 4.6 |
| Example 5b | R-5 | 23 | 20 | 4.5 |
| Example 6b | R-6 | 21 | 18 | 4.4 |
| Example 7b | R-7 | 22 | 18 | 4.5 |
| Example 8b | R-8 | 20 | 19 | 4.2 |
| Example 9b | R-9 | 21 | 19 | 4.2 |
| Example 10b | R-10 | 20 | 18 | 4.3 |
| Example 11b | R-11 | 21 | 19 | 4.2 |
| Example 12b | R-12 | 24 | 23 | 4.6 |
| Example 13b | R-13 | 25 | 23 | 4.8 |
| Example 14b | R-14 | 24 | 23 | 4.5 |
| Example 15b | R-15 | 23 | 22 | 4.5 |
| Example 16b | R-16 | 20 | 19 | 4.3 |
| Example 17b | R-17 | 26 | 23 | 4.7 |
| Example 18b | R-18 | 26 | 24 | 4.8 |
| Example 19b | R-19 | 21 | 18 | 4.4 |
| Example 20b | R-20 | 23 | 21 | 4.5 |

TABLE 8

| | Resist composition | L/S resolution [nm] | Isolated space pattern (IS) resolution [nm] | LWR [nm] |
|---|---|---|---|---|
| Example 21b | R-21 | 22 | 19 | 4.7 |
| Example 22b | R-22 | 21 | 18 | 4.2 |
| Example 23b | R-23 | 22 | 18 | 4.4 |
| Example 24b | R-24 | 24 | 22 | 4.6 |
| Example 25b | R-25 | 23 | 20 | 4.6 |
| Example 26b | R-26 | 21 | 18 | 4.4 |
| Example 27b | R-27 | 22 | 19 | 4.5 |
| Example 28b | R-28 | 25 | 23 | 4.7 |
| Example 29b | R-29 | 28 | 27 | 5.2 |
| Example 30b | R-30 | 27 | 25 | 4.9 |
| Example 31b | R-31 | 26 | 24 | 5.0 |
| Example 32b | R-32 | 24 | 23 | 4.7 |
| Example 33b | R-33 | 25 | 24 | 4.7 |
| Example 34b | R-34 | 24 | 24 | 4.8 |
| Example 35b | R-35 | 20 | 18 | 4.3 |
| Example 36b | R-36 | 21 | 19 | 4.2 |

TABLE 8-continued

| | Resist composition | L/S resolution [nm] | Isolated space pattern (IS) resolution [nm] | LWR [nm] |
|---|---|---|---|---|
| Comparative Example 1b | R-37 | 28 | 35 | 7.3 |
| Comparative Example 2b | R-38 | 29 | 28 | 6.9 |
| Comparative Example 3b | R-39 | 43 | 35 | 4.9 |
| Comparative Example 4b | R-40 | 43 | 35 | 4.9 |

From the results in Table 5, it can be seen that the pattern obtained by the pattern forming method of the present invention has excellent resolution and roughness performance.

According to the present invention, it is possible to provide an actinic ray-sensitive or radiation-sensitive resin composition capable of improving roughness performance and a resolving power at a high level in formation of an ultrafine pattern (particularly having a line width or space width or 30) nm or less). According to the embodiment of the present invention, it is also possible to provide an actinic ray-sensitive or radiation-sensitive film, a pattern forming method, and a method for manufacturing an electronic device, each of which uses the actinic ray-sensitive or radiation-sensitive resin composition.

Although the present invention has been described in detail with reference to specific embodiments, it will be apparent to those skilled in the art that various changes and modifications can be made without departing from the spirit and the scope of the present invention.

The present application is based on Japanese Patent Application (Patent Application No. 2020-65191) filed on Mar. 31, 2020, the contents of which are incorporated herein by reference.

What is claimed is:

1. An actinic ray-sensitive or radiation-sensitive resin composition comprising:

(A) a resin having a polarity that increases by an action of an acid; and (B) a compound that generates an acid upon irradiation with actinic rays or radiation, represented by the following General Formula (I), wherein the resin (A) includes a repeating unit represented by the following General Formula (AI), (AI)

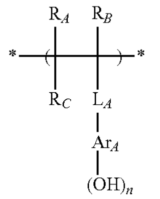

in the General Formula (AI), $R_A$, $R_B$, and $R_C$ each independently represent a hydrogen atom, an alkyl group, a cycloalkyl group, a halogen atom, a cyano group, or an alkoxycarbonyl group, provided that RC may be bonded to $Ar_A$ to form a ring, in which case RC represents a single bond or an alkylene group, $L_A$ represents a single bond or a divalent linking group, $Ar_A$ represents an (n+1)-valent aromatic ring group, and in a case where Are is bonded to $R_C$ to form a ring, $Ar_A$ represents an (n+2)-valent aromatic ring group, and n represents an integer of 1 to 5, (I)

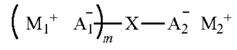

in the General Formula (I), $M_1^+$ and $M_2^+$ each independently represent a cation, X represents a single bond or an (m+1)-valent linking group, $A_1^-$ and $A_2^-$ each independently represent an anionic group, and $A_1^-$ represents a structure different from the anionic group represented by $A_2^-$, and m represents 1 or 2, and in a case where m represents 2, a plurality of $M_1^+$'s may be the same as or different from each other, and in a case where m represents 2, a plurality of $A_1^-$'s may be the same as or different from each other, provided that a compound (PI) in which $M_1^+$ and $M_2^+$ of the compound represented by the General Formula (I) are each substituted with a hydrogen atom having an acid dissociation constant a1 of a group represented by $HA_1$ and an acid dissociation constant a2 of a group represented by $A_2H$, the acid dissociation constant a1 is lower than the acid dissociation constant a2, and the acid dissociation constant a1 is −1.5 or more, wherein in the General Formula (I), $A_1^-$ and $A_2^-$ are each independently a group selected from the group consisting of groups represented by the following General Formulae (B-1) to (B-27), (B-1)

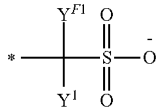

(B-2)

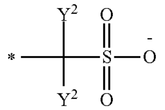

(B-3)

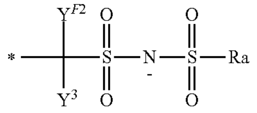

(B-4)

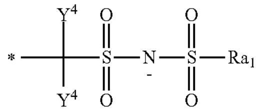

(B-5)

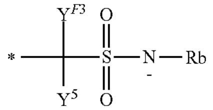

(B-6)

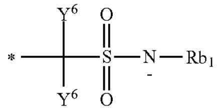

-continued
(B-7)
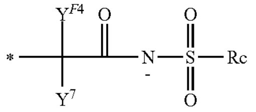
(B-8)
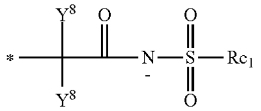
(B-9)
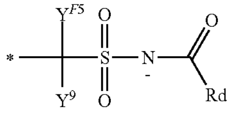
(B-10)
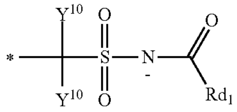
(B-11)
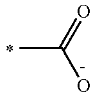
(B-12)
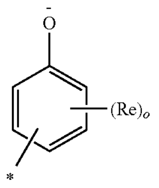
(B-13)
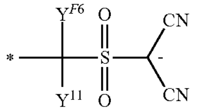
(B-14)
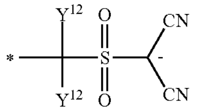
(B-15)
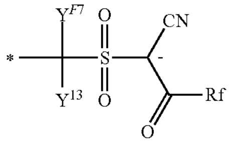
(B-16)
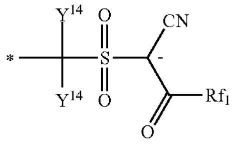
(B-17)
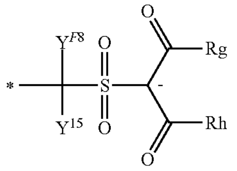
-continued
(B-18)
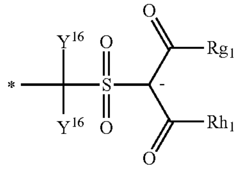
(B-19)
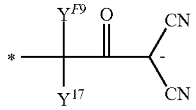
(B-20)
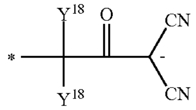
(B-21)
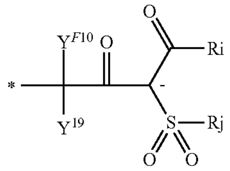
(B-22)
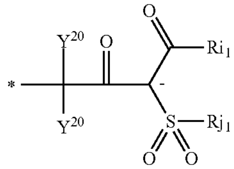
(B-23)
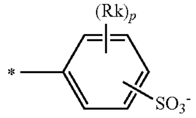
(B-24)
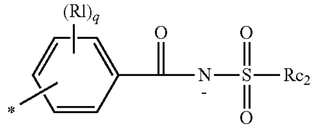
(B-25)
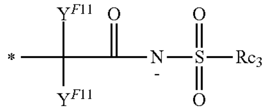
(B-26)
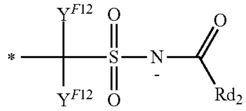
(B-27)
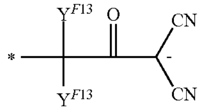
in the General Formula (B-1),
$Y^{F1}$ represents a fluorine atom or a perfluoroalkyl group, and
$Y^1$ represents a hydrogen atom or a substituent having no fluorine atom,
in the General Formula (B-2), $Y^2$'s each independently represent a hydrogen atom or a substituent having no fluorine atom, in the General Formula (B-3), $Y^{F2}$ represents a fluorine atom or a perfluoroalkyl group, $Y^3$ represents a hydrogen atom or a substituent having no fluorine atom, and Ra represents an organic group, in the General Formula (B-4), $Y^4$'s each independently represent a hydrogen atom or a substituent having no fluorine atom, and $Ra_1$ represents an organic group, in the General Formula (B-5), $Y^{F3}$ represents a fluorine atom or a perfluoroalkyl group, $Y^{5'}$ represents a hydrogen atom or a substituent having no fluorine atom, and Rb represents a hydrogen atom or an organic group, in the General Formula (B-6), $Y^6$'s each independently represent a hydrogen atom or a substituent having no fluorine atom, and $Rb_1$ represents a hydrogen atom or an organic group, in the General Formula (B-7), $Y^{F4}$ represents a fluorine atom or a perfluoroalkyl group, $Y^7$ represents a hydrogen atom or a substituent having no fluorine atom, and Rc represents an organic group, in the General Formula (B-8), $Y^8$'s each independently represent a hydrogen atom or a substituent having no fluorine atom, and $Rc_1$ represents an organic group, in the General Formula (B-9), $Y^{F5}$ represents a fluorine atom or a perfluoroalkyl group, $Y^9$ represents a hydrogen atom or a substituent having no fluorine atom, and Rd represents an organic group, in the General Formula (B-10), $Y^{10}$'s each independently represent a hydrogen atom or a substituent having no fluorine atom, and $Rd_1$ represents an organic group, in the General Formula (B-12), Re represents a hydrogen atom, an organic group, or a halogen atom, represents an integer of 1 to 4, and in a case where o represents an integer of 2 or more, a plurality of Re's may be the same as or different from each other, in the General Formula (B-13), $Y^{F6}$ represents a fluorine atom or a perfluoroalkyl group, and $Y^{11}$ represents a hydrogen atom or a substituent having no fluorine atom, in the General Formula (B-14), $Y^{12}$'s each independently represent a hydrogen atom or a substituent having no fluorine atom, in the General Formula (B-15), $Y^{F7}$ represents a fluorine atom or a perfluoroalkyl group, $Y^{13}$ represents a hydrogen atom or a substituent having no fluorine atom, and Rf represents an organic group, in the General Formula (B-16), $Y^{14}$'s each independently represent a hydrogen atom or a substituent having no fluorine atom, and $Rf_1$ represents an organic group, in the General Formula (B-17), $Y^{F8}$ represents a fluorine atom or a perfluoroalkyl group, $Y^{15}$ represents a hydrogen atom or a substituent having no fluorine atom, Rg represents an organic group, and Rh represents an organic group, in the General Formula (B-18), $Y^{16}$'s each independently represent a hydrogen atom or a substituent having no fluorine atom, $Rg_1$ represents an organic group, and $Rh_1$ represents an organic group, in the General Formula (B-19), $Y^{F9}$ represents a fluorine atom or a perfluoroalkyl group, and $Y^{17}$ represents a hydrogen atom or a substituent having no fluorine atom, in the General Formula (B-20), $Y^{18}$'s each independently represent a hydrogen atom or a substituent having no fluorine atom, in the General Formula (B-21), $Y^{F10}$ represents a fluorine atom or a perfluoroalkyl group, $Y^{19}$ represents a hydrogen atom or a substituent having no fluorine atom, Ri represents an organic group, and Rj represents an organic group, in the General Formula (B-22), $Y^{20}$'s each independently represent a hydrogen atom or a substituent having no fluorine atom, $Ri_1$ represents an organic group, and $Rj_1$ represents an organic group, in the General Formula (B-23), Rk represents a hydrogen atom or a substituent having no fluorine atom, p represents an integer of 1 to 4, and in a case where p represents an integer of 2 or more, a plurality of Rk's may be the same as or different from each other, in the General Formula (B-24), Rl represents a hydrogen atom, an organic group, or a halogen atom, q represents an integer of 1 to 4, in a case where q represents an integer of 2 or more, a plurality of Rl's may be the same as or different from each other, and $Rc_2$ represents an organic group, in the General Formula (B-25), $Y^{F11}$'s each independently represent a fluorine atom or a perfluoroalkyl group, and $Rc_3$ represents an organic group, in the General Formula (B-26), $Y^{F12}$'s each independently represent a fluorine atom or a perfluoroalkyl group, and $Rd_2$ represents an organic group, in the General Formula (B-27), $Y^{F13}$'s each independently represent a fluorine atom or a perfluoroalkyl group, and in the General Formulae (B-1) to (B-27),

* represents a bonding position.

2. The actinic ray-sensitive or radiation-sensitive resin composition according to claim 1, wherein a difference between the acid dissociation constant a1 and the acid dissociation constant a2 is 2.0 or more in the compound (PI).

3. The actinic ray-sensitive or radiation-sensitive resin composition according to claim 1, wherein the acid dissociation constant a2 is 2.0 or more in the compound (PI).

4. The actinic ray-sensitive or radiation-sensitive resin composition according to claim 1, wherein in the General Formula (I), A1 is the group represented by the General Formula (B-2) or (B-23).

5. The actinic ray-sensitive or radiation-sensitive resin composition according to claim 1, wherein in the General Formula (I), A1 is the group represented by the General Formula (B-2).

6. The actinic ray-sensitive or radiation-sensitive resin composition according to claim 1, wherein (A) the resin having a polarity that increases by an action of an acid includes a repeating unit having an acid-decomposable group, and the repeating unit having an acid-decomposable group is a repeating unit selected from the group consisting of a group that decomposes by an action of an acid to generate a carboxy group and a group that decomposes by an action of an acid to generate a phenolic hydroxyl group.

7. The actinic ray-sensitive or radiation-sensitive resin composition according to claim 6, wherein the repeating unit having an acid-decomposable group includes one or more selected from repeating units represented by the following General Formulae (3) to (7), (3)

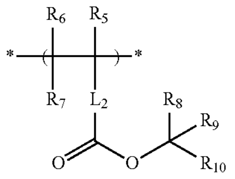

(4)

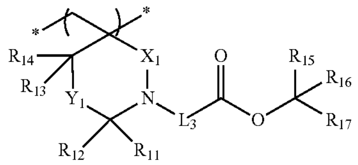

(5)

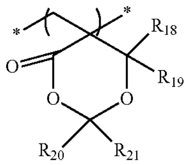

(6)

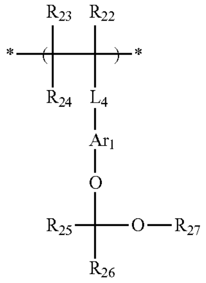

(7)

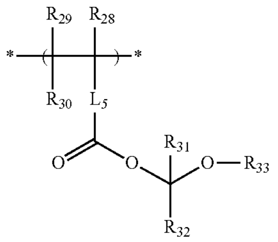

in the General Formula (3), $R_5$, $R_6$, and $R_7$ each independently represent a hydrogen atom, an alkyl group, a cycloalkyl group, a halogen atom, a cyano group, or an alkoxycarbonyl group, $L_2$ represents a single bond or a divalent linking group, $R_8$ to $R_{10}$ each independently represent an alkyl group, a cycloalkyl group, an aryl group, an aralkyl group, or an alkenyl group, and two of $R_8$ to $R_{10}$ may be bonded to each other to form a ring, in the General Formula (4), $R_{11}$ to $R_{14}$ each independently represent a hydrogen atom or an organic group, provided that at least one of $R_{11}$ or $R_{12}$ represents an organic group, $X_1$ represents —CO—, —SO—, or —$SO_2$—, $Y_1$ represents —O—, —S—, —SO—, —$SO_2$—, or —$NR_{34}$—, $R_{34}$ represents a hydrogen atom or an organic group, $L_3$ represents a single bond or a divalent linking group, $R_{15}$ to $R_{17}$ each independently represent an alkyl group, a cycloalkyl group which may have a fluorine atom, an aryl group, an aralkyl group, or an alkenyl group, and two of $R_{15}$ to $R_{17}$ may be bonded to each other to form a ring, in the General Formula (5), $R_{18}$ and $R_{19}$ each independently represent a hydrogen atom or an organic group, $R_{20}$ and $R_{21}$ each independently represent a hydrogen atom, an alkyl group, a cycloalkyl group, an aryl group, an aralkyl group, or an alkenyl group, and $R_{20}$ and $R_{21}$ may be bonded to each other to form a ring, in the General Formula (6), $R_{22}$, $R_{23}$, and $R_{24}$ each independently represent a hydrogen atom, an alkyl group, a cycloalkyl group, a halogen atom, a cyano group, or an alkoxycarbonyl group, $L_4$ represents a single bond or a divalent linking group, $Ar_1$ represents an aromatic ring group, $R_{25}$ to $R_{27}$ each independently represent a hydrogen atom, an alkyl group, a cycloalkyl group, an aryl group, an aralkyl group, or an alkenyl group, $R_{26}$ and $R_{27}$ may be bonded to each other to form a ring, and $Ar_1$ may be bonded to $R_{24}$ or $R_{25}$ to form a ring, and in the General Formula (7), $R_{28}$, $R_{29}$, and $R_{30}$ each independently represent a hydrogen atom, an alkyl group, a cycloalkyl group, a halogen atom, a cyano group, or an alkoxycarbonyl group, $L_5$ represents a single bond or a divalent linking group, $R_{31}$ and $R_{32}$ each independently represent a hydrogen atom, an alkyl group, a cycloalkyl group, an aryl group, an aralkyl group, or an alkenyl group, $R_{33}$ represents an alkyl group, a cycloalkyl group, an aryl group, an aralkyl group, or an alkenyl group, and $R_{32}$ and $R_{33}$ may be bonded to each other to form a ring.

8. The actinic ray-sensitive or radiation-sensitive resin composition according to claim 7, wherein the repeating unit having an acid-decomposable group includes one or more selected from the repeating unit represented by the General Formula (6) and the repeating unit represented by the General Formula (7).

9. The actinic ray-sensitive or radiation-sensitive resin composition according to claim 6, wherein the repeating unit having an acid-decomposable group includes no halogen atom.

10. An actinic ray-sensitive or radiation-sensitive film formed of the actinic ray-sensitive or radiation-sensitive resin composition according to claim 1.

11. A pattern forming method comprising:

forming a resist film using the actinic ray-sensitive or radiation-sensitive resin composition according to claim 1;

exposing the resist film; and developing the exposed resist film by a developer.

12. A method for manufacturing an electronic device, comprising the pattern forming method according to claim 11.

* * * * *